United States Patent
Maciag et al.

(10) Patent No.: US 9,644,212 B2
(45) Date of Patent: *May 9, 2017

(54) DUAL DELIVERY SYSTEM FOR HETEROLOGOUS ANTIGENS

(71) Applicant: Advaxis, Inc., East Princeton, NJ (US)

(72) Inventors: Paulo Maciag, Northbrook, IL (US); Anu Wallecha, Yardley, PA (US); Vafa Shahabi, Valley Forge, PA (US)

(73) Assignee: ADVAXIS, INC., East Princeton, NJ (US)

( * ) Notice: Subject to any disclaimer, the term of this patent is extended or adjusted under 35 U.S.C. 154(b) by 137 days.

This patent is subject to a terminal disclaimer.

(21) Appl. No.: 14/204,806

(22) Filed: Mar. 11, 2014

(65) Prior Publication Data

US 2014/0314708 A1    Oct. 23, 2014

Related U.S. Application Data

(62) Division of application No. 12/993,380, filed as application No. PCT/US2009/044538 on May 19, 2009.

(60) Provisional application No. 61/071,792, filed on May 19, 2008.

(51) Int. Cl.
| | | |
|---|---|---|
| C12N 1/20 | (2006.01) | |
| C12N 15/74 | (2006.01) | |
| A61K 39/00 | (2006.01) | |
| C07K 14/47 | (2006.01) | |
| C07K 14/515 | (2006.01) | |
| A61K 39/39 | (2006.01) | |

(52) U.S. Cl.
CPC .......... C12N 15/74 (2013.01); A61K 39/0011 (2013.01); A61K 39/39 (2013.01); C07K 14/4748 (2013.01); C07K 14/515 (2013.01); A61K 2039/523 (2013.01); A61K 2039/6006 (2013.01)

(58) Field of Classification Search
CPC ..................................................... C12N 15/74
See application file for complete search history.

(56) References Cited

U.S. PATENT DOCUMENTS

| | | | |
|---|---|---|---|
| 4,458,066 A | 7/1984 | Caruthers et al. | |
| 4,521,382 A | 6/1985 | Kessick | |
| 4,816,567 A | 3/1989 | Cabilly et al. | |
| 5,204,253 A | 4/1993 | Sanford et al. | |
| 5,262,177 A | 11/1993 | Brown et al. | |
| 5,580,859 A | 12/1996 | Felgner et al. | |
| 5,589,466 A | 12/1996 | Felgner et al. | |
| 5,643,599 A | 7/1997 | Lee et al. | |
| 5,679,647 A | 10/1997 | Carson et al. | |
| 5,681,570 A | 10/1997 | Yang et al. | |
| 5,736,524 A | 4/1998 | Content et al. | |
| 5,739,118 A | 4/1998 | Carrano et al. | |
| 5,804,566 A | 9/1998 | Carson et al. | |
| 5,824,538 A | 10/1998 | Branstrom et al. | |
| 5,830,702 A | 11/1998 | Portnoy et al. | |
| 5,858,682 A | 1/1999 | Gruenwald et al. | |
| 5,877,159 A | 3/1999 | Powell et al. | |
| 5,922,583 A | 7/1999 | Morsey et al. | |
| 5,922,687 A | 7/1999 | Mann et al. | |
| 6,004,815 A | 12/1999 | Portnoy et al. | |
| 6,015,567 A | 1/2000 | Hudziak et al. | |
| 6,017,705 A | 1/2000 | Lurquin et al. | |
| 6,051,237 A | 4/2000 | Paterson et al. | |
| 6,099,848 A | 8/2000 | Frankel et al. | |
| 6,287,556 B1 | 9/2001 | Portnoy et al. | |
| 6,306,404 B1 | 10/2001 | LaPosta et al. | |
| 6,329,511 B1 | 12/2001 | Vasquez et al. | |
| 6,479,258 B1 | 11/2002 | Short | |
| 6,500,432 B1 | 12/2002 | Dalemans et al. | |
| 6,504,020 B1 | 1/2003 | Frankel et al. | |
| 6,521,449 B1 | 2/2003 | Polack et al. | |
| 6,599,502 B2 | 7/2003 | Portnoy et al. | |
| 6,635,749 B2 | 10/2003 | Frankel et al. | |
| 6,740,516 B2 | 5/2004 | Savitzky et al. | |
| 6,767,542 B2 | 7/2004 | Paterson et al. | |
| 6,773,900 B2 | 8/2004 | Short et al. | |
| 6,855,320 B2 | 2/2005 | Paterson et al. | |
| 6,991,785 B2 | 1/2006 | Frey, II | |
| 7,135,188 B2 | 11/2006 | Paterson et al. | |
| 7,375,091 B2 | 5/2008 | Cheever et al. | |
| 7,425,449 B2 | 9/2008 | Portnoy et al. | |
| 7,488,487 B2 | 2/2009 | Frankel et al. | |

(Continued)

FOREIGN PATENT DOCUMENTS

| | | |
|---|---|---|
| CN | 1763093 A | 4/2006 |
| EP | 0902086 | 3/1999 |

(Continued)

OTHER PUBLICATIONS

U.S. Appl. No. 09/050,739, filed Jan. 22, 2004, Peter Andersen et al.
U.S. Appl. No. 13/290,783, filed May 31, 2012, Anu Wallecha.
U.S. Appl. No. 60/490,089, filed Jul. 24, 2003, Thomas W. Dubenksy.
Abachin et al., Formation of D-alanyl-lipoteichoic acid is required for adhesion and virulence of Listeria monocytogenes 2002, *Mol Microbiol* 43:1-14.
Ahmadzadeh M et al. Tumor antigen-specific CD8 T cells infiltrating the tumor express high levels of PD-1 and are functionally impaired. Blood (2009) 114: 1537-1544.
Alexander et al, Characterization of an Aromatic Amino Acid-Dependent Listeria monocytogenes Mutant: Attenuation, Persistence, and Ability To Induce Protective Immunity in Mice 1993, *Infection and Immunity* 10 61 :2245-2248.

(Continued)

*Primary Examiner* — Albert Navarro
(74) *Attorney, Agent, or Firm* — Alston & Bird LLP

(57) ABSTRACT

Provided herein are recombinant *Listeria* strains expressing a tumor-specific antigenic polypeptide and, optionally, an angiogenic polypeptide wherein a nucleic acid molecule encoding at least one of the polypeptides is operably integrated into the *Listeria* genome in an open reading frame with a nucleic acid sequence encoding a PEST-containing polypeptide, methods of preparing same, and methods of inducing an immune response, and treating, inhibiting, or suppressing cancer or tumors comprising administering same.

10 Claims, 12 Drawing Sheets

(56) References Cited

U.S. PATENT DOCUMENTS

| | | |
|---|---|---|
| 7,488,802 B2 | 2/2009 | Collins et al. |
| 7,521,051 B2 | 4/2009 | Collins et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,691,393 B2 | 4/2010 | Dubensky et al. |
| 7,700,344 B2 | 4/2010 | Paterson et al. |
| 7,786,288 B2 | 8/2010 | Karp |
| 7,790,177 B2 | 9/2010 | Karp |
| 7,794,728 B2 | 9/2010 | Portnoy et al. |
| 7,794,729 B2 | 9/2010 | Paterson et al. |
| 7,820,180 B2 | 10/2010 | Paterson et al. |
| 7,842,289 B2 | 11/2010 | Dubensky et al. |
| 7,855,064 B2 | 12/2010 | Paterson et al. |
| 7,858,097 B2 | 12/2010 | Paterson et al. |
| 7,871,604 B1 | 1/2011 | Curtiss, III et al. |
| 7,887,822 B2 | 2/2011 | Ferrone et al. |
| 7,935,804 B2 | 5/2011 | Dubensky et al. |
| 8,008,449 B2 | 8/2011 | Korman et al. |
| 8,114,414 B2 | 2/2012 | Paterson et al. |
| 8,168,757 B2 | 5/2012 | Finnefrock et al. |
| 8,287,883 B2 | 10/2012 | Dubensky et al. |
| 8,354,509 B2 | 1/2013 | Carven et al. |
| 8,383,796 B2 | 2/2013 | Korman et al. |
| 8,771,702 B2 | 7/2014 | Paterson et al. |
| 9,017,660 B2 | 4/2015 | Shahabi et al. |
| 2002/0025323 A1 | 2/2002 | Paterson et al. |
| 2002/0136737 A1 | 9/2002 | Frankel et al. |
| 2002/0165172 A1 | 11/2002 | Sallberg et al. |
| 2003/0220239 A1 | 11/2003 | Simard et al. |
| 2004/0013685 A1 | 1/2004 | Andersen et al. |
| 2004/0013690 A1 | 1/2004 | Portnoy et al. |
| 2004/0058342 A1 | 3/2004 | Yousef |
| 2004/0228877 A1 | 11/2004 | Dubensky et al. |
| 2005/0048081 A1 | 3/2005 | Frankel et al. |
| 2005/0118184 A1 | 6/2005 | Paterson et al. |
| 2005/0129715 A1 | 6/2005 | Paterson et al. |
| 2005/0281783 A1 | 12/2005 | Kinch et al. |
| 2006/0051380 A1 | 3/2006 | Schulick et al. |
| 2006/0073170 A1 | 4/2006 | Papierok |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2007/0154953 A1 | 7/2007 | Brunner et al. |
| 2007/0207170 A1 | 9/2007 | Dubensky et al. |
| 2007/0207171 A1 | 9/2007 | Dubensky et al. |
| 2007/0253976 A1 | 11/2007 | Paterson et al. |
| 2007/0264279 A1 | 11/2007 | Paterson et al. |
| 2008/0124354 A1 | 5/2008 | Paterson et al. |
| 2008/0131456 A1 | 6/2008 | Paterson et al. |
| 2008/0213295 A1 | 9/2008 | Cheever et al. |
| 2008/0241069 A1 | 10/2008 | Paterson |
| 2009/0202587 A1 | 8/2009 | Paterson et al. |
| 2010/0069344 A1 | 3/2010 | Wang et al. |
| 2010/0189739 A1 | 7/2010 | Frankel et al. |
| 2010/0233212 A1 | 9/2010 | Dubensky |
| 2011/0129499 A1 | 6/2011 | Maciag et al. |
| 2011/0142791 A1 | 6/2011 | Shahabi et al. |
| 2011/0223187 A1 | 9/2011 | Shahabi et al. |
| 2011/0271358 A1 | 11/2011 | Freeman et al. |
| 2012/0014984 A1 | 1/2012 | Shahabi |
| 2012/0135033 A1 | 5/2012 | Wallecha |
| 2014/0186387 A1 | 7/2014 | Lauer et al. |
| 2014/0199258 A1 | 7/2014 | Rothman |

FOREIGN PATENT DOCUMENTS

| | | |
|---|---|---|
| EP | 1408048 | 4/2004 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/34631 | 11/1996 |
| WO | WO 96/39154 | 12/1996 |
| WO | WO 97/03211 | 1/1997 |
| WO | WO 98/04720 | 2/1998 |
| WO | WO 98/48026 | 10/1998 |
| WO | WO 99/07861 | 2/1999 |
| WO | WO 99/25376 | 5/1999 |
| WO | WO 01/72329 | 10/2001 |
| WO | WO 01/79274 | 10/2001 |
| WO | WO 03/092600 | 11/2003 |
| WO | WO 03/102168 | 12/2003 |
| WO | WO2004/004771 | 1/2004 |
| WO | WO 2004/006837 | 1/2004 |
| WO | WO2004/056875 | 7/2004 |
| WO | WO2004/072286 | 8/2004 |
| WO | WO 2005/061534 | 7/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2008/045148 A2 | 4/2008 |
| WO | WO 2008/109155 | 9/2008 |
| WO | WO 2008/130551 | 10/2008 |
| WO | 2009/0143085 | 6/2009 |
| WO | WO 2009/110950 | 9/2009 |
| WO | WO2009/143085 | 11/2009 |
| WO | WO 2009/143167 | 11/2009 |
| WO | WO2010/027827 | 3/2010 |
| WO | WO2010/077634 | 7/2010 |
| WO | WO 2011/060260 A2 | 5/2011 |
| WO | WO2011/066342 | 6/2011 |
| WO | WO 2011/100754 A1 | 8/2011 |
| WO | WO2013/019906 | 2/2013 |
| WO | WO2014/100079 | 6/2014 |

OTHER PUBLICATIONS

Altschul, S.F ., et al., "Gapped BLAST and PSI-BLAST: a new generation of protein database search programs" (1997) Nucleic Acids Res. 25:3389-3402.

Angelakopoulos et al., "Safety and shedding of an attenuated strain of listeria monocytogenes with a delection of actA/plcB in adult volunteers: a dose escalation study of oral innoculation", Infection and Immunity 2002, 70(7): 3592-3601.

Anthony "Precursor Lesions for Liver Cancer in Humans" Cancer Res. (1976) 36:2579-2583.

Auchtung JM et al "Regulation of a *Bacillus subtilis* mobile genetic element by intercellular signaling and the global DNA damage response". *Proc Natl Acad Sci* USA. Aug. 30, 2005;102 (35): 12554-9.

Auerbuch, et al. "Development of a Competitive Index Assay To Evaluate the Virulence of *Listeria monocytogenes* actA Mutants during Primary and Secondary Infection of Mice" (2001) Infec. Immunity 69:5953-5957.

Baca et al., "Protein Chemistry and Structure: Antibody humanization using monovalent phage display", (1997) J. Biol. Chem. 272:10678-10684.

Baert et al. "Influence of Immunogenicity on the Long-Term Efficacy of Infliximab in Crohn's Disease" (2003) New Engl. J. Med. 348:601-608.

Baloglu et al. "Immune Responses Of Mice To Vaccinia Virus Recombinants Expressing Either Listeria Monocytogenes Partial Listeriolysin Or *Brucella abortus* Ribosomal L7/L12 Protein" Vet Microbiol.; 109(1-2) M., Aug. 10, 2005.

Bargmann et al. "The neu oncogene encodes an epidermal growth facor receptor-related protein" Nature 319, 226-230, Jan. 16, 1986.

Beatty and Paterson, IFN-gamma-dependent inhibition of tumor angiogenesis by tumor-infiltraing CD4+ T cells requires tumor responsiveness to IFN-gamma.J Immunol. Feb. 15, 2001;166(4):2276-82.

Beaucage et al. "Deoxynucleoside Phosphoramidites—A New Class of Key Intermediates For Deoxypolynucleotide Synthesis" Tetra Lett. 22:1859-1862 (1981).

(56) References Cited

OTHER PUBLICATIONS

Belt, P.B.G.M., et al (1991) Efficient cDNA cloning by direct phenotypic correction of a mutant human cell line (HPRT2) using an Epstein-Barr virus-derived cDNA expression vector. Nucleic Acids Res. 19, 4861-4866.
Beniaminovitz et al. "Prevention Of Rejection In Cardiac Transplantation By Blockade Of The Interleukin-2 Receptor With A Monoclonal Antibody" (2000) New Engl. J. Med. 342:613-619.
Boyer et al., "DNA prime Listeria boost induces a cellular immune response to SIV antigens in the Rhesus Macaque model that is capable of limited suppression of SIV239 viral replication", Virology. 333: 88-101, 2005.
Brantl et al, "Molecular analysis of the replication region of the conjugative *Streptococcus agalactiae* plasmid pIP501 in Bacillus subtilis. Comparision with plasmids pAM31 and pSM1 9035" Nucleic Acid Res 18: 4783-4790, 1990.
Brockstedt et al, "Listeria-based cancer vaccines that segregate immunogenicity from toxicity" 2004, *PNAS*, 101:13832-13837.
Bron et al, "Use of the air Gene as a Food-Grade Selection Marker in Lactic Acid Bacteria" 2002, Appl Environ Microbiol, 68: 5663-70.
Brundage et al, 1993. Expression and phosphorylation of the Listeria monocytogenes ActA protein in mammalian cells, *Proc. Natl. Acad. Sci.*, USA, 90:11890-11894.
Camilli et al, 1991, Listeria monocytogenes mutant lacking phosphatidylinositol-specific phospholipase C area virulent, *J. Exp. Med.*, 173:751-754.
Cenatiemp et al. "Prokaryotic gene expression in vitro: transcription-translation coupled systems" Biochimie 68:505-515 (1986).
Chen, B.J. et al., "PD-L1 Expression Is Characteristic of a Subset of Aggressive B-cell Lymphomas and Virus-Associated Malignancies" Clin Cancer Res 19: 3462-3473 (2013).
Clifton Guy et al., "Overcoming cancer immune intolerance and escape", Clinical Cancer Research : An Official Journal Of The Amirican Association For Cancer Research 2009, vol. 15, No. 3, pp. 749-751.
De Boer et al, "A division inhibitor and a topological specificity factor coded for by the minicell locus determine proper placement of the division septum in *E. coli*" 1989 *Cell* 56:641-649.
Dell'erba et al., "Immunohistochemical reactivity of anti-melanoma monoclonal antibody 225.28S in Human Breast Cancer Biopsies", Anticancer Res. 2001, vol. 21, No. 2A, pp. 925-930.
Disis, "Generation of immunity to the HER-2/neu oncogenic protein in patients with breast and ovarian cancer using a peptide-based vaccine" Clin Cancer Res. 5(6):1289-97, Jun. 1999.
Dzojic H et al "Adenovirus-mediated CD40 ligand therapy induces tumor cell apoptosis and systemic immunity in the TRAMP-C2 mouse prostate cancer model" The Prostate 66: 831-838 (2006).
European Search report Application No. 09751395.6 Date Of Mailing Jul. 11, 2012.
European Search report Application No. 10830785.1 Date Of Mailing Dec. 10, 2013.
Flint et al., "Overexpression of the erbB-2 proto-oncogene in canine osteosarcoma cell lines and tumors", Vet. Pathol. 41: 291-296, 2004.
Frankel et al., "Induction of a cell-mediated immune reponse to HIV gag using Listeria monocytogenes as a live vaccine vector", J. Immunol. 155: 4766-4774. 1995.
Gadiot, J., et al., "Overall survival and PD-L1 expression in metastasized malignant melanoma" Cancer 117:2192-2201 (2011).
Gao et al. Overexpression of PD-L1 significantly associates with tumor aggressiveness and postoperative recurrence in human hepatocellular carcinoma. Clincal Cancer Research (2009) 15: 971-979.
Garay-Malpartida HM, Occhiucci JM, Alves J, Belizario JE, Bioinformatics. Jun. 2005; 21 Suppl 1 :169-76.
Ghebeh et al. B7-H1 (PD-L1) T lymphocyte-inhibitory molecule is expressed in breast cancer patients with infiltrating ductal carcinoma: correlation with important high-risk propgnostic factors. Neoplasia (2006): 8: 190-198.
Ghebeh H. Foxp3+ tregs and B7-H1+/PD-1+ T lymphocytes co-infiltrate the tumor tissues of high-risk breast cancer patients: implication for immunotherapy. BMC Cancer. Feb. 23, 2008;8:57.
Ghosh et al. "Natalizumab for Active Crohn's Disease" (2003) New Engl. J. Med. 348:24-32.
Glick (1987). Factors affecting the expression of foreign proteins in *Escherichia coli*, *J. Ind. Microbiol.* 1:277-282.
Gottesman, (1984). Bacterial regulation: global regulatory networks Annu Rev Genet, *Ann. Rev. Genet.* 18:415-442.
Gunn et al., "Two Listeria monocytogenes vaccine vectors that express different molecular forms of human papilloma virus-16 E7 induce qualitatively different T cell immunity that correlated with their avility to induce regression of established tumors immortalized by HPV-16", Journal of Immunology, vol. 167, No. 11, 2001, pp. 6471-6479.
Hamanishi J et al. Programmed cell death 1 ligand 1 and tumor-infiltrating CD8+ T lymphocytes are prognostic factors of human ovarian cancer. Proceeding of the National Academy of Sciences (2007): 104: 3360-3365.
Heinrich JE et al (Vaccination against prostate cancer using a live tissue factor deficient cell line in Lobund-Wistar rats. Cancer Immunol Immunother 2007;56(5):725-30).
Henikoff, S., et al., "Amino acid substitution matrices from protein blocks" (1992) Proc. Nat. Acad. Sci. USA 89:10915-10919.
Herold et al. "Anti-Cd3 Monoclonal Antibody In New-Onset Type 1 Diabetes Mellitus" (2002) New Engl. J. Med. 346:1692-1698.
Hino et al. Tumor cell expression of programmed cell death-1 is a prognostic factor for malignant melanoma. Cancer (2010 116(7):1757-66.
Hjortland et al., "Immunotoxin treatment targeted to the higher-molecular weight melanoma-associated antigen prolonging the survival of immunodeficient rats with invasive intracranial human glioblastoma multiforme", J. Neurosurg. 2004, vol. 100, No. 2, pp. 320-327.
Inman et al. PD-L1 (B7-H1) expression by urothelial carcinoma of the bladder and BCG-induced granulomata: associations with localized stage progression. Cancer (2007): 109: 1499-1505.
International Search report Application No. PCT/US 10/56534 Date Of Mailing Jun. 27, 2011.
International Search report Application No. PCT/US2012/051187 Date Of Mailing Jan. 23, 2013.
International Search report Application No. PCT/US2009/44538 Date Of Mailing Aug. 14, 2009.
Jiang et al. "Characterization of a mutant Lysteria monocytogenes strain expressing green fluorescent protein" Acta. Biochim. Biophys Sin (Shanghai), 37(1): 19-24, (2005).
Johnson et al., "Kabat database and its applications: 30 years after the first variability plot", Nucleic Acids Research, 2000, vol. 28, No. 1, pp. 214-218.
Jones and Portnoy "Characterization of Listeria monocytogenes pathogenesis in a strain expressing perfringolysin O in place of listeriolysin O." (1994) Infect. Immunity 65:5608-5613.
Kabat, et al., "Unusual distrubtions of amino acids in complementarity -determining (hypervariable) segments of heavy and light chains of immunoglobulins and their possible roles in specificity of antibody-combining sites" (1977) J. Biol. Chem. 252:6609-6616.
Karlin, S., et al., "Methods for assessing the statistical significance of molecular sequence features by using general scoring schemes" (1990) Proc. Natl. Acad. Sci. USA 87:2264-2268.
Karlin, S., et al., "Applications and statistics for multiple high-scoring segments in molecular sequences" (1993) Proc. Natl. Acad. Sci. USA 90:5873-5877.
Kim Myoung-Song et al., "Coexpression of BiP increased antithrombotic hirudin production in recombinant *Saccharomyces cerevisiae*", Journal of Biotechnology, vol. 101, No. 1, pp. 81-87, 2003.
King et. al., "Amplification of a novel v-erbB-related gene in a human mammory carcinoma" (1985). Science 229:974-976.
Kohler et al, "Expression of the iap gene coding for protein p60 of Listeria monocytogenes is controlled on the posttranscriptional level" J Bacteriol 173: 4668-74, 1991.
Kucera et al., "Prostate Specific Antigen (PSA) in Breat and Ovarian Cancer", Anticancer Res 1997, vol. 17, No. 60, pp. 4735-4737.

(56) References Cited

OTHER PUBLICATIONS

Kyte et al., "A simple method for displaying the hydropathic character of a protein", J. Mol. Biol. 157, 105 (1982).
Landy, A., Mechanistic and structural complexity in the site-specific recombination pathways of Int and FLP Current Opinion in Genetics & Development 3:699-707; (1993).
Lauer, et al., "Construction, characterization, and use of two LM site-specific phageintegration vectors", 2002 *J Bacteliol*, 184:4177-4186.
Lenz, "Stable integration vector for nutrient broth-based selection of attenuated Listeria monocytogenes strains with recombinant antigen expression" Clin Vaccine Immunol. 15(9):1414-1419. Sep. 2008.
Li et al., "Conditional lethality yields a new vaccine strain of listeria monocytogenes for the induction of cell-mediated immunity", Infection and Immunity, 2005, 73(8): 5065-5073.
Lipsky et al, "Infliximab And Methotrexate In The Treatment Of Rheumatoid Arthritis" (2000) New Engl. J. Med. 343:1594-1602.
Liu et al. "Randomised, double blind, placebo controlled study of interferon beta-1a in relapsing-remitting multiple sclerosis analysed by area under disability/time curves" (1999) J. Neurol. Neurosurg. Psych. 67:451-456.
Loessner, M. J., I. B. Krause, T. Henle, and S. Scherer. 1994. Structural proteins and DNA characteristics of 14 Listeria typing bacteriophages. J. Gen. Virol. 75:701-710.
Mata (1997). A hexameric phosphorothioate oligonucleotide telomerase inhibitor arrests growth of Burkitt's lymphoma cells in vitro and in vivo. Toxicol. Appl. Pharmacol. 144:189-197.
Mazda, O., et al. (1997) Extremely efficient gene transfection in lympho-hematopoietic cell by Epstein-Barr virus-based vectors. J. Immunol. Methods 204, 143-151.
Mengaud et al., "Transcriptional mapping and nucleotide sequence of the Listeria monocytogenes hlyA region structural features that may be involved in regulation" Infect. Immun. 1989 57, 3695-3701.
Menne, et al. "A comparison of signal sequence predition methods using a test set of signal peptides" (2000) Bioinformatics 16: 741-742.
Meyaard et al. "LAIR-1, a Novel Inhibitory Receptor Expressed on Human Mononulcear Leukocytes" (1997) Immunity 7:283-290.
Milgrom et al. "Treatment Of Allergic Asthma With Monoclonal Anti-Ige Antibody" (1999) New Engl. J. Med. 341:1966-1973.
Milligan (1993) "Current concepts in antisense drug design", J. Med. Chem. 36:1923-1937; Antisense Research and Applications (1993, CRC Press).
Nagai et al, 1991 Isolation and partial characterization of major protein antigens in the culture fluid of *Mycobacterium tuberculosis*. Infect Immun. Jan. 1991;59(1):372-82.
Narang et al. (1979). Improved Phosphotriester Method for the Synthesis of Gene Fragments, *Meth. Enzymol.* 68: 90-99.
Naruishi K et al (Adenoviral vector-mediated RTVP-1 gene-modified tumor cell-based vaccine suppresses the development of experimental prostate cancer. Cancer Gene Ther. Jul. 2006;13(7):658-63).
Nielsen PE,(1999). Peptide nucleic acids as therapeutic agents *Current Opin Struct Biol* 9:353-57.
Nikodinovic J et al. A second generation snp-derived *Escherichia coli-Streptomyces* shuttle expression vector that is generally transferable by conjugation. *Plasmid.* Nov. 2006;56(3):223-7.
Nomi, T. Sho, M., Akahori, T., et al. Clinical significance and therapeutic potential of the programmed death-1 ligand/programmed death-1 pathway in human pancreatic cancer. Clinical Cancer Research (2007);13:2151-2157.
Ogasawara et al A strategy for making synthetic peptide vaccines Proc. Nati. Acad. Sci. USA vol. 89, pp. 8995-8999, Oct. 1992.
Ohigashi Y et al. Clinical significance of programmed death-1 ligand-1 and programmed death-1 ligand 2 expression in human esophageal cancer. Clin. Cancer Research (2005): 11: 2947-2953.
Parsa Saba et al., "Engineering bacterial vectors for delivery of genes and proteins to antigen-presenting cells", Molecular Pharmaceutics, vol. 4, No. 1, 2007, pp. 4-17.
Passos S. et al. Recombinant Leishmania Antigens for Serodiagnosis of Visceral Leishmaniasis *Clinical and Diagnostic Laboratory Immunology*, Oct. 2005, p. 1164-1167, vol. 12, No. 10.
Paterson et al., "Listeria-based vaccines for cancer treatment", Current Opinion in Molecular Therapeutics, vol. 7, No. 5, 2005, pp. 454-460.
Presta "Selection, design, and engineering of therapeutic antibodies" (2005), J. Allergy Clin. Immunol. 116:731.
Pucci et ai., "Staphylococcus haemolyticus Contains Two D-Glutamic Acid Biosynthetic Activities, a Glutamate Racemase and a D-Amino Acid Transaminase" 1995, J Bacteriol. 177: 336-342.
Rechstiner M et al (PEST sequences and regulation by proteolysis. Trends Biochem Sci 1996; 21(7):267-71.
Samstag (1996). Synthesis and properties of new antisense oligodeoxynucleotides containing benzylophosphonate linkages. Antisense Nucleic Acid Drug Dev. 6:153-156.
Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.
Seavy MM. "A novel human Her-2/neu chimeric molecule ecpressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sehgal I et al "Prostate cncaer cells show elevated urokinase receptor in a mouse model of metastasis" Cancer Cell Int. Aug. 23, 2006, 6:21.
Sewell et al., "Recombinant Listeria Vaccines Containing PEST Sequences are potent immune adjuvants for the tumor-associates antigen human pappilomavirus-16 E7", Cancer Research, American Association for Cancer Research, vol. 64, No. 24, 2004, pp. 8821-825.
Shahabi et al., "Live, attenuated strains of *Listeria* and *Salmonella* as vaccine vectors in cancer treatment", Bioeng. Bugs, 2010, vol. 1, No. 4, pp. 235-243.
Shimauchi T et al. Augmented expression of programmed death-1 in both neoplasmatic and nonneoplastic CD4+ T-cells in adult T-cell Leukemia/ Lymphoma. Int. J. Cancer (2007): 121:2585-2590.
Singh et al., "Cancer immunotherapy using recombinant Listeria monocytogenes transition from bench to clinic", Human Vaccines, 2011, vol. 7(5), pp. 497-505.
Singh et al., "Fusion to Listeriolysin O and Delivery by *Listeria monocytogenes* Enhances the Immunogenicity of HER-2/neu and Reveals Subdominant Epitopes in the FVB/N Mouse", The Journal of Immunology 2005, vol. 175, No. 6, pp. 3663-3673.
Skoble, et al. "Three Regions within ActA Promote Arp2/3 Complex0-mediated Actin Nucleation and *Listeria monocytogenes* Motility" 2000, J. Cell Biol. 150: 527-538.
Slamon et al. "Use Of Chemotherapy Plus A Monoclonal Antibody Against Her2 For Metastic Breast Cancer That Overexpresses Her2" 2001, New Engl. J. Med. 344:783-792.
Smith and Youngman, Biochimie. 1992. Use of a new integrational vector to investigate comparement-specific expression of the Bacillus subtilis spoIIM gene; 74 (7-8) p. 705-711.
Soussi et al., "Listeria monocytogenes as short lived delivery system for the induction of type 1 cell-mediated immunity againdt the p36/LACK antigen of Leishmania major", Infection and Immunity, vol. 68, No. 3, 2000, pp. 1498-1506.
Strauss-Soukup, "Effects of Neutralization Pattern and Stereochemistry on DNA Bending by Methylphosphonate Substitutions", 1997, Biochemistry 36:8692-8698.
Strych et al, "Mutant Analysis Shows that Alanine Racemases from *Pseudomonas aeruinosa* and *Escherichia coli* Are Dimeric" 2002, J. Bacteriol. 184:4321-4325.
Su et al., "Relevance of Hepatic Preneoplasia for Human Hepatocarcinogenesis" (2003) Toxicol. Pathol. 31:123-133.
Tang et al., "Protein Chemistry and Structure: Use of a Peptide Mimotope to Guide the Humanization of MRK-16, an Anti-P-glycoprotein Monoclonal Antibody", 1999 J. Biol. Chem. 274:27371-27378.

(56) References Cited

OTHER PUBLICATIONS

Tanghe, A., "Improved Immunogenicity and Protective Efficacy of Tuberculosis DNA Vaccine Encoding Ag85 by Protein Boosting" Infect. Immun. 69:3041-7 (2001).

Tauch et al, "The alanine racemase gene air is an alternative to antibiotic resistance genes in cloning systems for industrial Corynebacterium glutamicun strains" 2002, J. Biotechnol 99:79-91.

Thomas-Kaskel et al (Vaccination of advanced prostate cancer patients with PSCA and PSA peptide-loaded dendritic cells induces DTH responses that correlate with superior overall survival. Int J Cancer. Nov. 15, 2006;119(10)2428-34).

Thompson, R. H., et al., "Costimulatory B7-H1 in renal cell carcinoma patients: Indicator of tumor agressiveness and potential therapeutic target" PNAS 101 (49); 17174-17179 (2004).

Thompson, R. H. et al., "Overall Survival and PD-L1 Expresion in Metastasized Malignant Melanoma" Cancer Res. 66:3381-3385 (2006).

Thompson RH et al. "PD-1 is expressed by tumor infiltrating cells and is associated with poor outcome for patients with renal carcinoma" Clinical Cancer Research (2007) 15: 1757-1761.

Toplain, S. L. et al., "Safety, Activity, and Immune Correlates of Anti-PD-1 Antibody in Cancer" New Eng. J Med. 366 (26): 2443-2454 (2012).

Uenaka A et al (T cell immunomonitoring and tumor responses in patients immunized with a complex of cholesterol-bearing hydrophobized pullulan (CHP) and NY-ESO-1 protein. Cancer Immun. Apr. 19, 2007;7:9).

Ulmanen et al, "Transcription and Translation of Foreign Genes in Bacillus subtilis by the Aid of a Secretion Vector" 1985. *J. Bacterial.* 162:176-182.

Verch et al., *Listeria monocytogenes*-Based Antibiotic Resistance Gene-Free Antigen Delivery System Applicable to Other Bacterial Vectors and DNA Vaccines. Infect Immun, 2004, 72(11):648-25.

von Heijne, "A new method for predicting signal sequence cleavage sites" (1986) Nucleic Acids Res. 14:4683-4690.

Wallecha et al. "Construction and characterization of an attenuated Listeria monocytogenes strain for clincial use in cancer immunotherapy" Clin Vaccine Immunol. 16(1):96-103, Jan. 2009.

Wallecha et al., "Multiple effector mechanisms induced by recombinant listeria monocytogenes anticancer immunotherapeutics", Advances in Applied Microbiology, vol. 66, 2009, pp. 1-27.

Ward et al, 1986. Construction and characterisation of a series of multi-copy promoter-probe plasmid vectors for *Streptomyces* using the aminoglycoside phosphotransferase gene from Tn5 as indicator. *Mol. Gen. Genet.* 203:468-478.

Weber, "Assessing Tumor Reponse to Therapy" Nucl. Med. 50:1S-10S (2009).

Wirth R et al, "Highly efficient protoplast transformation system for *Streptococcus faecalis* and a new *Escherichia coli-S. faecalis* shuttle vector", J Bacteriol, 165: 831, 1986.

Wood et al. "Cancer immunotherapy using Listeria monocytogenese and listerial virulence factors" Immunol Res. ; 42(1-3):233-45. (2008).

Wright et al. "Lyphoid/Neuronal Cell Surface OX2 Glycoprotein Recognizes a Novel Receptor on Macrophages Implicated in the Control of Their Function", (2000) Immunity 13:233-242.

Yang et al. "A Randomized Trial of Bevacizumab, an Anti-Vascular Endothelial Growth Factor Antibody, for Metastatic Renal Cancer" (2003) New Engl. J. Med. 349:427-434.

Zhang, J. et al., "PowerBLAST: A New Network BLAST Application for Interactive or Automated Sequence Analysis and Annotation" (1997) Genome Res. 7:649-656.

Shahabi et al., "Development of a Listeria monocytogenes based vaccine against prostate cancer" Cancer Immunol Immunother (2008) 57:1301-1313.

Hussain et al., "CD4+CD25+ Regulatory T Cells That Secret TGF and IL-10 Are Preferentially Induced by a Vaccine Vector", 2004, *J Immunother* 27( 5):339-346.

Nitcheu-Tefit et al., "Listeriolysin O Expressed in a Bacterial Vaccine Suppresses CD4$^+$CD25$^{high}$ Regulatory T Cell Function In Vivo", 2007 *J. Immunol.* 179(3):1532-41.

Shahabi et al., "Development of a live and highly attenuated *Listeria monocytogenes*-based vaccine for the treatment of Her2/neu-overexpressing cancers in human", *Cancer Gene Therapy* (2010), 1-10.

Adams et al., 1992, "Cre-lox recombination in *Escherichia coli* cells Mechanistic differences from the in vitro reaction", J. Mol. Biol. 226:661-673

Al-Lazikani et al. JMB Standard Conformations for the Canonical Structures of Immunoglobulins., J. Mol. Biol. 273:927-948 (1997).

Allision et al., 1997, "Cloning and characterization of a Prevotelia melaninogenica hemolysin", Infect. Immun. 65(7):2765-71.

Altschul et al. Basic Local Alignment Search Tool Basic Local Alignment Search Tool; J. Mol. Biol. 215:403-410 (1990).

Altschul "Amino Acid Substitution Matrices from an Information Theoretic Perspective", J. Mol. Biol. 219:555-565 (1991).

Altschul et al. A Protein Alignment Scoring System Sensitive at all Evolutionary Distances; J. Mol. Evol. 36:290-300 (1993).

Amersham. Introduction to Glutathione S-transferase (GST) Gene Fusion System , Pharmacia Biotech; BioDirectory, Piscataway, N.J., (pp. 384-391) (2001).

An et al., 1996, "A recombinant minigene vaccine containing a nonameric cytotoxic-T-Lymphocyte epitope confers limited protection against Listeria monocytogenes infection", Infect. Immun., vol. 64, No. 5, p. 1685-1693

Anderson, 1998, "Human gene therapy", Nature, Apr. 30; 392 (6679 Suppl):25-30.

Attwood et al., "The Babel of Bioinformatics", Science, vol. 290, No. 5491: 471-473, 2000.

Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.

Barbas Synthetic Human Antibodies ; Nature Medicine, 1:837-839 (1995).

Bear, 1986, "Tumor-specific suppressor T-cells which inhibit the in vitro generation of cytolytic T-cells from immune and early tumor-bearing host spleens", Cancer Res., Apr.; 46(4 Pt 1):1805-12.

Beattie et al. "Cloning and characterization of T-cell-reactive protein antogens from Listeria monocytogenes", infect. Immune. Sep. 1990, 58(9):2792-803.

Becker at al., The changes in the T helper 1 (Th1) and T helper 2 (Th2) cytokine balance 3,4during HIV-1 infection are indicative of an allergic response in viral proteins that may bereversed by Th2 cytokine inhibitors and immune response modifiers—a review and hypothesis; Viruses Genes 28:5-18 (2004).

Benvegnu, et al. Space Occupying lesions of the liver detected by ultrasonography and their relation to hypatocellular Carcinoma in Cirrhosis; Liver 12:80-83 (1992).

Bernhard et al., 2002, "Vaccination against the HER-2/neu onco-genic protein", Endocrine-Related Cancer, 9:33-44.

Bielecki et al. "Bacillus subtilis expressing a haemolysin gene from Lesteria monocytogenes can grow in mammalian cells", Nature 1990, 354:175-176.

Billaut-Mulot, O. et al. Interleukin-18 modulates immune responses induced by HIV-1 Nef DNA prime/protein boost vaccine; Vaccine 19:95-102 (2000).

Billington et al., 1997, "The Arcanobacterium (Actinomyces) pyogenes hemolysin, pyolysin, is a novel member of the thiol-activated cytolysin family", J. Bacteriol. Oct; 179(19):6100-6.

Bird et al. "An autologous dendritic cell canine mammary tumor hybrid-cell fusion vaccine", Cancer Immunol Immunother. Jan. 2011:60(1):87-97.

Bishop et al. "Adoptive Transfer of Immunity to Listeria Monocytogenes The Influence of In Vitro Stimulation Lymphocyte Subset Requirements", J. Immunol. 139: 2005-2009 (1987).

Bodmer et al., 1988, "Enhanced recognition of a modified peptide antigen by cytotoxic T cells specific for infuenza nucleoprotein", Cell 52:253-258.

Boon et al., 2003, "Human T-cell responses against melanoma" Annu. Rev. Immunol. 24:175-208.

(56) References Cited

OTHER PUBLICATIONS

Bourquin et al., 2000, "Myelin oligodendrocyte glycoprotein-DNA vaccination induces antibody-mediated autoagression in experimental autoimmune ecephalomyelitis" Eur. J. Immunol. 30:3663-3671.
Bouwer et al. Acquired immunity to an intracellular pathogen: immunologic recognition of L. monocytogenes-infected cells, Immunol. Rev. Aug. 1997; 158:137-46.
Bouwer et al. Cytotoxic-T-lymphocyte responses to epitopes of listeriolysin O and p60 following infection with Listeria monocytogenes, Infect. Immune. Jul. 1996; 64(7):2515-22.
Brett et al. "Comparison of antigen presentation of influenza A nucleoprotein expressed in attenuated AroA− *Salmonella typhimurium* with that of live virus", J. Immunol. Apr. 1 1993;150(7):2869-84.
Bron et al., 2004, "Identification of Lactobacillus plantarum genes that are induced in the gastrointestinal tract of mice", J. Bacteriol. Sep.; 186(17):5721-9.
Brown et al., 1988, "Site-specific integration in Saccharopolyspora erthraea and multisite integration in Streptomyces lividans of actinomycete plasmid pSE101", J. Bacteriology 170: 2287-2295.
Brown et al. "Chemical synthesis and cloning of a tyrosine tRNA gene" 1979, Meth. Enzymol. 68:109-151.
Bruder et al. "Efficient induction of cytotoxic CD8+ T cells against exogenous proteins: establishment and characterization of a T cell line specific for the membrane protein ActA OF Listeria monocytogenes", Eur. J. Immunol. Sep. 1998; 28(9):2630-9.
Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.
Bubert et al., 1997, "The Listeria monocytogenes iap gene as an indicator gene for the study of PrfA-dependent regulation", Mol. Gen. Genet. Sep.; 256(1):54-62.
Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.
Camilli et al., 1993, "Dual roles in plcA in Listeria monocytogenes pathogenesis", Mol. Microbiol. 8:143-157.
Camilli et al. "Insertional mutagenesis of Listeria monocytogenes with a novel Tn917 derivative that allows direct cloning of DNA flanking transposon insertions", J Bacteriol, Jul. 1990;172(7):3738-44.
Carbone, 1989, "Induction of ovalbumin-specific cytotoxic T cells by in vivo peptide immunization" J. Ecp. Med. 169:603-612.
Carbone, 1990, "Class I-restricted processing and presentation of exogenou cell-associated antigen in vivo", J. Exp. Med. 171:377-387.
Carpenter et al. Non-Fc Receptor-Binding Humanized Anti-CD3 Antibodies Induce Apoptosis of Activated Human T Cells; J. Immunol. 165:6205-6213 (2000).
Catic et al. "Introduction of protein or DNA delivered via recombinant *Salmonella typhimurium* into the major histocompatibility complex class I presentation of pathway of macrophages", Microbes Infect., Feb. 1999, 1(2):113-21.
Cenatiempo, "Prokaryotic gene expression in vitro: transcription-translation coupled systems." 1986, Biochimie 68:505-516.
Chen et al. "Episomal Expression Of Truncated Listeriolysin O in LmddA-LLO-E7 Vaccine Enhances Antitumor Efficacy by Preferentially Inducting Expansions of CD4FoxP3_ andCD8 T Cells", Cancer Immunol Res; 2(9) Sep. 2014, pp. 911-922.
Chothia et al. Canonical Structures for the Hypervariable Regions of Immunoglobulins; J Mol. Biol. 196:901-917 (1987).
Chothia et al. Confirmations of immunoglobulin hypervariable Regions; Nature 342:878-883 (1989).
Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).

Clackson et al. Making Antibody Fragments Using Phage Display Libraries; Nature 352: 624-628 (1991).
Clark et al., "Clinical use of steptolysin-O to facilitate antisense oligodeoxyribonucleotide delivery for purging autografts in chronic myeloid leukaemia", Bone Marrow Transplantion, vol. 23, No. 12, 1999, pp. 1303/1308.
Collins et al. "Directional cloning of DNA fragments at a large distance from an initial probe: a circularization method", Proc Natl Acad Sci U S A. Nov. 1984;81(21):6812-6.
Courvalin et al., 1995, "Gene transfer from bacteria to mammalian cells", C R Acad Sci III, Dec; 318(12):1207-12.
Coynault et al. "Virulence and vaccine potential of *Salmonella typhimurium* mutants deficient in the expression of the RpoS (sigma S) regulon", Mol Microbiol. Oct. 1996;22(1):149-60.
Cunto-Amesty et al., 2003, "Strategies in cancer vaccines development", Int. J. Parasitol. 33(5-6):597-613.
Da'Dara et al. Elimination of helminth infection restores HIV-1C vaccine-specific T cellresponses independent of helminth-induced IL-10; Vaccine; 3;28(5):1310-7 (2010).
Dakappagari et al., 2000, "Prevention of mammary tumors with a chimeric HER-2 B-cell epitope peptide vaccine", Cancer Res. Jul. 15; 60(14):3782-9.
Darji et al. The role of the bacterial membrane protein ActA in immunity and protection against Listeria monocytogenes, J. Immunol. Sep. 1, 1998, 161(5):2414-20.
Darji et al. "Antigen-specific T cell receptor antagonism by antigen-presenting cells treated with the hemolysin of Listeria monocytogenes: a noval type of immune escape", Eur. J. Immunol. Jul. 1997; 27(7):1696-703.
Darji et al. T-cell anergy induced by antigen presenting cells treated with the hemolysin of Listeria monocytogenes, Immunol. Lett. Jun. 1, 1997, 57(1-3):33-7.
Darji et al., 1995, "Hyperexpression of listeriolysin in the nonpathogenic species *Listeria innocua* and high yield purification", J. Biotechnol. Dec. 15; 43(3):205-12.
Darji et al., 1995, "Listeriolysin generates a route for the presentation of exogenous antigens by major histocompatibility complex class I", Eur. J. Immunol. Oct.; 25(10):2967-71.
Darji et al., 1997, "Oral somatic transgene vaccination using attenuated S. typhimurium" Cell 91:765-775.
Darji et al., 1997, "TAP-dependent major histocompatibility complex class I presentation of soluble proteins using listeriolysin", Eur. J. Immunol. Jun; 27(6):1353-9.
Darji et al., 2003, "Induction of immune responses by attenuated isogenic mutant strains of Listeria monocytoge" Vaccine 1; 21 Suppl. 2:S102-9.
De Bruin et al. Selection of high-affinity phage antibodies from phage display libraries; Nature Biotechnol. 17:397-399 (1999).
Decatur et al., "A PEST-Like Sequence in Listeriolysin O Essential for Listeria monocytogenes Pathogenicity", Science 2000, 290:992-995.
Dembo, A et al. Limit Distribution of Maximal Non-Aligned Two-Sequence Segmental Score Ann. Prob. 22:2022-2039; (1994).
Dermime et al., 2004, "Vaccine and antibody-directed T cell tumour immunotherapy" Biochim Biophys Acta. 1704(1):11-35.
Deshpande et al., 1997, "Isolation of a contact-dependent haemolysin from *Mycobacterium tuberculosis*", J. Med. Microbiol. Mar.; 46(3):233-8.
Dietrich et al., 1998, "Delivery of antigen-encoding plasmid DNA into the cytosol of macrophages by attenuated suicide Listeria monocytogenes" Nature Biotechnology 15:181-185.
Dietrich et al., 2001, "From evil to good: a cytolysin in vaccine development", Trends Microbiol. Jan.; 9(1):23-8.
Doling et al. Cytotoxic T-lymphocyte epitopes fused to anthrax toxin induce protective antiviral immunity, Infect. Immun. Jul. 1999; 67(7):3290-6.
Dominiecki et al. Tumor sensitivity to IFN-γ is required for successful antigen-specific immunotherapy of a transplantable mouse tumor model for HPV-transformed tumors; Cancer Immunol Immunother ;54(5):477-88 (2005).
Dons et al. "Cloning and characterization of a gene encoding flagelin of Listeria monocytogenes", Mol Microbiol. Oct. 1992;6(20):2919-29.

(56) References Cited

OTHER PUBLICATIONS

Dramsi et al., 1995, "Entry of Listeria monocytogenes into hepatocytes requires expression of inlB, a surface protein of the internalin multigene family", Mol. Microbiol. 16(2):251-61.

Dunn et al., 1991, "Selective radiation resistance of immunologically induced T cells as the basis for irradiation-inducted T-cell-mediated regression of immunogenic tumor", J. Leukoc Biol. 49(4):388-396.

Dustoor, "Antitumor activity of listeria monocytogenes on a guinea pig fibrosarcoma", Infection and Immunity, 1979, vol. 23, No. 1, pp. 54-60.

Ebbeson et al. "Rhabdomyolysis, acute renal failure, and compartment syndrome in a child with parainfluenza type 1 infection", The Pediatric Infectious Disease Journal vol. 28, No. 9, Sep. 2009.

Ebert et al., 1990, "Selective immunosuppressive action of a factor produced by colon cancer cells", Cancer Res. 50(19):6158-6161.

Edman et al. A Protein Sequenator; Eur. J. Biochem . 80: 116-132, (1967).

Eisenhauer et al. New response evaluation criteria in solid tumours: Revised RECIST guideline (version 1.1), Eur. J. Cancer 45:228-247 (2009).

Emond et al. "A ribosomal DNA fragment of Listeria monocytogenes and its use as a genus-specific probe in an aqueous-phase hybridization assay", Appl Environ Microbiol. Aug. 1993;59(8):2690-7.

Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.

European Search Report for European Application No. 14190388.0 dated Mar. 2, 2015.

Everts et al. Selective Intracellular Delivery of Dexamethasone into Activated Endothelial Cells Using an E-Selectin-Directed Immunoconjugate; J. Immunol. 168:883-889 (2002).

Ezzel, 1995, "Cancer Vaccines: An Idea Whose Time Has Come?" J. NIH Res., 7:46-49.

Falk et al., 1991, "Identification of naturally processed viral nonapeptides allows their quantification in infected cells and suggests an allele-specific T cell epitope forecast" J. Exp. Med. 174(2):425-434.

Ferrari et al. "Isolation of an Alanine Racemase Gene from Bacillus subtilis and its Use for Plasmid Maintenance in B. subtilis", Nature Biotechnology 3, 1003-1007 (1985).

Finn et al., 2003, "Cancer vaccines: between the idea and the reality" Nature Reviews Immunology 3:630-641.

Foote et al. "Antibody Framework Residues Affecting the Conformation of the Hypervariable Loops", J. Mol. Biol. 224:487-499 (1992).

Fouts et al. "Construction and immunogenicity of *Salmonella typhimurium* vaccine vectors that express HIV-1 gp-120", Vaccine. Dec. 1995;13(17):1697-705.

Frankel et al. "Induction of cell-mediated immune responses to human immunodeficiency virus type 1 Gag protein by using Listeria monocytogenes as a live vaccine vector", J. Immunol. Nov. 15, 1995;155(10):4775-82.

Frey, 1993, "Rat adenocarcinoma 13762 expresses tumor rejection antigens but tumor bearing animals exhibit tumor-specific immunosuppression", Clin. Immunol. Immunopathol. 69(2):223-233.

Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.

Fu et al., 1990, "Expansion of Immunoregulatory macrophages by granulocyte-macrophage colony-stimulating factor derived from a murine mammory tumor", Cancer Res. 50(2):227-234.

Fuji, 1987, "Significance of suppressor macrophages for immunosurveillance of tumor-bearing mice" J. Natl. Inst. 78(3):509-517.

Furukawa, 1993, "Nude mouse metastatic models of human stomach cancer constructed using orthotopic implantation of histologically intact tissue" Cancer Res. 53(5):1204-1208.

Galakatos et al. "Biosynthetic air alanine racemase from *Salmonella typhimurium*: DNA and protein sequence determination", Biochemistry. Jun. 3, 1986;25(11):3255-60.

Galen et al., 2001, "Can a 'flawless' live vector vaccine strain be engineered?", Trends Microbiol. 9(8):372-6.

Gentschev et al. "*Salmonella* Strain Secreting Active Listeriolysin Changes Its Intracellular Localization", Infect. Immun., 1995, 65:4202-4205.

Gentschev et al. 1996, "Development of antigen-delivery systems, based on the *Escherichia coli* hemolysin secreatiohn pathway" Gene 179:133-140.

Giannini et al. Morphological Precursors of Hepatocellular Carcinoma: A Morphometrical Analysis; Hepatogastroenterol. 34:95-97 (1987).

Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells; J. Immunol. 160:3891-3898 (1998).

Gilbert et al. Enhanced CD8 T cell immunogenicity and protective efficacyin a mouse malaria model using a recombinant adenoviral vaccine in heterologous prime—boost immunization regimes; Vaccine 20:1039-45 (2002).

Gilman et al. "Isolation of sigma-28-specific promoters from Bacillus subtilis DNA" 1984, Gene 32:11-20.

Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.

Gish, W et al. Identification of protein coding regions by database similarity search; Nature Genet. 3:266-272 (1993).

Glomski et al., 2002, "The Listeria monocytogenes hemolysin has an acidic pH optimum to compartmentalize activity and prevent damage to infected host cells" J. Cell Biol. Mar. 18; 156(6):1029-38.

Goebel et al., 1993, "Listeria monocytogenes—a model system for studying the pathomechanisms of an intracellular microorganism", Zbl. Bakt. 278:334-347.

Gold et al., "Translational initiation in prokaryotes." 1981, Ann. Rev. Microbiol. 35:365-404.

Gonzalo et al. A heterologou prime-boost regime using DNA and recombinant vaccinia virus expressing the Leishmania infantum P36/LACK antigen protects BALB/c mice from cutaneous leishmaniasis; Vaccine 20:1226-31 (2002).

Goossens et al., 1992, "Induction of protective CD8+ T lymphocytes by an attenuated Listeria monocytogenes actA mutant" Int. Immunol. Dec.; 4(12):1413-8.

Goossens et al., 1992, "Attenuated Listeria monocytogenes as a live vector for induction of CD8+ T cells in vivo: a study with the nucleoprotein of the lymphocytic choriomeningitis virus", Int. Immunol. May; 7(5):797-805.

Graham et al. "Candidate AIDS vaccines", N Engl J Med Nov. 16, 1995;333(20):1331-9.

Gregory et al., 1997, "Internalin B promotes the replication of Listeria monoctyogenes in mouse hepatocytes" Infect. Immun. 65(12):5137-41.

Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.

Guzman et al. "Attenuated Listeria monocytogenes carrier strains can deliver an HIV-1 jp120 T helper epitope to MCH class II-restricted human CD4+ T cells", European Journal of Immunology, vol. 28, No. 6, Jun. 1998, pp. 1807-1814.

Hancock et al. SIMPLE34: An Improved And Enhanced Implementation for VAX and Sun computers of the SIMPLE algorithm for analysis of clustered repetitive motifs in nucleotide sequences; Comput. Appl. Biosci. 10:67-70 (1994).

Harty et al. "CD8 T lymphocytes specific for the secreted p60 antigen protect against Listeria monocytogenes infection", J. Immunol. May 1, 1995; 154(9):4642-50.

(56) References Cited

OTHER PUBLICATIONS

Harty et al. "CD8+ T cells specific for a single nonamer epitope of Listeria monocytogenes are protective in vivo", J Exp Med. Jun. 1, 1992;175(6):1531-8.

Hassan et al., 2004, "Mesothelin: a new target for immunotherapy" Clin. Cancer Res. 10(12 Pt 1):3937-42.

Hauf et al., 1997 "Listeria monocytogenes infection of P388D1 macrophages results in a biphasic NF-kappaB (RelA/p50) activation induced by lipoteichoic acid and Bacterial phospholipases and mediated by IkappaBalpha and IkappBbeta degradation", Proc. Natl. Acad. Sci. U.S.A. Aug. 19; 94(17):9394-9.

Haynes et al. "Update on the issues of HIV vaccine development", Ann Med. Feb. 1996;28(1):39-41.

Haynes et al. "Scientific and social issues of human immunodeficiency virus vaccine development", Science. May 28, 1993;260(5112):1279-86.

He et al. Humanization and Pharmacokinetics of a Monoclonal Antibody with Specificity for Both E- and P-Selectin; J. Immunol. 160:1029 (1998).

Hess et al., 1995, "Listeria monocytogenes p60 supports host cell invasion by and in vivo survival of attenuated *Solmonella typhimurium*" Infect. Immun. May; 63(5):2047-53.

Hess et al., 1996, "Salmonella typhimurium aroA- infection in gene-targeted immunodeficient mice: major role of CD4+ TCR-alpha beta cells and IFN-gamma in bacterial clearance independent of intracellular location" J. Immunol. May 1;156(9):3321-6.

Hess et al., 1996, "Superior efficacy of secreted over somatic antigen display in recombinant *Salmonella* vaccine induced protection against listeriosis" Proc. Nat. Acad. Sci. 93:1458-1463.

Hess et al., 1997, "Protection against murine listeriosis by an attenuated recombinant *Salmonella typhimurium* vaccine strain that secretes the naturally somatic antigen superoxide dismutase", Infect. Immun. Apr.; 65(4):1286-92.

Hess et al, "*Mycobacterium bovis* Bacille Calmette-Guerin strains secreting listeriolysin of Listeria monocytogenes", Proc. Natl. Acad. Sci. U.S.A. Apr. 28, 1998;95(9):5299-304.

Hess et al. Abstract, "Live antigen carriers as tools for improved anti-tuberculosis vaccines", FEMS Immunol. Med. Microbiol. Feb. 1999; 23(2):165-73.

Higgins et al., Abstract, "Delivery of protein to the cytosol of macrophages using *Escherichia coli* K-12", Mol. Microbiol. Mar. 1999 31(6):1631-41.

Higgins et al., 1998, "Bacterial delivery of DNA evolves" Nat. Biotechnol. Feb.; 16(2):138-9.

Hiltbold et al. "The presentation of class I and class II epitopes of listeriolysin O is regulated by intracellular localization and by intracellular spread of Listeria monocytogenes", J. Immunol. Aug. 1, 1996; 157(3):1163-75.

Hiltbold et al. "Mechanisms of processing and presentation of the antigens of Listeria monocytogenes", Infect. Agents Dis. Oct. 1993; 2(5):314-23.

Hodgson, 2000, "Generalized transduction of serotype 1/2 and serotype 4b strains of Listeria monocytogenes" Mol. Microbiol. 35(2):312-23.

Hoogenboom et al. "Natural and designer binding sites made by phage display technology", Immunol. Today 21:371-377 (2000).

Hsing et al. "Requirement for Nuclear Factor-kB activation by a Distinct Subset of CD40-Meidated Effector Functions in B Lymphoctyes", J. Immunol. 162:2804-2811 (1999).

Huang et al., 1994, "Role of bone marrow-derrived cells in presenting MHC class I-restricted tumor antigens" Science 264:961-965.

Hussain et al., "What is needed for effective anitumor immunotherapy? Lessons learned using Listeria Monocytogenes as a live vector for HPV-associated tumors", Cancer Immunology, Immunotherapy, vol. 54, No. 6, 2005, pp. 577-586.

Ikonomidis et al., 1994, Abstract E-90, Abstracts, 94th General Meeting of the American society for Microbiology, May 23-27.

Ikonomidis et al., "Influenze-specific immunity induced by recombinant Listeria monoctogenese vaccines", Vaccine, vol. 15, No. 4, 1997, pp. 433-440.

Ikonomidis et al. "Delivery of a viral antigen to the class I processing and presentation pathway of Listeria monocytogenes", J Exp Med. Dec 1, 1994;180(6):2209-18.

International Search Report for PCT/US15/40911 mailed Nov. 2, 2015.

Jensen et al., 1997, "Recombinant Listeria monoctyogenes as a live vaccine vehicle and a probe for studying-cell-meidated immunity" Immunological Review 158:147-157.

Jensen, 1997, "Recombinant Liseria monocytogenes vaccination elminates papillomavirus-induced tumors and prevents papilloma formation from viral DNA", J. Virol. 71(11):8467-8474.

Kabat "The Structural Basis Of Antibody Complementarity", Adv. Prot. Chem. 32:1-75 (1978).

Kaithamana et al. Induction of Experimental Autoimmune Graves' Dises in BALB/c Mice; J. Immunol. 163:5157-5164 (1999).

Kaufman et al., "Impact of intracellular location of and antigen display by intracelluar bacteria:implications for vaccine development", J. Immunol. Lett. 1999, 65(1-2):81-84.

Kaufmann "Immunity to intracellular bacteria", Annu Rev Immunol. 1993;11:12-63.

Knutson et al., "Immunization with a HER-2/neu helper peptide vaccine generates HER-2/neu CD8 T-cell immunity in cancer patients." The Journal of Clinical Investegation, 107:477-484, 2001.

Kocks et al., 1992, "L monocytogenes-induced act in assembly requires the actA gene product", Cell, vol. 68, No. 3, p. 521-531.

Kohler et al. Continuous Cultures Of Fused Cells Secreting Antibody Of Predefined Specificity; Nature 256: 495 (1975).

Kovacsovics-Bankowski et al., 1993, "Efficient major histocompatibility complex class I peresentation of exogenous antigen upon phagocytosis by macrophages", Proc. Natl. Acad. Sci. USA 90:4942-4946.

Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.

Lasa et al., 1997, "Identification of two regions of the N-terminal domain of ActA involved in the actin comet tail formation by Listeria monocytogenes" EMBO 16(7):1531-40.

Lauer et al., "Characterization of the Attachment Site of Bacteriophage U153 within the Listeria monocytogenes comK Gene" ASM Meeting, Abstract 1999.

Lauer et al., "Systematic mutational analysis of the amino-terminal domain of the Listeria monocytogenes ActA protein reveals novel functions in actin-based motility" Molecular Microbiology 42(5):1163-1177, 2001.

Le Doussal et al. Enhanced In Vivo Targeting Of An Asymmetric Bivalent Hapten Antibody Conjugate CockTailsTo Double-Antigen-Positive Mouse B Cells With Monoclonal ; J. Immunol. 146:169-175 (1991).

Leao et al., 1995, "A species-specific nucleotide sequence of *Mycobacterium tuberculosis* encodes a protein that exhibits hemolytic activity when expressed in *Escherichia coli*" Infect. Immun. Nov.;63(11):4301-6.

Lebrun et al., Aug. 1996, "Internallan must be on the Bacterial Surface to mediate Entry of Listeria monocytogenes into Epihalial Cells", Molecullar Microbiology 21:579-592.

Lee et al., 1991, "Construction of single-copy integration vectors for *Staphylococcus aureus*", Gene 103:101-5.

Lee et al. Delivery of macromolecules into cytosol using liposomes containig hemolysin from Listeria monocytogenes, J. Biol. Chem., Mar. 29, 1996 271(13):7249-52.

Lehner et al., 1996, "Processing and delivery of peptides presented by MHC class I molecules", Curr. Opin. Immunol. 8(1):59-67.

Lejeune, 1994, "Nitric oxide involvement in tumor-induced immunosuppression" J. Immunol. 152(10):5077-5083.

Liau et al., 2002, "Tumor immunity within the central nervous system stimulated by recombinant Listeria monocytogenes vaccination", Cancer Res., 62(8):2287-93.

(56) References Cited

OTHER PUBLICATIONS

Lieberman et al. "Engineered Listeria monocytogenes as an AIDs vaccine", Vaccine. May 6, 2002;20(15):2007-10.
Lin et al., "Treatment of Established Tumors with a Novel Vaccine that Enhances Major Histocompatibility Class II Presentation of Tumor Antigen", Cancer Res. 1996, 56:21-26.
Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.
Lingnau et al., 1995, "Expression of the Listeria monocytogenes EGD inlA and inlB genes, whose products meidate bacterial entry into tissue culture cell lines, by PrfA-dependent and independent mechanisms" Infect. Immun. Oct.; 63(10):3896-903.
Lipford et al. "Vaccination with immunodominant peptides encapsulated in Quil A-containing liposomes induces peptide-specific primary CD8+ cytotoxic T cells", Vaccine Jan. 1994; 12(1):73-80.
Lobocka et al. "Organization and expression of the *Escherichia coli* K-12 dad operon encoding the smaller sunbunit of D-amino acid dehydrogenase and the catabolic alanine racemase", J Bacteriol. Mar. 1994;176(5):1500-10.
Loeffler et al., 2006, "Comparison of different live vaccine strategies in vivo for delivery of protein antigen or antigen-encoding DNA and mRNA by virulence-attenuated Listeria monocytogenes" Infect. Immun. Jul.; 74(7):3946-57.
Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.
Loessner et al., 2000, "Complete nucleotide sequence, molecular analysis and genome structure of bacteriophage A118 of Listeria monocytogenes: implications for phage evolution", Molecular Microbiology 35(2):324-40.
Maciag et al. "The first clinical use of a live-attenuated Listeria monocytogenes vaccine: a Phase I safety study of Lm-LLO-E7 in patients with advanced carcinoma of the cervix", Vaccine. Jun. 19, 2009;27(30):3975-83.
Madden et al. Applications of Network BLAST Server; Meth. Enzymol. 266:131-141 (1996).
Makela et al., Hand book of Experimental Immunology vol. 1, Chapter 3—"Haptens and carriers", pp. 3-1-3.13; 1987.
Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.
Marks et al. By-passing Immunization Human Antibodies from V-gene Libraries Displayed on Phage; J. Mol. Biol. 222: 581-597 (1991).
Marquis et al., 1997, "Proteolytic pathways of activation and degradation of a bacterial phospholipase C during intracellular infection by Listeria monocytogenes" J. Cell Biol. 137:1381-1392.
Marquis et al. "Intracytoplasmic growth and virulence of Listeria monocytogenes auxorophic mutants", Infect. Immun. Sep. 1993;61(9):3756-60.
Martin et al., 1986, "Necleotide sequence of the tetM tetracycline resistance determinant of the streptococcal conjugative shuttle transpson Tn1545", Nucleic Acid Res. 14:7047-7058.
Marx et al., 2002, "Broad-host-range cre-lox system for antibiotic marker recycling in gramnegativ bacteria" Biotechniques, Nov.;33(5):1062-7.
Mata et al. "Evaluation of a recombinant Listeria monocytogenes expressing an HIV protein that protects mice against viral challenge", Vaccine 19:1435-45, 2001.
Mata et al. Th1 T.cell responses to HIV•1 Gag protein delivered by Listeria monocytogenes vaccine are similar to those induced by endogenous listerial antigen's; J. Immunol 163:1449-1456. (1999).
Mazzaccaro et al. "Major histocompatibility class I presentation of soluble antigen facilitated by *Mycobacterium tuberculosis* infection", Proc. Natl. Acad. U.S.A. Oct. 15, 1996; 93(21):11786-91.

McLaughlin et al., 1998, "Molecular characterization of an autolytic amidase of Listeria monocytogenes EDG", Microbiology, May; 144(Pt 5):1359-67.
Mendez et al. Functional Transplant Of Megabase Humanimmunoglobulin Loci Recapitulates Human Antibody Response In Mice; Nature Genetics 15:146-156 (1997).
Mengaud et al., 1988, "Expression in *Escherichia coli* and sequence analysis of the listeriolysin O determinant of listeria monocytogenes", Infect. Immun., vol. 56, No. 4, 766-772.
Merrifield et al., "Solid phase peptide synthesis. 1. The synthesis of a tetrapeptide" J. Am. Chem. Soc., 85:2149-2156 (1963).
Mikayama et al. "Molecular cloning and functional expression of a cDNA encoding gycosylation-inhibiting factor", Nov. 1993, Pro Natl. Acad. Sci., USA, vol. 90:10056-10060.
Miller et al, "Targeted vectors for gene therapy" 1995, FASEB J., 9:190-199.
Mkrtichyan et al. "Anti-PD-1 antibody significantly increases therapeutic efficacy of Listeria monocytogenes (Lm)-LLO immunotherapy", Journal for ImmunoTherapy of Cancer 2013, 1:15.
Mlynarova et al., 2002, "The promiscutiy of heterospecifc lox sites increases dramatically in the presence of palindromic DNA", Gene, Aug. 21;296(1-2):129-37.
Mollet et al., 1993, "Directed genomic integration gene replacement, and integrative gene expression in *Streptococcus thermophilus*" J. Bacteriology 175:4315-4324.
Moriishi et al., 1998, "Sequence analysis of the actA gene of Listeria monocytogenes isoluted from human", Microbiol. Immunol., vol. 42, No. 2, p. 129-132.
Nakanuma, et al. Anatomic and molecular pathology of intrahepatic cholangiocarcinoma, J. Hepatobiliary Pancreat. Surg. 10:265-281 (2003).
Naz et al. "Novel human prostate-specific cDNA: molecular cloning, expression, and immunobiology of the recombinant protein" Biochem Biophys Res Commun. 297:1075-84, 2002.
Ngo et al., 1994, "The Protein Folding Problem and Tertiary Structure Prediction", pp. 492-495.
Nitcheu-Tefit et al. "Listeriolysin O Expressed in a Bacterial Vaccine Suppresses CD4_CD25high Regulatory T Cell Function In Vivo", J. Immunol. Aug. 1, 2007;179(3):1532-41.
Noriega et al. "Engineered deltagua-B-A deltavirG Shigella flexneri 2a strain CVD 1205: construction, safety, immunogenicity, and potential efficacy as a mucosal vaccine", Infect. Immun. Aug. 1996;64(8):3055-61.
Ochsenbein et al., 1999, "A comparison of T cell memory against the same antigen induced by virus versus intracellular bacteria" Proc. Natl. Acad. U.S.A. Aug. 3;96(16):9293-8.
Offit et al. "Addressing Parents' Concerns: Do Mulitple Vaccines Overwhelm or Weaken the Infant's Immune System?", Pediatrics vol. 109 No. 1 Jan. 2002.
O'Riordan, et al. Listeria Intracellular Growth and Virulence Require Host-Derived Lipoic Acid, Science 302: 462-464(2003).
Oscarsson et al., 1996, "Induction of haemolytic activity in *Escherichia coli* by the slyA gene product" Mol. Microbiol. Apr.; 20(1):191-9.
Paglia et al., 1997, "The defined attenuated Listeria monocytogenes delta mp12 mutant is an effect oral vaccine carrier to trigger long-lasting immune response against a mouse fibrosarcoma" Eur. J. Immunol. 27:1570-1575.
Palmeros et al., 2000, "A family of removable cassettes designed to obtain antibiotic-resistance-free genomic modifications of *Escherichia coli* and other bacteria" Gene, Apr. 18; 247(1-2):255-64.
Pamer et al. "Precise prediction of a dominant class I MHC-restricted epitope of Listeria monocytogenes", Nature. Oct. 31, 1991;353(6347):852-5.
Pan et al., "Regression of Established Tumors in Mice Mediated by the Oral Administration of a Recombinant Listeria monocytogenes Vaccine", Cancer Res., 1995, 55:4776-4779.
Pan et al., 1995, "A recombinant Listeria monocytogenes vaccine expressing a model tumor antigen protects mice against lethal tumour cell challenge and causes regression of established tumors" Nature Med. 1:471-477.

(56) References Cited

OTHER PUBLICATIONS

Parida et al, 1998, "Internalin B is essential for adhesion and mediates the invasion of Listeria monocytogenes into human endothelial cells" Mol. Microbiol. Apr.; 28(1):81-93.
Paterson, "Rational approaches to immune regulation", Immunologic Research, 2003; 27/2-3:451-462.
Paterson et al. "Recombinant Listeria monocytogenes cancer vaccines", Curr Opin Immuno. Oct. 1996;8(5):664-9.
Paul et al., 1989, "Fundamental Immunology", Second Edition, Raven Press, 987-988.
Paul et al. Frequent associations between CTI and T-Helper epitopes in HIV-1 genomes and 12, 13 implications for multi-epitope vaccine designs. BMC Microbiology 10:1-16 (2010).
Paul et al. An IL-4 Receptor Region Containing an Insulin Receptor Motif Is Important for IL+Mediated IRS-1 Phosphorylation and Cell Growth, Cell 76 241-251 (1994).
Pawelek et al. "Tumor-targeted *Salmonella* as a novel anticancer vector", Cancer Res. Oct. 15, 1997;57(20):4537-44.
Peng et al. "Adjuvant properties of listeriolysin O in a DNA vaccine strategy", Cancer Immunol Immunother, Jun. 2007;56(6):797-806.
Penichet et al., 2001, "Antibody-cytokine fusion proteins for the therapy of cancer" J. Immunological Methods 248:91-101.
Peters et al. "Tailoring host immune responses to Listeria by manipulation of virulence genes—the interface between innate and acquired immunity", FEMS Immunol Med Microbiol. Apr. 1, 2003;35(3):243-53.
Peters et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).
Peters et al. "Enhancing the immunogenicity of bioengineered Listeria monocytogenes by passaging through live animal hosts", Vaccine. 21.:1187-94. (2003).
Pfeifer et al., 1993, "Phagocytic processing of bacterial antigens for class I MHC presentation to T cells" Nature, Jan. 28; 361(6410):359-62.
Portielji et al. IL-12: a promising adjuvant for cancer vaccination, Cancer Immunol. Immunother. 52:133-144 (2003).
Portnoy et al. "Molecular determinants of Listeria monocytogenes pathogenesis", Infect Immun. Apr. 1992;60(4):1263-7.
Pupa et al., 2001, "Prevention of spontaneous neu-expressing mammary tumor development in mice transgenic or rat proto-neu by DNA vaccination" Gene Ther. Jan.;8(1):75-9.
Purchio et al. "Methods in Enzymology: Methods for molecular cloning in eukaryotic cells", (2003).
Quenee et al., 2005, "Combined sacB-based negative selection and cre-lox antibiotic marker recycling for efficient gene deletion in pseudomonas aeruginosa", Biotechniques, Jan.; 38(1):63-7.
Raveneau et al., 1992, "Reduced virulence of a Listeria monoctyogenes phospholipase-deficient mutant obtained by transposon insertion into the zinc metalloproteas gene" Infect. Immune., 60:916-921.
Realini et al., "Proposed roles in protein-protein association and presentation of peptides by MHC Class I receptors", FEBS Lett., 1994, 348:109-113.
Riegler. Preneoplastic Conditions of the Liver; Seminars in Gastrointestinal Disease vol. 7, No. 2:pp. 74-87 (1996).
Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec;23 (12):899-904 (2004).
Reiter et al., 1989, "Transfer RNA genes frequently serve as integration sites for porkaryotic genetic elements", Nucleic Acids Research 17(5):1907-14.
Renard et al., "HER-2 DNA and protein vaccines containing potent Th cell epitopes induce distinct protective and therapeutic antitumor responses in HER-2 transgenic mice", The Journal of Immunology, 171(3):1588-1595, 2003.

Repique, 1992, "Immunosuppression derived from human B-lymphoblastoid and melanoma cell lines" Cancer Invest. 10(3):201-208.
Robinson et al. "New Hope For An Aids Vaccine", Nat. Rev. Immunol. 2:239-50 (2002).
Rocken et al. "Pathology and Pathogenesis of Hepatocellular", Digestive Diseases 19:269-278 (2001).
Roden et al., 2004, "Vaccination to prevent and treat cervical cancer", Hum. Pathol. 35(8):971-82.
Rogers et al. "Amino acid sequences common to rapidly degraded proteins: the PEST hypothesis", Science 1986; 234(4774):364-8.
Rothman et. al. "The use of lving listeria monocytogenes as an active immunotherapy for the treatment of cancer", Emerging Cancer Therapy: Microbial Approaches and Biotechnological Tools, Edited by Arsénio M. Fialho and Ananda M. Chakrabarty Copyright © 2010 John Wiley & Sons, Inc.
Rubin et al. "Cloning, sequence determination, and regulation of the ribonucleotide reductase subunits from Plasmodium falciparum: a target for antimalarial therapy", Proc Natl Acad Sci U S A. Oct. 15, 1993;90(20):9280-4.
Russmann et al., 1998, "Delivery of epitopes by the *Salmonella* type III secretion system for vaccine system for vaccine development", Science, Jul. 24; 281(5376):565-8.
Safely et al., "Role of listeriolysin-O (LLO) in the T lymphocyte response to infection with Listeria monocytogenes. Identification of T cell epitopes of LLO" J. Immunology 146(10):3604-3616; May 1991.
Sambrook et al. "Molecular cloning: a laboratory manual", Cold Spring Harbor Laboratory Press, Cold Spring Harbor, New York 2 (2001).
Schafer et al. "Induction of a cellular immune response to a foreign antigen by a recombinant Listeria monocytogenes vaccine", J. Immunol. Jul. 1, 1992;149(1):53-9.
Scheirlinck et al., 1989, "Integration and expression of alpha-amylase and endoglucansase genes in the Lactobacillus plantarum chromosome", Appl. Environ Microbiol. 55(9):2130-7.
Schmidt et al., 1995, "Molecular Analysis of the Plasmid-Encoded Hemolysin of *Escherichia coli* O157:H7 Strain EDL 933", Infection and Immunity, 63(3):1055-1061.
Schneider et al. Induction of CD8+ T cells using heterologus prime-boost immunisation strategies, Immunol.Rev. 170:29-38 (1999).
Schnupf et al., "Phosphorylation, ubiquitination and degradation of listeriolysic O in mammalian cells: role of the PEST-like sequence" Cellular microbiology 8(2):353-364, 2006.
Schnupf et al. "ListeriolysinO: a phagosome-specific lysine", Microbes & Infect. 2007, 9:1176-1187.
Scortti et al., 2007, "The PrfA virulence regulon", Microbes Infect. Aug.; 9(10):1196-207.
Scott, P. et al. Amino Acid Sequences Common to Rapidly Degraded Proteins: The PEST Hypothesis; Immunol. Today vol. 364-348.,(1991).
Sewell et al. Regression of HPV-Positive Tumors Treated with a New Listeria monocytogenes Vaccine Arch Otolaryngol., Head Neck Surg., Jan. 2004, vol. 130, pp. 92-97.
Shahabi et al. "A live, attenuated Listeria-based immunotherapeutic for the treatment of breast cancer", 2009 ASCO Breast Cancer Symposium, Oct. 8, 2009, abstract.
Shahabi et al. "Development of a live and highly attenuated Listeria monocytogenes-based vaccine for the treatment of Her2/neu-expressing cancers in human", Cancer Gene Therapy, vol. 18, No. 1, Jan. 1, 2011, pp. 53-62.
Shahabi et al. "Development of a live and highly attenuated Listeria monocytogenes-based vaccine for the treatment of Her2/neu-overexpressing cancers in human", Cancer Gene Therapy, 2010, pp. 1-10.
Shahabi et al., "Development of Listeria monocytogenes based vaccine against prostate cancer" Cancer Immunol Immunother (2008) 57:1301-1313.
Sharpe et al. "The function of programmed cell death 1 and its ligands in regulating autoimmunity and infection", Nature Immunology ; 8:239-245 (2007).

(56) References Cited

OTHER PUBLICATIONS

Shaw et al. "Complete nucleotide sequence of macrolide-lincosamide-streptogramin B-resistance tansposon Tn917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: differential effects on priming of CD8 T cells and protective immunity" Cell., Feb. 20; 92(4):535-45.
Shetron-Rama et al., 2002, "Intracellular induction of Listeria monocytogenes actA expression" Infect. Immun. 70:1087-1096.
Shimizu et al., 1994, "Effects of CD4+ and CD8+ T cells in tumor-bearing mice on antibody production" Cancer Immunol. Immunother 38(4):272-276.
Shiver et al., Replication-incompetent adenoviral vaccine vector elicits effective antiimmunode ® ciency-virus immunity, Nature 415: 331-5 (2002).
Sin et al. DNA Priming—Protein Boosting Enhances Both Antigen-Specific Antibody and Th1-Type Cellular Immune Responses in a Murine Herpes Simplex Virus-2 gD Vaccine Model, DNA Cell Biol. 18:771-9 (1999).
Singh et al. "Immunoediting sculpts tumor epitopes during immunotherapy", Cancer Res.67(5):1887-92. Mar. 1, 2007.
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-443.
Sizemore et al. "Attenuated Shigella as a DNA delivery vehicle for DNA-mediated immunization", Science. Oct. 13, 1995;270(5234):299-302.
Skolnick et al. "Form genes to protein structure and function: novel applications of computational approaches in the genomic era", Jan. 2000, Trends in Biotech., 18(1):34-39.
Slifka et al., 1996, "Arrival cytotoxic T-cell memory by vaccination with recombinant Listeria monocytogenes" J. Virol. 70(5):2902-10.
Smith et al., 1995, "The two distinct phospholipases C of Listeria monocytogenes have overlapping roles in escape from a vacuole and cell-to-cell spread", Infect. Immun. 63:4231-4237.
Smith et al., Sep. 1995, "Asymmetric Distribution of the Listeria monocytogenes ActA Protein is Required and Sufficient to Direct Actin-Based Motility", Molecular Microbiology 17:945-951.
Souders et al., 2006, "In vivo bactofection: listeriacan function as a DNA-cancer vaccine" DNA Cell Biol. Mar.; 25(3):142-51.
Stahl et al., 1984, "Replacement of the Bacillus subtillisin structural gene with an in vitro-derived deletion mutation", J. Bacteriol. 158:411-418.
States, D.J. et al. Improved Sensitivity of Nucleic Acid Database Searches Using Application-Specific Scoring Matrices, Methods 3:66-70 (1991).
Stitz et al., 1990, "Characterization and immunological properties of influenza A virus nucleoprotein (NP): cell-associated NP isolated from infected cells or viral NP expressed by vaccinia recombinant virus do no confer protection" J. Gen. Virol., 71(Pt 5):1169-1179.
Strungnell et al., 1990, "Stable expression of forgein antigens from the chromsome of *Salmonella typhimurium* vaccine strains", Gene 88:57-63.
Strych et al. "Characterization of the alanine racemases from two mycobacteria", FEMS Microbiol Lett. Mar. 15, 2001;196(2):93-8.
Stryer et al., "Levels of structure in protein architecture", Biochemistry, Third Edition, W H Freeman Company, New York, pp. 31-33, 1998.
Sun et al., "Isolation of Listeria monocytogenes small-plaque mutants defective intracellular growth and cell-to-cell spread", Infect. Immun. Nov. 1990;58(11):3770-8.
Szalay et al. "Presentation of Listeria monoctyogenes antigenes by major histocompatibility complex class I molecules to CD8 cytotoxic T lymphocytes independent of listeriolysin secretion and virulence", Eur. J. Immuno. Jul. 1994; 24(7):1471-7.

Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun. 1999, 67(2):568-575.
Tanizawa et al. "The primary structure of thermostable D-amino acid aminotransferase from a thermophilic *Bacillus* species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Taube, J. M. et al. Colocalization of Inflammatory Response with B7-H1 Expression in Human Melanocytic Lesions Supports an Adaptive Resistance Mechanism of Immune Espace, Sci Transl Med 4, 127ra37 (2012).
Teitelbaum et al. "Mycobacterial infection of macrophages results in membrane-permeable phagosomes", Proc. Natl. Acad. Sci. U S A, Dec. 21, 1999, 96(26):15190-5.
Terracciano et al. "Cytogenetic alterations in liver cell tumors as detected by Comparitive Genomic Hybridization", Pathologica 95:71-82 (2003).
Thompson et al. "Pathogenicity and immunogenicity of Listeria monocytogenes strain that requires D-alanine for growth", Infect Immun. Aug. 1998;66(8):3552-61.
Tilney et al., 1989, "Actin filaments and the growth, momvement, and speard of the intracellular bacterial parasite, Listeria monocytogenes" J. Cell Biol., Oct.; 109(4 Pt 1):1597-608.
Triglia et al. "A procedure for in vitro amplification of DNA segments that lie outside the boundaries of know sequences", Nucleic Acids Res. Aug. 25, 1988;16(16):8186.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinites Isolated from a Large Non-immunized Phage Display Library, Nature Biotechnol. 14:309-314 (1996).
Vazquez et al. Differential regulation of Ia expression and antigen presentation by listeriolysin-producting versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verma et al., 1995, "Delivery of class I and class II MHC-restricted T-cell epitopes of listeriolysin of listeria monocytogenes by attenuated *Salmonella*", Vacine, vol. 13, No. 2, p. 142-150.
Villanueva et al. "Listeriolysin is processed efficiently into an MHC class I-associated epitope in Listeria monocytogenes-infected cells", J. Immunol. Dec. 1, 1995; 155(11):5227-33.
Vines et al. "Identification and characterization of nucleotide sequence difference in three virulence-associate genes of listeria monocytogenes strains representing clinically important serotypes", Current Microbiology, May 1998, vol. 36, No. 5, pp. 309-318.
Von Heijne. Patterns of Amino Acids near Signal-Sequence Cleavage Sites Eur. J. Biochem. 133:17-21 (1983).
Walker et al., 1994, "Tumor growth Alters T cell and macrophage production of and responsiveness to granulocyte-macrophage colony-stimulating factor: partial dysregulation through interleukin-10" Cell Immunol. 154(1):342-357.
Wasserman et al. "Catabolic alanine racemase from *Salmonella typhimurium*: DNA sequence, enzyme purfication, and characterization", Biochemistry, Oct. 23, 1984; 23(22):5182-7.
Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.
Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.

(56) References Cited

OTHER PUBLICATIONS

Weidt et al., 1994, "CD8+ T lymphocyte-mediated antiviral immunity in mice as a result of injection of recombinant viral proteins", J. Immunol. Sep. 15; 153(6):2554-61.
Weiskirch "Listeria monocytognes: a potent vaccine vector for neoplastic and infectious disease" Immunol. Rev., vol. 158, Aug. 1997, p. 159-169.
Welch et al., Jul. 3, 1998, "Interaction of Human Arp2/3 Complex and the Listeria monocytogenes ActA Protein in Actin Filament Nucleation" Science 281:105-108; pa-998020.
Wilson et al. "Transient expression of bacterial gene fragments in eukaryotic cells: implications for CD8(+) T cell epitope analaysis", J. Immunol. Methods, Feb. 3, 2000; 234 (1-2):137-47.
Wipke et al. "Variable binding affinities of liseriolysin O peptides for the H-2Kd class I molecule", Eur J Immunol. Aug. 1993;23(8):2005-10.
Wolff et. al. "Direct Gene Transfer into Mouse Muscle in Vivo", Science 247:1465(1990).
Wootton et al. Statistics of Local Complexity in Amino Acid Sequences and Sequence Databases, Comput. Chem. 17:149-163 (1993).
Wu et al., "Engineering an itracellular pathway for major histocompatibility complex class II presentation of antigens", Proc. Natl. Acad. Sci. USA, 1995, 92:11671-5.
Young et al., 1992, "Tumor-derived cytokines induce bone marrow suppressor cells that mediate immunosuppression through transforming growth factor beta", Cancer Immunol. Immunother. 35(1):14-18.
Young et al., 1995, "Holins: form and function in bacteriophage lysis" FEMS Microbiol Rev., Aug., 17 (1-2):191-205.
Zhang et al., 1993, "Functional replacement of the hemolysin A transport signal by a different primary sequence", Proc. Natl. Acad. Sci. U.S.A May 1; 90(9):4211-5.
Zhao et al. "Pathogenicity and immunogenicity of a vaccine strain of Listeria monocytogenes that relies on a suicide plasmid to supply an essential gene product", Infect Immun. Sep. 2005;73(9):5789-98.
Caudy et al., "Fragile X-related protein and VIG associate with RNA interference machinery" Genes and Development 16: 2491-96, 2002.
Genbank Accession No. AF103807, Nov. 1, 1999.
GenBank Acc. No. NC_003210, Dec. 17, 2014.
GenBank Accession No. DQ054588, Aug. 21, 2006.
GenBank Accession No. DQ054589, Aug. 21, 2006.
GenBank Accession No. AY878649, Feb. 6, 2005.
GenBank Accession No. U25452, Jul. 16, 2001.
Gouin et al. "The Listeria monocytogenes InlC protein interferes with innate immune responses by targeting the I B kinase subunit IKK", Proceedings of the National Academy of Sciences, vol. 107, No. 40, Sep. 20, 2010 (Sep. 20, 2010), pp. 17333-17338.
International Search Report for PCT Application No. PCT/US15/040855 mailed Dec. 18, 2015.
Naz et al., "Novel human prostate-specific cDNA; molecular cloning, expression, and immunobiology of the recombinant protein" *Biochem Biohphys Res Commun.* 297:1075-84, 2002.
Soussi et al., "Effect of intragastric and intraperitoneal immunization with attenuated and wild-type LACK-expressing Listeria monocytogenes on control murine Leishmania major infection", Vaccine, vol. 20, No. 21-22, pp. 2702-2712, 2002.

SEQUENCE LISTING

```
<160> NUMBER OF SEQ ID NOS: 55

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 2
```

```
<211> LENGTH: 19
<212> TYPE: PRT
<213> ORGANISM: Listeria monocytogenes

<400> SEQUENCE: 2

Lys Glu Asn Ser Ile Ser Ser Met Ala Pro Pro Ala Ser Pro Pro Ala
1               5                   10                  15

Ser Pro Lys

<210> SEQ ID NO 3
<211> LENGTH: 14
<212> TYPE: PRT
<213> ORGANISM: Listeria monocytogenes

<400> SEQUENCE: 3

Lys Thr Glu Glu Gln Pro Ser Glu Val Asn Thr Gly Pro Arg
1               5                   10

<210> SEQ ID NO 4
<211> LENGTH: 28
<212> TYPE: PRT
<213> ORGANISM: Listeria monocytogenes

<400> SEQUENCE: 4

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 5
<211> LENGTH: 20
<212> TYPE: PRT
<213> ORGANISM: Listeria monocytogenes

<400> SEQUENCE: 5

Lys Asn Glu Glu Val Asn Ala Ser Asp Phe Pro Pro Pro Pro Thr Asp
1               5                   10                  15

Glu Glu Leu Arg
            20

<210> SEQ ID NO 6
<211> LENGTH: 33
<212> TYPE: PRT
<213> ORGANISM: Listeria monocytogenes

<400> SEQUENCE: 6

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 7
<211> LENGTH: 19
<212> TYPE: PRT
<213> ORGANISM: Listeria seeligeri

<400> SEQUENCE: 7

Arg Ser Glu Val Thr Ile Ser Pro Ala Glu Thr Pro Glu Ser Pro Pro
1               5                   10                  15

Ala Thr Pro
```

<210> SEQ ID NO 8
<211> LENGTH: 17
<212> TYPE: PRT
<213> ORGANISM: Streptococcus pyogenes

<400> SEQUENCE: 8

Lys Gln Asn Thr Ala Ser Thr Glu Thr Thr Thr Thr Asn Glu Gln Pro
1               5                   10                  15

Lys

<210> SEQ ID NO 9
<211> LENGTH: 17
<212> TYPE: PRT
<213> ORGANISM: Streptococcus equisimilis

<400> SEQUENCE: 9

Lys Gln Asn Thr Ala Asn Thr Glu Thr Thr Thr Thr Asn Glu Gln Pro
1               5                   10                  15

Lys

<210> SEQ ID NO 10
<211> LENGTH: 441
<212> TYPE: PRT
<213> ORGANISM: Listeria monocytogenes

<400> SEQUENCE: 10

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

```
Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
            435                 440

<210> SEQ ID NO 11
<211> LENGTH: 416
<212> TYPE: PRT
<213> ORGANISM: Listeria monocytogenes

<400> SEQUENCE: 11

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
            85                  90                  95

Glu Tyr Ile Val Val Glu Lys Lys Lys Ser Ile Asn Gln Asn Asn
        100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
            165                 170                 175
```

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 12
<211> LENGTH: 529
<212> TYPE: PRT
<213> ORGANISM: Listeria monocytogenes

<400> SEQUENCE: 12

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val

```
            130                 135                 140
Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu

<210> SEQ ID NO 13
<211> LENGTH: 416
```

<212> TYPE: PRT
<213> ORGANISM: Listeria monocytogenes

<400> SEQUENCE: 13

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 14
<211> LENGTH: 390
<212> TYPE: PRT
<213> ORGANISM: Listeria monocytogenes

<400> SEQUENCE: 14

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Lys Thr Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser

```
              355                 360                 365
Gln Asn Phe Ser Asp Phe Pro Pro Ile Pro Thr Glu Glu Glu Leu Asn
    370                 375                 380

Gly Arg Gly Gly Arg Pro
385                 390

<210> SEQ ID NO 15
<211> LENGTH: 1200
<212> TYPE: DNA
<213> ORGANISM: Listeria monocytogenes

<400> SEQUENCE: 15
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata aagtgagaaa tacgaacaaa     240
gcagacctaa tagcaatgtt gaaagaaaaa gcagaaaaag tccaaatat caataataac      300 aacagtgaac aaactgagaa tgcggctata aatgaagagg cttcaggagc cgaccgacca     360
gctatacaag tggagcgtcg tcatccagga ttgccatcgg atagcgcagc ggaaattaaa     420 aaagaagga agccatagc atcatcggat agtgagcttg aaagccttac ttatccggat      480
aaaccaacaa agtaaataa gaaaaaagtg gcgaaagagt cagttgcgga tgcttctgaa     540
agtgacttag attctagcat gcagtcagca gatgagtctt caccacaacc tttaaaagca     600
aaccaacaac cattttttcc ctaaagtattt aaaaaaataa agatgcgggg aaatgggta     660 cgtgataaaa tcgacgaaaa tcctgaagta agaaagcga ttgttgataa aagtgcaggg     720
ttaattgacc aattattaac caaaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc     1020
atccgggaaa cagcatcctc gctagattct agttttacaa gagggatttt agctagtttg     1080
agaaatgcta ttaatcgcca tagtcaaaat ttctctgatt tcccaccaat cccaacagaa     1140
gaagagttga cgggagagg cggtagacca gaagagttga cgggagagg cggtagacca     1200

<210> SEQ ID NO 16
<211> LENGTH: 390
<212> TYPE: PRT
<213> ORGANISM: Listeria monocytogenes

<400> SEQUENCE: 16

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Glu Glu Leu Glu Lys Ser Asn Lys Val Lys Asn Thr Asn Lys
65                  70                  75                  80
```

Ala Asp Leu Ile Ala Met Leu Lys Ala Lys Ala Glu Lys Gly Pro Asn
                85                  90                  95

Asn Asn Asn Asn Asn Gly Glu Gln Thr Gly Asn Val Ala Ile Asn Glu
            100                 105                 110

Glu Ala Ser Gly Val Asp Arg Pro Thr Leu Gln Val Glu Arg Arg His
        115                 120                 125

Pro Gly Leu Ser Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Ala Asn Lys Arg Lys Val Ala Lys Glu Ser Val Val
                165                 170                 175

Asp Ala Ser Glu Ser Asp Leu Asp Ser Ser Met Gln Ser Ala Asp Glu
            180                 185                 190

Ser Thr Pro Gln Pro Leu Lys Ala Asn Gln Lys Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Thr Pro Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Met Arg Glu Thr Ala Pro Ser Leu Asp Ser Ser Phe
            340                 345                 350

Thr Ser Gly Asp Leu Ala Ser Leu Arg Ser Ala Ile Asn Arg His Ser
        355                 360                 365

Glu Asn Phe Ser Asp Phe Pro Leu Ile Pro Thr Glu Glu Leu Asn
    370                 375                 380

Gly Arg Gly Gly Arg Pro
385                 390

<210> SEQ ID NO 17
<211> LENGTH: 1200
<212> TYPE: DNA
<213> ORGANISM: Listeria monocytogenes

<400> SEQUENCE: 17
atgcgtgcga tgatggtagt tttcattact gccaactgca ttacgattaa ccccgacata    60
atatttgcag cgacagatag cgaagattcc agtctaaaca cagatgaatg gaagaagaa    120 aaaacagaag agcagccaag cgaggtaaat acgggaccaa gatacgaaac tgcacgtgaa    180
gtaagttcac gtgatattga ggaactagaa aaatcgaata agtgaaaaa tacgaacaaa    240 gcagacctaa tagcaatgtt gaaagcaaaa gcagagaaag gtccgaataa caataataac    300
aacggtgagc aaacaggaaa tgtggctata aatgaagagg cttcaggagt cgaccgacca    360

```
actctgcaag tggagcgtcg tcatccaggt ctgtcatcgg atagcgcagc ggaaattaaa    420
aaaagaagaa aagccatagc gtcgtcggat agtgagcttg aaagccttac ttatccagat    480
aaaccaacaa aagcaaataa gagaaaagtg gcgaaagagt cagttgtgga tgcttctgaa    540
agtgacttag attctagcat gcagtcagca gacgagtcta caccacaacc tttaaaagca    600
aatcaaaaac cattttttccc taaagtattt aaaaaaataa agatgcggg gaaatgggta    660 cgtgataaaa tcgacgaaaa tcctgaagta aagaagcga ttgttgataa agtgcaggg    720 ttaattgacc aattattaac caaaagaaa agtgaagagg taaatgcttc ggacttcccg    780
ccaccaccta cggatgaaga gttaagactt gctttgccag agacaccgat gcttctcggt    840
tttaatgctc ctactccatc ggaaccgagc tcattcgaat tccgccgcc acctacggat    900 gaagagttaa gacttgcttt gccagagacg ccaatgcttc ttggttttaa tgctcctgct    960
acatcggaac cgagctcatt cgaatttcca ccgcctccaa cagaagatga actagaaatt   1020
atgcgggaaa cagcaccttc gctagattct agttttacaa gcggggattt agctagttg   1080 agaagtgcta ttaatcgcca tagcgaaaat ttctctgatt tcccactaat cccaacagaa   1140
gaagagttga acgggagagg cggtagacca gaagagttga acgggagagg cggtagacca   1200
```

<210> SEQ ID NO 18
<211> LENGTH: 1256
<212> TYPE: DNA
<213> ORGANISM: Listeria monocytogenes

<400> SEQUENCE: 18

```
gcgccaaatc attggttgat tggtgaggat gtctgtgtgc gtgggtcgcg agatgggcga     60
ataagaagca ttaaagatcc tgacaaatat aatcaagcgg ctcatatgaa agattacgaa    120
tcgcttccac tcacagagga aggcgactgg ggcggagttc attataatag tggtatcccg    180
aataaagcag cctataatac tatcactaaa cttggaaaag aaaaaacaga acagctttat    240
tttcgcgcct taaagtacta tttaacgaaa aaatcccagt ttaccgatgc gaaaaaagcg    300
cttcaacaag cagcgaaaga tttatatggt gaagatgctt ctaaaaaagt tgctgaagct    360
tgggaagcag ttggggttaa ctgattaaca aatgttagag aaaaattaat tctccaagtg    420
atattcttaa ataattcat gaatatttt tcttatatta gctaattaag aagataacta    480
actgctaatc caattttaa cggaacaaat tagtgaaaat gaaggccgaa ttttccttgt    540
tctaaaaagg ttgtattagc gtatcacgag gagggagtat aagtgggatt aaacagattt    600
atgcgtgcga tgatggtggt tttcattact gccaattgca ttacgattaa ccccgacgtc    660
gacccatacg acgttaattc ttgcaatgtt agctattggc gtgttctctt taggggcgtt    720
tatcaaaatt attcaattaa gaaaaaataa ttaaaaacac agaacgaaag aaaaagtgag    780
gtgaatgata tgaaattcaa aaaggtggtt ctaggtatgt gcttgatcgc aagtgttcta    840
gtctttccgg taacgataaa agcaaatgcc tgttgtgatg aatacttaca acacccgca    900 gctccgcatg atattgacag caaattacca cataaactta gttggtccgc ggataacccg    960
acaaatactg acgtaaatac gcactattgg ctttttaaac aagcggaaaa aatactagct   1020
aaagatgtaa atcatatgcg agctaattta atgaatgaac ttaaaaaatt cgataaacaa   1080
atagctcaag gaatatatga tgcggatcat aaaaatccat attatgatac tagtacattt   1140
ttatctcatt tttataatcc tgatagagat aatacttatt tgcccgggttt tgctaatgcg   1200 aaaataacag gagcaaagta tttcaatcaa tcggtgactg attaccgaga agggaa       1256
```

<210> SEQ ID NO 19
<211> LENGTH: 2322
<212> TYPE: PRT
<213> ORGANISM: Homo sapiens

<400> SEQUENCE: 19

```
Met Gln Ser Gly Arg Gly Pro Pro Leu Pro Ala Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
                35                  40                  45

Ile Asp Leu Gln Leu Gln Phe Ser Thr Ser Gln Pro Glu Ala Leu Leu
        50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                    85                  90                  95

Gln Thr Pro Ala Glu Thr Leu Leu Ser Asp Ser Ile Pro His Thr Val
                100                 105                 110

Val Leu Thr Val Val Glu Gly Trp Ala Thr Leu Ser Val Asp Gly Phe
            115                 120                 125

Leu Asn Ala Ser Ser Ala Val Pro Gly Ala Pro Leu Glu Val Pro Tyr
        130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380
```

```
Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
            405                 410                 415

Pro Glu Pro Gly Leu Pro Pro Val Phe Ala Asn Phe Thr Gln Leu Leu
        420                 425                 430

Thr Ile Ser Pro Leu Val Val Ala Glu Gly Thr Ala Trp Leu Glu
        435                 440                 445

Trp Arg His Val Gln Pro Thr Leu Asp Leu Met Glu Ala Glu Leu Arg
        450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
        530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
        610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Ala Thr Leu Lys Val
            645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
        690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
            725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
        770                 775                 780

Trp Met Leu Arg Leu Glu Pro Leu His Thr Gln Asn Thr Gln Gln Glu
785                 790                 795                 800
```

-continued

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
        995                 1000                1005

Val Ala Ile Gln Pro Val Asn Asp His Ala Pro Val Gln Thr Ile
    1010                1015                1020

Ser Arg Ile Phe His Val Ala Arg Gly Gly Arg Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly

```
            1205                1210                1215

Pro Val His Thr Asp Ala Thr Leu Gln Val Thr Ile Ala Leu Glu
            1220                1225                1230

Gly Pro Leu Ala Pro Leu Lys Leu Val Arg His Lys Lys Ile Tyr
            1235                1240                1245

Val Phe Gln Gly Glu Ala Ala Glu Ile Arg Arg Asp Gln Leu Glu
            1250                1255                1260

Ala Ala Gln Glu Ala Val Pro Pro Ala Asp Ile Val Phe Ser Val
            1265                1270                1275

Lys Ser Pro Pro Ser Ala Gly Tyr Leu Val Met Val Ser Arg Gly
            1280                1285                1290

Ala Leu Ala Asp Glu Pro Pro Ser Leu Asp Pro Val Gln Ser Phe
            1295                1300                1305

Ser Gln Glu Ala Val Asp Thr Gly Arg Val Leu Tyr Leu His Ser
            1310                1315                1320

Arg Pro Glu Ala Trp Ser Asp Ala Phe Ser Leu Asp Val Ala Ser
            1325                1330                1335

Gly Leu Gly Ala Pro Leu Glu Gly Val Leu Val Glu Leu Glu Val
            1340                1345                1350

Leu Pro Ala Ala Ile Pro Leu Glu Ala Gln Asn Phe Ser Val Pro
            1355                1360                1365

Glu Gly Gly Ser Leu Thr Leu Ala Pro Pro Leu Leu Arg Val Ser
            1370                1375                1380

Gly Pro Tyr Phe Pro Thr Leu Leu Gly Leu Ser Leu Gln Val Leu
            1385                1390                1395

Glu Pro Pro Gln His Gly Ala Leu Gln Lys Glu Asp Gly Pro Gln
            1400                1405                1410

Ala Arg Thr Leu Ser Ala Phe Ser Trp Arg Met Val Glu Glu Gln
            1415                1420                1425

Leu Ile Arg Tyr Val His Asp Gly Ser Glu Thr Leu Thr Asp Ser
            1430                1435                1440

Phe Val Leu Met Ala Asn Ala Ser Glu Met Asp Arg Gln Ser His
            1445                1450                1455

Pro Val Ala Phe Thr Val Thr Val Leu Pro Val Asn Asp Gln Pro
            1460                1465                1470

Pro Ile Leu Thr Thr Asn Thr Gly Leu Gln Met Trp Glu Gly Ala
            1475                1480                1485

Thr Ala Pro Ile Pro Ala Glu Ala Leu Arg Ser Thr Asp Gly Asp
            1490                1495                1500

Ser Gly Ser Glu Asp Leu Val Tyr Thr Ile Glu Gln Pro Ser Asn
            1505                1510                1515

Gly Arg Val Val Leu Arg Gly Ala Pro Gly Thr Glu Val Arg Ser
            1520                1525                1530

Phe Thr Gln Ala Gln Leu Asp Gly Gly Leu Val Leu Phe Ser His
            1535                1540                1545

Arg Gly Thr Leu Asp Gly Gly Phe Arg Phe Arg Leu Ser Asp Gly
            1550                1555                1560

Glu His Thr Ser Pro Gly His Phe Phe Arg Val Thr Ala Gln Lys
            1565                1570                1575

Gln Val Leu Leu Ser Leu Lys Gly Ser Gln Thr Leu Thr Val Cys
            1580                1585                1590

Pro Gly Ser Val Gln Pro Leu Ser Ser Gln Thr Leu Arg Ala Ser
            1595                1600                1605
```

-continued

```
Ser Ser Ala Gly Thr Asp Pro Gln Leu Leu Tyr Arg Val Val
1610                1615                1620

Arg Gly Pro Gln Leu Gly Arg Leu Phe His Ala Gln Gln Asp Ser
1625                1630                1635

Thr Gly Glu Ala Leu Val Asn Phe Thr Gln Ala Glu Val Tyr Ala
1640                1645                1650

Gly Asn Ile Leu Tyr Glu His Glu Met Pro Pro Glu Pro Phe Trp
1655                1660                1665

Glu Ala His Asp Thr Leu Glu Leu Gln Leu Ser Ser Pro Pro Ala
1670                1675                1680

Arg Asp Val Ala Ala Thr Leu Ala Val Ala Val Ser Phe Glu Ala
1685                1690                1695

Ala Cys Pro Gln Arg Pro Ser His Leu Trp Lys Asn Lys Gly Leu
1700                1705                1710

Trp Val Pro Glu Gly Gln Arg Ala Arg Ile Thr Val Ala Ala Leu
1715                1720                1725

Asp Ala Ser Asn Leu Leu Ala Ser Val Pro Ser Pro Gln Arg Ser
1730                1735                1740

Glu His Asp Val Leu Phe Gln Val Thr Gln Phe Pro Ser Arg Gly
1745                1750                1755

Gln Leu Leu Val Ser Glu Glu Pro Leu His Ala Gly Gln Pro His
1760                1765                1770

Phe Leu Gln Ser Gln Leu Ala Ala Gly Gln Leu Val Tyr Ala His
1775                1780                1785

Gly Gly Gly Gly Thr Gln Gln Asp Gly Phe His Phe Arg Ala His
1790                1795                1800

Leu Gln Gly Pro Ala Gly Ala Ser Val Ala Gly Pro Gln Thr Ser
1805                1810                1815

Glu Ala Phe Ala Ile Thr Val Arg Asp Val Asn Glu Arg Pro Pro
1820                1825                1830

Gln Pro Gln Ala Ser Val Pro Leu Arg Leu Thr Arg Gly Ser Arg
1835                1840                1845

Ala Pro Ile Ser Arg Ala Gln Leu Ser Val Val Asp Pro Asp Ser
1850                1855                1860

Ala Pro Gly Glu Ile Glu Tyr Glu Val Gln Arg Ala Pro His Asn
1865                1870                1875

Gly Phe Leu Ser Leu Val Gly Gly Leu Gly Pro Val Thr Arg
1880                1885                1890

Phe Thr Gln Ala Asp Val Asp Ser Gly Arg Leu Ala Phe Val Ala
1895                1900                1905

Asn Gly Ser Ser Val Ala Gly Ile Phe Gln Leu Ser Met Ser Asp
1910                1915                1920

Gly Ala Ser Pro Pro Leu Pro Met Ser Leu Ala Val Asp Ile Leu
1925                1930                1935

Pro Ser Ala Ile Glu Val Gln Leu Arg Ala Pro Leu Glu Val Pro
1940                1945                1950

Gln Ala Leu Gly Arg Ser Ser Leu Ser Gln Gln Gln Leu Arg Val
1955                1960                1965

Val Ser Asp Arg Glu Glu Pro Glu Ala Ala Tyr Arg Leu Ile Gln
1970                1975                1980

Gly Pro Gln Tyr Gly His Leu Leu Val Gly Gly Arg Pro Thr Ser
1985                1990                1995
```

| | | | | | | | | | | |
|---|---|---|---|---|---|---|---|---|---|---|
| Ala | Phe | Ser | Gln | Phe | Gln | Ile | Asp | Gln | Gly | Glu | Val | Val | Phe | Ala |
| | 2000 | | | | 2005 | | | | 2010 | |

Ala Phe Ser Gln Phe Gln Ile Asp Gln Gly Glu Val Val Phe Ala
     2000                2005              2010

Phe Thr Asn Phe Ser Ser Ser His Asp His Phe Arg Val Leu Ala
     2015                2020              2025

Leu Ala Arg Gly Val Asn Ala Ser Ala Val Val Asn Val Thr Val
     2030                2035              2040

Arg Ala Leu Leu His Val Trp Ala Gly Pro Trp Pro Gln Gly
     2045                2050              2055

Ala Thr Leu Arg Leu Asp Pro Thr Val Leu Asp Ala Gly Glu Leu
     2060                2065              2070

Ala Asn Arg Thr Gly Ser Val Pro Arg Phe Arg Leu Leu Glu Gly
     2075                2080              2085

Pro Arg His Gly Arg Val Val Arg Val Pro Arg Ala Arg Thr Glu
     2090                2095              2100

Pro Gly Gly Ser Gln Leu Val Glu Gln Phe Thr Gln Gln Asp Leu
     2105                2110              2115

Glu Asp Gly Arg Leu Gly Leu Glu Val Gly Arg Pro Glu Gly Arg
     2120                2125              2130

Ala Pro Gly Pro Ala Gly Asp Ser Leu Thr Leu Glu Leu Trp Ala
     2135                2140              2145

Gln Gly Val Pro Pro Ala Val Ala Ser Leu Asp Phe Ala Thr Glu
     2150                2155              2160

Pro Tyr Asn Ala Ala Arg Pro Tyr Ser Val Ala Leu Leu Ser Val
     2165                2170              2175

Pro Glu Ala Ala Arg Thr Glu Ala Gly Lys Pro Glu Ser Ser Thr
     2180                2185              2190

Pro Thr Gly Glu Pro Gly Pro Met Ala Ser Ser Pro Glu Pro Ala
     2195                2200              2205

Val Ala Lys Gly Gly Phe Leu Ser Phe Leu Glu Ala Asn Met Phe
     2210                2215              2220

Ser Val Ile Ile Pro Met Cys Leu Val Leu Leu Leu Ala Leu
     2225                2230              2235

Ile Leu Pro Leu Leu Phe Tyr Leu Arg Lys Arg Asn Lys Thr Gly
     2240                2245              2250

Lys His Asp Val Gln Val Leu Thr Ala Lys Pro Arg Asn Gly Leu
     2255                2260              2265

Ala Gly Asp Thr Glu Thr Phe Arg Lys Val Glu Pro Gly Gln Ala
     2270                2275              2280

Ile Pro Leu Thr Ala Val Pro Gly Gln Gly Pro Pro Gly Gly
     2285                2290              2295

Gln Pro Asp Pro Glu Leu Leu Gln Phe Cys Arg Thr Pro Asn Pro
     2300                2305              2310

Ala Leu Lys Asn Gly Gln Tyr Trp Val
     2315                2320

<210> SEQ ID NO 20
<211> LENGTH: 7011
<212> TYPE: DNA
<213> ORGANISM: Homo sapiens

<400> SEQUENCE: 20

| | |
|---|---|
| atgcagtccg gccgcggccc cccacttcca gcccccggcc tggccttggc tttgaccctg | 60 |
| actatgttgg ccagacttgc atccgcggct tccttcttcg gtgagaacca cctggaggtg | 120 |
| cctgtggcca cggctctgac cgacatagac ctgcagctgc agttctccac gtcccagccc | 180 |

```
gaagccctcc ttctcctggc agcaggccca gctgaccacc tcctgctgca gctctactct    240
ggacgcctgc aggtcagact tgttctgggc caggaggagc tgaggctgca gactccagca    300
gagacgctgc tgagtgactc catccccac actgtggtgc tgactgtcgt agagggctgg     360
gccacgttgt cagtcgatgg gtttctgaac gcctcctcag cagtcccagg agcccccta    420 gaggtcccct atgggctctt tgttggggc actgggaccc ttggcctgcc ctacctgagg     480
ggaaccagcc gacccctgag gggttgcctc catgcagcca ccctcaatgg ccgcagcctc    540
ctccggcctc tgaccccga tgtgcatgag ggctgtgctg aagagttttc tgccagtgat     600
gatgtgcccc tgggcttctc tgggccccac tctctggctg ccttccctgc ctggggcact    660
caggacgaag gaaccctaga gtttacactc accacacaga gccggcaggc acccttggcc    720
ttccaggcag gggccggcg tggggacttc atctatgtgg acatatttga gggccacctg     780
cgggccgtgg tggagaaggg ccagggtacc gtattgctcc acaacagtgt gcctgtggcc    840
gatgggcagc cccatgaggt cagtgtccac atcaatgctc accggctgga aatctccgtg    900
gaccagtacc ctacgcatac ttcgaaccga ggagtcctca gctacctgga gccacggggc    960
agtctccttc tcgggggct ggatgcagag gcctctcgtc acctccagga acaccgcctg    1020
ggcctgacac cagaggccac caatgcctcc ctgctgggct gcatggaaga cctcagtgtc   1080
aatggccaga gcgggggct gcgggaagct ttgctgacgc gcaacatggc agccggctgc   1140
aggctggagg aggaggagta tgaggacgat gcctatggac attatgaagc tttctccacc   1200
ctggcccctg aggcttggcc agccatggag ctgcctgagc catgcgtgcc tgagccaggg   1260
ctgcctcctg tctttgccaa tttcacccag ctgctgacta tcagcccact ggtggtggcc   1320
gaggggggca cagcctggct tgagtggagg catgtgcagc ccacgctgga cctgatggag   1380
gctgagctgc gcaaatccca ggtgctgttc agcgtgaccc gaggggcacg ccatggcgag   1440
ctcgagctgg acatcccggg agcccaggca cgaaaaatgt tcaccctcct ggacgtggtg   1500
aaccgcaagg cccgcttcat ccacgatggc tctgaggaca cctccgacca gctggtgctg   1560
gaggtgtcgg tgacggctcg ggtgccatg ccctcatgcc ttcggagggg ccaaacatac   1620
ctcctgccca tccaggtcaa ccctgtcaat gaccccacccc acatcatctt cccacatggc   1680
agcctcatgg tgatcctgga acacacgcag aagccgctgg ggcctgaggt tttccaggcc   1740
tatgacccgg actctgcctg tgagggcctc accttccagg tccttggcac ctcctctggc   1800
ctccccgtgg agcgccgaga ccagcctggg gagccggcga ccgagttctc ctgccgggag   1860
ttggaggccg gcagcctagt ctatgtccac cgcggtggtc ctgcacagga cttgacgttc   1920
cgggtcagcg atggactgca ggccagcccc ccggccacgc tgaaggtggt ggccatccgg   1980
ccggccatac agatccaccg cagcacaggg ttgcgactgg cccaaggctc tgccatgccc   2040
atcttgcccg ccaacctgtc ggtggagacc aatgccgtgg ggcaggatgt gagcgtgctg   2100
ttccgcgtca ctgggccct gcagtttggg gagctgcaga gcaggggc aggtggggtg   2160 gagggtgctg agtggtgggc cacacaggcg ttccaccagc gggatgtgga gcagggccgc   2220
gtgaggtacc tgagcactga cccacagcac cacgcttacg acaccgtgga gaacctggcc   2280
ctggaggtgc aggtgggcca ggagatcctg agcaatctgt ccttcccagt gaccatccag   2340
agagccactg tgtggatgct gcggctggag ccactgcaca ctcagaacac ccagcaggag   2400
accctcacca cagcccacct ggaggccacc ctggaggagg caggcccaag ccccccaacc   2460
ttccattatg aggtggttca ggctcccagg aaaggcaacc ttcaactaca gggcacaagg   2520
```

```
ctgtcagatg gccagggctt cacccaggat gacatacagg ctggccgggt gacctatggg    2580
gccacagcac gtgcctcaga ggcagtcgag gacaccttcc gtttccgtgt cacagctcca    2640
ccatatttct ccccactcta taccttcccc atccacattg gtggtgaccc agatgcgcct    2700
gtcctcacca atgtcctcct cgtggtgcct gagggtggtg agggtgtcct ctctgctgac    2760
cacctctttg tcaagagtct caacagtgcc agctacctct atgaggtcat ggagcggccc    2820
cgccatggga ggttggcttg gcgtgggaca caggacaaga ccactatggt gacatccttc    2880
accaatgaag acctgttgcg tggccggctg gtctaccagc atgatgactc cgagaccaca    2940
gaagatgata tcccatttgt tgctacccgc cagggcgaga gcagtggtga catggcctgg    3000
gaggaggtac ggggtgtctt ccgagtggcc atccagcccg tgaatgacca cgccctgtg    3060
cagaccatca gccggatctt ccatgtggcc cggggtgggc ggcggctgct gactacagac    3120
gacgtggcct tcagcgatgc tgactcgggc tttgctgacg cccagctggt gcttacccgc    3180
aaggacctcc tctttggcag tatcgtggcc gtagatgagc ccacgcgcc catctaccgc    3240
ttcacccagg aggacctcag gaagaggcga gtactgttcg tgcactcagg ggctgaccgt    3300
ggctggatcc agctgcaggt gtccgacggg caacaccagg ccactgcgct gctggaggtg    3360
caggcctcgg aaccctacct ccgtgtgcc aacggctcca gccttgtggt ccctcaaggg    3420
ggccagggca ccatcgacac ggccgtgctc cacctggaca ccaacctcga catccgcagt    3480
ggggatgagg tccactacca cgtcacagct ggccctcgct ggggacagct agtccgggct    3540
ggtcagccag ccacagcctt ctcccagcag gacctgctgg atggggccgt tctctatagc    3600
cacaatggca gcctcagccc ccgcgacacc atggccttct ccgtggaagc agggccagtg    3660
cacacggatg ccaccctaca agtgaccatt gccctagagg gcccactggc cccactgaag    3720
ctggtccggc acaagaagat ctacgtcttc caggagagg cagctgagat cagaagggac    3780
cagctggagg cagcccagga ggcagtgcca cctgcagaca tcgtattctc agtgaagagc    3840
ccaccgagtg ccggctacct ggtgatggtg tcgcgtggcg ccttggcaga tgagccaccc    3900
agcctggacc ctgtgcagag cttctcccag gaggcagtgg acacaggcag gtcctgtac    3960
ctgcactccc gccctgaggc ctggagcgat gccttctcgc tggatgtggc ctcaggcctg    4020
ggtgctcccc tcgagggcgt ccttgtggag ctggaggtgc tgcccgctgc catcccacta    4080
gaggcgcaaa acttcagcgt ccctgagggt ggcagcctca ccctggcccc tccactgctc    4140
cgtgtctccg ggccctactt ccccactctc ctgggcctca gctgcaggt gctggagcca    4200
ccccagcatg gagccctgca gaaggaggac ggacctcaag ccaggaccct cagcgccttc    4260
tcctggagaa tggtggaaga gcagctgatc cgctacgtgc atgacgggag cgagacactg    4320
acagacagtt ttgtcctgat ggctaatgcc tccgagatgg atcgccagag ccatcctgtg    4380
gccttcactg tcactgtcct gcctgtcaat gaccaacccc ccatcctcac tacaaacaca    4440
ggcctgcaga tgtgggaggg ggccactgcg cccatccctg cggaggctct gaggagcacg    4500
gacggcgact ctgggtctga ggatctggtc taccaccatcg agcagcccag caacgggcgg    4560
gtagtgctgc ggggggcgcc gggcactgag gtgcgcagct tcacgcaggc ccagctggac    4620
ggcgggctcg tgctgttctc acacagagga accctggatg gaggcttccg cttccgcctc    4680
tctgacggcg agcacacttc ccccggacac ttcttccgag tgacggccca gaagcaagtg    4740
ctcctctcgc tgaagggcag ccagacactg actgtctgcc cagggtccgt ccagccactc    4800
agcagtcaga ccctcagggc cagctccagc gcaggcactg accccagct cctgctctac    4860
cgtgtggtgc ggggcccca gctaggccgg ctgttccacg cccagcagga cagcacaggg    4920
```

```
gaggccctgg tgaacttcac tcaggcagag gtctacgctg ggaatattct gtatgagcat    4980
gagatgcccc ccgagccctt ttgggaggcc catgataccc tagagctcca gctgtcctcg    5040
ccgcctgccc gggacgtggc cgccaccctt gctgtggctg tgtcttttga ggctgcctgt    5100
ccccagcgcc ccagccacct ctggaagaac aaaggtctct gggtcccccga gggccagcgg    5160 gccaggatca ccgtggctgc tctggatgcc tccaatctct tggccagcgt ccatcaccc    5220 cagcgctcag agcatgatgt gctcttccag gtcacacagt tccccagccg gggccagctg    5280
ttggtgtccg aggagcccct ccatgctggg cagccccact tcctgcagtc ccagctggct    5340
gcagggcagc tagtgtatgc ccacggcggt gggggcaccc agcaggatgg cttccacttt    5400
cgtgcccacc tccaggggcc agcaggggcc tccgtggctg accccaaac ctcagaggcc    5460 tttgccatca cggtgaggga tgtaaatgag cggccccctc agccacaggc ctctgtccca    5520
ctccggctca cccgaggctc tcgtgccccc atctcccggg cccagctgag tgtggtggac    5580
ccagactcag ctcctgggga gattgagtac gaggtccagc gggcacccca caacggcttc    5640
ctcagcctgg tgggtggtgg cctggggccc gtgacccgct tcacgcaagc cgatgtggat    5700
tcagggcggc tggccttcgt ggccaacggg agcagcgtgg caggcatctt ccagctgagc    5760
atgtctgatg gggccagccc accctgcccc atgtccctgg ctgtggacat cctaccatcc    5820
gccatcgagt gcagctgcg ggcaccctg gaggtgcccc aagctttggg gcgctcctca    5880
ctgagccagc agcagctccg ggtggtttca gatcgggagg agccagaggc agcataccgc    5940
ctcatccagg gacccagta tgggcatctc ctggtgggcg gcggccccac ctcggccttc    6000
agccaattcc agatagacca gggcgaggtg gtctttgcct tcaccaactt ctcctcctct    6060
catgaccact tcagagtcct ggcactggct aggggtgtca atgcatcagc cgtagtgaac    6120
gtcactgtga gggctctgct gcatgtgtgg gcaggtgggc catggcccca gggtgccacc    6180
ctgcgcctgg accccaccgt cctagatgct ggcgagctgg ccaaccgcac aggcagtgtg    6240
ccgcgcttcc gcctcctgga gggaccccgg catggccgcg tggtccgcgt gccccgagcc    6300
aggacggagc ccgggggcag ccagctggtg gagcagttca ctcagcagga ccttgaggac    6360
gggaggctgg ggctggaggt gggcaggcca gaggggaggg cccccggccc cgcaggtgac    6420
agtctcactc tggagctgtg ggcacagggc gtcccgcctg ctgtggcctc cctggacttt    6480
gccactgagc cttacaatgc tgcccggccc tacagcgtgg ccctgctcag tgtccccgag    6540
gccgcccgga cggaagcagg gaagccagag agcagcaccc ccacaggcga gccaggcccc    6600
atggcatcca gccctgagcc cgctgtgcc aaggagggct tcctgagctt ccttgaggcc    6660
aacatgttca gcgtcatcat ccccatgtgc ctggtacttc tgctcctggc gctcatcctg    6720
cccctgctct tctacctccg aaaacgcaac aagacgggca agcatgacgt ccaggtcctg    6780
actgccaagc cccgcaacgg cctggctggt gacaccgaga cctttcgcaa ggtggagcca    6840
ggccaggcca tcccgctcac agctgtgcct ggccagggggc cccctccagg aggccagcct    6900
gacccagagc tgctgcagtt ctgccggaca cccaaccctg cccttaagaa tggccagtac    6960
tgggtgtgag gcctggcctg ggcccagatg ctgatcgggc cagggacagg c            7011
```

<210> SEQ ID NO 21
<211> LENGTH: 261
<212> TYPE: PRT
<213> ORGANISM: Homo sapiens

<400> SEQUENCE: 21

```
Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 22
<211> LENGTH: 237
<212> TYPE: PRT
<213> ORGANISM: Homo sapiens

<400> SEQUENCE: 22

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
                20                  25                  30

Pro Gln Trp Val Leu Thr Ala Ala His Cys Ile Arg Asn Lys Ser Val
            35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
                100                 105                 110
```

```
Lys Val Met Asp Leu Pro Thr Gln Glu Pro Ala Leu Gly Thr Thr Cys
            115                 120                 125
Tyr Ala Ser Gly Trp Gly Ser Ile Glu Pro Glu Phe Leu Thr Pro
    130                 135                 140
Lys Lys Leu Gln Cys Val Asp Leu His Val Ile Ser Asn Asp Val Cys
145                 150                 155                 160
Ala Gln Val His Pro Gln Lys Val Thr Lys Phe Met Leu Cys Ala Gly
                165                 170                 175
Arg Trp Thr Gly Gly Lys Ser Thr Cys Ser Gly Asp Ser Gly Gly Pro
            180                 185                 190
Leu Val Cys Tyr Gly Val Leu Gln Gly Ile Thr Ser Trp Gly Ser Glu
            195                 200                 205
Pro Cys Ala Leu Pro Glu Arg Pro Ser Leu Tyr Thr Lys Val Val His
            210                 215                 220
Tyr Arg Lys Trp Ile Lys Asp Thr Ile Val Ala Asn Pro
225                 230                 235

<210> SEQ ID NO 23
<211> LENGTH: 237
<212> TYPE: PRT
<213> ORGANISM: Homo sapiens

<400> SEQUENCE: 23

Ile Val Gly Gly Trp Glu Cys Glu Lys His Ser Gln Pro Trp Gln Val
1               5                   10                  15
Leu Val Ala Ser Arg Gly Arg Ala Val Cys Gly Gly Val Leu Val His
            20                  25                  30
Pro Gln Trp Val Leu Thr Ala Ala His Cys Ile Arg Asn Lys Ser Val
            35                  40                  45
Ile Leu Leu Gly Arg His Ser Leu Phe His Pro Glu Asp Thr Gly Gln
50                  55                  60
Val Phe Gln Val Ser His Ser Phe Pro His Pro Leu Tyr Asp Met Ser
65                  70                  75                  80
Leu Leu Lys Asn Arg Phe Leu Arg Pro Gly Asp Asp Ser Ser His Asp
                85                  90                  95
Leu Met Leu Leu Arg Leu Ser Glu Pro Ala Glu Leu Thr Asp Ala Val
            100                 105                 110
Lys Val Met Asp Leu Pro Thr Gln Glu Pro Ala Leu Gly Thr Thr Cys
            115                 120                 125
Tyr Ala Ser Gly Trp Gly Ser Ile Glu Pro Glu Phe Leu Thr Pro
    130                 135                 140
Lys Lys Leu Gln Cys Val Asp Leu His Val Ile Ser Asn Asp Val Cys
145                 150                 155                 160
Ala Gln Val His Pro Gln Lys Val Thr Lys Phe Met Leu Cys Ala Gly
                165                 170                 175
Arg Trp Thr Gly Gly Lys Ser Thr Cys Ser Gly Asp Ser Gly Gly Pro
            180                 185                 190
Leu Val Cys Asn Gly Val Leu Gln Gly Ile Thr Ser Trp Gly Ser Glu
            195                 200                 205
Pro Cys Ala Leu Pro Glu Arg Pro Ser Leu Tyr Thr Lys Val Val His
            210                 215                 220
Tyr Arg Lys Trp Ile Lys Asp Thr Ile Val Ala Asn Pro
225                 230                 235
```

```
<210> SEQ ID NO 24
<211> LENGTH: 5873
<212> TYPE: DNA
<213> ORGANISM: Homo sapiens

<400> SEQUENCE: 24
ggtgtcttag gcacactggt cttggagtgc aaaggatcta ggcacgtgag gctttgtatg     60
aagaatcggg gatcgtaccc accccctgtt tctgtttcat cctgggcatg tctcctctgc    120
ctttgtcccc tagatgaagt ctccatgagc tacaagggcc tggtgcatcc agggtgatct    180
agtaattgca gaacagcaag tgctagctct ccctcccctt ccacagctct gggtgtggga    240
gggggttgtc cagcctccag cagcatgggg agggccttgg tcagcctctg ggtgccagca    300
gggcaggggc ggagtcctgg ggaatgaagg ttttataggg ctcctggggg aggctcccca    360
gccccaagct taccacctgc acccggagag ctgtgtcacc atgtgggtcc cggttgtctt    420
cctcaccctg tccgtgacgt ggattggtga gaggggccat ggttgggggg atgcaggaga    480
gggagccagc cctgactgtc aagctgaggc tctttccccc caacccagc accccagccc     540 agacagggag ctgggctctt ttctgtctct cccagcccca cttcaagccc ataccccag     600 tccctccat attgcaacag tcctcactcc cacaccaggt ccccgctccc tcccacttac     660
cccagaactt tcttcccatt tgcccagcca gctccctgct cccagctgct ttactaaagg    720
ggaagttcct gggcatctcc gtgtttctct ttgtggggct caaaacctcc aaggacctct    780
ctcaatgcca ttggttcctt ggaccgtatc actggtccat ctcctgagcc cctcaatcct    840
atcacagtct actgactttt cccattcagc tgtgagtgtc caaccctatc ccagagacct    900
tgatgcttgg cctcccaatc ttgccctagg atacccagat gccaaccaga cacctccttc    960
tttcctagcc aggctatctg gcctgagaca acaaatgggt ccctcagtct ggcaatggga   1020
ctctgagaac tcctcattcc ctgactctta gccccagact cttcattcag tggcccacat   1080
tttccttagg aaaaacatga gcatcccag ccacaactgc cagctctctg agtccccaaa    1140
tctgcatcct tttcaaaacc taaaaacaaa agaaaaaca aataaaacaa aaccaactca    1200
gaccagaact gttttctcaa cctgggactt cctaaacttt ccaaaacctt cctcttccag   1260
caactgaacc tcgccataag gcacttatcc ctggttccta gcacccctta tcccctcaga   1320
atccacaact tgtaccaagt ttcccttctc ccagtccaag accccaaatc accacaaagg   1380
acccaatccc cagactcaag atatggtctg ggcgctgtct tgtgtctcct accctgatcc   1440
ctgggttcaa ctctgctccc agagcatgaa gcctctccac cagcaccagc caccaacctg   1500
caaacctagg gaagattgac agaattccca gcctttccca gctcccctg cccatgtccc     1560 aggactccca gccttggttc tctgcccccg tgtcttttca aacccacatc ctaaatccat   1620
ctcctatccg agtcccccag ttcccctgt caacctgat tccctgatc tagcaccccc      1680 tctgcaggcg ctgcgcccct catcctgtct cggattgtgg gaggctggga gtgcgagaag   1740
cattcccaac cctggcaggt gcttgtggcc tctcgtggca gggcagtctg cggcggtgtt   1800
ctggtgcacc cccagtgggt cctcacagct gcccactgca tcaggaagtg agtagggcc    1860 tggggtctgg ggagcaggtg tctgtgtccc agaggaataa cagctgggca ttttccccag   1920
gataacctct aaggccagcc ttgggactgg gggagagagg gaaagttctg gttcaggtca   1980
catggggagg cagggttggg gctggaccac cctccccatg gctgcctggg tctccatctg   2040
tgtccctcta tgtctctttg tgtcgctttc attatgtctc ttggtaactg gcttcggttg   2100
tgtctctccg tgtgactatt tgttctctc tctccctctc ttctctgtct tcagtctcca    2160
```

```
tatctccccc tctctctgtc cttctctggt ccctctctag ccagtgtgtc tcaccctgta    2220
tctctctgcc aggctctgtc tctcggtctc tgtctcacct gtgccttctc cctactgaac    2280
acacgcacgg gatgggcctg ggggaccctg agaaaaggaa gggctttggc tgggcgcggt    2340
ggctcacacc tgtaatccca gcactttggg aggccaaggc aggtagatca cctgaggtca    2400
ggagttcgag accagcctgg ccaactggtg aaaccccatc tctactaaaa atacaaaaaa    2460
ttagccaggc gtggtggcgc atgcctgtag tcccagctac tcaggagctg agggaggaga    2520
attgcattga acctggaggt tgaggttgca gtgagccgag accgtgccac tgcactccag    2580
cctgggtgac agagtgagac tccgcctcaa aaaaaaaaaa aaaaaaaaaa aaaaaaagaa    2640
aaagaaaaga aaagaaaagg aagtgtttta tccctgatgt gtgtgggtat gagggtatga    2700
gagggcccct ctcactccat tccttctcca ggacatccct ccactcttgg gagacacaga    2760
gaagggctgg ttccagctgg agctgggagg ggcaattgag ggaggaggaa ggagaagggg    2820
gaaggaaaac agggtatggg ggaaaggacc ctggggagcg aagtggagga tacaaccttg    2880
ggcctgcagg caggctacct acccacttgg aaacccacgc caaagccgca tctacagctg    2940
agccactctg aggcctcccc tccccggcgg tccccactca gctccaaagt ctctctccct    3000
tttctctccc acactttatc atcccccgga ttcctctcta cttggttctc attcttcctt    3060
tgacttcctg cttccctttc tcattcatct gtttctcact ttctgcctgg ttttgttctt    3120
ctctctctct ttctctggcc catgtctgtt tctctatgtt tctgtctttt ctttctcatc    3180
ctgtgtattt tcggctcacc ttgtttgtca ctgttctccc ctctgcectt tcattctctc    3240 tgccctttta ccctcttcct tttcccttgg ttctctcagt tctgtatctg cccttcaccc    3300
tctcacactg ctgtttccca actcgttgtc tgtattttgg cctgaactgt gtcttcccaa    3360
ccctgtgttt tctcactgtt tcttttttctc ttttggagcc tcctccttgc tcctctgtcc    3420
cttctctctt tccttatcat cctcgctcct cattcctgcg tctgcttcct ccccagcaaa    3480
agcgtgatct tgctgggtcg gcacagcctg tttcatcctg aagacacagg ccaggtattt    3540
caggtcagcc acagcttccc acacccgctc tacgatatga gcctcctgaa gaatcgattc    3600
ctcaggccag gtgatgactc cagccacgac ctcatgctgc tccgcctgtc agagcctgcc    3660
gagctcacgg atgctgtgaa ggtcatggac ctgcccaccc aggagccagc actggggacc    3720
acctgctacg cctcaggctg gggcagcatt gaaccagagg agtgtacgcc tgggccagat    3780
ggtgcagccg ggagcccaga tgcctgggtc tgagggagga ggggacagga ctcctgggtc    3840
tgagggagga gggccaagga accaggtggg gtccagccca caacagtgtt tttgcctggc    3900
ccgtagtctt gaccccaaag aaacttcagt gtgtggacct ccatgttatt tccaatgacg    3960
tgtgtgcgca agttcaccct cagaaggtga ccaagttcat gctgtgtgct ggacgctgga    4020 caggggcaa aagcacctgc tcggtgagtc atccctactc ccaagatctt gagggaaagg    4080
tgagtgggac cttaattctg ggctggggtc tagaagccaa caaggcgtct gcctcccctg    4140
ctccccagct gtagccatgc cacctccccg tgtctcatct cattccctcc ttccctcttc    4200
tttgactccc tcaaggcaat aggttattct tacagcacaa ctcatctgtt cctgcgttca    4260
gcacacggtt actaggcacc tgctatgcac ccagcactgc cctagagcct gggacatagc    4320
agtgaacaga cagagagcag cccctccctt ctgtagcccc caagccagtg aggggcacag    4380
gcaggaacag ggaccacaac acagaaaagc tggagggtgt caggaggtga tcaggctctc    4440
ggggagggag aaggggtggg gagtgtgact gggaggagac atcctgcaga aggtgggagt    4500
gagcaaacac ctgcgcaggg gaggggaggg cctgcggcac ctgggggagc agagggaaca    4560
```

```
gcatctggcc aggcctggga ggaggggcct agagggcgtc aggagcagag aggaggttgc   4620
ctggctggag tgaaggatcg gggcagggtg cgagagggaa caaaggaccc ctcctgcagg   4680
gcctcacctg ggccacagga ggacactgct tttcctctga ggagtcagga actgtggatg   4740
gtgctggaca gaagcaggac agggcctggc tcaggtgtcc agaggctgcg ctggcctcct   4800
atgggatcag actgcaggga gggagggcag cagggatgtg gagggagtga tgatggggct   4860
gacctggggg tggctccagg cattgtcccc acctgggccc ttacccagcc tccctcacag   4920
gctcctggcc ctcagtctct cccctccact ccattctcca cctacccaca gtgggtcatt   4980
ctgatcaccg aactgaccat gccagccctg ccgatggtcc tccatggctc cctagtgccc   5040
tggagaggag gtgtctagtc agagagtagt cctggaaggt ggcctctgtg aggagccacg   5100
gggacagcat cctgcagatg gtcctggccc ttgtcccacc gacctgtcta caaggactgt   5160
cctcgtggac cctcccctct gcacaggagc tggaccctga agtcccttcc taccggccag   5220
gactggagcc cctaccoctc tgttggaatc cctgcccacc ttcttctgga agtcggctct   5280
ggagacattt ctctcttctt ccaaagctgg gaactgctat ctgttatctg cctgtccagg   5340
tctgaaagat aggattgccc aggcagaaac tgggactgac ctatctcact ctctccctgc   5400
ttttacccctt agggtgattc tgggggccca cttgtctgta atggtgtgct tcaaggtatc   5460
acgtcatggg gcagtgaacc atgtgccctg cccgaaaggc cttccctgta caccaaggtg   5520
gtgcattacc ggaagtggat caaggacacc atcgtggcca cccctgagc accctatca    5580
agtccctatt gtagtaaact tggaaccttg gaaatgacca ggccaagact caagcctccc   5640
cagttctact gacctttgtc cttaggtgtg aggtccaggg ttgctaggaa agaaatcag    5700
cagacacagg tgtagaccag agtgtttctt aaatggtgta attttgtcct ctctgtgtcc   5760
tggggaatac tggccatgcc tggagacata tcactcaatt tctctgagga cacagttagg   5820
atggggtgtc tgtgttattt gtgggataca gagatgaaag aggggtggga tcc          5873
```

<210> SEQ ID NO 25
<211> LENGTH: 238
<212> TYPE: PRT
<213> ORGANISM: Homo sapiens

<400> SEQUENCE: 25

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140
```

```
Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Trp Val Ile Leu Ile Thr Glu Leu Thr Met Pro Ala Leu Pro
210                 215                 220

Met Val Leu His Gly Ser Leu Val Pro Trp Arg Gly Gly Val
225                 230                 235

<210> SEQ ID NO 26
<211> LENGTH: 1906
<212> TYPE: DNA
<213> ORGANISM: Homo sapiens

<400> SEQUENCE: 26
agccccaagc ttaccacctg cacccggaga gctgtgtcac catgtgggtc ccggttgtct    60
tcctcaccct gtccgtgacg tggattggtg ctgcacccct catcctgtct cggattgtgg   120
gaggctggga gtgcgagaag cattcccaac cctggcaggt gcttgtggcc tctcgtggca   180 ggcagtctg cggcggtgtt ctggtgcacc cccagtgggt cctcacagct gcccactgca   240
tcaggaacaa aagcgtgatc ttgctgggtc ggcacagctt gtttcatcct gaagacacag   300
gccaggtatt tcaggtcagc cacagcttcc cacacccgct ctacgatatg agcctcctga   360
agaatcgatt cctcaggcca ggtgatgact ccagccacga cctcatgctg ctccgcctgt   420
cagagcctgc cgagctcacg gatgctgtga aggtcatgga cctgcccacc aggagccag   480 cactggggac cacctgctac gcctcaggct ggggcagcat tgaaccagag gagttcttga   540
ccccaaagaa acttcagtgt gtggacctcc atgttatttc caatgacgtg tgtgcgcaag   600
ttcaccctca gaaggtgacc aagttcatgc tgtgtgctgg acgctggaca ggggcaaaa   660 gcacctgctc gtgggtcatt ctgatcaccg aactgaccat gccagccctg ccgatggtcc   720
tccatggctc cctagtgccc tggagaggag gtgtctagtc agagagtagt cctggaaggt   780
ggcctctgtg aggagccacg gggacagcat cctgcagatg gtcctggccc ttgtcccacc   840
gacctgtcta caaggactgt cctcgtggac cctcccctct gcacaggagc tggaccctga   900
agtcccttcc ccaccggcca ggactggagc ccctacccct ctgttggaat ccctgcccac   960
cttcttctgg aagtcggctc tggagacatt tctctcttct tccaaagctg gaactgcta   1020 tctgttatct gcctgtccag gtctgaaaga taggattgcc caggcagaaa ctgggactga  1080
cctatctcac tctctccctg cttttaccct tagggtgatt ctgggggccc acttgtctgt  1140
aatggtgtgc ttcaaggtat cacgtcatgg ggcagtgaac catgtgccct gcccgaaagg  1200
ccttccctgt acaccaaggt ggtgcattac cggaagtgga tcaaggacac catcgtggcc  1260 aaccctgag cacccctatc aaccccctat tgtagtaaac ttggaacctt ggaaatgacc  1320
aggccaagac tcaagcctcc ccagttctac tgacctttgt ccttaggtgt gaggtccagg  1380
gttgctagga aagaaatca gcagacacag gtgtagacca gagtgtttct taaatggtgt  1440
aattttgtcc tctctgtgtc ctggggaata ctgccatgc ctggagacat atcactcaat  1500
ttctctgagg acacagatag gatggggtgt ctgtgttatt tgtggggtac agagatgaaa  1560
```

```
gaggggtggg atccacactg agagagtgga gagtgacatg tgctggacac tgtccatgaa    1620
gcactgagca gaagctggag gcacaacgca ccagacactc acagcaagga tggagctgaa    1680
aacataaccc actctgtcct ggaggcactg ggaagcctag agaaggctgt gagccaagga    1740
gggagggtct tcctttggca tgggatgggg atgaagtaag gagagggact ggaccccctg    1800
gaagctgatt cactatgggg ggaggtgtat tgaagtcctc cagacaaccc tcagatttga    1860
tgatttccta gtagaactca cagaaataaa gagctgttat actgtg                  1906
```

<210> SEQ ID NO 27
<211> LENGTH: 69
<212> TYPE: PRT
<213> ORGANISM: Homo sapiens

<400> SEQUENCE: 27

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65
```

<210> SEQ ID NO 28
<211> LENGTH: 554
<212> TYPE: DNA
<213> ORGANISM: Homo sapiens

<400> SEQUENCE: 28

```
agccccaagc ttaccacctg caccccggaga gctgtgtcac catgtgggtc ccggttgtct    60
tcctcaccct tccgtgacgt ggattggtgc tgcacccctc atcctgtctc ggattgtggg   120
aggctgggag tgcgagaagc attcccaacc ctggcaggtg cttgtggcct ctcgtggcag   180
ggcagtctgc ggcggtgttc tggtgcaccc ccagtgggtc ctcacagctg cccactgcat   240
caggaagtga gtaggggcct ggggtctggg gagcaggtgt ctgtgtccca gaggaataac   300
agctgggcat tttccccagg ataacctcta aggccagcct tgggactggg ggagagaggg   360
aaagttctgg ttcaggtcac atggggaggc agggttgggg ctggaccacc ctccccatgg   420
ctgcctgggt ctccatctgt gttcctctat gtctctttgt gtcgctttca ttatgtctct   480
tggtaactgg cttcggttgt gtctctccgt gtgactattt tgttctctct ctccctctct   540
tctctgtctt cagt                                                     554
```

<210> SEQ ID NO 29
<211> LENGTH: 220
<212> TYPE: PRT
<213> ORGANISM: Homo sapiens

<400> SEQUENCE: 29

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45
```

Val Cys Gly Gly Val Leu Val His Pro Gln Trp Val Leu Thr Ala Ala
 50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
                100                 105                 110

Pro Gly Asp Asp Ser Ser Ile Glu Pro Glu Glu Phe Leu Thr Pro Lys
            115                 120                 125

Lys Leu Gln Cys Val Asp Leu His Val Ile Ser Asn Asp Val Cys Ala
        130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
                180                 185                 190

Cys Ala Leu Pro Glu Arg Pro Ser Leu Tyr Thr Lys Val Val His Tyr
                195                 200                 205

Arg Lys Trp Ile Lys Asp Thr Ile Val Ala Asn Pro
210                 215                 220

<210> SEQ ID NO 30
<211> LENGTH: 1341
<212> TYPE: DNA
<213> ORGANISM: Homo sapiens

<400> SEQUENCE: 30
agccccaagc ttaccacctg cacccggaga gctgtgtcac catgtgggtc ccggttgtct     60
tcctcaccct gtccgtgacg tggattggtg ctgcacccct catcctgtct cggattgtgg    120
gaggctggga gtgcgagaag cattcccaac cctggcaggt gcttgtggcc tctcgtggca    180
gggcagtctg cggcggtgtt ctggtgcacc ccagtgggt cctcacagct gcccactgca    240
tcaggaacaa aagcgtgatc ttgctgggtc ggcacagcct gtttcatcct gaagacacag    300
gccaggtatt tcaggtcagc cacagcttcc cacacccgct ctacgatatg agcctcctga    360
agaatcgatt cctcaggcca ggtgatgact ccagcattga accagaggag ttcttgaccc    420
caaagaaact tcagtgtgtg gacctccatg ttatttccaa tgacgtgtgt gcgcaagttc    480
accctcagaa ggtgaccaag ttcatgctgt gtgctggacg ctggacaggg ggcaaaagca    540
cctgctcggg tgattctggg gcccacttg tctgtaatgg tgtgcttcaa ggtatcacgt    600 catgggcag tgaaccatgt gccctgcccg aaaggccttc cctgtacacc aaggtggtgc    660
attaccggaa gtggatcaag gacaccatcg tggccaaccc ctgagcaccc ctatcaaccc    720
cctattgtag taaacttgga accttggaaa tgaccaggcc aagactcaag cctccccagt    780
tctactgacc tttgtcctta ggtgtgaggt ccagggttgc taggaaaaga aatcagcaga    840
cacaggtgta gaccagagtg tttcttaaat ggtgtaattt tgtcctctct gtgtcctggg    900
gaatactggc catgcctgga gacatatcac tcaatttctc tgaggacaca gataggatgg    960
ggtgtctgtg ttatttgtgg ggtacagaga tgaaagaggg gtgggatcca cactgagaga   1020
gtggagagtg acatgctgtg acactgtcc atgaagcact gagcagaagc tggaggcaca   1080
acgcaccaga cactcacagc aaggatggag ctgaaaacat aacccactct gtcctggagg   1140

| | |
|---|---|
| cactgggaag cctagagaag gctgtgagcc aaggagggag ggtcttcctt tggcatggga | 1200 |
| tggggatgaa gtaaggagag ggactggacc ccctggaagc tgattcacta tgggggagg | 1260 |
| tgtattgaag tcctccagac aaccctcaga tttgatgatt tcctagtaga actcacagaa | 1320 |
| ataaagagct gttatactgt g | 1341 |

<210> SEQ ID NO 31
<211> LENGTH: 218
<212> TYPE: PRT
<213> ORGANISM: Homo sapiens

<400> SEQUENCE: 31

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys Pro Gly Asp Asp Ser Ser His Asp Leu Met Leu
65                  70                  75                  80

Leu Arg Leu Ser Glu Pro Ala Glu Leu Thr Asp Ala Val Lys Val Met
                85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
    130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215

<210> SEQ ID NO 32
<211> LENGTH: 1325
<212> TYPE: DNA
<213> ORGANISM: Homo sapiens

<400> SEQUENCE: 32

| | |
|---|---|
| agccccaagc ttaccacctg cacccggaga gctgtgtcac catgtgggtc ccggttgtct | 60 |
| tcctcaccct gtccgtgacg tggattggtg ctgcaccct catcctgtct cggattgtgg | 120 |
| gaggctggga gtgcgagaag cattcccaac cctggcaggt gcttgtggcc tctcgtggca | 180 |
| gggcagtctg cggcggtgtt ctggtgcacc ccagtgggt cctcacagct gcccactgca | 240 |
| tcaggaagcc aggtgatgac tccagccacg acctcatgct gctccgcctg tcagagcctg | 300 |
| ccgagctcac ggatgctgtg aaggtcatgg acctgcccac ccaggagcca gcactgggga | 360 |

```
ccacctgcta cgcctcaggc tgggcagca ttgaaccaga ggagttcttg accccaaaga    420
aacttcagtg tgtggacctc catgttattt ccaatgacgt gtgtgcgcaa gttcaccctc    480
agaaggtgac caagttcatg ctgtgtgctg acgctggac aggggggcaaa agcacctgct    540
cgggtgattc tgggggccca cttgtctgta atggtgtgct tcaaggtatc acgtcatggg    600
gcagtgaacc atgtgccctg cccgaaaggc cttccctgta caccaaggtg gtgcattacc    660
caaggacacc atcgtggcca acccctgagc accccatca accccctatt gtagtaaact    720
tggaaccttg gaaatgacca ggccaagact caagcctccc cagttctact gacctttgtc    780
cttaggtgtg aggtccaggg ttgctaggaa aagaaatcag cagacacagg tgtagaccag    840
agtgtttctt aaatggtgta atttgtcct ctctgtgtcc tggggaatac tggccatgcc    900
tggagacata tcactcaatt tctctgagga cacagatagg atgggtgtc tgtgttattt    960
gtggggtaca gagatgaaag aggggtggga tccacactga gagagtggag agtgacatgt    1020
gctggacact gtccatgaag cactgagcag aagctggagg cacaacgcac cagacactca    1080
cagcaaggat ggagctgaaa acataaccca ctctgtcctg gaggcactgg gaagcctaga    1140
gaaggctgtg agccaaggag ggagggtctt cctttggcat gggatgggga tgaagtaagg    1200
agagggactg gaccccctgg aagctgattc actatggggg gaggtgtatt gaagtcctcc    1260
agacaaccct cagatttgat gatttcctag tagaactcac agaaataaag agctgttata    1320
ctgtg                                                                1325

<210> SEQ ID NO 33
<211> LENGTH: 261
<212> TYPE: PRT
<213> ORGANISM: Homo sapiens

<400> SEQUENCE: 33

Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
```

```
            195                 200                 205
Cys Ser Gly Asp Ser Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 34
<211> LENGTH: 1464
<212> TYPE: DNA
<213> ORGANISM: Homo sapiens

<400> SEQUENCE: 34
```

| | | | | | |
|---|---|---|---|---|---|
| agccccaagc | ttaccacctg | cacccggaga | gctgtgtcac | catgtgggtc | ccggttgtct | 60 |
| tcctcaccct | gtccgtgacg | tggattggtg | ctgcacccct | catcctgtct | cggattgtgg | 120 |
| gaggctggga | gtgcgagaag | cattcccaac | cctggcaggt | gcttgtggcc | tctcgtggca | 180 |
| gggcagtctg | cggcggtgtt | ctggtgcacc | cccagtgggt | cctcacagct | gcccactgca | 240 |
| tcaggaacaa | aagcgtgatc | ttgctgggtc | ggcacagcct | gtttcatcct | gaagacacag | 300 |
| gccaggtatt | tcaggtcagc | cacagcttcc | cacacccgct | ctacgatatg | agcctcctga | 360 |
| agaatcgatt | cctcaggcca | ggtgatgact | ccagccacga | cctcatgctg | ctccgcctgt | 420 |
| cagagcctgc | cgagctcacg | gatgctgtga | aggtcatgga | cctgcccacc | caggagccag | 480 |
| cactggggac | cacctgctac | gcctcaggct | ggggcagcat | tgaaccagag | gagttcttga | 540 |
| ccccaaagaa | acttcagtgt | gtggacctcc | atgttatttc | caatgacgtg | tgtgcgcaag | 600 |
| ttcaccctca | gaaggtgacc | aagttcatgc | tgtgtgctgg | acgctggaca | gggggcaaaa | 660 |
| gcacctgctc | gggtgattct | gggggcccac | ttgtctgtaa | tggtgtgctt | caaggtatca | 720 |
| cgtcatgggg | cagtgaacca | tgtgccctgc | ccgaaaggcc | ttccctgtac | accaaggtgg | 780 |
| tgcattaccg | gaagtggatc | aaggacacca | tcgtggccaa | cccctgagca | ccccctatcaa | 840 |
| cccctattg | tagtaaactt | ggaaccttgg | aaatgaccag | gccaagactc | aagcctcccc | 900 |
| agttctactg | acctttgtcc | ttaggtgtga | ggtccagggt | tgctaggaaa | agaaatcagc | 960 |
| agacacaggt | gtagaccaga | gtgtttctta | aatggtgtaa | ttttgtcctc | tctgtgtcct | 1020 |
| ggggaatact | ggccatgcct | ggagacatat | cactcaattt | ctctgaggac | acagatagga | 1080 |
| tggggtgtct | gtgttatttg | tggggtacag | agatgaaaga | ggggtgggat | ccacactgag | 1140 |
| agagtggaga | gtgacatgtg | ctggacactg | tccatgaagc | actgagcaga | agctggaggc | 1200 |
| acaacgcacc | agacactcac | agcaaggatg | gagctgaaaa | cataacccac | tctgtcctgg | 1260 |
| aggcactggg | aagcctagag | aaggctgtga | gccaaggagg | gagggtcttc | ctttggcatg | 1320 |
| ggatggggat | gaagtaagga | gagggactgg | accccctgga | agctgattca | ctatgggggg | 1380 |
| aggtgtattg | aagtcctcca | gacaacccto | agatttgatg | atttcctagt | agaactcaca | 1440 |
| gaaataaaga | gctgttatac | tgtg | | | | 1464 |

```
<210> SEQ ID NO 35
<211> LENGTH: 261
<212> TYPE: PRT
<213> ORGANISM: Homo sapiens

<400> SEQUENCE: 35
```

```
Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 36
<211> LENGTH: 1495
<212> TYPE: DNA
<213> ORGANISM: Homo sapiens

<400> SEQUENCE: 36
gggggagccc caagcttacc acctgcaccc ggagagctgt gtcaccatgt gggtcccggt      60
tgtcttcctc accctgtccg tgacgtggat tggtgctgca cccctcatcc tgtctcggat     120
tgtgggaggc tgggagtgcg agaagcattc ccaaccctgg caggtgcttg tggcctctcg     180
tggcagggca gtctgcggcg gtgttctggt gcacccccag tgggtcctca gctgcccca     240 ctgcatcagg aacaaaagcg tgatcttgct gggtcggcac agcctgtttc atcctgaaga     300
cacaggccag gtatttcagg tcagccacag cttcccacac ccgctctacg atatgagcct     360
cctgaagaat cgattcctca ggccaggtga tgactccagc cacgacctca tgctgctccg     420
cctgtcagag cctgccgagc tcacggatgc tgtgaaggtc atggacctgc ccacccagga     480
gccagcactg gggaccacct gctacgcctc aggctgggc agcattgaac cagaggagtt      540
cttgacccca aagaaacttc agtgtgtgga cctccatgtt atttccaatg acgtgtgtgc     600
```

-continued

```
gcaagttcac cctcagaagg tgaccaagtt catgctgtgt gctggacgct ggacaggggg      660
caaaagcacc tgctcgggtg attctggggg cccacttgtc tgtaatggtg tgcttcaagg      720
tatcacgtca tggggcagtg aaccatgtgc cctgcccgaa aggccttccc tgtacaccaa      780
ggtggtgcat taccggaagt ggatcaagga caccatcgtg gccaacccct gagcacccct      840
atcaactccc tattgtagta aacttggaac cttggaaatg accaggccaa gactcaggcc      900
tccccagttc tactgacctt tgtccttagg tgtgaggtcc agggttgcta ggaaaagaaa      960
tcagcagaca caggtgtaga ccagagtgtt tcttaaatgg tgtaattttg tcctctctgt     1020
gtcctgggga atactggcca tgcctggaga catatcactc aatttctctg aggacacaga     1080
taggatgggg tgtctgtgtt atttgtgggg tacagagatg aaagaggggt gggatccaca     1140
ctgagagagt ggagagtgac atgtgctgga cactgtccat gaagcactga gcagaagctg     1200
gaggcacaac gcaccagaca ctcacagcaa ggatggagct gaaaacataa cccactctgt     1260
cctggaggca ctgggaagcc tagagaaggc tgtgagccaa ggagggaggg tcttcctttg     1320
gcatgggatg gggatgaagt agggagaggg actggacccc ctggaagctg attcactatg     1380
gggggaggtc tattgaagtc ctccagacaa ccctcagatt tgatgatttc ctagtagaac     1440
tcacagaaat aaagagctgt tatactgcga aaaaaaaaaa aaaaaaaaaa aaaaa          1495
```

<210> SEQ ID NO 37
<211> LENGTH: 218
<212> TYPE: PRT
<213> ORGANISM: Homo sapiens

<400> SEQUENCE: 37

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser Ile Glu Pro Glu Glu Phe Leu Thr Pro Lys
        115                 120                 125

Lys Leu Gln Cys Val Asp Leu His Val Ile Ser Asn Asp Val Cys Ala
    130                 135                 140

Gln Val His Pro Gln Lys Val Thr Lys Phe Met Leu Cys Ala Gly Arg
145                 150                 155                 160

Trp Thr Gly Gly Lys Ser Thr Cys Ser Gly Asp Ser Gly Gly Pro Leu
                165                 170                 175

Val Cys Asn Gly Val Leu Gln Gly Ile Thr Ser Trp Gly Ser Glu Pro
            180                 185                 190

Cys Ala Leu Pro Glu Arg Pro Ser Leu Tyr Thr Lys Val Val His Tyr
        195                 200                 205

Arg Lys Trp Ile Lys Asp Thr Ile Val Ala
    210                 215
```

<210> SEQ ID NO 38
<211> LENGTH: 227
<212> TYPE: PRT
<213> ORGANISM: Homo sapiens

<400> SEQUENCE: 38

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Lys Ser Thr
        195                 200                 205

Cys Ser Val Ser His Pro Tyr Ser Gln Asp Leu Glu Gly Lys Gly Glu
        210                 215                 220

Trp Gly Pro
225
```

<210> SEQ ID NO 39
<211> LENGTH: 104
<212> TYPE: PRT
<213> ORGANISM: Homo sapiens

<400> SEQUENCE: 39

```
Met Trp Val Pro Val Val Phe Leu Thr Leu Ser Val Thr Trp Ile Gly
1               5                   10                  15

Glu Arg Gly His Gly Trp Gly Asp Ala Gly Gly Ala Ser Pro Asp
                20                  25                  30

Cys Gln Ala Glu Ala Leu Ser Pro Pro Thr Gln His Pro Ser Pro Asp
            35                  40                  45

Arg Glu Leu Gly Ser Phe Leu Ser Leu Pro Ala Pro Leu Gln Ala His
        50                  55                  60

Thr Pro Ser Pro Ser Ile Leu Gln Gln Ser Ser Leu Pro His Gln Val
65                  70                  75                  80

Pro Ala Pro Ser His Leu Pro Gln Asn Phe Leu Pro Ile Ala Gln Pro
```

```
                    85                  90                  95
Ala Pro Cys Ser Gln Leu Leu Tyr
                100

<210> SEQ ID NO 40
<211> LENGTH: 261
<212> TYPE: PRT
<213> ORGANISM: Homo sapiens

<400> SEQUENCE: 40

Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 41
<211> LENGTH: 1778
<212> TYPE: DNA
<213> ORGANISM: Homo sapiens

<400> SEQUENCE: 41
aagtttccct tctcccagtc caagacccca aatcaccaca aaggacccaa tccccagact      60
caagatatgg tctgggcgct gtcttgtgtc tcctaccctg atccctgggt tcaactctgc    120
tcccagagca tgaagcctct ccaccagcac cagccaccaa cctgcaaacc tagggaagat    180
tgacagaatt cccagccttt cccagctccc cctgcccatg tcccaggact cccagccttg    240
```

```
gttctctgcc cccgtgtctt ttcaaaccca catcctaaat ccatctccta tccgagtccc    300
ccagttcctc ctgtcaaccc tgattcccct gatctagcac cccctctgca ggtgctgcac    360
ccctcatcct gtctcggatt gtgggaggct gggagtgcga gaagcattcc caaccctggc    420
aggtgcttgt agcctctcgt ggcagggcag tctgcggcgg tgttctggtg caccccccagt  480
gggtcctcac agctacccac tgcatcagga acaaaagcgt gatcttgctg gtcggcaca    540
gcctgtttca tcctgaagac acaggccagg tatttcaggt cagccacagc ttcccacacc    600
cgctctacga tatgagcctc ctgaagaatc gattcctcag gccaggtgat gactccagcc    660
acgacctcat gctgctccgc ctgtcagagc ctgccgagct cacggatgct atgaaggtca    720
tggacctgcc cacccaggag ccagcactgg ggaccacctg ctacgcctca ggctggggca    780
gcattgaacc agaggagttc ttgaccccaa agaaacttca gtgtgtggac ctccatgtta    840
tttccaatga cgtgtgtgcg caagttcacc ctcagaaggt gaccaagttc atgctgtgtg    900
ctggacgctg gacaggggc aaaagcacct gctcgggtga ttctgggggc ccacttgtct     960
gtaatggtgt gcttcaaggt atcacgtcat ggggcagtga accatgtgcc ctgcccgaaa   1020
ggccttccct gtacaccaag gtggtgcatt accggaagtg gatcaaggac accatcgtgg   1080
ccaaccctg agcaccccta tcaactccct attgtagtaa acttggaacc ttggaaatga   1140
ccaggccaag actcaggcct ccccagttct actgacctttt gtccttaggt gtgaggtcca   1200
gggttgctag gaaaagaaat cagcagacac aggtgtagac cagagtgttt cttaaatggt   1260
gtaattttgt cctctctgtg tcctggggaa tactggccat gctggagac atatcactca    1320
atttctctga ggacacagat aggatggggt gtctgtgtta tttgtggggt acagagatga   1380
aagaggggtg ggatccacac tgagagagtg gagagtgaca tgtgctggac actgtccatg   1440
aagcactgag cagaagctgg aggcacaacg caccagacac tcacagcaag gatggagctg   1500
aaaacataac ccactctgtc ctggaggcac tgggaagcct agagaaggct gtgaaccaag   1560
gagggagggt cttcctttgg catgggatgg ggatgaagta aggagaggga ctgacccct    1620
ggaagctgat tcactatggg gggaggtgta ttgaagtcct ccagacaacc ctcagatttg   1680
atgatttcct agtagaactc acagaaataa agagctgtta tactgtgaaa tgatttccta   1740
gtagaactca cagaaataaa gagctgttat actgtgaa                            1778
```

<210> SEQ ID NO 42
<211> LENGTH: 1134
<212> TYPE: DNA
<213> ORGANISM: Listeria monocytogenes

<400> SEQUENCE: 42

```
atggtgacag gctggcatcg tccaacatgg attgaaatag accgcgcagc aattcgcgaa     60
aatataaaaa atgaacaaaa taaactcccg gaaagtgtcg acttatgggc agtagtcaaa    120
gctaatgcat atggtcacgg aattatcgaa gttgctagga cggcgaaaga agctggagca    180
aaaggtttct gcgtagccat tttagatgag gcactggctc ttagagaagc tggatttcaa    240
gatgacttta ttcttgtgct tggtgcaacc agaaaagaag atgctaatct ggcagccaaa    300
aaccacattt cacttactgt ttttagagaa gattggctag agaatctaac gctagaagca    360
acacttcgaa ttcatttaaa agtagatagc ggtatggggc gtctcggtat tcgtacgact    420
gaagaagcac ggcgaattga agcaaccagt actaatgatc accaattaca actgaaggt    480
atttacacgc attttgcaac agccgaccag ctagaaacta gttattttga caacaattga    540
```

```
gctaagttcc aaacgatttt aacgagttta aaaaaacgac caacttatgt tcatacagcc    600
aattcagctg cttcattgtt acagccacaa atcgggtttg atgcgattcg ctttggtatt    660
tcgatgtatg gattaactcc ctccacagaa atcaaaacta gcttgccgtt tgagcttaaa    720
cctgcacttg cactctatac cgagatggtt catgtgaaag aacttgcacc aggcgatagc    780
gttagctacg gagcaactta tacagcaaca gagcgagaat gggttgcgac attaccaatt    840
ggctatgcgg atggattgat tcgtcattac agtggtttcc atgttttagt agacggtgaa    900
ccagctccaa tcattggtcg agtttgtatg gatcaaacca tcataaaact accacgtgaa    960
tttcaaactg gttcaaaagt aacgataatt ggcaaagatc atggtaacac ggtaacagca   1020
gatgatgccg ctcaatattt agatacaatt aattatgagg taacttgttt gttaaatgag   1080 cgcatacccta gaaatacat ccattagcgc atacctagaa aatacatcca ttag         1134
```

<210> SEQ ID NO 43
<211> LENGTH: 368
<212> TYPE: PRT
<213> ORGANISM: Listeria monocytogenes

<400> SEQUENCE: 43

```
Met Val Thr Gly Trp His Arg Pro Thr Trp Ile Glu Ile Asp Arg Ala
1               5                   10                  15

Ala Ile Arg Glu Asn Ile Lys Asn Glu Gln Asn Lys Leu Pro Glu Ser
            20                  25                  30

Val Asp Leu Trp Ala Val Val Lys Ala Asn Ala Tyr Gly His Gly Ile
        35                  40                  45

Ile Glu Val Ala Arg Thr Ala Lys Glu Ala Gly Ala Lys Gly Phe Cys
    50                  55                  60

Val Ala Ile Leu Asp Glu Ala Leu Ala Leu Arg Glu Ala Gly Phe Gln
65                  70                  75                  80

Asp Asp Phe Ile Leu Val Leu Gly Ala Thr Arg Lys Glu Asp Ala Asn
                85                  90                  95

Leu Ala Ala Lys Asn His Ile Ser Leu Thr Val Phe Arg Glu Asp Trp
            100                 105                 110

Leu Glu Asn Leu Thr Leu Glu Ala Thr Leu Arg Ile His Leu Lys Val
        115                 120                 125

Asp Ser Gly Met Gly Arg Leu Gly Ile Arg Thr Thr Glu Glu Ala Arg
    130                 135                 140

Arg Ile Glu Ala Thr Ser Thr Asn Asp His Gln Leu Gln Leu Glu Gly
145                 150                 155                 160

Ile Tyr Thr His Phe Ala Thr Ala Asp Gln Leu Glu Thr Ser Tyr Phe
                165                 170                 175

Glu Gln Gln Leu Ala Lys Phe Gln Thr Ile Leu Thr Ser Leu Lys Lys
            180                 185                 190

Arg Pro Thr Tyr Val His Thr Ala Asn Ser Ala Ala Ser Leu Leu Gln
        195                 200                 205

Pro Gln Ile Gly Phe Asp Ala Ile Arg Phe Gly Ile Ser Met Tyr Gly
    210                 215                 220

Leu Thr Pro Ser Thr Glu Ile Lys Thr Ser Leu Pro Phe Glu Leu Lys
225                 230                 235                 240

Pro Ala Leu Ala Leu Tyr Thr Glu Met Val His Val Lys Glu Leu Ala
                245                 250                 255

Pro Gly Asp Ser Val Ser Tyr Gly Ala Thr Tyr Thr Ala Thr Glu Arg
            260                 265                 270
```

```
Glu Trp Val Ala Thr Leu Pro Ile Gly Tyr Ala Asp Gly Leu Ile Arg
            275                 280                 285

His Tyr Ser Gly Phe His Val Leu Val Asp Gly Glu Pro Ala Pro Ile
        290                 295                 300

Ile Gly Arg Val Cys Met Asp Gln Thr Ile Ile Lys Leu Pro Arg Glu
305                 310                 315                 320

Phe Gln Thr Gly Ser Lys Val Thr Ile Ile Gly Lys Asp His Gly Asn
                325                 330                 335

Thr Val Thr Ala Asp Asp Ala Ala Gln Tyr Leu Asp Thr Ile Asn Tyr
            340                 345                 350

Glu Val Thr Cys Leu Leu Asn Glu Arg Ile Pro Arg Lys Tyr Ile His
        355                 360                 365

<210> SEQ ID NO 44
<211> LENGTH: 870
<212> TYPE: DNA
<213> ORGANISM: Listeria monocytogenes

<400> SEQUENCE: 44
atgaaagtat tagtaaataa ccatttagtt gaaagagaag atgccacagt tgacattgaa    60
gaccgcggat atcagtttgg tgatggtgta tatgaagtag ttcgtctata taatggaaaa   120
ttctttactt ataatgaaca cattgatcgc ttatatgcta gtgcagcaaa aattgactta   180
gttattcctt attccaaaga agagctacgt gaattacttg aaaaattagt tgccgaaaat   240
aatatcaata cagggaatgt ctatttacaa gtgactcgtg tgttcaaaa  cccacgtaat   300 catgtaatcc ctgatgattt ccctctagaa ggcgttttaa cagcagcagc tcgtgaagta   360
cctagaaacg agcgtcaatt cgttgaaggt ggaacggcga ttacagaaga agatgtgcgc   420
tggttacgct gtgatattaa gagcttaaac cttttaggaa atattctagc aaaaaataaa   480
gcacatcaac aaaatgcttt ggaagctatt ttacatcgcg gggaacaagt aacagaatgt   540
tctgcttcaa acgtttctat tattaaagat ggtgtattat ggacgcatgc ggcagataac   600
ttaatcttaa atggtatcac tcgtcaagtt atcattgatg ttgcgaaaaa gaatggcatt   660
cctgttaaag aagcggattt cactttaaca gaccttcgtg aagcggatga agtgttcatt   720
tcaagtacaa ctattgaaat tacacctatt acgcatattg acggagttca gtagctgac    780 ggaaaacgtg gaccaattac agcgcaactt catcaatatt ttgtagaaga aatcactcgt   840
gcatgtggcg aattagagtt tgcaaaataa                                    870

<210> SEQ ID NO 45
<211> LENGTH: 289
<212> TYPE: PRT
<213> ORGANISM: Listeria monocytogenes

<400> SEQUENCE: 45

Met Lys Val Leu Val Asn Asn His Leu Val Glu Arg Glu Asp Ala Thr
1               5                   10                  15

Val Asp Ile Glu Asp Arg Gly Tyr Gln Phe Gly Asp Gly Val Tyr Glu
            20                  25                  30

Val Val Arg Leu Tyr Asn Gly Lys Phe Phe Thr Tyr Asn Glu His Ile
        35                  40                  45

Asp Arg Leu Tyr Ala Ser Ala Ala Lys Ile Asp Leu Val Ile Pro Tyr
    50                  55                  60

Ser Lys Glu Glu Leu Arg Glu Leu Leu Glu Lys Leu Val Ala Glu Asn
65                  70                  75                  80
```

```
Asn Ile Asn Thr Gly Asn Val Tyr Leu Gln Val Thr Arg Gly Val Gln
                85                  90                  95

Asn Pro Arg Asn His Val Ile Pro Asp Asp Phe Pro Leu Glu Gly Val
            100                 105                 110

Leu Thr Ala Ala Ala Arg Glu Val Pro Arg Asn Glu Arg Gln Phe Val
        115                 120                 125

Glu Gly Gly Thr Ala Ile Thr Glu Glu Asp Val Arg Trp Leu Arg Cys
    130                 135                 140

Asp Ile Lys Ser Leu Asn Leu Leu Gly Asn Ile Leu Ala Lys Asn Lys
145                 150                 155                 160

Ala His Gln Gln Asn Ala Leu Glu Ala Ile Leu His Arg Gly Glu Gln
                165                 170                 175

Val Thr Glu Cys Ser Ala Ser Asn Val Ser Ile Ile Lys Asp Gly Val
            180                 185                 190

Leu Trp Thr His Ala Ala Asp Asn Leu Ile Leu Asn Gly Ile Thr Arg
        195                 200                 205

Gln Val Ile Ile Asp Val Ala Lys Lys Asn Gly Ile Pro Val Lys Glu
    210                 215                 220

Ala Asp Phe Thr Leu Thr Asp Leu Arg Glu Ala Asp Glu Val Phe Ile
225                 230                 235                 240

Ser Ser Thr Thr Ile Glu Ile Thr Pro Ile Thr His Ile Asp Gly Val
                245                 250                 255

Gln Val Ala Asp Gly Lys Arg Gly Pro Ile Thr Ala Gln Leu His Gln
            260                 265                 270

Tyr Phe Val Glu Glu Ile Thr Arg Ala Cys Gly Glu Leu Glu Phe Ala
        275                 280                 285

Lys

<210> SEQ ID NO 46
<211> LENGTH: 6523
<212> TYPE: DNA
<213> ORGANISM: Artificial Sequence
<220> FEATURE:
<223> OTHER INFORMATION: plasmid pAdv142

<400> SEQUENCE: 46
cggagtgtat actggcttac tatgttggca ctgatgaggg tgtcagtgaa gtgcttcatg    60
tggcaggaga aaaaaggctg caccggtgcg tcagcagaat atgtgataca ggatatattc   120
cgcttcctcg ctcactgact cgctacgctc ggtcgttcga ctgcggcgag cggaaatggc   180
ttacgaacgg ggcggagatt tcctggaaga tgccaggaag atacttaaca gggaagtgag   240
agggccgcgg caaagccgtt tttccatagg ctccgccccc ctgacaagca tcacgaaatc   300
tgacgctcaa atcagtggtg gcgaaacccg acaggactat aaagatacca ggcgtttccc   360
cctggcggct ccctcgtgcg ctctcctgtt cctgcctttc ggtttaccgg tgtcattccg   420
ctgttatggc cgcgtttgtc tcattccacg cctgacactc agttccgggt aggcagttcg   480
ctccaagctg gactgtatgc acgaaccccc cgttcagtcc gaccgctgcg ccttatccgg   540
taactatcgt cttgagtcca acccggaaag acatgcaaaa gcaccactgg cagcagccac   600
tggtaattga tttagaggag ttagtcttga agtcatgcgc cggttaaggc taaactgaaa   660
ggacaagttt ggtgactgcg ctcctccaa gccagttacc tcggttcaaa gagttggtag    720
ctcagagaac cttcgaaaaa ccgccctgca aggcggtttt tcgttttca gagcaagaga    780
ttacgcgcag accaaaacga tctcaagaag atcatcttat taatcagata aaatatttct   840
```

```
agccctcctt tgattagtat attcctatct taaagttact tttatgtgga ggcattaaca      900
tttgttaatg acgtcaaaag gatagcaaga ctagaataaa gctataaagc aagcatataa      960
tattgcgttt catctttaga agcgaatttc gccaatatta taattatcaa agagagggg     1020
tggcaaacgg tatttggcat tattaggtta aaaaatgtag aaggagagtg aaacccatga     1080
aaaaaataat gctagttttt attacactta tattagttag tctaccaatt gcgcaacaaa     1140
ctgaagcaaa ggatgcatct gcattcaata agaaaattc aatttcatcc atggcaccac      1200
cagcatctcc gcctgcaagt cctaagacgc caatcgaaaa gaaacacgcg gatgaaatcg     1260
ataagtatat acaaggattg gattacaata aaaacaatgt attagtatac cacggagatg     1320
cagtgacaaa tgtgccgcca agaaaaggtt acaaagatgg aaatgaatat attgttgtgg     1380
agaaaaagaa gaaatccatc aatcaaaata atgcagacat tcaagttgtg aatgcaattt     1440
cgagcctaac ctatccaggt gctctcgtaa aagcgaattc ggaattagta gaaaatcaac     1500
cagatgttct ccctgtaaaa cgtgattcat taacactcag cattgatttg ccaggtatga     1560
ctaatcaaga caataaaata gttgtaaaaa atgccactaa atcaaacgtt aacaacgcag     1620
taaatacatt agtggaaaga tggaatgaaa aatatgctca agcttatcca aatgtaagtg     1680
caaaaattga ttatgatgac gaaatggctt acagtgaatc acaattaatt gcgaaatttg     1740
gtacagcatt taaagctgta aataatagct tgaatgtaaa cttcggcgca atcagtgaag     1800
ggaaaatgca agaagaagtc attagtttta aacaaattta ctataacgtg aatgttaatg     1860
aacctacaag accttccaga tttttcggca aagctgttac taaagagcag ttgcaagcgc     1920
ttggagtgaa tgcagaaaat cctcctgcat atatctcaag tgtggcgtat ggccgtcaag     1980
tttatttgaa attatcaact aattcccata gtactaaagt aaaagctgct tttgatgctg     2040
ccgtaagcgg aaaatctgtc tcaggtgatg tagaactaac aaatatcatc aaaaattctt     2100
ccttcaaagc cgtaatttac ggaggttccg caaagatga agttcaaatc atcgacggca      2160
acctcggaga cttacgcgat attttgaaaa aaggcgctac ttttaatcga gaaacaccag     2220
gagttcccat tgcttataca acaaacttcc taaaagacaa tgaattagct gttattaaaa     2280
acaactcaga atatattgaa acaacttcaa aagcttatac agatggaaaa attaacatcg     2340
atcactctgg aggatacgtt gctcaattca acatttcttg ggatgaagta aattatgatc     2400
tcgagattgt gggaggctgg gagtgcgaga agcattccca accctggcag gtgcttgtgg     2460
cctctcgtgg cagggcagtc tgcggcggtg ttctggtgca cccccagtgg gtcctcacag     2520
ctgcccactg catcaggaac aaaagcgtga tcttgctggg tcggcacagc ctgtttcatc     2580
ctgaagacac aggccaggta tttcaggtca gccacagctt cccacacccg ctctacgata     2640
tgagcctcct gaagaatcga ttcctcaggc caggtgatga ctccagccac gacctcatgc     2700
tgctccgcct gtcagagcct gccgagctca cggatgctgt gaaggtcatg gacctgccca     2760
cccaggagcc agcactgggg accacctgct acgcctcagg ctgggcagc attgaaccag     2820
aggagttctt gaccccaaag aaacttcagt gtgtggacct ccatgttatt ccaatgacg      2880
tgtgtgcgca agttcaccct cagaaggtga ccaagttcat gctgtgtgct ggacgctgga     2940
caggggcaa aagcacctgc tcgggtgatt ctggggccc acttgtctgt tatggtgtgc       3000
ttcaaggtat cacgtcatgg ggcagtgaac catgtgccct gcccgaaagg ccttccctgt     3060
acaccaaggt ggtgcattac cggaagtgga tcaggacac catcgtggcc aacccctaac      3120
ccgggccact aactcaacgc tagtagtgga tttaatccca aatgagccaa cagaaccaga     3180
accagaaaca gaacaagtaa cattggagtt agaaatggaa gaagaaaaaa gcaatgattt     3240
```

-continued

```
cgtgtgaata atgcacgaaa tcattgctta ttttttaaa aagcgatata ctagatataa    3300
cgaaacaacg aactgaataa agaatacaaa aaaagagcca cgaccagtta aagcctgaga    3360
aactttaact gcgagcctta attgattacc accaatcaat taaagaagtc gagacccaaa    3420
atttggtaaa gtatttaatt actttattaa tcagatactt aaatatctgt aaacccatta    3480
tatcgggttt ttgaggggat ttcaagtctt taagaagata ccaggcaatc aattaagaaa    3540
aacttagttg attgccttt tgttgtgat tcaactttga tcgtagcttc taactaatta    3600
attttcgtaa gaaggagaa cagctgaatg aatatccctt ttgttgtaga aactgtgctt    3660
catgacggct tgttaaagta caaatttaaa aatagtaaaa ttcgctcaat cactaccaag    3720
ccaggtaaaa gtaaagggc tattttgcg tatcgctcaa aaaaagcat gattggcgga    3780
cgtggcgttt ttctgacttc cgaagaagcg attcacgaaa tcaagatac atttacgcat    3840
tggacaccaa acgtttatcg ttatggtacg tatgcagacg aaaaccgttc atacactaaa    3900
ggacattctg aaaacaattt aagacaaatc aatacctcct tattgattt tgatattcac    3960
acggaaaaag aaactattc agcaagcgat atttaacaa cagctattga tttaggtttt    4020
atgcctacgt taattatcaa atctgataaa ggttatcaag catattttgt tttagaaacg    4080
ccagtctatg tgacttcaaa atcagaattt aaatctgtca aagcagccaa aataatctcg    4140
caaaatatcc gagaatattt tggaaagtct ttgccagttg atctaacgtg caatcatttt    4200
gggattgctc gtataccaag aacggacaat gtagaatttt ttgatcccaa ttaccgttat    4260
tctttcaaag aatggcaaga ttggtctttc aaacaaacag ataataaggg ctttactcgt    4320
tcaagtctaa cggtttaag cggtacagaa ggcaaaaaac aagtagatga accctggttt    4380
aatctcttat tgcacgaaac gaaattttca ggagaaaagg gtttagtagg gcgcaatagc    4440
gttatgttta ccctctcttt agcctacttt agttcaggct attcaatcga aacgtgcgaa    4500
tataatatgt ttgagtttaa taatcgatta gatcaaccct tagaagaaaa agaagtaatc    4560
aaaattgtta gaagtgccta ttcagaaaac tatcaagggg ctaataggga atacattacc    4620
attctttgca aagcttgggt atcaagtgat ttaaccagta aagatttatt tgtccgtcaa    4680
gggtggttta aattcaagaa aaaaagaagc gaacgtcaac gtgttcattt gtcagaatgg    4740
aaagaagatt taatggctta tattagcgaa aaaagcgatg tatacaagcc ttatttagcg    4800
acgaccaaaa aagagattag agaagtgcta ggcattcctg aacggacatt agataaattg    4860
ctgaaggtac tgaaggcgaa tcaggaaatt ttctttaaga ttaaaccagg aagaaatggt    4920
ggcattcaac ttgctagtgt taaatcattg ttgctatcga tcattaaatt aaaaaaagaa    4980
gaacgagaaa gctatataaa ggcgctgaca gcttcgttta atttagaacg tacatttatt    5040
caagaaactc taaacaaatt ggcagaacgc cccaaaacgg acccacaact cgatttgttt    5100
agctacgata caggctgaaa ataaaacccg cactatgcca ttacatttat atctatgata    5160
cgtgtttgtt tttctttgct ggctagctta attgcttata tttacctgca ataaaggatt    5220
tcttacttcc attatactcc cattttccaa aaacatacgg ggaacacggg aacttattgt    5280
acaggccacc tcatagttaa tggtttcgag ccttcctgca atctcatcca tggaaatata    5340
ttcatccccc tgccggccta ttaatgtgac ttttgtgccc ggcggatatt cctgatccag    5400
ctccaccata aattggtcca tgcaaattcg gccggcaatt tcaggcgtt ttcccttcac    5460
aaggatgtcg gtccctttca attttcggag ccagccgtcc gcatagccta caggcaccgt    5520
cccgatccat gtgtcttttt ccgctgtgta ctcggctccg tagctgacgc tctcgccttt    5580
```

```
tctgatcagt tgacatgtg acagtgtcga atgcagggta aatgccggac gcagctgaaa    5640
cggtatctcg tccgacatgt cagcagacgg gcgaaggcca tacatgccga tgccgaatct    5700
gactgcatta aaaaagcctt ttttcagccg gagtccagcg gcgctgttcg cgcagtggac    5760
cattagattc tttaacggca gcggagcaat cagctcttta aagcgctcaa actgcattaa    5820
gaaatagcct ctttcttttt catccgctgt cgcaaaatgg gtaaatacccc ctttgcactt    5880 taaacgaggg ttgcggtcaa gaattgccat cacgttctga acttcttcct ctgttttac     5940 accaagtctg ttcatccccg tatcgacctt cagatgaaaa tgaagagaac cttttttcgt    6000
gtggcgggct gcctcctgaa gccattcaac agaataaccct gttaaggtca cgtcatactc    6060
agcagcgatt gccacatact ccgggggaac cgcgccaagc accaatatag gcgccttcaa    6120 tcccttttg cgcagtgaaa tcgcttcatc caaaatggcc acggccaagc atgaagcacc     6180
tgcgtcaaga gcagccttg ctgttctgc atcaccatgc ccgtaggcgt ttgctttcac      6240
aactgccatc aagtggacat gttcaccgat atgtttttc atattgctga catttccttt    6300
tatcgcggac aagtcaattt ccgcccacgt atctctgtaa aaaggttttg tgctcatgga    6360
aaactcctct cttttttcag aaaatcccag tacgtaatta agtatttgag aattaatttt    6420
atattgatta atactaagtt tacccagttt tcacctaaaa aacaaatgat gagataatag    6480
ctccaaaggc taaagaggac tataccaact atttgttaat taa                      6523
```

```
<210> SEQ ID NO 47
<211> LENGTH: 36
<212> TYPE: DNA
<213> ORGANISM: Artificial Sequence
<220> FEATURE:
<223> OTHER INFORMATION: Adv271-actAF1 primer

<400> SEQUENCE: 47
cggaattcgg atccgcgcca aatcattggt tgattg                              36

<210> SEQ ID NO 48
<211> LENGTH: 37
<212> TYPE: DNA
<213> ORGANISM: Artificial Sequence
<220> FEATURE:
<223> OTHER INFORMATION: Adv272-actAR1 primer

<400> SEQUENCE: 48
gcgagtcgac gtcggggtta atcgtaatgc aattggc                             37

<210> SEQ ID NO 49
<211> LENGTH: 35
<212> TYPE: DNA
<213> ORGANISM: Artificial Sequence
<220> FEATURE:
<223> OTHER INFORMATION: Adv273-actAF2 primer

<400> SEQUENCE: 49
gcgagtcgac ccatacgacg ttaattcttg caatg                               35

<210> SEQ ID NO 50
<211> LENGTH: 39
<212> TYPE: DNA
<213> ORGANISM: Artificial Sequence
<220> FEATURE:
<223> OTHER INFORMATION: Adv274-actAR2 primer

<400> SEQUENCE: 50
gatactgcag ggatccttcc cttctcggta atcagtcac                           39
```

```
<210> SEQ ID NO 51
<211> LENGTH: 19
<212> TYPE: DNA
<213> ORGANISM: Artificial Sequence
<220> FEATURE:
<223> OTHER INFORMATION: primer 3 which binds externally to actA region

<400> SEQUENCE: 51
tgggatggcc aagaaattc                                                    19

<210> SEQ ID NO 52
<211> LENGTH: 22
<212> TYPE: DNA
<213> ORGANISM: Artificial Sequence
<220> FEATURE:
<223> OTHER INFORMATION: primer 4 which binds externally to actA region

<400> SEQUENCE: 52
ctaccatgtc ttccgttgct tg                                                22

<210> SEQ ID NO 53
<211> LENGTH: 10
<212> TYPE: PRT
<213> ORGANISM: Homo sapiens

<400> SEQUENCE: 53

His Cys Ile Arg Asn Lys Ser Val Ile Leu
1               5                   10

<210> SEQ ID NO 54
<211> LENGTH: 9
<212> TYPE: PRT
<213> ORGANISM: Human papilloma virus type 16

<400> SEQUENCE: 54

Arg Ala His Tyr Asn Ile Val Thr Phe
1               5

<210> SEQ ID NO 55
<211> LENGTH: 24
<212> TYPE: PRT
<213> ORGANISM: Homo sapiens

<400> SEQUENCE: 55

Met Trp Val Pro Val Val Phe Leu Thr Leu Ser Val Thr Trp Ile Gly
1               5                   10                  15

Ala Ala Pro Leu Ile Leu Ser Arg
            20
```

DUAL DELIVERY SYSTEM FOR HETEROLOGOUS ANTIGENS

CROSS-REFERENCE TO RELATED APPLICATIONS

This application is a Divisional of U.S. patent application Ser. No. 12/993,380, filed Feb. 7, 2011, which is a National Phase Application of PCT International Application No. PCT/US09/44538, filed on May 19, 2009, which claims the benefit of priority to U.S. Provisional Application No. 61/071,792, filed May 19, 2008. These applications are hereby incorporated by reference herein.

FIELD OF INVENTION

Provided herein are recombinant *Listeria* strains expressing a tumor-specific antigenic polypeptide and, optionally, an angiogenic polypeptide wherein a nucleic acid molecule encoding at least one of the polypeptides is operably integrated into the *Listeria* genome in an open reading frame with a nucleic acid sequence encoding a PEST-containing polypeptide, methods of preparing same, and methods of inducing an immune response, and treating, inhibiting, or suppressing cancer or tumors comprising administering same.

BACKGROUND OF THE INVENTION

A great deal of pre-clinical evidence and early clinical trial data suggests that the anti-tumor capabilities of the immune system can be harnessed to treat patients with established cancers. The vaccine strategy takes advantage of tumor antigens associated with various types of cancers. Immunizing with live vaccines such as viral or bacterial vectors expressing a tumor-associated antigen is one strategy for eliciting strong CTL responses against tumors.

*Listeria monocytogenes* (Lm) is a gram positive, facultative intracellular bacterium that has direct access to the cytoplasm of antigen presenting cells, such as macrophages and dendritic cells, largely due to the pore-forming activity of listeriolysin-O (LLO). LLO is secreted by Lm following engulfment by the cells and perforates the phagolysosomal membrane, allowing the bacterium to escape the vacuole and enter the cytoplasm. LLO is very efficiently presented to the immune system via MHC class I molecules. Furthermore, Lm-derived peptides also have access to MHC class II presentation via the phagolysosome.

Cancer is a complex disease and combined therapeutic approaches are more likely to succeed. Not only tumor cells, but also the microenvironment that supports tumor growth, must be targeted to maximize the therapeutic efficacy. Most immunotherapies focus on single antigens to target tumor cells and therefore they have shown limited success against human cancers. A single therapeutic agent capable of targeting tumor cells and tumor microenvironment simultaneously would have an advantage over other immunotherapeutic approaches, especially if it results in a synergistic anti-tumor effect.

SUMMARY OF THE INVENTION

In one embodiment, provided herein is a recombinant *Listeria* strain comprising a first and second nucleic acid molecule, each said nucleic acid molecule encoding a heterologous antigenic polypeptide or fragment thereof, wherein said first nucleic acid molecule is operably integrated into the *Listeria* genome in an open reading frame with an endogenous PEST-containing gene. In another embodiment, the present invention provides a vaccine comprising such a recombinant *Listeria* strain.

In another embodiment, provided herein is a method of inducing an immune response to an antigen in a subject comprising administering a recombinant *Listeria* strain to said subject, wherein said recombinant *Listeria* strain comprises a first and second nucleic acid molecule, each said nucleic acid molecule encoding a heterologous antigenic polypeptide or fragment thereof, wherein said first nucleic acid molecule is operably integrated into the *Listeria* genome in an open reading frame with an endogenous PEST-containing gene.

In another embodiment, provided herein is a method of treating, suppressing, or inhibiting a cancer in a subject comprising administering a recombinant *Listeria* strain comprising a first and second nucleic acid molecule, each said nucleic acid molecule encoding a heterologous antigenic polypeptide or fragment thereof, wherein said first nucleic acid molecule is operably integrated into the *Listeria* genome in an open reading frame with an endogenous PEST-containing gene.

In another embodiment, provided herein is a method of treating, suppressing, or inhibiting at least one tumor in a subject comprising administering a recombinant *Listeria* strain comprising a first and second nucleic acid molecule, each said nucleic acid molecule encoding a heterologous antigenic polypeptide or fragment thereof, wherein said first nucleic acid molecule is operably integrated into the *Listeria* genome in an open reading frame with an endogenous PEST-containing gene.

In another embodiment, provided herein is a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, provided herein is a method of producing a recombinant *Listeria* strain expressing two antigens, the method comprising genetically fusing a first nucleic acid encoding a first antigen and a second nucleic acid encoding a second antigen into the *Listeria* genome in an open reading frame with an endogenous PEST-containing gene; and expressing said first and second antigens under conditions conducive to antigenic expression in said recombinant *Listeria* strain.

In another embodiment, provided herein is a method of producing a recombinant *Listeria* strain expressing two antigens. In one embodiment, the method comprises genetically fusing a first nucleic acid encoding a first antigen into the *Listeria* genome in an open reading frame with an endogenous PEST-containing gene; transforming said recombinant *Listeria* with an episomal expression vector comprising a second nucleic acid encoding a second antigen; and expressing said first and second antigens under conditions conducive to antigenic expression in said recombinant *Listeria* strain.

Figure 2:
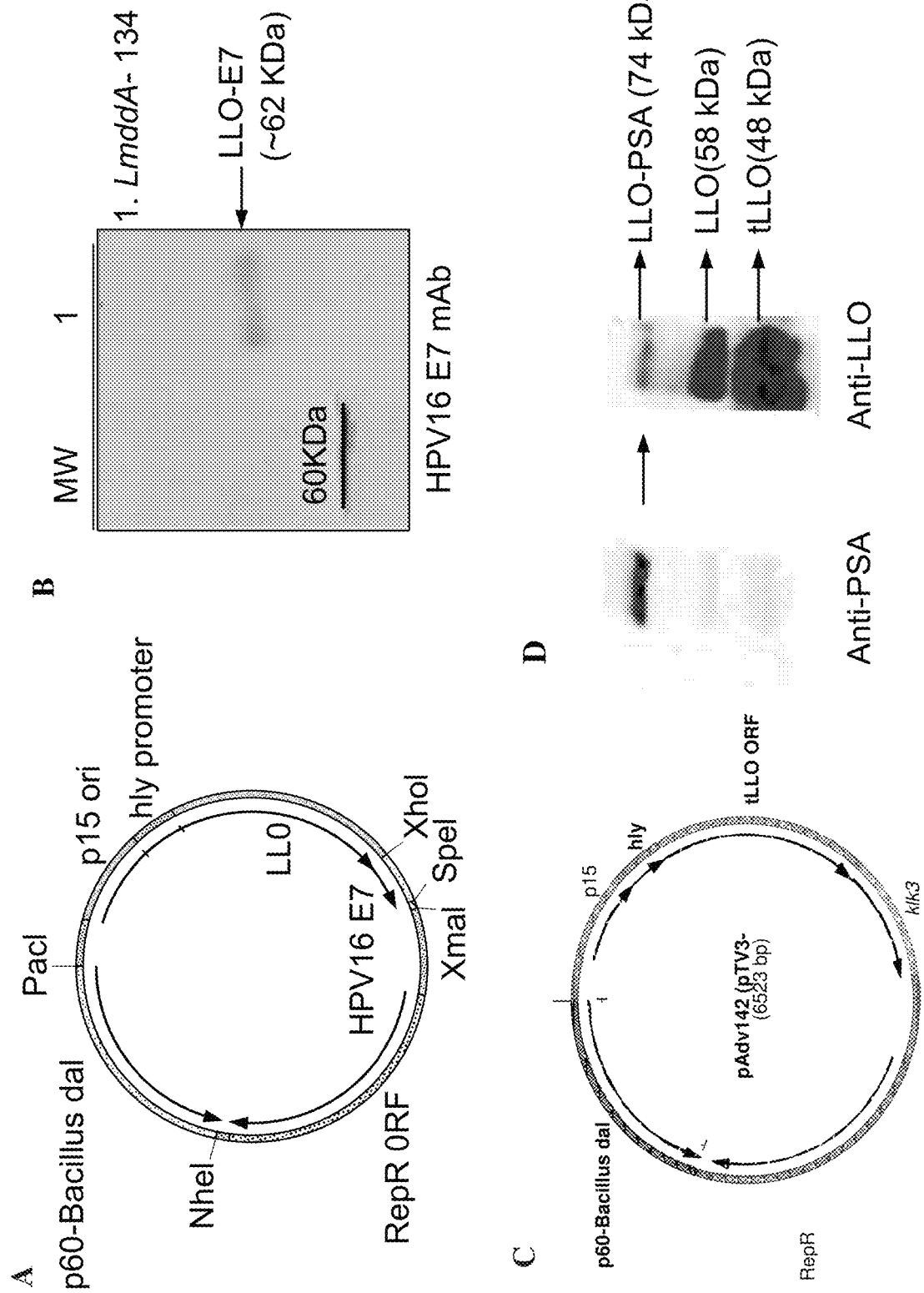

FIG. 2. (A) Map of the pADV134 plasmid. (B) Proteins from LmddA-134 culture supernatant were precipitated, separated in a SDS-PAGE, and the LLO-E7 protein detected by Western-blot using an anti-E7 monoclonal antibody. The antigen expression cassette consists of hly promoter, ORF for truncated LLO and human PSA gene (klk3). (C) Map of the pADV142 plasmid. (D) Western blot showed the expression of LLO-PSA fusion protein using anti-PSA and anti-LLO antibody.

Figure 3:
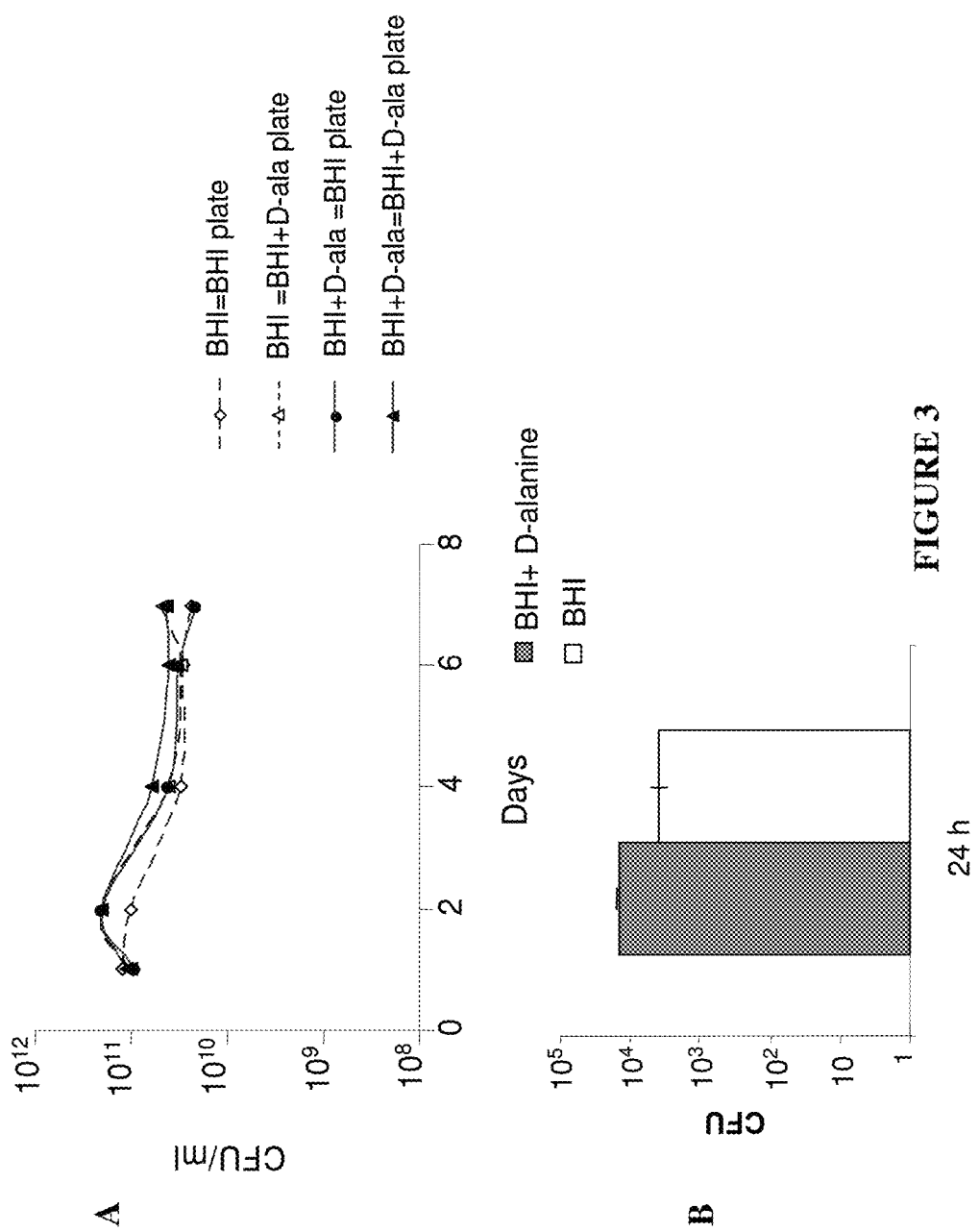

FIG. 3. (A) Plasmid stability in vitro of LmddA-LLO-PSA if cultured with and without selection pressure (D-alanine). Strain and culture conditions are listed first and plates used for CFU determination are listed after. (B) Clearance of LmddA-LLO-PSA in vivo and assessment of potential plasmid loss during this time. Bacteria were injected i.v. and isolated from spleen at the time point indicated. CFUs were determined on BHI and BHI+D-alanine plates.

Figure 4:
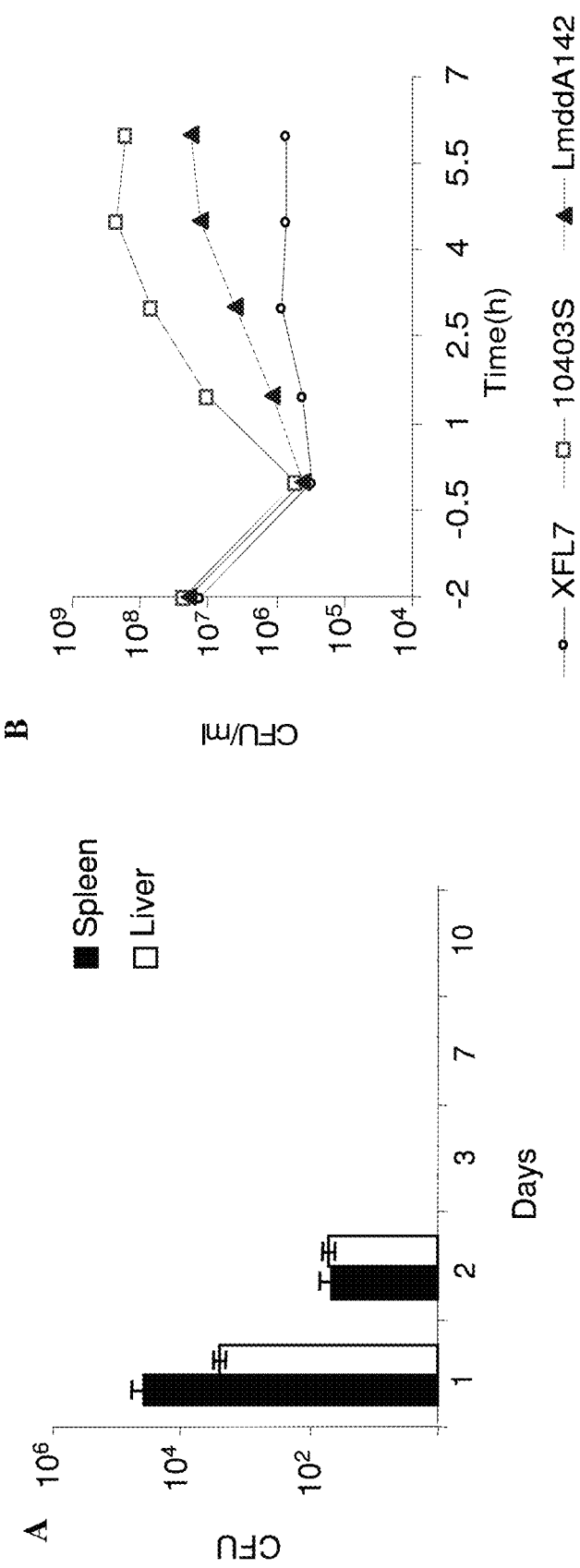

FIG. 4. (A) In vivo clearance of the strain LmddA-LLO-PSA after administration of $10^8$ CFU in C57BL/6 mice. The number of CFU were determined by plating on BHI/str plates. The limit of detection of this method was 100 CFU. (B) Cell infection assay of J774 cells with 10403S, LmddA-LLO-PSA and XFL7 strains.

Figure 5:
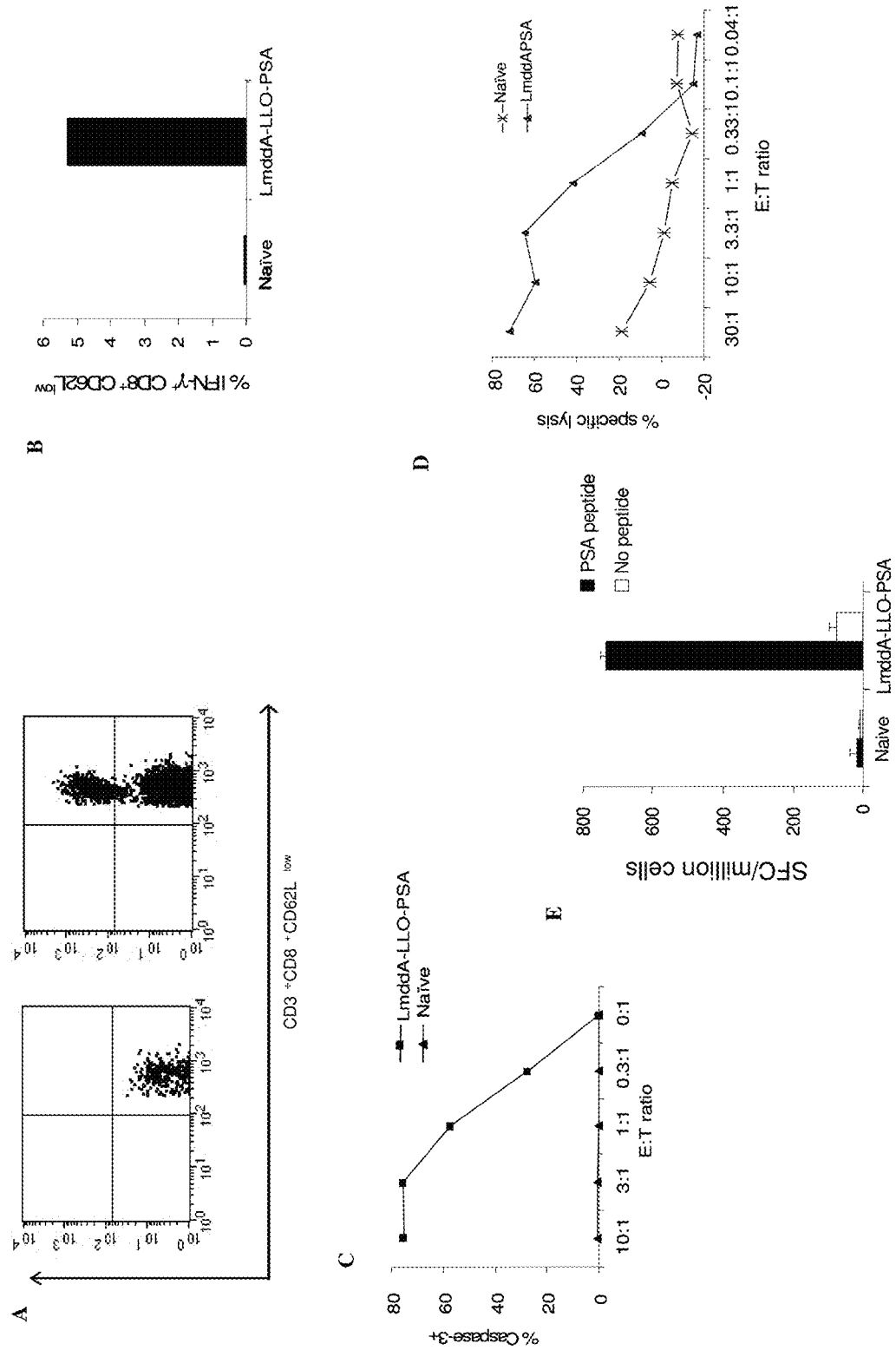

FIG. 5. (A) PSA tetramer-specific cells in the splenocytes of naïve and LmddA-LLO-PSA immunized mice on day 6 after the booster dose. (B) Intracellular cytokine staining for IFN-γ in the splenocytes of naïve and LmddA-LLO-PSA immunized mice were stimulated with PSA peptide for 5 h. Specific lysis of EL4 cells pulsed with PSA peptide with in vitro stimulated effector T cells from LmddA-LLO-PSA immunized mice and naïve mice at different effector/target ratio using a caspase based assay (C) and a europium based assay (D). Number of IFNγ spots in naïve and immunized splenocytes obtained after stimulation for 24 h in the presence of PSA peptide or no peptide (E).

Figure 6:
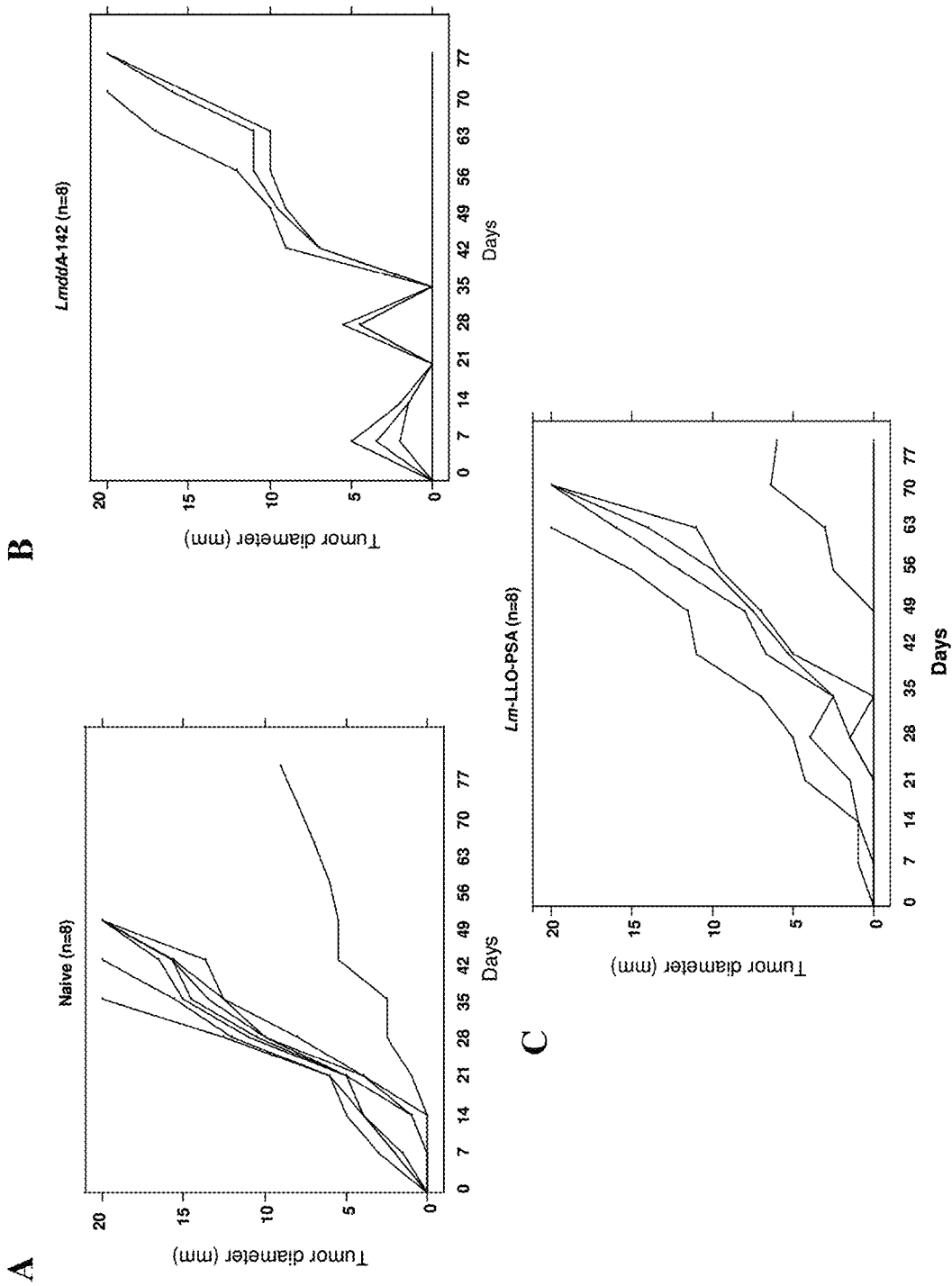

FIG. 6. Immunization with LmddA-142 induces regression of Tramp-C1-PSA (TPSA) tumors. Mice were left untreated (n=8) (A) or immunized i.p. with LmddA-142 ($1\times10^8$ CFU/mouse) (n=8) (B) or Lm-LLO-PSA (n=8) (C) on days 7, 14 and 21. Tumor sizes were measured for each individual tumor and the values expressed as the mean diameter in millimeters. Each line represents an individual mouse.

Figure 7:
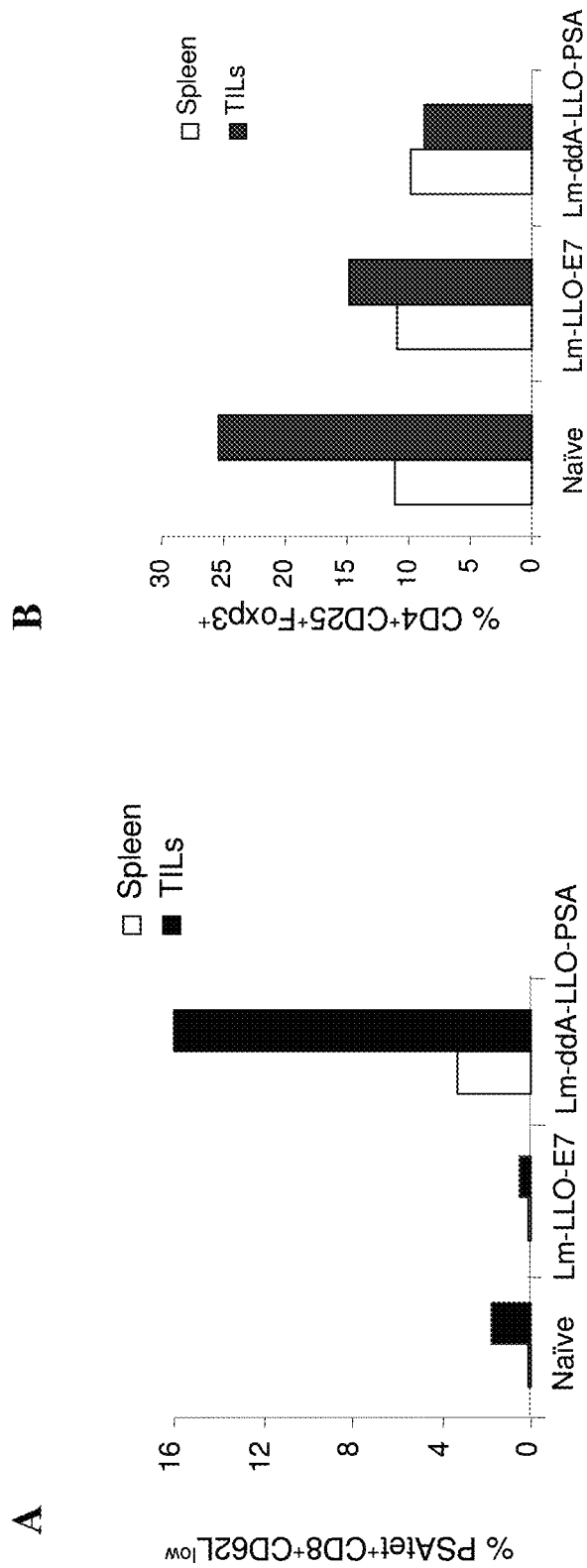

FIG. 7. (A) Analysis of PSA-tetramer$^+$CD8$^+$ T cells in the spleens and infiltrating T-PSA-23 tumors of untreated mice and mice immunized with either an Lm control strain or Lm-ddA-LLO-PSA (LmddA-142). (B) Analysis of CD4$^+$ regulatory T cells, which were defined as CD25$^+$FoxP3$^+$, in the spleens and infiltrating T-PSA-23 tumors of untreated mice and mice immunized with either an Lm control strain or Lm-ddA-LLO-PSA.

Figure 8:
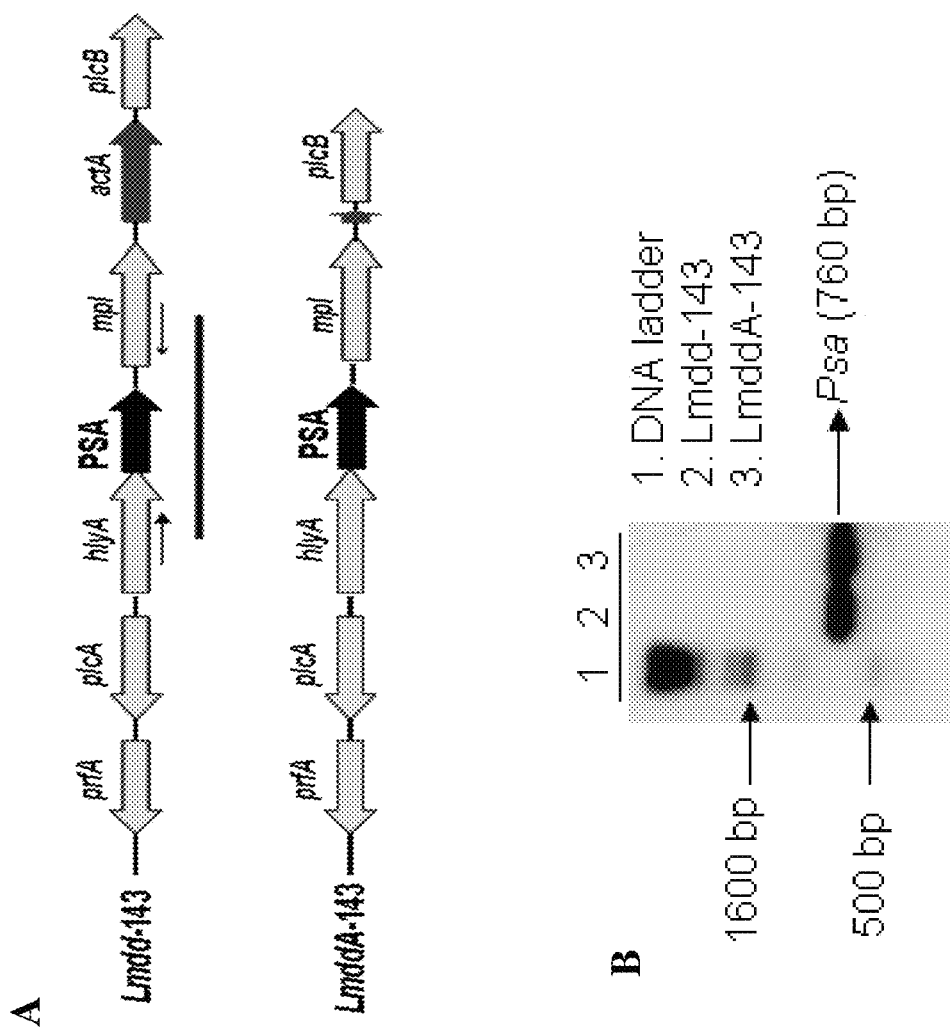

FIG. 8. (A) Schematic representation of the chromosomal region of the Lmdd-143 and LmddA-143 after klk3 integration and actA deletion; (B) The klk3 gene is integrated into the Lmdd and LmddA chromosome. PCR from chromosomal DNA preparation from each construct using klk3 specific primers amplifies a band of 760 bp corresponding to the klk3 gene.

Figure 9:
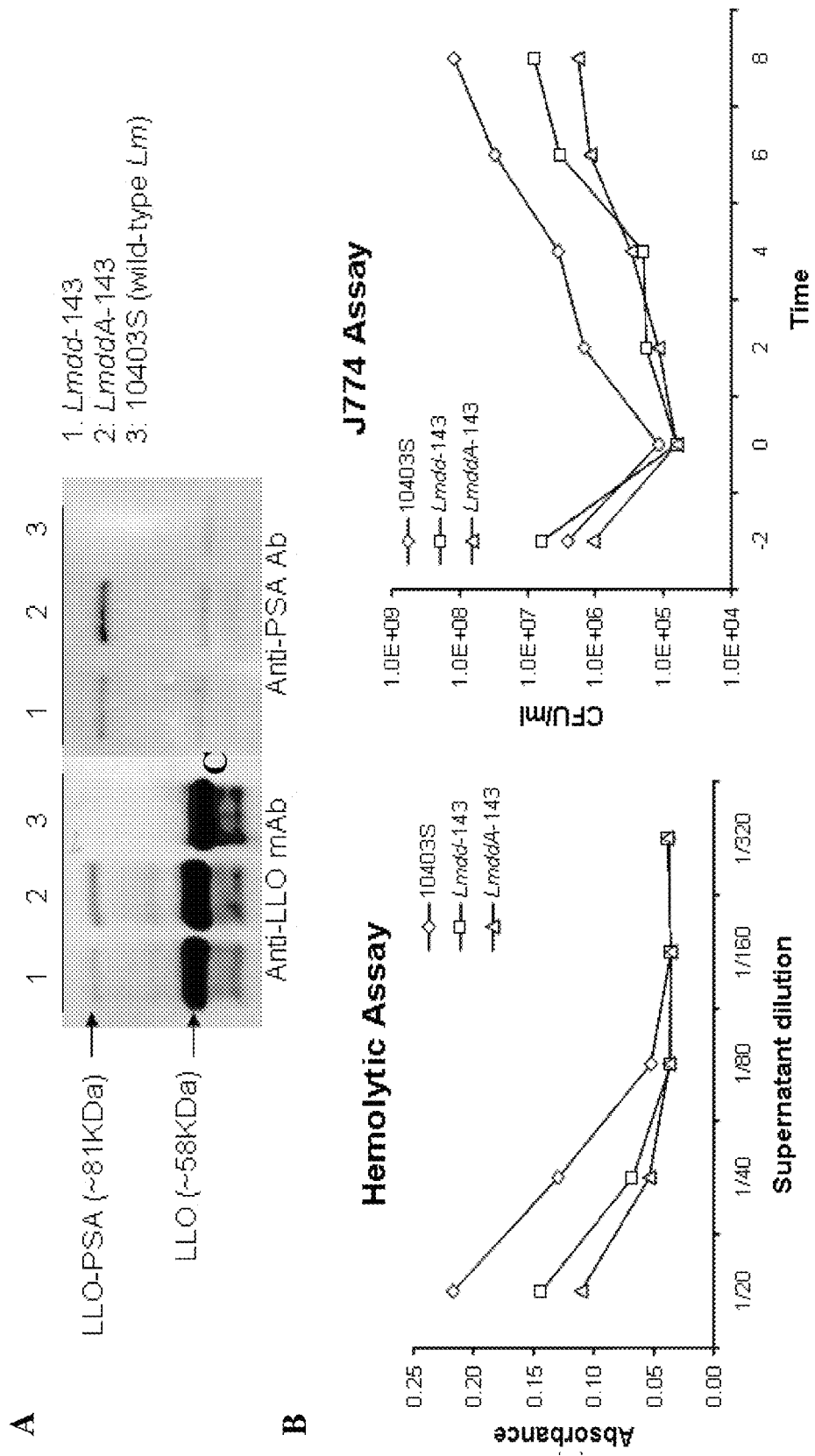

FIG. 9. (A) Lmdd-143 and LmddA-143 secretes the LLO-PSA protein. Proteins from bacterial culture supernatants were precipitated, separated in a SDS-PAGE and LLO and LLO-PSA proteins detected by Western-blot using an anti-LLO and anti-PSA antibodies; (B) LLO produced by Lmdd-143 and LmddA-143 retains hemolytic activity. Sheep red blood cells were incubated with serial dilutions of bacterial culture supernatants and hemolytic activity measured by absorbance at 590 nm; (C) Lmdd-143 and LmddA-143 grow inside the macrophage-like J774 cells. J774 cells were incubated with bacteria for 1 hour followed by gentamicin treatment to kill extracellular bacteria. Intracellular growth was measured by plating serial dilutions of J774 lysates obtained at the indicated timepoints. Lm 10403S was used as a control in these experiments.

Figure 10:
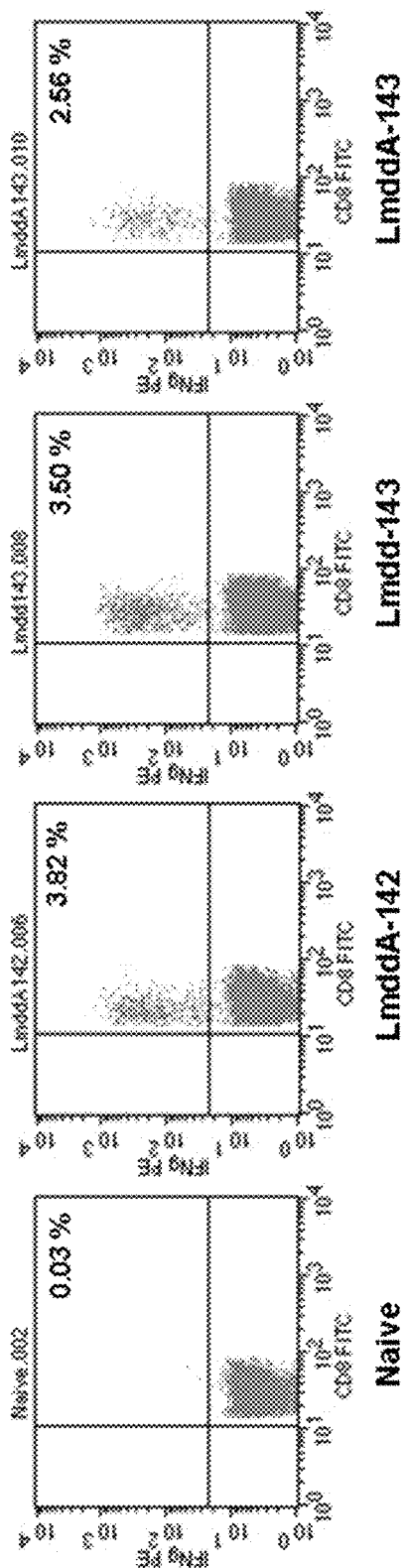

FIG. 10. Immunization of mice with Lmdd-143 and LmddA-143 induces a PSA-specific immune response. C57BL/6 mice were immunized twice at 1-week interval with $1\times10^8$ CFU of Lmdd-143, LmddA-143 or LmddA-142 and 7 days later spleens were harvested. Splenocytes were stimulated for 5 hours in the presence of monensin with 1 M of the PSA$_{65-74}$ peptide. Cells were stained for CD8, CD3, CD62L and intracellular IFN-γ and analyzed in a FACS Calibur cytometer.

Figure 11:
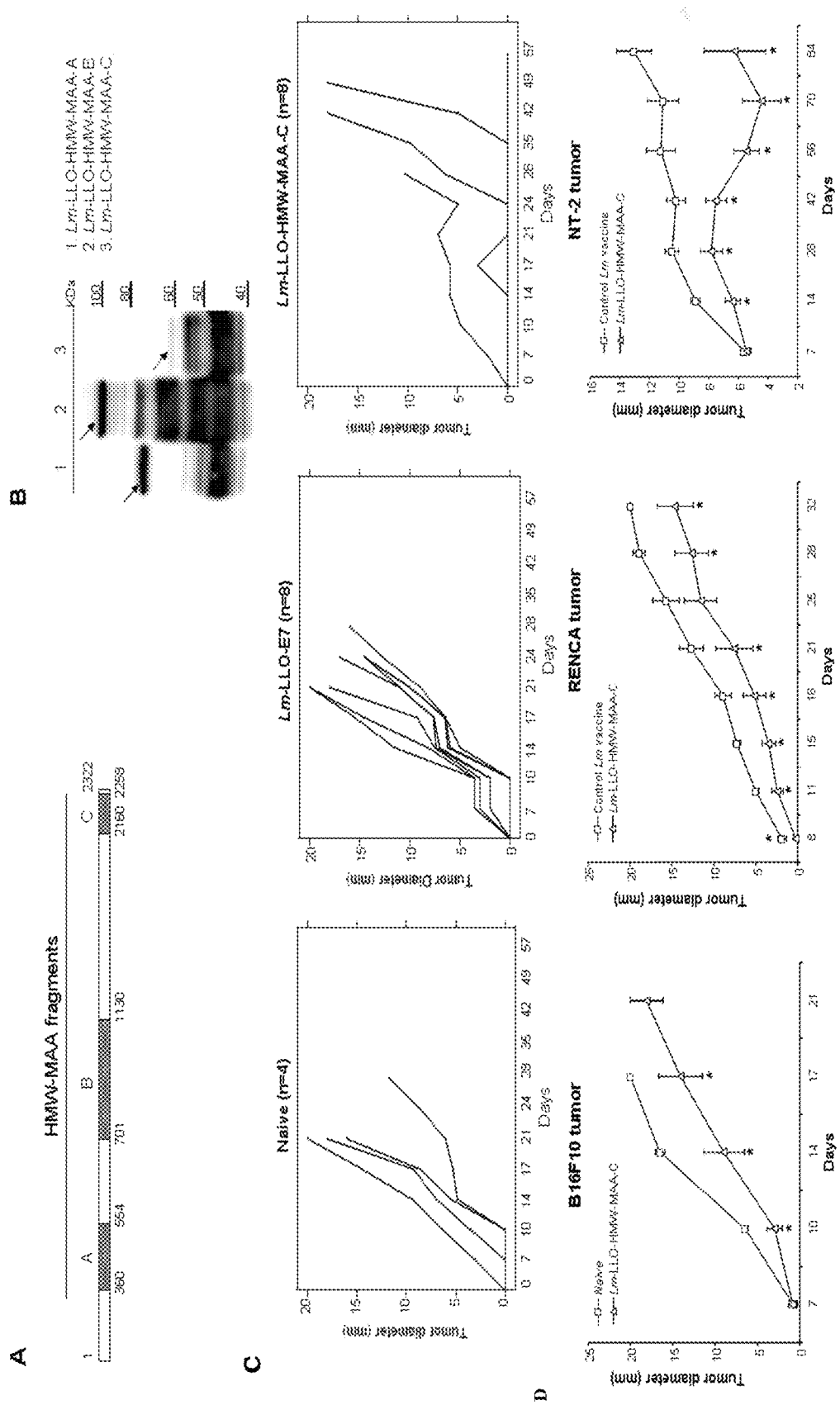

FIG. 11. Three Lm-based vaccines expressing distinct HMW-MAA fragments based on the position of previously mapped and predicted HLA-A2 epitopes were designed (A). The Lm-tLLO-HMW-MMA$_{2160-2258}$ (also referred as Lm-LLO-HMW-MAA-C) strain secretes a ~62 kDa band corresponding to the tLLO-HMW-MAA$_{2160-2258}$ fusion protein (B). C57BL/6 mice (n=15) were inoculated s.c. with B16F10 cells and either immunized i.p. on days 3, 10 and 17 with Lm-tLLO-HMW-MAA$_{2160-2258}$ (n=8) or left untreated (n=7). BALB/c mice (n=16) were inoculated s.c. with RENCA cells and immunized i.p. on days 3, 10 and 17 with either Lm-HMW-MAA-C (n=8) or an equivalent dose of a control Lm vaccine. Mice immunized with the Lm-LLO-HMW-MAA-C impeded the growth of established tumors (C). FVB/N mice (n=13) were inoculated s.c. with NT-2 tumor cells and immunized i.p. on days 7, 14 and 21 with either Lm-HMW-MAA-C (n=5) or an equivalent dose of a control Lm vaccine (n=8). Immunization of mice with Lm-LLO-HMW-MAA-C significantly impaired the growth of tumors not engineered to express HMW-MAA, such as B16F10, RENCA and NT-2 (D). Tumor sizes were measured for each individual tumor and the values expressed as the mean diameter in millimeters±SEM. *, P≤0.05, Mann-Whitney test.

Figure 12:
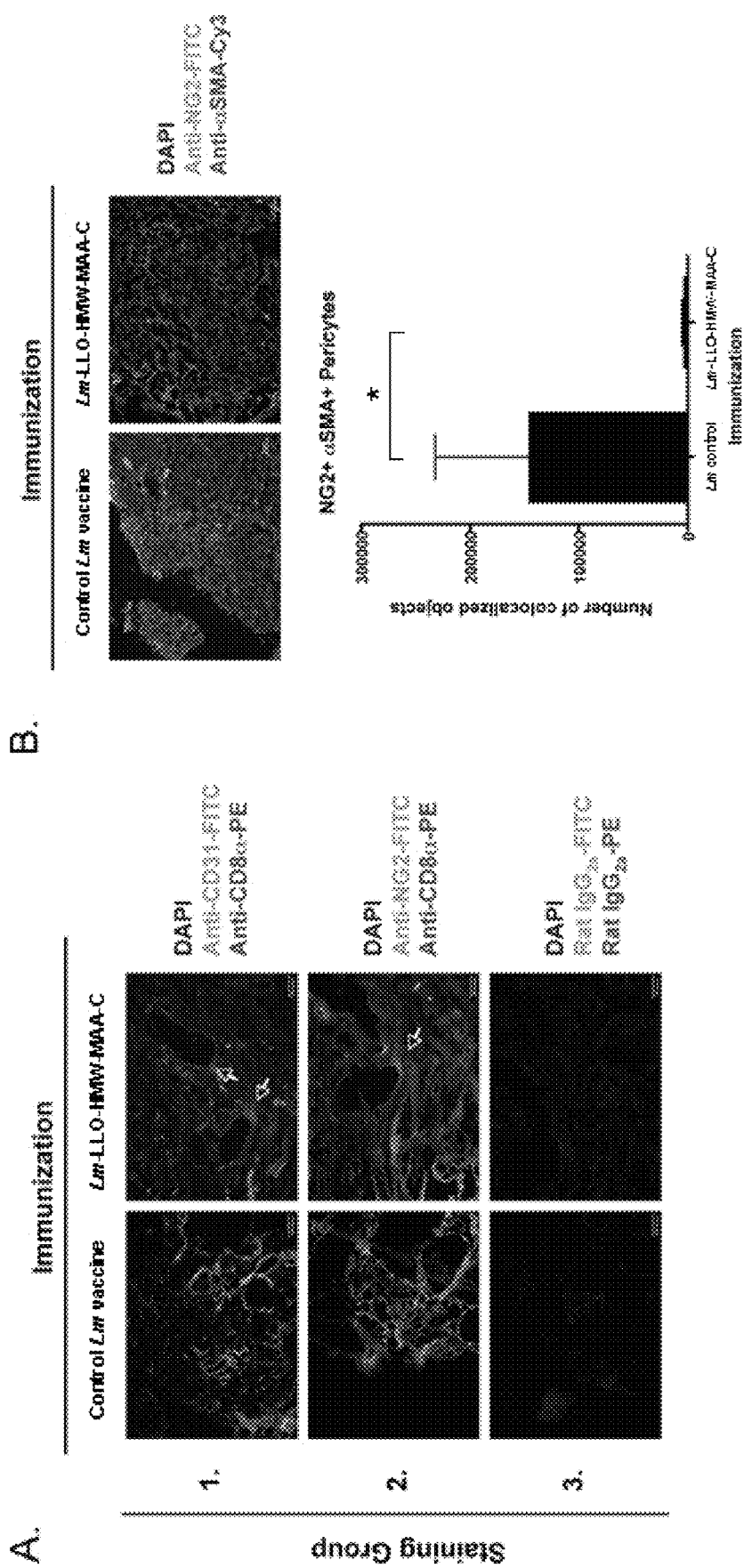

FIG. 12. Immunization with Lm-HMW-MAA-C promotes tumor infiltration by CD8$^+$ T cells and decreases the number of pericytes in blood vessels. (A) NT-2 tumors were removed and sectioned for immunofluorescence. Staining groups are numbered (1-3) and each stain is indicated on the right. Sequential tissues were either stained with the pan-vessel marker anti-CD31 or the anti-NG2 antibody for the HMW-MAA mouse homolog AN2, in conjunction with anti-CD8α for possible TILs. Group 3 shows isotype controls for the above antibodies and DAPI staining used as a nuclear marker. A total of 5 tumors were analyzed and a single representative image from each group is shown. CD8$^+$ cells around blood vessels are indicated by arrows. (B) Sequential sections were stained for pericytes by using the anti-NG2 and anti-alpha-smooth-muscle-cell-actin (α-SMA) antibodies. Double staining/colocalization of these two antibodies (yellow in merge image) are indicative of pericyte staining (top). Pericyte colocalization was quantitated using Image Pro Software and the number of colocalized objects is shown in the graph (bottom). A total of 3 tumors were analyzed and a single representative image from each group is shown. *, P≤0.05, Mann-Whitney test. Graph shows mean±SEM.

DETAILED DESCRIPTION OF THE INVENTION

This invention relates, in one embodiment, to a recombinant *Listeria* strain expressing an antigenic polypeptide in which the nucleic acid encoding the polypeptide is operably integrated into the *Listeria* genome in an open reading frame with an endogenous PEST-containing gene, which in one embodiment, is LLO. In one embodiment, the *Listeria* expresses two polypeptides, one of which is a tumor-associated antigen, and one of which is an angiogenic polypeptide.

In one embodiment, the present invention provides a recombinant *Listeria* strain comprising a first and second nucleic acid molecule, each said nucleic acid molecule encoding a heterologous antigenic polypeptide or fragment thereof, wherein the first nucleic acid molecule is integrated into the *Listeria* genome in an open reading frame with an endogenous LLO gene and wherein the second nucleic acid molecule is present in an episomal expression vector within the recombinant *Listeria* strain. In one embodiment, the first nucleic acid molecule encodes a KLK3 protein and the second nucleic acid molecule encodes an HMW-MAA peptide, and in one embodiment, is in an open reading frame with a nucleic acid encoding a non-hemolytic LLO, truncated ActA, or PEST sequence.

In one embodiment, this invention provides a recombinant *Listeria* strain comprising a first and second nucleic acid molecule, each said nucleic acid molecule encoding a heterologous antigenic polypeptide.

In one embodiment, the first nucleic acid molecule is operably integrated into the *Listeria* genome as an open reading frame with an endogenous nucleic acid sequence encoding a polypeptide comprising a PEST sequence. In one embodiment, the first nucleic acid molecule is operably integrated into the *Listeria* genome as an open reading frame with a nucleic acid sequence encoding LLO. In another embodiment, the first nucleic acid molecule is operably integrated into the *Listeria* genome as an open reading frame with a nucleic acid sequence encoding ActA.

In one embodiment, the first nucleic acid molecule is operably integrated into the *Listeria* genome in an open reading frame with an endogenous nucleic acid sequence encoding LLO. In one embodiment, the integration does not eliminate the functionality of LLO. In another embodiment, the integration does not eliminate the functionality of ActA. In one embodiment, the functionality of LLO or Acta is its native functionality. In one embodiment, the LLO functionality is allowing the organism to escape from the phagolysosome, while in another embodiment, the LLO functionality is enhancing the immunogenicity of a polypeptide to which it is fused. In one embodiment, a recombinant *Listeria* of the present invention retains LLO function, which in one embodiment, is hemolytic function and in another embodiment, is antigenic function. Other functions of LLO are known in the art, as are methods of and assays for evaluating LLO functionality. In one embodiment, a recombinant *Listeria* of the present invention has wild-type virulence, while in another embodiment, a recombinant *Listeria* of the present invention has attenuated virulence. In another embodiment, a recombinant *Listeria* of the present invention is avirulent. In one embodiment, a recombinant *Listeria* of the present invention is sufficiently virulent to escape the phagolysosome and enter the cytosol. In one embodiment, a recombinant *Listeria* of the present invention expresses a fused antigen-LLO protein. Thus, in one embodiment, the integration of the first nucleic acid molecule into the *Listeria* genome does not disrupt the structure of the endogenous PEST-containing gene, while in another embodiment, it does not disrupt the function of the endogenous PEST-containing gene. In one embodiment, the integration of the first nucleic acid molecule into the *Listeria* genome does not disrupt the ability of said *Listeria* to escape the phagolysosome.

In another embodiment, the second nucleic acid molecule is operably integrated into the *Listeria* genome with said first nucleic acid molecule in an open reading frame with an endogenous polypeptide comprising a PEST sequence. Thus, in one embodiment, the first and second nucleic acid molecules are integrated in frame with a nucleic acid sequence encoding LLO, while in another embodiment, they are integrated in frame with a nucleic acid sequence encoding ActA. In another embodiment, the second nucleic acid molecule is operably integrated into the *Listeria* genome in an open reading frame with a nucleic acid sequence encoding a polypeptide comprising a PEST sequence in a site that is distinct from the integration site of the first nucleic acid molecule. In one embodiment, the first nucleic acid molecule is integrated in frame with a nucleic acid sequence encoding LLO, while the second nucleic acid molecule is integrated in frame with a nucleic acid sequence encoding ActA, while in another embodiment, the first nucleic acid molecule is integrated in frame with a nucleic acid sequence encoding ActA, while the second nucleic acid molecule is integrated in frame with a nucleic acid sequence encoding LLO.

In another embodiment, this invention provides a recombinant *Listeria* strain comprising a first nucleic acid molecule encoding a first heterologous antigenic polypeptide or fragment thereof and a second nucleic acid molecule encoding a second heterologous antigenic polypeptide or fragment thereof, wherein said first nucleic acid molecule is integrated into the *Listeria* genome such that the first heterologous antigenic polypeptide and an endogenous PEST-containing polypeptide are expressed as a fusion protein. In one embodiment, the first heterologous antigenic polypeptide and the endogenous PEST-containing polypeptide are translated in a single open reading frame, while in another embodiment, the first heterologous antigenic polypeptide and the endogenous PEST-containing polypeptide are fused after being translated separately.

In one embodiment, the *Listeria* genome comprises a deletion of the endogenous ActA gene, which in one embodiment is a virulence factor. In one embodiment, such a deletion provides a more attenuated and thus safer *Listeria* strain for human use. According to this embodiment, the antigenic polypeptide is integrated in frame with LLO in the *Listeria* chromosome. In another embodiment, the integrated nucleic acid molecule is integrated into the ActA locus. In another embodiment, the chromosomal nucleic acid encoding ActA is replaced by a nucleic acid molecule encoding an antigen.

In another embodiment, the integrated nucleic acid molecule is integrated into the *Listeria* chromosome.

In one embodiment, said first nucleic acid molecule is a vector designed for site-specific homologous recombination into the *Listeria* genome. In another embodiment, the construct or heterologous gene is integrated into the Listerial chromosome using homologous recombination.

Techniques for homologous recombination are well known in the art, and are described, for example, in Frankel, F R, Hegde, S, Lieberman, J, and Y Paterson. Induction of a cell-mediated immune response to HIV gag using *Listeria monocytogenes* as a live vaccine vector. J. Immunol. 155: 4766-4774. 1995; Mata, M, Yao, Z, Zubair, A, Syres, K and Y Paterson, Evaluation of a recombinant *Listeria monocytogenes* expressing an HIV protein that protects mice against viral challenge. Vaccine 19:1435-45, 2001; Boyer, J D, Robinson, T M, Maciag, P C, Peng, X, Johnson, R S, Pavlakis, G, Lewis, M G, Shen, A, Siliciano, R, Brown, C R, Weiner, D, and Y Paterson. DNA prime *Listeria* boost induces a cellular immune response to SIV antigens in the Rhesus Macaque model that is capable of limited suppression of SIV239 viral replication. Virology. 333: 88-101, 2005. In another embodiment, homologous recombination is performed as described in U.S. Pat. No. 6,855,320. In another embodiment, a temperature sensitive plasmid is used to select the recombinants. Each technique represents a separate embodiment of the methods and compositions as provided herein.

In another embodiment, the construct or heterologous gene is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in one embodiment, that a stable genomic insertion mutant can be formed. In another embodiment, the position in the genome where the foreign gene has been inserted by transposon mutagenesis is unknown.

In another embodiment, the construct or heterologous gene is integrated into the Listerial chromosome using phage integration sites (Lauer P, Chow M Y et al, Construction, characterization, and use of two LM site-specific phage integration vectors. J Bacteriol 2002; 184(15): 4177-86). In another embodiment, an integrase gene and attachment site of a bacteriophage (e.g. U153 or PSA listeriophage) is used to insert the heterologous gene into the corresponding attachment site, which can be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment as provided herein.

In another embodiment, the first nucleic acid sequence of methods and compositions as provided herein is operably linked to a promoter/regulatory sequence. In another embodiment, the second nucleic acid sequence is operably linked to a promoter/regulatory sequence. In another embodiment, each of the nucleic acid sequences is operably linked to a promoter/regulatory sequence. In one embodiment, the promoter/regulatory sequence is present on an episomal plasmid comprising said nucleic acid sequence. In one embodiment, endogenous *Listeria* promoter/regulatory sequence controls the expression of a nucleic acid sequence of the methods and compositions of the present invention. Each possibility represents a separate embodiment of the methods and compositions as provided herein.

In another embodiment, a nucleic acid sequence as provided herein is operably linked to a promoter, regulatory sequence, or combination thereof that drives expression of the encoded peptide in the *Listeria* strain. Promoter, regulatory sequences, and combinations thereof useful for driving constitutive expression of a gene are well known in the art and include, but are not limited to, for example, the $P_{hlyA}$, $P_{ActA}$, hly, ActA, and p60 promoters of *Listeria*, the *Streptococcus* bac promoter, the *Streptomyces griseus* sgiA promoter, and the *B. thuringiensis* phaZ promoter. In another embodiment, inducible and tissue specific expression of the nucleic acid encoding a peptide as provided herein is accomplished by placing the nucleic acid encoding the peptide under the control of an inducible or tissue-specific promoter/regulatory sequence. Examples of tissue-specific or inducible regulatory sequences, promoters, and combinations thereof which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter or regulatory sequence, which is either known or unknown, and which is capable of driving expression of the desired protein operably linked thereto. In one embodiment, a regulatory sequence is a promoter, while in another embodiment, a regulatory sequence is an enhancer, while in another embodiment, a regulatory sequence is a suppressor, while in another embodiment, a regulatory sequence is a repressor, while in another embodiment, a regulatory sequence is a silencer.

In one embodiment, the nucleic acid construct used for integration to the *Listeria* genome contains an integration site. In one embodiment, the site is a PhSA (phage from Scott A) attPP' integration site. PhSA is, in another embodiment, the prophage of *L. monocytogenes* strain ScottA (Loessner, M. J., I. B. Krause, T. Henle, and S. Scherer. 1994. Structural proteins and DNA characteristics of 14 *Listeria* typing bacteriophages. J. Gen. Virol. 75:701-710, incorporated herein by reference), a serotype 4b strain that was isolated during an epidemic of human listeriosis. In another embodiment, the site is any another integration site known in the art. Each possibility represents a separate embodiment of the methods and compositions as provided herein.

In another embodiment, the nucleic acid construct contains an integrase gene. In another embodiment, the integrase gene is a PhSA integrase gene. In another embodiment, the integrase gene is any other integrase gene known in the art. Each possibility represents a separate embodiment of the methods and compositions as provided herein.

In one embodiment, the nucleic acid construct is a plasmid. In another embodiment, the nucleic acid construct is a shuttle plasmid. In another embodiment, the nucleic acid construct is an integration vector. In another embodiment, the nucleic acid construct is a site-specific integration vector. In another embodiment, the nucleic acid construct is any other type of nucleic acid construct known in the art. Each possibility represents a separate embodiment of the methods and compositions as provided herein.

The integration vector of methods and compositions as provided herein is, in another embodiment, a phage vector. In another embodiment, the integration vector is a site-specific integration vector. In another embodiment, the vector further comprises an attPP' site. Each possibility represents a separate embodiment of the methods and compositions as provided herein.

In another embodiment, the integration vector is a U153 vector. In another embodiment, the integration vector is an A118 vector. In another embodiment, the integration vector is a PhSA vector.

In another embodiment, the vector is an A511 vector (e.g. GenBank Accession No: X91069). In another embodiment, the vector is an A006 vector. In another embodiment, the vector is a B545 vector. In another embodiment, the vector is a B053 vector. In another embodiment, the vector is an A020 vector. In another embodiment, the vector is an A500 vector (e.g. GenBank Accession No: X85009). In another embodiment, the vector is a B051 vector. In another embodiment, the vector is a B052 vector. In another embodiment, the vector is a B054 vector. In another embodiment, the vector is a B055 vector. In another embodiment, the vector is a B056 vector. In another embodiment, the vector is a B101 vector. In another embodiment, the vector is a B110 vector. In another embodiment, the vector is a B111 vector. In another embodiment, the vector is an A153 vector. In another embodiment, the vector is a D441 vector. In another embodiment, the vector is an A538 vector. In another embodiment, the vector is a B653 vector. In another embodiment, the vector is an A513 vector. In another embodiment, the vector is an A507 vector. In another embodiment, the vector is an A502 vector. In another embodiment, the vector is an A505 vector. In another embodiment, the vector is an A519 vector. In another embodiment, the vector is a B604 vector. In another embodiment, the vector is a C703 vector. In another embodiment, the vector is a B025 vector. In another embodiment, the vector is an A528 vector. In another embodiment, the vector is a B024 vector. In another embodiment, the vector is a B012 vector. In another embodiment, the vector is a B035 vector. In another embodiment, the vector is a C707 vector.

In another embodiment, the vector is an A005 vector. In another embodiment, the vector is an A620 vector. In another embodiment, the vector is an A640 vector. In another embodiment, the vector is a B021 vector. In another embodiment, the vector is an HSO47 vector. In another embodiment, the vector is an H10G vector. In another embodiment, the vector is an H8/73 vector. In another embodiment, the vector is an H19 vector. In another embodiment, the vector is an H21 vector. In another embodiment, the vector is an H43 vector. In another embodiment, the vector is an H46 vector. In another embodiment, the vector is an H107 vector. In another embodiment, the vector is an H108 vector. In another embodiment, the vector is an H110 vector. In another embodiment, the vector is an H163/84 vector. In another embodiment, the vector is an H312 vector. In another embodiment, the vector is an H340 vector. In another embodiment, the vector is an H387 vector. In another embodiment, the vector is an H391/73 vector. In another embodiment, the vector is an H684/74 vector. In another embodiment, the vector is an H924A vector. In another embodiment, the vector is an fMLUP5 vector. In another embodiment, the vector is a syn (=P35) vector. In another embodiment, the vector is a 00241 vector. In another embodiment, the vector is a 00611 vector. In another embodiment, the vector is a 02971A vector. In another embodiment, the vector is a 02971C vector. In another embodiment, the vector is a 5/476 vector. In another embodiment, the vector is a 5/911 vector. In another embodiment, the vector is a 5/939 vector. In another embodiment, the vector is a 5/11302 vector. In another embodiment, the vector is a 5/11605 vector. In another embodiment, the vector is a 5/11704 vector. In another embodiment, the vector is a 184 vector. In another embodiment, the vector is a 575 vector. In another embodiment, the vector is a 633 vector. In another embodiment, the vector is a 699/694 vector. In another embodiment, the vector is a 744 vector. In another embodiment, the vector is a 900 vector. In another embodiment, the vector is a 1090 vector. In another embodiment, the vector is a 1317 vector. In another embodiment, the vector is a 1444 vector. In another embodiment, the vector is a 1652 vector. In another embodiment, the vector is a 1806 vector. In another embodiment, the vector is a 1807 vector. In another embodiment, the vector is a 1921/959 vector. In another embodiment, the vector is a 1921/11367 vector. In another embodiment, the vector is a 1921/11500 vector. In another embodiment, the vector is a 1921/11566 vector. In another embodiment, the vector is a 1921/12460 vector. In another embodiment, the vector is a 1921/12582 vector. In another embodiment, the vector is a 1967 vector. In another embodiment, the vector is a 2389 vector. In another embodiment, the vector is a 2425 vector. In another embodiment, the vector is a 2671 vector. In another embodiment, the vector is a 2685 vector. In another embodiment, the vector is a 3274 vector. In another embodiment, the vector is a 3550 vector. In another embodiment, the vector is a 3551 vector. In another embodiment, the vector is a 3552 vector. In another embodiment, the vector is a 4276 vector. In another embodiment, the vector is a 4277 vector. In another embodiment, the vector is a 4292 vector. In another embodiment, the vector is a 4477 vector. In another embodiment, the vector is a 5337 vector. In another embodiment, the vector is a 5348/11363 vector. In another embodiment, the vector is a 5348/11646 vector. In another embodiment, the vector is a 5348/12430 vector. In another embodiment, the vector is a 5348/12434 vector. In another embodiment, the vector is a 10072 vector. In another embodiment, the vector is a 11355C vector. In another embodiment, the vector is a 11711A vector. In another embodiment, the vector is a 12029 vector. In another embodiment, the vector is a 12981 vector. In another embodiment, the vector is a 13441 vector. In another embodiment, the vector is a 90666 vector. In another embodiment, the vector is a 90816 vector. In another embodiment, the vector is a 93253 vector. In another embodiment, the vector is a 907515 vector. In another embodiment, the vector is a 910716 vector. In another embodiment, the vector is a N,N-*Listeria* vector. In another embodiment, the vector is a O1761 vector. In another embodiment, the vector is a 4211 vector. In another embodiment, the vector is a 4286 vector.

In another embodiment, the integration vector is any other site-specific integration vector known in the art that is capable of infecting *Listeria*. Each possibility represents a separate embodiment of the methods and compositions as provided herein. In another embodiment, the integration vector or plasmid of methods and compositions as provided herein does not confer antibiotic resistance to the *Listeria* vaccine strain. In another embodiment, the integration vector or plasmid does not contain an antibiotic resistance gene. Each possibility represents a separate embodiment of the methods and compositions as provided herein.

In another embodiment, the present invention provides an isolated nucleic acid encoding a recombinant polypeptide. In one embodiment, the isolated nucleic acid comprises a sequence sharing at least 85% homology with a nucleic acid encoding a recombinant polypeptide as provided herein. In another embodiment, the isolated nucleic acid comprises a sequence sharing at least 90% homology with a nucleic acid encoding a recombinant polypeptide as provided herein. In another embodiment, the isolated nucleic acid comprises a sequence sharing at least 95% homology with a nucleic acid encoding a recombinant polypeptide as provided herein. In another embodiment, the isolated nucleic acid comprises a sequence sharing at least 97% homology with a nucleic acid encoding a recombinant polypeptide as provided herein. In another embodiment, the isolated nucleic acid comprises a sequence sharing at least 99% homology with a nucleic acid encoding a recombinant polypeptide as provided herein.

In one embodiment, provided herein is a method of producing a recombinant *Listeria* strain expressing two distinct heterologous antigens. In another embodiment, the recombinant *Listeria* expresses at least 3 or more distinct heterologous antigens. In another embodiment, the recombinant *Listeria* expresses 4 or more distinct heterologous antigens. In another embodiment, the recombinant *Listeria* expresses 5 or more distinct heterologous antigens.

In another embodiment, the method comprises genetically fusing a first nucleic acid encoding a first antigen into the *Listeria* genome in an open reading frame with an endogenous polypeptide comprising a PEST sequence. In another embodiment, the method comprises genetically fusing at least 2 nucleic acids encoding two distinct heterologous antigens in the *Listeria* genome in an open reading frame with an endogenous polypeptide comprising a PEST sequence. In another embodiment, the method comprises genetically fusing at least 3 nucleic acids encoding two distinct heterologous antigens in the *Listeria* genome in an open reading frame with an endogenous polypeptide comprising a PEST sequence. In another embodiment, the method comprises genetically fusing at least 4 nucleic acids encoding two distinct heterologous antigens in the *Listeria* genome in an open reading frame with an endogenous polypeptide comprising a PEST sequence. In another embodiment, the method comprises genetically fusing at least 5 nucleic acids encoding two distinct heterologous antigens in the *Listeria* genome in an open reading frame with an endogenous polypeptide comprising a PEST sequence.

In another embodiment, the method comprises transforming said recombinant *Listeria* with an episomal expression vector comprising a second nucleic acid encoding a second antigen. In another embodiment, the method comprises transforming said recombinant *Listeria* with an episomal expression vector comprising at least 2 nucleic acids encoding at least two distinct heterologous antigens. In another embodiment, the method comprises transforming said recombinant *Listeria* with an episomal expression vector comprising at least 3 nucleic acids encoding at least three distinct heterologous antigens. In another embodiment, the method comprises transforming said recombinant *Listeria* with an episomal expression vector comprising at least 4 nucleic acids encoding at least four distinct heterologous antigens. In another embodiment, the method comprises transforming said recombinant *Listeria* with an episomal expression vector comprising at least 5 nucleic acids encoding at least five distinct heterologous antigens.

In yet another embodiment, the method comprises expressing said first and second antigens under conditions conducive to antigenic expression, that are known in the art, in said recombinant *Listeria* strain.

In another embodiment, the method comprises transforming said recombinant *Listeria* with at least 1 episomal expression vector comprising heterologous antigens as described hereinabove. In another embodiment, the method comprises transforming said recombinant *Listeria* with at least 2 episomal expression vector comprising heterologous antigens as described hereinabove. In another embodiment, the method comprises transforming said recombinant *Listeria* with at least 3 episomal expression vector comprising heterologous antigens as described hereinabove. In another embodiment, the method comprises transforming said recombinant *Listeria* with at least 4 episomal expression vector comprising heterologous antigens as described hereinabove.

In another embodiment, the recombinant *Listeria* strain may express more than two antigens, some of which are expressed from one or more nucleic acid molecules integrated into the *Listeria* chromosome and some of which are expressed via one or more episomal expression vectors present in the recombinant *Listeria* strain. Thus, as described hereinabove, in one embodiment, a recombinant *Listeria* strain as provided herein comprises two or more episomal expression vectors, each of which expresses a separate antigenic polypeptide, in one embodiment. In one embodiment, one or more of the antigens are expressed as a fusion protein with LLO, which in one embodiment, is non-hemolytic LLO, and, in another embodiment, truncated LLO. In one embodiment, a recombinant *Listeria* strain as provided herein targets tumors by eliciting immune responses to two separate antigens, which are expressed by two different cell types, which in one embodiment are a cell surface antigen and an anti-angiogenic polypeptide, while in another embodiment, a recombinant *Listeria* strain as provided herein targets tumors by eliciting an immune response to two different antigens expressed by the same cell type, which in one embodiment are prostate specific antigen (PSA) and prostate-specific membrane antigen (PSMA), which in one embodiment is FOLH1. In another embodiment, a recombinant *Listeria* strain as provided herein targets tumors by eliciting an immune response to two different antigens as described hereinbelow or as are known in the art.

In one embodiment, a first antigen of the compositions and methods of the present invention is directed against a specific cell surface antigen or tumor target, and a second antigen is directed against an angiogenic antigen or tumor microenvironment. In another embodiment, the first and second antigens of the compositions and methods of the present invention are polypeptides expressed by tumor cells, or in another embodiment, polypeptides expressed in a tumor microenvironment. In another embodiment, the first antigen of the compositions and methods of the present invention is a polypeptide expressed by a tumor and the second antigen of the compositions and methods of the present invention is a receptor target, NO Synthetase, Arg-1, or other enzyme known in the art.

In one embodiment, provided herein is a method of producing a recombinant *Listeria* strain expressing two antigens, the method comprising, in one embodiment, genetically fusing a first nucleic acid encoding a first antigen and a second nucleic acid encoding a second antigen into the *Listeria* genome in an open reading frame with a native polypeptide comprising a PEST sequence. In another embodiment, the expressing said first and second antigens are produced under conditions conducive to antigenic expression in said recombinant *Listeria* strain.

In one embodiment, the recombinant *Listeria* strain of the composition and methods as provided herein comprises an episomal expression vector comprising the second nucleic acid molecule encoding a heterologous antigen. In another embodiment, the second nucleic acid molecule encoding a heterologous antigen is present in said episomal expression vector in an open reading frame with a polypeptide comprising a PEST sequence.

In another embodiment, an episomal expression vector of the methods and compositions as provided herein comprises an antigen fused in frame to a nucleic acid sequence encoding a PEST-like AA sequence. In one embodiment, the antigen is HMW-MAA, and in another embodiment, a HMW-MAA fragment. In another embodiment, the PEST-like AA sequence is KENSISSMAPPASPPASPKTPIEK-KHADEIDK (SEQ ID NO: 1). In another embodiment, the PEST-like sequence is KENSISSMAPPASPPASPK (SEQ ID No: 2). In another embodiment, fusion of an antigen to any LLO sequence that includes one of the PEST-like AA sequences enumerated herein can enhance cell mediated immunity against HMW-MAA.

In another embodiment, the PEST-like AA sequence is a PEST-like sequence from a *Listeria* ActA protein. In another embodiment, the PEST-like sequence is KTEEQPSEVNT-GPR (SEQ ID NO: 3), KASVTDT-SEGDLDSSMQSADESTPQPLK (SEQ ID NO: 4), KNEEVNASDFPPPPTDEELR (SEQ ID NO: 5), or RGGIPTSEEFSSLNSGDFTDDENSETTEEEIDR (SEQ ID NO: 6). In another embodiment, the PEST-like sequence is from *Listeria seeligeri* cytolysin, encoded by the iso gene. In another embodiment, the PEST-like sequence is RSE-VTISPAETPESPPATP (SEQ ID NO: 7). In another embodiment, the PEST-like sequence is from Streptolysin O protein of *Streptococcus* sp. In another embodiment, the PEST-like sequence is from *Streptococcus pyogenes* Streptolysin O, e.g. KQNTASTETTTTNEQPK (SEQ ID NO: 8) at AA 35-51. In another embodiment, the PEST-like sequence is from *Streptococcus equisimilis* Streptolysin O, e.g. KQN-TANTETTTTNEQPK (SEQ ID NO: 9) at AA 38-54. In another embodiment, the PEST-like sequence has a sequence selected from SEQ ID NO: 3-9. In another embodiment, the PEST-like sequence has a sequence selected from SEQ ID NO: 1-9. In another embodiment, the PEST-like sequence is another PEST-like AA sequence derived from a prokaryotic organism.

Identification of PEST-like sequences is well known in the art, and is described, for example in Rogers S et al (Amino acid sequences common to rapidly degraded proteins: the PEST hypothesis. Science 1986; 234(4774):364-8, incorporated herein by reference) and Rechsteiner M et al (PEST sequences and regulation by proteolysis. Trends Biochem Sci 1996; 21(7):267-71, incorporated herein by reference). "PEST-like sequence" refers, in another embodiment, to a region rich in proline (P), glutamic acid (E), serine (S), and threonine (T) residues. In another embodiment, the PEST-like sequence is flanked by one or more clusters containing several positively charged amino acids. In another embodiment, the PEST-like sequence mediates rapid intracellular degradation of proteins containing it. In another embodiment, the PEST-like sequence fits an algorithm disclosed in Rogers et al. In another embodiment, the PEST-like sequence fits an algorithm disclosed in Rechsteiner et al. In another embodiment, the PEST-like sequence contains one or more internal phosphorylation sites, and phosphorylation at these sites precedes protein degradation. In one embodiment, a sequence referred to herein as a PEST-like sequence is a PEST sequence.

In one embodiment, PEST-like sequences of prokaryotic organisms are identified in accordance with methods such as described by, for example Rechsteiner and Rogers (1996, Trends Biochem. Sci. 21:267-271) for LM and in Rogers S et al (Science 1986; 234(4774):364-8). Alternatively, PEST-like AA sequences from other prokaryotic organisms can also be identified based on this method. Other prokaryotic organisms wherein PEST-like AA sequences would be expected to include, but are not limited to, other *Listeria* species. In one embodiment, the PEST-like sequence fits an algorithm disclosed in Rogers et al. In another embodiment, the PEST-like sequence fits an algorithm disclosed in Rechsteiner et al. In another embodiment, the PEST-like sequence is identified using the PEST-find program.

In another embodiment, identification of PEST motifs is achieved by an initial scan for positively charged amino acids R, H, and K within the specified protein sequence. All amino acids between the positively charged flanks are counted and only those motifs are considered further, which contain a number of amino acids equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical amino acids as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, R F. J. Mol. Biol. 157, 105 (1982), incorporated herein by reference. For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine.

Hydropathy index=10*Kyte-Doolittle hydropathy index+45

In another embodiment, a potential PEST motif's hydrophobicity is calculated as the sum over the products of mole percent and hydrophobicity index for each amino acid species. The desired PEST score is obtained as combination of local enrichment term and hydrophobicity term as expressed by the following equation:

PEST score=0.55*DEPST−0.5*hydrophobicity index.

In another embodiment, "PEST sequence," "PEST-like sequence" or "PEST-like sequence peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the methods and compositions as provided herein.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:1169-76). In another embodiment, the following method is used:

A PEST index is calculated for each stretch of appropriate length (e.g. a 30-35 amino acid stretch) by assigning a value of 1 to the amino acids Ser, Thr, Pro, Glu, Asp, Asn, or Gln. The coefficient value (CV) for each of the PEST residue is 1 and for each of the other amino acids (non-PEST) is 0.

Each method for identifying a PEST-like sequence represents a separate embodiment as provided herein.

In another embodiment, the PEST-like sequence is any other PEST-like sequence known in the art. Each PEST-like sequence and type thereof represents a separate embodiment as provided herein.

In one embodiment, the present invention provides fusion proteins, which in one embodiment, are expressed by *Listeria*. In one embodiment, such fusion proteins are fused to a PEST-like sequence which, in one embodiment, refers to fusion to a protein fragment comprising a PEST-like sequence. In another embodiment, the term includes cases wherein the protein fragment comprises surrounding sequence other than the PEST-like sequence. In another embodiment, the protein fragment consists of the PEST-like sequence. Thus, in another embodiment, "fusion" refers to two peptides or protein fragments either linked together at their respective ends or embedded one within the other. Each possibility represents a separate embodiment of the methods and compositions as provided herein.

In another embodiment, a recombinant *Listeria* strain of the compositions and methods as provided herein comprises a full length LLO polypeptide, which in one embodiment, is hemolytic.

In another embodiment, the recombinant *Listeria* strain comprises a non-hemolytic LLO polypeptide. In another embodiment, the polypeptide is an LLO fragment. In another embodiment, the oligopeptide is a complete LLO protein. In another embodiment, the polypeptide is any LLO protein or fragment thereof known in the art. Each possibility represents a separate embodiment of the methods and compositions as provided herein.

In another embodiment, an LLO protein fragment is utilized in compositions and methods as provided herein. In one embodiment, a truncated LLO protein is encoded by the episomal expression vector as provided herein that expresses a polypeptide, that is, in one embodiment, an antigen, in another embodiment, an angiogenic factor, or, in another embodiment, both an antigen and angiogenic factor. In another embodiment, the LLO fragment is an N-terminal fragment.

In another embodiment, the N-terminal LLO fragment has the sequence:
MKKIMLVFITLILVSLPIAQQTEAKDASAFNKENSIS SVAPPASPPASPKTPIE KKHADEIDKYIQGLDYNKNNVLVYHGDAVTNVPPRKGYKDGNEYIVVEKKKKSIN QNNADIQVVNAISSLTYPGALVKANSELVENQPDVLPVKRDSLTLSIDLPGMTNQDN KIVVKNATKSNVNNAVNTLVERWNEKYAQAYSNVSAKIDYDDEMAYSESQLIAKF GTAFKAVNNSLNVNFGAISEGKMQEEVISFKQIYYNVNVNEPTRPSRFFGKAVTKEQ LQALGVNAENPPAYISSVAYGRQVYLKLSTNSHSTKVKAAFDAAVSGKSVSGDVEL TNIIKNSSFKAVIYGGSAKDEVQIIDGNLGDLRDILKKGATFNRETPGVPIAYTTNFLK DNELAVIKNNSEYIETTSKAYTDGKINIDHSGGYVAQFNISWDEVNYD (SEQ ID NO: 10). In another embodiment, an LLO AA sequence of methods and compositions as provided herein comprises the sequence set forth in SEQ ID No: 10. In another embodiment, the LLO AA sequence is a homologue of SEQ ID No: 10. In another embodiment, the LLO AA sequence is a variant of SEQ ID No: 10. In another embodiment, the LLO AA sequence is a fragment of SEQ ID No: 10. In another embodiment, the LLO AA sequence is an isoform of SEQ ID No: 10. Each possibility represents a separate embodiment of the methods and compositions as provided herein.

In another embodiment, the LLO fragment has the sequence:
mkkimlvfitlilvslpiaqqteakdasafnkensissvappasppaspktpiekkhadeidkyiqgldynknnylv yhgdavtnvpprkgykdgneyivvekkkksinqnnadiqvvnaissltypgalvkanselvenqpdvlpvkrdsltlsidlpgm tnqdnkivvknatksnvnnavntlverwnekyaqaysnvsakidyddemaysesqliakfgtafkavnnslnvnfgaisegk mqeevisfkqiyynvnvneptrpsrffgkavtkeqlqalgvnaenppayissvaygrqvylklstnshstkvkaafdaavsgksv sgdveltniiknssfkaviyggsakdevqiidgnlgdlrdilkkgatfnretpgvpiayttnflkdnelaviknnseyiettskaytd (SEQ ID NO: 11). In another embodiment, an LLO AA sequence of methods and compositions as provided herein comprises the sequence set forth in SEQ ID No: 11. In another embodiment, the LLO AA sequence is a homologue of SEQ ID No: 11. In another embodiment, the LLO AA sequence is a variant of SEQ ID No: 11. In another embodiment, the LLO AA sequence is a fragment of SEQ ID No: 11. In another embodiment, the LLO AA sequence is an isoform of SEQ ID No: 11. Each possibility represents a separate embodiment of the methods and compositions as provided herein.

The LLO protein used in the compositions and methods as provided herein has, in another embodiment, the sequence:
MKKIMLVFITLILVSLPIAQQTEAKDASAFNKENSISSMAPPASPPASPKTPIE KKHADEIDKYIQGLDYNKNNVLVYHGDAVTNVPPRKGYKDGNEYIVVEKKKKSIN QNNADIQVVNAISSLTYPGALVKANSELVENQPDVLPVKRDSLTLSIDLPGMTNQD NKIVVKNATKSNVNNAVNTLVERWNEKYAQAYPNVSAKIDYDDEMAYSESQLIAK FGTAFKAVNNSLNVNFGAISEGKMQEEVISFKQIYYNVNVNEPTRPSRFFGKAVTKE QLQALGVNAENPPAYISSVAYGRQVYLKLSTNSHSTKVKAAFDAAVSGKSVSGDV ELTNIIKNSSFKAVIYGGSAKDEVQIIDGNLGDLRDILKKGATFNRETPGVPIAYTTNF LKDNELAVIKNNSEYIETTSKAYTDGKINIDHSGGYVAQFNISWDEVNYDPEGNEIV QHKNWSENNKSKLAHFTSSIYLPGNARNINVYAKECTGLAWEWWRTVIDDRNLPL VKNRNISIWGTTLYPKYSNKVDNPIE (GenBank Accession No. P13128; SEQ ID NO: 12; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a vaccine as provided herein. In another embodiment, an LLO AA sequence of methods and compositions as provided herein comprises the sequence set forth in SEQ ID NO: 12. In another embodiment, the LLO AA sequence is a homologue of SEQ ID NO: 12. In another embodiment, the LLO AA sequence is a variant of SEQ ID NO: 12. In another embodiment, the LLO AA sequence is a fragment of SEQ ID NO: 12. In another embodiment, the LLO AA sequence is an isoform of SEQ ID NO: 12. Each possibility represents a separate embodiment as provided herein.

The LLO protein used in the compositions and methods as provided herein has, in another embodiment, the sequence:

MKKIMLVFITLILVSLPIAQQTEAKDASAFNKEN-SISSVAPPASPPASPKTPIEKKHAD EIDKYIQGL-DYNKNNVLVYHGDAVTNVPPRKGYKDGNEYIV-VEKKKKSINQNNADI QVVNAISSLTYPGALVKANSELVENQPDVLPVKRD-SLTLSIDLPGMTNQDNKIVVKN ATKSNVN-NAVNTLVERWNEKYAQAYSNVSAKIDYDDEMAY-SESQLIAKFGTAFKA VNNSLNVNFGAISEGKMQEEVISFKQIYYNVNVNEP-TRPSRFFGKAVTKEQLQALGV NAENPPAYISS-VAYGRQVYLKLSTNSHSTKVKAAFDAAVSGKSVS-GDVELTNIIKNS SFKAVIYGGSAKDEVQIIDGNLGDLRDILKKGATFN-RETPGVPIAYTTNFLKDNELAV IKNNSEYIETTS-KAYTD (SEQ ID NO: 13). In another embodiment, an LLO AA sequence of methods and compositions as provided herein comprises the sequence set forth in SEQ ID NO: 13. In another embodiment, the LLO AA sequence is a homologue of SEQ ID NO: 13. In another embodiment, the LLO AA sequence is a variant of SEQ ID NO: 13. In another embodiment, the LLO AA sequence is a fragment of SEQ ID NO: 13. In another embodiment, the LLO AA sequence is an isoform of SEQ ID NO: 13. Each possibility represents a separate embodiment as provided herein.

In one embodiment, the amino acid sequence of the LLO polypeptide of the compositions and methods as provided herein is from the *Listeria monocytogenes* 10403S strain, as set forth in Genbank Accession No.: ZP_01942330, EBA21833, or is encoded by the nucleic acid sequence as set forth in Genbank Accession No.: NZ_AARZ01000015 or AARZ01000015.1. In another embodiment, the LLO sequence for use in the compositions and methods as provided herein is from *Listeria monocytogenes*, which in one embodiment, is the 4b F2365 strain (in one embodiment, Genbank accession number: YP_012823), the EGD-e strain (in one embodiment, Genbank accession number: NP_463733), or any other strain of *Listeria monocytogenes* known in the art.

In another embodiment, the LLO sequence for use in the compositions and methods as provided herein is from Flavobacteriales bacterium HTCC2170 (in one embodiment, Genbank accession number: ZP_01106747 or EAR01433; in one embodiment, encoded by Genbank accession number: NZ_AAOC01000003). In one embodiment, proteins that are homologous to LLO in other species, such as alveolysin, which in one embodiment, is found in *Paenibacillus alvei* (in one embodiment, Genbank accession number: P23564 or AAA22224; in one embodiment, encoded by Genbank accession number: M62709) may be used in the compositions and methods as provided herein. Other such homologous proteins are known in the art.

Each LLO protein and LLO fragment represents a separate embodiment of the methods and compositions as provided herein.

In another embodiment, homologues of LLO from other species, including known lysins, or fragments thereof may be used to create a fusion protein of LLO with an antigen of the compositions and methods as provided herein, which in one embodiment, is HMW-MAA, and in another embodiment is a fragment of HMW-MAA.

In another embodiment, the LLO fragment of methods and compositions as provided herein, is a PEST-like domain. In another embodiment, an LLO fragment that comprises a PEST sequence is utilized as part of a composition or in the methods as provided herein.

In another embodiment, the LLO fragment does not contain the activation domain at the carboxy terminus. In another embodiment, the LLO fragment does not include cysteine 484. In another embodiment, the LLO fragment is a non-hemolytic fragment. In another embodiment, the LLO fragment is rendered non-hemolytic by deletion or mutation of the activation domain. In another embodiment, the LLO fragment is rendered non-hemolytic by deletion or mutation of cysteine 484. In another embodiment, an LLO sequence is rendered non-hemolytic by deletion or mutation at another location.

In another embodiment, the LLO fragment consists of about the first 441 AA of the LLO protein. In another embodiment, the LLO fragment comprises about the first 400-441 AA of the 529 AA full length LLO protein. In another embodiment, the LLO fragment corresponds to AA 1-441 of an LLO protein disclosed herein. In another embodiment, the LLO fragment consists of about the first 420 AA of LLO. In another embodiment, the LLO fragment corresponds to AA 1-420 of an LLO protein disclosed herein. In another embodiment, the LLO fragment consists of about AA 20-442 of LLO. In another embodiment, the LLO fragment corresponds to AA 20-442 of an LLO protein disclosed herein. In another embodiment, any ΔLLO without the activation domain comprising cysteine 484, and in particular without cysteine 484, are suitable for methods and compositions as provided herein.

In another embodiment, the LLO fragment corresponds to the first 400 AA of an LLO protein. In another embodiment, the LLO fragment corresponds to the first 300 AA of an LLO protein. In another embodiment, the LLO fragment corresponds to the first 200 AA of an LLO protein. In another embodiment, the LLO fragment corresponds to the first 100 AA of an LLO protein. In another embodiment, the LLO fragment corresponds to the first 50 AA of an LLO protein, which in one embodiment, comprises one or more PEST-like sequences.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

In another embodiment, a recombinant *Listeria* strain of the methods and compositions as provided herein comprise a nucleic acid molecule operably integrated into the *Listeria* genome as an open reading frame with an endogenous ActA sequence. In another embodiment, an episomal expression vector as provided herein comprises a fusion protein comprising an antigen fused to an ActA or a truncated ActA. In one embodiment, the antigen is HMW-MAA, while in another embodiment, it's an immunogenic fragement of HMW-MAA.

In one embodiment, an antigen of the methods and compositions as provided herein is fused to an ActA protein, which in one embodiment, is an N-terminal fragment of an ActA protein, which in one embodiment, comprises or consists of the first 390 AA of ActA, in another embodiment, the first 418 AA of ActA, in another embodiment, the first 50 AA of ActA, in another embodiment, the first 100 AA of ActA, which in one embodiment, comprise a PEST-like sequence such as that provided in SEQ ID NO: 2. In another embodiment, an N-terminal fragment of an ActA protein utilized in methods and compositions as provided herein comprises or consists of the first 150 AA of ActA, in another embodiment, the first approximately 200 AA of ActA, which in one embodiment comprises 2 PEST-like sequences as described herein. In another embodiment, an N-terminal fragment of an ActA protein utilized in methods and compositions as provided herein comprises or consists of the first 250 AA of ActA, in another embodiment, the first 300 AA of ActA. In another embodiment, the ActA fragment contains residues of a homologous ActA protein that correspond to one of the above AA ranges. The residue numbers need not, in another embodiment, correspond exactly with the residue numbers enumerated above; e.g. if the homologous ActA protein has an insertion or deletion, relative to an ActA protein utilized herein, then the residue numbers can be adjusted accordingly, as would be routine to a skilled artisan using sequence alignment tools such as NCBI BLAST that are well-known in the art.

In another embodiment, the N-terminal portion of the ActA protein comprises 1, 2, 3, or 4 PEST-like sequences, which in one embodiment are the PEST-like sequences specifically mentioned herein, or their homologs, as described herein or other PEST-like sequences as can be determined using the methods and algorithms described herein or by using alternative methods known in the art.

An N-terminal fragment of an ActA protein utilized in methods and compositions as provided herein has, in another embodiment, the sequence set forth in SEQ ID NO: 14: MRAMMVVFITANCITINPDIIFAATDSEDSSLNT-DEWEEEKTEEQPSEVNTGPRYETA REVSSRDIKELEKSNKVRNTNKADLIAMLKEKAEK-GPNINNNNSEQTENAAINEEAS GADRPAIQVERRH-PGLPSDSAAEIKKRRKAIASSDSELESLTYPDKPTK-VNKKKVAK ESVADASESDLDSSMQSADESSPQPLKANQQPFFPK-VFKKIKDAGKWVRDKIDENPE VKKAIVDKSA-GLIDQLLTKKKSEEVNASDFPPPPTDEELRLALPETP-MLLGFNAPATS EPSSFEFPPPPTDEELRLALPETPMLLGFNAPAT-SEPSSFEFPPPPTEDELEIIRETASSLD SSFTRGDLASL-RNAINRHSQNFSDFPPIPTEEELNGRGGRP (SEQ ID NO: 14). In another embodiment, the ActA fragment comprises the sequence set forth in SEQ ID NO: 14. In another embodiment, the ActA fragment is any other ActA fragment known in the art. In another embodiment, the ActA protein is a homologue of SEQ ID NO: 14. In another embodiment, the ActA protein is a variant of SEQ ID NO: 14. In another embodiment, the ActA protein is an isoform of SEQ ID NO: 14. In another embodiment, the ActA protein is a fragment of SEQ ID NO: 14. In another embodiment, the ActA protein is a fragment of a homologue of SEQ ID NO: 14. In another embodiment, the ActA protein is a fragment of a variant of SEQ ID NO: 14. In another embodiment, the ActA protein is a fragment of an isoform of SEQ ID NO: 14. Each possibility represents a separate embodiment as provided herein. Each possibility represents a separate embodiment as provided herein.

In another embodiment, the recombinant nucleotide encoding a fragment of an ActA protein comprises the sequence set forth in SEQ ID NO: 15: atgcgtgcgatgatggtg-gttttcattactgccaattgcattacgattaaccccgacataatatttgcagcgaca-gatagcgaagattcta gtctaaacacagatgaatgggaagaagaaaaaaca-gaagagcaaccaagcgaggtaaatacgggaccaagatacgaaactgcac gtgaagtaagttcacgtgatattaaagaactagaaaaatcgaataaagt-gagaaatacgaacaaagcagacctaatagcaatgttgaa agaaaagca-gaaaaaggtccaaatatcaataataacaacagtgaacaaactgaagaatgcggc-tataaatgaagaggcttcaggag ccgaccgaccagctatacaagtggagcgtcgtcatccaggattgccatcgga-tagcgcagcggaaattaaaaaaagaaggaaagc catagcatcatcggatagt-gagcttgaaagccttacttatccggataaaccaacaaaag-taaataagaaaaaagtggcgaaagagtc agttgcggatgcttctgaaagtgacttagattctagcatgcagtcagcagat-gagtcttcaccacaacctttaaaagcaaaccaacaac cattttccctaaagtatt-taaaaaaataaaagatgcggggaaatgggtacgtgataaaatcgacgaaaatcct-gaagtaaagaaagc gattgttgataaaagtgcagggttaattgaccaattattaaccaaaaagaaaagt-gaagaggtaaatgcttcggacttcccgccaccac ctacggatgaagagt-taagacttgctttgccagagacaccaatgcttcttggttttaatgctcctgctacatca-gaaccgagctcattcg aatttccaccaccacctacggatgaagagttaagacttgctttgccagagacgc-caatgcttcttggttttaatgctcctgctacatcgga accgagctcgttcgaatttc-caccgcctccaacagaagatgaactagaaatcatccgggaaacagcatc-ctcgctagattctagtttta caagaggggatttagctagtttgagaaatgctattaatcgccatagt-caaaatttctctgatttcccaccaatcccaacagaagaagagt tgaacgggagag-gcggtagacca (SEQ ID NO: 15). In another embodiment, the recombinant nucleotide has the sequence set forth in SEQ ID NO: 15. In another embodiment, the recombinant nucleotide comprises any other sequence that encodes a fragment of an ActA protein. Each possibility represents a separate embodiment of the methods and compositions as provided herein.

An N-terminal fragment of an ActA protein utilized in methods and compositions as provided herein has, in another embodiment, the sequence set forth in SEQ ID NO: 16: MRAMMVVFITANCITINPDIIFAATDSEDSSLNT-DEWEEEKTEEQPSEVNTGPRYETA REVSSRDIEELEKSNKVKNTNKADLIAMLKAKAEK-GPNNNNNNGEQTGNVAINEEA SGVDRPTLQVERRH-PGLSSDSAAEIKKRRKAIASSDSELESLTYPDKPT-KANKRKVA KESVVDASESDLDSSMQSADESTPQPLKANQKPFFP-KVFKKIKDAGKWVRDKIDEN PEVKKAIVDKSA-GLIDQLLTKKKSEEVNASDFPPPPTDEELRLALPETP-MLLGFNAPT PSEPSSFEFPPPPTDEELRLALPETPMLLGFNAPAT-SEPSSFEFPPPPTEDELEIMRETAP SLDSSFTSGDLASL-RSAINRHSENFSDFPLIPTEEELNGRGGRP (SEQ ID NO: 16), which in one embodiment is the first 390 AA for ActA from *Listeria monocytogenes*, strain 10403S. In another embodiment, the ActA fragment comprises the sequence set forth in SEQ ID NO: 16. In another embodiment, the ActA fragment is any other ActA fragment known in the art. In another embodiment, the ActA protein is a homologue of SEQ ID NO: 16. In another embodiment, the ActA protein is a variant of SEQ ID NO: 16. In another embodiment, the ActA protein is an isoform of SEQ ID NO: 16. In another embodiment, the ActA protein is a fragment of SEQ ID NO: 16. In another embodiment, the ActA protein is a fragment of a homologue of SEQ ID NO: 16. In another embodiment, the ActA protein is a fragment of a variant of SEQ ID NO: 16. In another embodiment, the ActA protein is a fragment of an isoform of SEQ ID NO: 16. Each possibility represents a separate embodiment of the methods and compositions as provided herein.

In another embodiment, the recombinant nucleotide encoding a fragment of an ActA protein comprises the sequence set forth in SEQ ID NO: 17: atgcgtgcgatgatgg-tagttttcattactgccaactgcattacgattaaccccgacataatatttgcagcgaca-gatagcgaagattcc a gtctaaacacagatgaatgggaagaagaaaaaaca-gaagagcagccaagcgaggtaaatacgggaccaagatacgaaactgcac gtgaagtaagttcacgtgatattgaggaactagaaaaatcgaataaagt-gaaaaatacgaacaaagcagacctaatagcaatgttgaa agcaaaagcaga-gaaaggtccgaataacaataataacaacggtgagcaaacaggaaatgtggc-tataaatgaagaggcttcaggag tcgaccgaccaactctgcaagtggagcgtcgtcatccaggtctgtcatcgga-tagcgcagcggaaattaaaaaaagaagaaaagcc atagcgtcgtcggatagt-gagcttgaaagccttacttatccagataaaccaacaaaagcaaataaga-gaaaagtggcgaaagagtca gttgtggatgcttctgaaagtgacttagattctagcatgcagtcagcagacgagtctacaccacaacctttaaaagcaaatcaaaaacca tttttccctaaagtatt-
taaaaaaataaaagatgcggggaaatgggtacgtgataaaatcgacgaaaatcct-
gaagtaaagaaagcgatt
gttgataaaagtgcagggttaattgaccaattattaaccaaaaagaaaagt-
gaagaggtaaatgcttcggacttcccgccaccacctac ggatgaagagt-
taagacttgctttgccagagacaccgatgcttctcggttttaatgctcctactccateg-
gaaccgagctcattcgaatttc
cgccgccacctacggatgaagagttaagacttgctttgccagagacgccaatgct-
tcttggttttaatgctcctgctacatcggaaccga gctcattcgaatttccaccgc-
ctccaacagaagatgaactagaaattatgcgggaaacagcaccttcgctagat-
tctagttttacaagcg
gggatttagctagtttgagaagtgctattaatcgccatagcgaaaatttctctgatttc-
ccactaatcccaacagaagaagagttgaacgg gagaggcggtagacca (SEQ
ID NO: 17), which in one embodiment, is the first 1170
nucleotides encoding ActA in *Listeria monocytogenes*
10403S strain. In another embodiment, the recombinant nucleotide has the sequence set forth in SEQ ID NO: 17. In another embodiment, the recombinant nucleotide comprises any other sequence that encodes a fragment of an ActA protein. Each possibility represents a separate embodiment of the methods and compositions as provided herein.

In another embodiment, the ActA fragment is another ActA fragment known in the art, which in one embodiment, is any fragment comprising a PEST sequence. Thus, in one embodiment, the ActA fragment is amino acids 1-100 of the ActA sequence. In another embodiment, the ActA fragment is amino acids 1-200 of the ActA sequence. In another embodiment, the ActA fragment is amino acids 200-300 of the ActA sequence. In another embodiment, the ActA fragment is amino acids 300-400 of the ActA sequence. In another embodiment, the ActA fragment is amino acids 1-300 of the ActA sequence. In another embodiment, a recombinant nucleotide as provided herein comprises any other sequence that encodes a fragment of an ActA protein. In another embodiment, the recombinant nucleotide comprises any other sequence that encodes an entire ActA protein. Each possibility represents a separate embodiment of the methods and compositions as provided herein.

In one embodiment, the ActA sequence for use in the compositions and methods as provided herein is from *Listeria monocytogenes*, which in one embodiment, is the EGD strain, the 10403S strain (Genbank accession number: DQ054585) the NICPBP 54002 strain (Genbank accession number: EU394959), the S3 strain (Genbank accession number: EU394960), the NCTC 5348 strain (Genbank accession number: EU394961), the NICPBP 54006 strain (Genbank accession number: EU394962), the M7 strain (Genbank accession number: EU394963), the S19 strain (Genbank accession number: EU394964), or any other strain of *Listeria monocytogenes* which is known in the art.

In one embodiment, the sequence of the deleted actA region in the strain, (SEQ ID NO: 18)

gcgccaaatcattggttgattggtgaggatgtctgtgtgcgtgggtcg cgagatgggcgaataagaagcattaaagatcctgacaaatataatcaa gcggctcatatgaaagattacgaatcgcttccactcacagaggaaggc gactggggcggagttcattataatagtggtatcccgaataaagcagcc tataatactatcactaaacttggaaaagaaaaaacagaacagctttat tttcgcgccttaaagtactatttaacgaaaaaatcccagtttaccgat gcgaaaaaagcgcttcaacaagcagcgaaagatttatatggtgaagat -continued gcttctaaaaaagttgctgaagcttgggaagcagttggggttaactga ttaacaaatgttagagaaaaattaattctccaagtgatattcttaaaa taattcatgaatatttttttcttatattagctaattaagaagataacta actgctaatccaatttttaacggaacaaattagtgaaaatgaaggccg aattttccttgttctaaaaaggttgtattagcgtatcacgaggaggga gtataagtgggattaaacagatttatgcgtgcgatgatggtggttttc attactgccaattgeattacgattaaccccgacgtcgacccatacgac gttaattcttgcaatgttagctattggcgtgttctctttaggggcgtt tatcaaaattattcaattaagaaaaaataattaaaaacacagaacgaa agaaaaagtgaggtgaatgatatgaaattcaaaaaggtggttctaggt atgtgcttgatcgcaagtgttctagtctttccggtaacgataaaagca aatgcctgttgtgatgaatacttacaaacacccgcagctccgcatgat attgacagcaaattaccacataaacttagttggtccgcggataacccg acaaatactgacgtaaatacgcactattggctttttaaacaagcggaa aaaatactagctaaagatgtaaatcatatgcgagctaatttaatgaat gaacttaaaaaattcgataaacaaatagctcaaggaatatatgatgcg gatcataaaaatccatattatgatactagtacatttttatctcatttt tataatcctgatagagataatacttatttgccgggttttgctaatgcg aaaataacaggagcaaagtatucaatcaatcggtgactgattaccgag aagggaa.

In one embodiment, the underlined region contains actA sequence element that is present in the LmddΔactA strain. In one embodiment, the bold sequence gtcgac represent the site of junction of the N-T and C-T sequence.

In one embodiment, the recombinant *Listeria* strain of the compositions and methods as provided herein comprise a first or second nucleic acid molecule that encodes a High Molecular Weight-Melanoma Associated Antigen (HMW-MAA), or, in another embodiment, a fragment of HMW-MAA.

In one embodiment, HMW-MAA is also known as the melanoma chondroitin sulfate proteoglycan (MCSP), and in another embodiment, is a membrane-bound protein of 2322 residues. In one embodiment, HMW-MAA is expressed on over 90% of surgically removed benign nevi and melanoma lesions, and is also expressed in basal cell carcinoma, tumors of neural crest origin (e.g. astrocytomas, gliomas, neuroblastomas and sarcomas), childhood leukemias, and lobular breast carcinoma lesions. In another embodiment, HMW-MAA is highly expressed on both activated pericytes and pericytes in tumor angiogeneic vasculature which, in another embodiment is associated with neovascularization in vivo. In another embodiment, immunization of mice with the recombinant *Listeria*, as provided herein, that expresses a fragment of HMW-MAA (residues 2160 to 2258), impairs the growth of tumors not engineered to express HMW-MAA (FIG. 9D). In another embodiment, immunization of mice with the recombinant *Listeria* expressing a fragment of HMW-MAA (residues 2160 to 2258) decreases the number of pericytes in the tumor vasculature. In another embodiment, immunization of mice with the recombinant *Listeria* expressing a fragment of HMW-MAA (residues 2160 to 2258) causes infiltration of $CD8^+$ T cells around blood vessels and into the tumor.

In one embodiment, a murine homolog of HMW-MAA, known as NG2 or AN2, has 80% homology to HMW-MAA, as well as similar expression pattern and function. In another embodiment, HMW-MAA is highly expressed on both activated pericytes and pericytes in tumor angiogenic vasculature. In one embodiment, activated pericytes are associated with neovascularization in vivo. In one embodiment, activated pericytes are involved in angiogenesis. In another embodiment, angiogenesis is important for survival of tumors. In another embodiment, pericytes in tumor angiogenic vasculature are associated with neovascularization in vivo. In another embodiment, activated pericytes are important cells in vascular development, stabilization, maturation and remodeling. Therefore, in one embodiment, besides its role as a tumor-associated antigen, HMW-MAA is also a potential universal target for anti-angiogenesis using an immunotherapeutic approach. As described herein (Example 8), results obtained using an Lm-based vaccine against this antigen has supported this possibility.

In another embodiment, one of the antigens of the methods and compositions provided herein is expressed in activated pericytes. In another embodiment, at least one of the antigens is expressed in activated pericytes.

The HMW-MAA protein from which HMW-MAA fragments as provided herein are derived is, in another embodiment, a human HMW-MAA protein. In another embodiment, the HMW-MAA protein is a mouse protein. In another embodiment, the HMW-MAA protein is a rat protein. In another embodiment, the HMW-MAA protein is a primate protein. In another embodiment, the HMW-MAA protein is from any other species known in the art. In another embodiment, the HMW-MAA protein is melanoma chondroitin sulfate proteoglycan (MCSP). In another embodiment, an AN2 protein is used in methods and compositions as provided herein. In another embodiment, an NG2 protein is used in methods and compositions as provided herein.

In another embodiment, the HMW-MAA protein of methods and compositions as provided herein has the sequence:
MQSGRGPPLPAPGLALALTLTMLARLASAASFF-GENHLEVPVATALTDIDL QLQFSTSQPEALLLLAAG-PADHLLLQLYSGRLQVRLVLGQEELRLQT-PAETLLSDSIP HTVVLTVVEGWATLSVDGFLNASSAVPGAPLEV-PYGLFVGGTGTLGLPYLRGTSRP LRGCLHAATLN-GRSLLRPLTPDVHEGCAEEFSASDDVALGFSGPHS-LAAFPAWGTQ DEGTLEFTLTTQSRQAPLAFQAGGRRGDFI-YVDIFEGHLRAVVEKGQGTVLLHNSVP VADGQPHEVSVHINAHRLEISVDQYPTHTSNRGVL-SYLEPRGSLLLGGLDAEASRHL QEHRLGLTPEAT-NASLLGCMEDLSVNGQRRGLREALLTRNMAAGCR-LEEEEYEDD AYGHYEAFSTLAPEAWPAMELPEPCVPEPGLPPV-FANFTQLLTISPLVVAEGGTAWL EWRHVQPTLDLME-AELRKSQVLFSVTRGARHGELELDIPGAQARKM-FTLLDVVNR KARFIHDGSEDTSDQLVLEVSVTARVPMPSCLRRGQ-TYLLPIQVNPVNDPPHIIFPHG SLMVILEHTQKPLG-PEVFQAYDPDSACEGLTFQVLGTSSGLP-VERRDQPGEPATEFSC RELEAGSLVYVHRGGPAQDLTFRVSDGLQASP-PATLKVVAIRPAIQIHRSTGLRLAQ GSAMPILPANLS-VETNAVGQDVSVLFRVTGALQFGELQKQGAGGVEG-AEWWATQA FHQRDVEQGRVRYLSTDPQHHAYDTVENLA-LEVQVGQEILSNLSFPVTIQRATVWM LRLE-PLHTQNTQQETLTTAHLEATLEEAGPSPPTFHYEV-VQAPRKGNLQLQGTRLSD GQGFTQDDIQAGRVTYGATARASEAVEDT-FRFRVTAPPYFSPLYTFPIHIGGDPDAPV LTNVLL-VVPEGGEGVLSADHLFVKSLNSASYLYEVMERPRH-GRLAWRGTQDKTTM VTSFTNEDLLRGRLVYQHDDSETTEDDIPFVATRQ-GESSGDMAWEEVRGVFRVAIQP VNDHAPVQTISRIF-HVARGGRRLLTTDDVAFSDADSGFADAQLVL-TRKDLLFGSIVA VDEPTRPIYRFTQEDLRKRRVLFVHSGADRG-WIQLQVSDGQHQATALLEVQASEPY LRVANGSSLV-VPQGGQGTIDTAVLHLDTNLDIRSGDEVHYHVTAG-PRWGQLVRAG QPATAFSQQDLLDGAVLYSHNGSLSPRDTMA-FSVEAGPVHTDATLQVTIALEGPLAP LKLVRHKKI-YVFQGEAAEIRRDQLEAAQEAVPPADIVFSVK-SPPSAGYLVMVSRGAL ADEPPSLDPVQSFSQEAVDTGRVLYLHSR-PEAWSDAFSLDVASGLGAPLEGVLVELE VLPAAIPLEAQNFSVPEGGSLTLAPPLLRVSGPY-FPTLLGLSLQVLEPPQHGALQKED GPQARTLSAF-SWRMVEEQLIRYVHDGSETLTDSFVLMANASEM-DRQSHPVAFTVTV LPVNDQPPILTTNTGLQMWEGATAPIPAEALRST-DGDSGSEDLVYTIEQPSNGRVVL RGAPGTEVRS-FTQAQLDGGLVLFSHRGTLDGGFRFRLS-DGEHTSPGHFFRVTAQKQ VLLSLKGSQTLTVCPGSVQPLSSQTLRASSSAGTD-PQLLLYRVVRGPQLGRLFHAQQ DSTGEALVN-FTQAEVYAGNILYEHEMPPEPFWEAHDTLELQLSSP-PARDVAATLAV AVSFEAACPQRPSHLWKNKGLWVPEGQRARIT-VAALDASNLLASVPSPQRSEHDVL FQVTQFPSRGQLLVSEEPLHAGQPHFLQSQ-LAAGQLVYAHGGGGTQQDGFHFRAHL QGPAGAS-VAGPQTSEAFAITVRDVNERPPQPQASVPLRLTRG-SRAPISRAQLSVVDPD SAPGEIEYEVQRAPHNGFLSLVGGGLGPVTRFTQAD-VDSGRLAFVANGSSVAGIFQL SMSDGASP-PLPMSLAVDILPSAIEVQLRAPLEVPQAL-GRSSLSQQQLRVVSDREEPEA AYRLIQGPQYGHLLVGGRPTSAFSQFQIDQGEV-VFAFTNFSSSHDHFRVLALARGVN ASAVVNVT-VRALLHVWAGGPWPQGATLRLDPTVLDAGELAN-RTGSVPRFRLLEGP RHGRVVRVPRARTEPGGSQLVEQFTQQDLEDGRLG-LEVGRPEGRAPGPAGDSLTLE LWAQGVPPAVASLD-FATEPYNAARPYSVALLSVPEAARTEAGKPESSTPT-GEPGPM ASSPEPAVAKGGFLSFLEANMFSVIIPMCLVLLLLAL-ILPLLFYLRKRNKTGKHDVQV LTAKPRNGLAGDTET-FRKVEPGQAIPLTAVPGQGPPPGGQPDPELLQFCRTP-NPALK NGQYWV (SEQ ID No: 19). In another embodiment, an HMW-MAA AA sequence of methods and compositions as provided herein comprises the sequence set forth in SEQ ID No: 19. In another embodiment, the HMW-MAA AA sequence is a homologue of SEQ ID No: 19. In another embodiment, the HMW-MAA AA sequence is a variant of SEQ ID No: 19. In another embodiment, the HMW-MAA AA sequence is a fragment of SEQ ID No: 19. In another embodiment, the HMW-MAA AA sequence is an isoform of SEQ ID No: 19. Each possibility represents a separate embodiment of the methods and compositions as provided herein.

In another embodiment, the HMW-MAA protein of methods and compositions as provided herein is encoded by the sequence:

atgcagtccggccgcggccccccacttccagcccccggcctggccttggctttgaccctgactatgttggccagacttg catccgcggcttccttcttcggtgagaaccacctggaggtgcctgtggccacggctctgaccgacatagacctgcagctgcagttctc cacgtcccagcccgaagccctccttctcctggcagcaggcccagctgaccacctcctgctgcagctctactctggacgcctgcaggt cagacttgttctgggccaggaggagctgaggctgcagactccagcagagacgctgctgagtgactccatccccacactgtggtgct gactgtcgtagagggctgggccacggttgtcagtcgatgggtttctgaacgcctctcagcagtcccaggagccccccctagaggtccc ctatgggctctttgttggggggcactgggacccttggcctgccctacctgaggggaaccagccgaccctgagggttgcctccatgc agccaccctcaatggccgcagcctcctccggcctctgaccccgatgtgcatgagggctgtgctgaagagttttctgccagtgatgat gtgccctgggctctctgggccccactctctggctgcctccctgcctggggcactcaggacgaaggaaccctagagtttacactca ccacacagagccggcaggcacccttggccttccaggcaggggccgcgtggggacttcatctatgtggacatatttgagggccac ctgcgggccgtggtgagaaggggccagggtaccgtattgctccacaacagtgtgcctgtggccgatgggcagccccatgaggtca gtgtccacatcaatgctcaccggctggaaatctccgtggaccagtaccctacgcatacttcgaaccgaggagtcctcagctacctgga gccacggggcagtctcctctctgggggctggatgcagaggcctctcgtcacctccaggaacaccgctgggcctgacaccgag gccaccaatgcctccctgctgggctgcatggaagaccctcagtgtcaatggccagaggcgggggctgcgggaagctttgctgacgcg caacatggcagccggctgcaggctggaggaggaggagtatgaggacgatgcctatggacattatgaagctttctccaccctggccc ctgaggcttggccagccatggagctgcctgagccatgcgtgcctgagccagggctgcctcctgtctttgccaatttcacccagctgctg actatcagcccactggtggtgggccgagggggcacagcctggcttgagtggaggcatgtgcagcccacgctggacctgatggagg ctgagctgcgcaaatcccaggtgctgttcagcgtgacccgagggggcacgccatggcgagctcgagctggacatcccgggagccca ggcacgaaaaatgttcacctcctggacgtggtgaaccgcaaggcccgcttcatccacgatggctctgaggacacctccgaccagct ggtgctggaggtgtcggtgacggctcgggtgcccatgcccatgccttcggaggggccaaacatacctcctgcccatccaggtcaa ccctgtcaatgacccaccccacatcatcttcccacatgcagcctcatggtgatcctggaacacacgcagaagccgctggggcctga ggttttccaggcctatgacccggactctgcctgtgagggcctcaccttccaggtccttggcacctcctctggcctccccgtggagcgcc gagaccagcctggggagccgcgaccgagttctcctgccgggagttggaggccggcagcctagtctatgtccaccgcggtggtcct gcacaggacttgacgttccgggtcagcgatggactgcaggccagccccccggccacgctgaaggtggtggccatccggccggcc atacagatccaccgcagcagggggttgcgactggccccaaggctctgccatgcccatcttgcccgccaacctgtcggtggagaccaat gccgtggggcaggatgtgagcgtgctgttccgcgtcactgggggccctgcagttttggggagctgcagaagcaggggcaggtggg gtggaggtgctgagtggtgggccacacaggcgttccaccagcgggatgtggagcagggccgcgtgaggtacctgagcactgac ccacagcaccacgcttacgacaccgtggagaacctggccctggaggtgcaggtggggccaggagatcctgagcaatctgtcctccc agtgaccatccagagagccactgtgtggatgctgcggctggagccactgcacactcagaacacccagcaggagccctcaccaca gcccacctggaggccaccctggaggaggcagcccaagcccccaaccttccattatgaggtggttcaggctcccaggaaaggcaaccttcaactacagggcacaaggcgtcagatggccagggcttcacccaggatgacatacaggctggccgggtgacctatggggcc acagcacgtgcctcagagcagtcgaggacaccttccgtttccgtgtcacagctccaccatatttctccccactctataccttccccatc cacattggtggtgacccagatgcgcctgtcctcgtggtgcctgagggtggtgagggtgtcctctctgctgacca cctctttgtcaagagtctcaacagtgccagctacctctatgaggtcatggagcggccccgccatggaggttggcttggcgtgggaca caggacaagaccactatggtgacatccttcaccaatgaagaccgttgcgtggccggctggtctaccagcatgatgactccgagacca cagaagatgatatcccatttgt tgctacccgccagggcgagagcagtggtgacatggcctgggaggaggtacggggtgtcttccgag tggccatccagcccgtgaatgaccacgcccctgtgcagaccatcagccggatcttccatgtggcccggggtgggcggcggctgctg actacagacgacgtggcctcagcgatgctgactcgggctttgctgacgcccagctggtgcttacccgcaaggacctcctcttggca gtatcgtggccgtagatgagccccacgcggcccatctaccgcttcacccaggagacctcaggaagaggcgagtactgttcgtgcact caggggctgaccgtggctgatccagctgcaggtgtccgacggggcaacaccaggccactgcgctgctggaggtgcaggcctcgg aaccctacctccgtgtggccaacggctccagccttgtggtccctcaaggggccagggcaccatcgacacggccgtgctccacctg gacaccaacctcgacatccgcagtggggatgaggtccactaccacgtcacagctggccctcgctggggacagctagtccgggctg gtcagccagccacagccttcccagcaggacctgctggatggggccgttctctatagccacaatggcagcctcagcccccgcgac accatggcctctccgtggaagcagggccagtgcacacggatgccaccctacaagtgaccattgccctagagggcccactggcccc actgaagctggtccggcacaagaagatctacgtcttccagggagaggcagctgagatcagaagggaccagctggaggcagccca ggaggcagtgccacctgcagacatcgtattctcagtgaagagcccaccgagtgccggctacctggtgatggtgtcgcgtggcgcctt ggcagatgagccacccagcctggacccgtgcagagcttctcccaggaggcagtggacacaggcagggtcctgtacctgcactccc gccctgaggcctggagcgatgccttctcgctggatgtggcctcaggcctgggtgctccctcgagggcgtcctgtgtggagctggagg tgctgcccgctgccatcccactagaggcgcaaaacttcagcgtccctgagggtgcagcctcacccggcccctccactgctccgtgt ctccgggccctacttcccactctcctgggcctcagcctgcaggtgctggagccaccccagcatggagccctgcagaaggaggacg gacctcaagccaggaccctcagccgccttctcctggagaatggtggaagagcagctgatccgctacgtgcatgacgggagcgagac actgacagacagttttgtcctgatggctaatgcctccgagatggatcgccagagccatcctgtggccttcactgtcactgtcctgcctgtc aatgaccaacccccatcctcactacaaacaggcctgcagatgtgggaggggccactgcgcccatccctgcggaggctctgag gagcacggacggcgactctgggtctgaggatcggtctacaccatcgagcagcccagcaacgggcgggtagtgctgcggggggc gccgggcactgaggtgcgcagcttcacgcaggcccagctggacggcgggctcgtgctgttctcacacagaggaacctggatgga ggcttccgcttcgcctctctgacggcgagcacacttcccccggacacttcttccgagtgacggcccagaagcaagtgctcctctcgc tgaagggcagccagacactgactgtctgcccagggtccgtcagccactcagcagtcagacccctcagggccagctccagcgcagg cactgaccccagctcctgctctaccgtgtggtgcgggggccccagctaggccggctgttccacgcccagcagacagcacaggg gaggccctggtgaacttcactcaggcagaggtctacgctgggaatattctgtatgagcatgagatgccccccgagccctttttgggagg cccatgatacccctagagctccagctgtcctcgccgcctgcccgggacgtggccgccacccttgctgtggctgtgtcttttgaggctgcc tgtcccagcgccccagccacctctggaagaacaaaggtctctgggtccccgagggccagcgggccaggatcaccgtggctgctct ggatgcctcaatctcttggccagcgttccatcaccccagcgctcagagcatgatgtgctcttccaggtcacacagttcccagccgg ggccagctgttggtgtccgaggagcccctccatgctgggcagcccccacttcctgcagtcccagctggctcagggcagctagtgtat gcccacgcgtgtgggggcacccagcaggatgcttccactttcgtgcccacctccaggggccagcaggggcctccgtggctggac cccaaacctcagaggcctttgccatcacggtgagggatgtaaatgagcggccccctcagccacaggcctctgtcccactccggctca cccgagggctctcgtcccccatctcccgggcccagctgagtgtggtggacccagactcagtcctggggagattgagtacgaggtc cagcggggcaccccacaacggcttcctcagcctggtgggtggtggcctggggccgtgacccgcttcacgcaagccgatgtggattc agggcgctggccttcgtggccaacgggagcagctggcaggcatcttccagctgagcatgtctgatggggcagcccaccctg cccatgtcccttggctgtggacatcctaccatccgccatcgaggtgcagct gcgggcacccctggaggtgccccaagctttggggcgc tcctcactgagcagcagcagctccgggtggtttcagatcgggaggagccagaggcagcataccgcctcatccagggaccccagta
tgggcatctcctggtgggcgggcggccacctcggccttcagccaattccagatagaccagggcgaggtggtctttgccttcaccaa cttctcctcctctcatgaccacttcagagtcctggcactggctaggggtgtcaatgcatcagccgtagtgaacgtcactgtgagggctct
gctgcatgtgtgggcaggtgggccatggccccagggtgccaccctgcgcctggaccccaccgtcctagatgctggcgagctggcc aaccgcacaggcagtgtgccgcgcttccgcctcctggagggaccccggcatggccgcgtggtccgcgtgccccgagccaggacg
gagcccgggggcagccagctggtggagcagttcactcagcaggaccttgaggacgggaggctggggctggaggtgggcaggcc agaggggagggcccccggccccgcaggtgacagtctcactctggagctgtgggcacagggcgtcccgcctgctgtggcctccctg
gactttgccactgagccttacaatgctgcccggccctacagcgtggccctgctcagtgtccccgaggccgcccggacggaagcagg gaagccagagagcagcaccccacaggcgagccaggcccccatggcatccagccctgagcccgctgtggccaagggaggcttcct
gagcttccttgaggccaacatgttcagcgtcatcatcccatgtgcctggtacttctgctcctggcgctcatcctgcccctgctcttctacc tccgaaaacgcaacaagacgggcaagcatgacgtccaggtcctgactgccaagccccgcaacggcctggctggtgacaccgaga
cctttcgcaaggtggagccaggccaggccatcccgctcacagctgtgcctggccagggccccctccaggaggccagcctgaccc agagctgctgcagttctgccggacacccaaccctgcccttaagaatggccagtactgggtgtgaggcctggcctggg
cccagatgct gatcgggccagggacaggc (SEQ ID No: 20). In another embodiment, the recombinant nucleotide has the sequence set forth in SEQ ID NO: 20. In another embodiment, an HMW-MAA-encoding nucleotide of methods and compositions as provided herein comprises the sequence set forth in SEQ ID No: 20. In another embodiment, the HMW-MAA-encoding nucleotide is a homologue of SEQ ID No: 20. In another embodiment, the HMW-MAA-encoding nucleotide is a variant of SEQ ID No: 20. In another embodiment, the HMW-MAA-encoding nucleotide is a fragment of SEQ ID No: 20. In another embodiment, the HMW-MAA-encoding nucleotide is an isoform of SEQ ID No: 20. Each possibility represents a separate embodiment of the methods and compositions as provided herein.

In another embodiment, the HMW-MAA protein of methods and compositions as provided herein has an AA sequence set forth in a GenBank entry having an Accession Numbers selected from NM_001897 and X96753. In another embodiment, the HMW-MAA protein is encoded by a nucleotide sequence set forth in one of the above GenBank entries. In another embodiment, the HMW-MAA protein comprises a sequence set forth in one of the above GenBank entries. In another embodiment, the HMW-MAA protein is a homologue of a sequence set forth in one of the above GenBank entries. In another embodiment, the HMW-MAA protein is a variant of a sequence set forth in one of the above GenBank entries. In another embodiment, the HMW-MAA protein is a fragment of a sequence set forth in one of the above GenBank entries. In another embodiment, the HMW-MAA protein is an isoform of a sequence set forth in one of the above GenBank entries. Each possibility represents a separate embodiment of the methods and compositions as provided herein.

The HMW-MAA fragment utilized in the present invention comprises, in another embodiment, AA 360-554. In another embodiment, the fragment consists essentially of AA 360-554. In another embodiment, the fragment consists of AA 360-554. In another embodiment, the fragment comprises AA 701-1130. In another embodiment, the fragment consists essentially of AA 701-1130. In another embodiment, the fragment consists of AA 701-1130. In another embodiment, the fragment comprises AA 2160-2258. In another embodiment, the fragment consists essentially of 2160-2258. In another embodiment, the fragment consists of 2160-2258. Each possibility represents a separate embodiment of the methods and compositions as provided herein.

In another embodiment, the recombinant Listeria of the compositions and methods as provided herein comprise a plasmid that encodes a recombinant polypeptide that is, in one embodiment, angiogenic, and in another embodiment, antigenic. In one embodiment, the polypeptide is HMW-MAA, and in another embodiment, the polypeptide is a HMW-MAA fragment. In another embodiment, the plasmid further encodes a non-HMW-MAA peptide. In one embodiment, the non-HMW-MAA peptide enhances the immunogenicity of the polypeptide. In one embodiment, the HMW-MAA fragment of methods and compositions as provided herein is fused to the non-HMW-MAA AA sequence. In another embodiment, the HMW-MAA fragment is embedded within the non-HMW-MAA AA sequence. In another embodiment, an HMW-MAA-derived peptide is incorporated into an LLO fragment, ActA protein or fragment, or PEST-like sequence. Each possibility represents a separate embodiment of the methods and compositions as provided herein.

The non-HMW-MAA peptide is, in one embodiment, a listeriolysin (LLO) oligopeptide. In another embodiment, the non-HMW-MAA peptide is an ActA oligopeptide. In another embodiment, the non-HMW-MAA peptide is a PEST-like oligopeptide. In one embodiment, fusion to LLO, ActA, PEST-like sequences and fragments thereof enhances the cell-mediated immunogenicity of antigens. In one embodiment, fusion to LLO, ActA, PEST-like sequences and fragments thereof enhances the cell-mediated immunogenicity of antigens in a variety of expression systems. In another embodiment, the non-HMW-MAA peptide is any other immunogenic non-HMW-MAA peptide known in the art. Each possibility represents a separate embodiment of the methods and compositions as provided herein.

In one embodiment, the recombinant Listeria strain of the compositions and methods as provided herein express a heterologous antigenic polypeptide that is expressed by a tumor cell. In one embodiment, the recombinant Listeria strain of the compositions and methods as provided herein comprise a first or second nucleic acid molecule that encodes a Prostate Specific Antigen (PSA), which in one embodiment, is a marker for prostate cancer that is highly expressed by prostate tumors, which in one embodiment is the most frequent type of cancer in American men and, in another embodiment, is the second cause of cancer related death in American men. In one embodiment, PSA is a kallikrein serine protease (KLK3) secreted by prostatic epithelial cells, which in one embodiment, is widely used as a marker for prostate cancer.

In one embodiment, the recombinant Listeria strain as provided herein comprises a nucleic acid molecule encoding KLK3 protein.

In another embodiment, the KLK3 protein has the sequence:
MWVPVVFLTLSVTWIGAAPLILSRIVGGWECEKH-SQPWQVLVASRGRAVC GGVLVHPQWVLTAAH-CIRNKSVILLGRHSLFHPEDTGQVFQVSHSFPHPLY-DMSLLK NRFLRPGDDSSHDLMLLRLS EPAEL TDAVKVMDLPTQEPALGTTCYASGWGSIEPEE FLTP-KKLQCVDLHVISNDVCAQVHPQKVTKFMLCAGR-WTGGKSTCSGDSGGPLVC NGVLQGITSWGSEP-CALPERPSLYTKVVHYRKWIKDTIVANP (SEQ ID No: 21; GenBank Accession No. CAA32915). In another embodiment, the KLK3 protein is a homologue of SEQ ID No: 21. In another embodiment, the KLK3 protein is a variant of SEQ ID No: 21. In another embodiment, the KLK3 protein is an isomer of SEQ ID No: 21. In another embodiment, the KLK3 protein is a fragment of SEQ ID No: 21. Each possibility represents a separate embodiment of the methods and compositions as provided herein.

In another embodiment, the KLK3 protein has the sequence:
IVGGWECEKHSQPWQVLVASRGRAVCGGVLVH-PQWVLTAAHCIRNKSVIL LGRHSLFHPEDT-GQVFQVSHSFPHPLYDMSLLKNRFLRPGDDSSH-DLMLLRLSEPAE LTDAVKVMDLPTQEPALGTTCYASGWGSIEPEEFLTP-KKLQCVDLHVISNDVCAQV HPQKVTKFMLCAGR-WTGGKSTCSGDSGGPLVCYGVLQGITSWGSEP-CALPERPSLY TKVVHYRKWIKDTIVANP (SEQ ID No: 22). In another embodiment, the KLK3 protein is a homologue of SEQ ID No: 22. In another embodiment, the KLK3 protein is a variant of SEQ ID No: 22. In another embodiment, the KLK3 protein is an isomer of SEQ ID No: 22. In another embodiment, the KLK3 protein is a fragment of SEQ ID No: 22. Each possibility represents a separate embodiment of the methods and compositions as provided herein.

In another embodiment, the KLK3 protein has the sequence: IVGGWECEKHSQPWQVLVASRGRAVCGGV-LVHPQWVLTAAHCIRNKSVILLGRHS LFHPEDT-GQVFQVSHSFPHPLYDMSLLKNRFLRPGDDSSH-DLMLLRLSEPAELTDAV KVMDLPTQEPALGTTCYASGWGSIEPEEFLTPK-KLQCVDLHVISNDVCAQVHPQKV TKFMLCAGR-WTGGKSTCSGDSGGPLVCNGVLQGITSWGSEP-CALPERPSLYTKVVH YRKWIKDTIVANP (SEQ ID No: 23; GenBank Accession No. AAA59995.1). In another embodiment, the KLK3 protein is a homologue of SEQ ID No: 23. In another embodiment, the KLK3 protein is a variant of SEQ ID No: 23. In another embodiment, the KLK3 protein is an isomer of SEQ ID No: 23. In another embodiment, the KLK3 protein is a fragment of SEQ ID No: 23. Each possibility represents a separate embodiment of the methods and compositions as provided herein.

In another embodiment, the KLK3 protein is encoded by a nucleotide molecule having the sequence: ggtgtcttaggca-cactggtcttggagtgcaaaggatctaggcacgtgaggctttgtat-gaagaatcggggatcgtacccaccccctgt ttctgttcatcctggcatgtctc-ctctgcctttgtccctagatgaagtctccatgagctacaaggctggtgca tccagggtgatcta gtaattgcagaacagcaagtgctagctctccctccccttc-cacagctctgggtgtgggagggggttgtccagcctccagcagcatggg gagggccttggtcagcctctgggtgccagcagggcagggcggagtc-ctggggaatgaaggttttatagggctcctgggggaggc tccccagccccaagct-taccacctgcaccccgagagctgtgtcaccatgtgggtcccggttgtcttcctcac-cctgtccgtgacgtgga ttggtgagaggggccatggttggggggatgcaggagagggagccagccct-gactgtcaagctgaggctctttcccccccaacccag caccccagcccagaca-gggagctgggctcttttctgtctctcccagccccacttcaagcccataccccagtc-ccctcatattgcaac agtcctcactcccacaccaggtccccgctccctcccacttacccagaactttcttc-ccatttgcccagccagctccctgctcccagctg ctttactaaagggaagttc-ctgggcatctccgt gtttctctttgtggggctcaaaacctccaaggacctctctcaat-gccattggttcctg gaccgtatcactggtccatctcctgagcccctcaatcctatcacagtctact-gacttttccattcagctgtgagtgtccaacccctatccca gagaccttgatgcttg-gcctcccaatcttgcccctaggatacccagatgcaaccagacacctccttctttc-ctagccaggctatctggcc tgagacaacaaatgggtccctcagtctggcaatgggactctgagaactcctcattc-cctgactcttagccccagactcttcattcagtgg cccacattttccttaggaaaaacatgagcatccccagccacaactgccagctctctgagtccccaaatctg-catccttttcaaaacctaaa aacaaaaagaaaaacaaataaaacaaaaccaactcagaccagaactgttttct-caacctgggacttcctaaactttccaaaaccttcctc ttccagcaactgaacctcgc-cataaggcacttatccctggttcctagcacccccttatccccctcagaatccacaacttg-taccaagtttccct tctcccagtccaagaccccaaatcaccacaaaggacccaatcccagact-caagatatggtctgggcgctgtcttgtgtctcctaccct gatccctgggttcaactct-gctcccagagcatgaagcctctccaccagcaccagccaccaacctgcaaac-ctagggaagattgacag aattcccagcctttcccagctccccctgcccatgtcccaggactcccagccttggt-tctctgccccgtgtcttttcaaacccacatccta aatccatctcctatccgagtc-ccccagttcccctgtcaaccctgattccctgatctagcaccccctctgcag-gcgctgcgcccctcat cctgtctcggattgtggaggctgggagtgcgagaagcattcccaaccctggca-ggtgcttgtggcctctcgtggcagggcagtctg cggcggtgttctggtgcac-cccagtgggtcctcacagctgcccactgcatcaggaagtgagtaggggc-ctgggggtctggggagca ggtgtctgtgtcccagagggaataacagctgggcatttccccaggataac-ctctaaggccagccttgggactggggagagagggaa agttctggttcaggtca-catggggaggcagggttggggctggaccaccctccccatggctgcctgggtctc-catctgtgtccctctatg tctctttgtgtcgctttcattatgtctcttggtaactggcttcggttgtgtctctccgt-gtgactattttgttctctctccctctcttctctgtcttc agtctccatatctc-ccctctctctgtccttctctggtccctctctagccagtgtgtctcaccctg-tatctctctgccaggctctgtctctcggt ctctgtctcacctgtgccttctccctactgaacacacgcacgggatgggc-ctggggacctgagaaaaggaagggctttggctggg cgcggtggctcacac-ctgtaatcccagcactttgggaggccaaggcaggtagatcacctgaggtcag-gagttcgagaccagcctgg ccaactggtgaaacccatctctactaaaaatacaaaaaattagccaggcgtggtg-gcgcatgcctgtagtcccagctactcaggagc tgagggaggagaattgcatt-gaacctggaggttgaggttgcagtgagccgagaccgtgccactgcactccagc-ctgggtgacagag tgagactccgcctcaaaaaaaaaaaaaaaaaaaaaaaaaaaaaaaaaagaa aagaaaagaaaagaaaaggaagtgtttatccctgatgtg tgtgggtatgaggg-tatgagagggcccctctcactccattccttctccaggacatccctccactcttggga-gacacagagaagggctg gttccagctggagctgggaggggcaattgagggag-gaggaaggagaaggggggaaggaaaacagggtatggggaaaggaccc tggggagcgaagtggaggatacaaccttgggcctgcaggcaggctacctac-ccacttggaaacccacgccaaagccgcatctaca gctgagccactctgaggc-ctcccctccccgccggtccccactcagctccaaagtctctctccctttttctctccca-cactttatcatccccc ggattcctctctacttggttctcattcttcctttgacttcctgcttccctttctcat-tcatctgtttctcactttctgcctgttttgttcttctctctc tttctctggcccatgtct-gtttctctatgtttctgtctttctttctcatcctgtgtattttcggctcaccttgttt-gtcactgttctccctctgccctt tcattctctctgcccttttaccctcttccttttcccttggttctctcagttctgtatct-gcccttcaccctctcacactgctgtttcccaactcgttg tctgtattttggcctgaact-gtgtcttcccaaccctgtgtttctcactgtttcttttttctcttttggagcctcctccttt-gctcctctgtcccttctct ctttccttatcatcctcgctcctccattcc tgcgtctgcttcctccccagcaaaagcgtgatcttgctgggtcggcacagcct-gtttcatcctg aagacacaggccaggtatttcaggtcagccacagcttcccacac-ccgctctacgatatgagcctcctgaagaatcgattcctcaggcc aggtgatgactc-cagccacgacct catgctgctccgcctgtcagagcctgcc gagctcacggatgctgtgaaggtcatggacctgcc cacccaggagccag-cactggggaccacctgctacgcctcaggctggggcagcattgaaccagaggagt-gtacgcctgggccagat ggtgcagccgggagcccagatgcctgggtct-gaggaggagggacaggactcctg ggtctgagggaggagg gccaaggaaccaggtggggtccagcccacaacagt-gttttgcctggcccgtagtcttgacccaaagaaacttcagtgtgtggacctccat-gttatttcc aatgacgtgtgtgcgcaagttcaccctc agaaggtgaccaagttcat-gctgtgtgctggacgctggacaggggcaaaagcacctgc tcggtga gtcatccctactcccaagatcttgagggaaggtgagtgggaccttaat-tctggctggggtctagaagccaacaaggcgt ctgcctcccctgctcccagct-gtagccatgccacctcccccgtgtctcatctcattcc ctccttccctcttctttgactccctcaaggcaata ggttattcttacagcacaactcatctgttcctgcgttcagcacacggttactaggcacctgctatgcacccagcact-gccctagagcctg ggacatagcagtgaacagacagagagcagccctccttct-gtagcccccaagccagtgaggggcacaggcaggaacagggacc acaacacagaaaagctggagggtgtcaggaggtgatcag-gctctcggggagggagaagggtggggagtgtgactgggaggag acatcct-gcagaaggtgggagtgagcaaacacctgcgcaggggagggagggcctgcg-gcacctgggggagcagagggaaca gcatctggccaggcctgggaggaggggcctagagggcgtcaggagcagagag-gaggttgcctggctggagtgaaggatcgggg cagggtgcga-gagggaacaaaggacccctcctgcagggcctcacctgggccacaggagga-cactgcttttcctctgaggagtcag gaactgtggatggtgctggacagaagcaggacagggcctggctcaggtgtcca-gaggctgcgctggcctcctatgggatcagactg cagggagggagggcagca-gggatgtggagggagtgatgatggggctgacctggggtggctccaggcatt-gtccccacctgggc ccttacccagcctccctcacaggctcctggccctcagtctctcccctccactccat-tctccacctacccacagtgggtcattctgatcacc gaactgaccatgccagccct-gccgatggtcctccatggctcccagtgccctggagaggaggtgtctagtcaga-gagtagtcctgga aggtggcctgtgaggagccacggggacagcatcctgcagatggtcctggc-ccttgtcccaccgacctgtctacaaggactgtcct cgtggaccctcccctg-cacaggagctggaccctgaagtcccttcctaccggccaggactggagccctac-ccctctgttggaatcc ctgcccaccttcttctggaagtcggctctggagacatttctctcttcttc-caaagctgggaactgctatctgttatctgcctgtccaggtctg aaagataggatt-gcccaggcagaaactgggactgacctatctcactctctccctgcttttaccct-tagggtgattctgggggcccacttgt ctgtaatggtgtgcttcaaggtatcacgtcatggggcagtgaaccatgtgccctgc-ccgaaaggccttccctgtacaccaaggtggtgc attaccggaagtggat-caaggacaccatcgtggccaaccctgagcaccctatcaagtccctattgtag-taaacttggaaccttggaa atgaccaggccaagactcaagcctcccagttctactgaccttgtccttaggtgt-gaggtccaggttgctaggaaaagaaatcagca gacacaggtgtagacca-gagtgtttcttaaatggtgtaattttgtcctctctgtgtcctggggaatactggccat-gcctggagacatatca ctcaatttctctgaggacacagttaggatggggtgtctgttatttgtgggataca-gagatgaaagaggggtgggatcc (SEQ ID No: 24; GenBank Accession No. X14810). In another embodiment, the KLK3 protein is encoded by residues 401 . . . 446, 1688 . . . 1847, 3477 . . . 3763, 3907 . . . 4043, and 5413 . . . 5568 of SEQ ID No: 24. In another embodiment, the KLK3 protein is encoded by a homologue of SEQ ID No: 24. In another embodiment, the KLK3 protein is encoded by a variant of SEQ ID No: 24. In another embodiment, the KLK3 protein is encoded by an isomer of SEQ ID No: 24. In another embodiment, the KLK3 protein is encoded by a fragment of SEQ ID No: 24. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSHDLMLLRLSEPAELTDAVKVMDLPTQEPAL-GTTCYASGWGSIEPEEFLTPK KLQCVDLHVISNDV-CAQVHPQKVTKFMLCAGRWTGGKSTCSWVI-LITELTMPALPM VLHGSLVPWRGGV (SEQ ID No: 25; GenBank Accession No. NP_001025218) In another embodiment, the KLK3 protein is a homologue of SEQ ID No: 25. In another embodiment, the KLK3 protein is a variant of SEQ ID No: 25. In another embodiment, the KLK3 protein is an isomer of SEQ ID No: 25. In another embodiment, the KLK3 protein is a fragment of SEQ ID No: 25. Each possibility represents a separate embodiment as provided herein.

In another embodiment, the KLK3 protein is encoded by a nucleotide molecule having the sequence: agccccaagcttac-cacctgcacccggagagctgtgtcaccatgtgggtcccggttgtcttcctcaccct-gtccgtgacgtggattggt gctgcaccccctcatcctgtctcggattgtgggag-gctgggagtgcgagaagcattcccaaccctggcaggtgcttgtggcctctcgtg gcagggcagtctgcggccggtgttctggtgcacccccagtgggtcctcacagct-gcccactgcatcaggaacaaaagcgtgatcttgc tgggtcggcacagcct-gtttcatcctgaagacacaggccaggtatttcaggtcagccacagcttcccacac-ccgctctacgatatgag cctcctgaagaatcgattcctcaggccaggtgatgactccagccacgacctcat-gctgctccgcctgtcagagcctgccgagctcacg gatgctgtgaaggtcatg-gacctgcccacccaggagccagcactggggaccacctgctacgcctcag-gctggggcagcattgaac cagaggagttcttgaccccaaagaaacttcagtgtgtggacctccatgttatttc-caatgacgtgtgtgcgcaagttcaccctcagaagg tgaccaagttcatgctgtgt-gctggacgctggacaggggggcaaaagcacctgctcgtgggtcattctgatcac-cgaactgaccatgcc agccctgccgatggtcctccatggctcccagtgccctggagaggaggt-gtctagtcagagagtagtcctggaaggtggcctctgtga ggagc-cacggggacagcatcctgcagatggtcctggcccttgtcccaccgacctgtcta-caaggactgtcctcgtggaccctcccct ctgcacaggagctggaccctgaagtcccttcccaccggccaggactggagc-ccctaccccctctgttggaatccctgcccaccttctt ctggaagtcggctctggaga-catttctctcttcttccaaagctgggaactgctatctgttatctgcctgtccaggtct-gaaagataggattg cccaggcagaaactgggactgacctatctcactctctccctgcttttaccct-tagggtgattctgggggcccacttgtctgtaatggtgtg cttcaaggtatcacgt-catgggcagtgaaccatgtgccctgcccgaaaggccttccctgtacac-caaggtggtgcattaccggaagt ggatcaaggacaccatcgtggccaaccctgagcaccctatcaacccctattg-tagtaaacttggaaccttggaaatgaccaggcc aagactcaagcctcccagttc-tactgacctttgtccttaggtgtgaggtccagggttgctaggaaaagaaatcagca-gacacaggtgt agaccagagtgtttcttaaatggtgtaattttgtcctctctgtgtcctggggaatactg-gccatgcctggagacatatcactcaatttctctg aggacacagataggatgggt-gtctgtgttatttgtggggtacagagatgaaagaggggtgggatccacactgaga-gagtggagagt gacatgtgctggacactgtccatgaagcactgagcagaagctggaggcacaacg-caccagacactcacagcaaggatggagctga aaacataacccactctgtcctg-gaggcactgggaagcctagagaaggctgtgagccaaggagggagggtcttc-ctttggcatgggat ggggatgaagtaaggagagggactggaccccctggaagctgattcac-tatggggggaggtgtattgaagtcctccagacaaccctc agatttgatgatttc-ctagtagaactcacagaaataaagagctgttatactgtg (SEQ ID No: 26; GenBank Accession No. NM_001030047). In another embodiment, the KLK3 protein is encoded by residues 42-758 of SEQ ID No: 26. In another embodiment, the KLK3 protein is encoded by a homologue of SEQ ID No: 26. In another embodiment, the KLK3 protein is encoded by a variant of SEQ ID No: 26. In another embodiment, the KLK3 protein is encoded by an isomer of SEQ ID No: 26. In another embodiment, the KLK3 protein is encoded by a fragment of SEQ ID No: 26. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRK (SEQ ID No: 27; GenBank Accession No. NP_001025221). In another embodiment, the KLK3 protein is a homologue of SEQ ID No: 27. In another embodiment, the KLK3 protein is a variant of SEQ ID No: 27. In another embodiment, the sequence of the KLK3 protein comprises SEQ ID No: 27. In another embodiment, the KLK3 protein is an isomer of SEQ ID No: 27. In another embodiment, the KLK3 protein is a fragment of SEQ ID No: 27. Each possibility represents a separate embodiment of the methods and compositions as provided herein.

In another embodiment, the KLK3 protein is encoded by a nucleotide molecule having the sequence: agccccaagcttaccacctgcacccggagagctgtgtcaccatgtgggtcccggttgtcttcctcaccct- tccgtgacgtggattggtg ctgcacccctcatcctgtctcggattgtgggag- gctgggagtgcgagaagcattcccaaccctggcaggtgcttgtggcctctcgtg cagggcagtctgcggcggtgttctggtgcacccccagtgggtcctcacagct- gcccactgcatcaggaagtgagtaggggcctggg gtctggggagcaggtgtctgt- gtcccagaggaataacagctgggcattttccccaggataacctctaaggccagc- cttgggactggg ggagagagggaaagttctggttcaggtcacatggggaggcagggttgggg- ctggaccaccctccccatggctgcctgggtctccat ctgtgttcctctatgtctctttgt- gtcgctttcattatgtctcttggtaactggcttcggttgtgtctctccgtgtgact- attttgttctctctctccct ctcttctctgtcttcagt (SEQ ID No: 28; GenBank Accession No. NM_001030050). In another embodiment, the KLK3 protein is encoded by residues 42-758 of SEQ ID No: 28. In another embodiment, the KLK3 protein is encoded by a homologue of SEQ ID No: 28. In another embodiment, the KLK3 protein is encoded by a variant of SEQ ID No: 28. In another embodiment, the KLK3 protein is encoded by an isomer of SEQ ID No: 28. In another embodiment, the KLK3 protein is encoded by a fragment of SEQ ID No: 28. Each possibility represents a separate embodiment of the methods and compositions as provided herein.

In another embodiment, the KLK3 protein that is the source of the KLK3 peptide has the sequence: MWVPV- VFLTLSVTWIGAAPLILSRIVGGWECEKHSQPWQV- LVASRGRAVCGGVLV HPQWVLTAAHCIRNKS- VILLGRHSLFHPEDTGQVFQVSHSFPHPLYDMSLLK NRFLR PGDDSSIEPEEFLTPKKLQCVDLHVISNDV- CAQVHPQKVTKFMLCAGRWTGGKSTCS GDSGG- PLVCNGVLQGITSWGSEPCALPERPSLYTKVVHYRK- WIKDTIVANP (SEQ ID No: 29; GenBank Accession No. NP_001025220). In another embodiment, the KLK3 protein is a homologue of SEQ ID No: 29. In another embodiment, the KLK3 protein is a variant of SEQ ID No: 29. In another embodiment, the KLK3 protein is an isomer of SEQ ID No: 29. In another embodiment, the KLK3 protein is a fragment of SEQ ID No: 29. Each possibility represents a separate embodiment of the methods and compositions as provided herein.

In another embodiment, the KLK3 protein is encoded by a nucleotide molecule having the sequence: agccccaagcttac- cacctgcacccggagagctgtgtcaccatgtgggtcccggttgtcttcctcaccct- gtccgtgacgtggattggt gctgcacccctcatcctgtctcggattgtgggag- gctgggagtgcgagaagcattcccaaccctggcaggtgcttgtggcctctcgtg gcagggcagtctgcggcggtgttctggtgcacccccagtgggtcctcacagct- gcccactgcatcaggaacaaaagcgtgatcttgc tgggtcggcacagcct- gtttcatcctgaagacacaggccaggtatttcaggtcagccacagcttcccacac- ccgctctacgatatgag cctcctgaagaatcgattcctcaggccaggtgatgactccagcattgaaccagag- gagttcttgacccaaagaaacttcagtgtgtgg acctccatgttatttccaat- gacgtgtgtgcgcaagttcaccctcagaaggtgaccaagttcatgctgtgtgctg- acgctggacaggg ggcaaaagcacctgctcgggtgattctgggggcccacttgtctgtaatggtgtgct- tcaaggtatcacgtcatggggcagtgaaccatg tgccctgcccgaaaggccttc- cctgtacaccaaggtggtgcattaccggaagtggatcaaggacaccatcgtggc- caacccctgagc accccctatcaaccccctattgtagtaaacttggaaccttggaaatgaccaggc- caagactcaagcctcccagttctactgacctttgtc cttaggtgtgaggtcca- gggttgctaggaaaagaaatcagcagacacaggtgtagaccagagtgtttct- taaatggtgtaattttgtcct ctctgtgtcctggggaatactggcc atgcctggagacatatcactcaatttctctgaggacacagataggatggggtgtct- gtgttatttgt ggggtacagagatgaaagaggggtgggatccacactgaga- gagtggagagtgacatgtgctggacactgtccatgaagcactgag cagaagctggaggcacaacgcaccagacactcacagcaaggatggagctgaaaacataac ccactctgtcctggaggcactggga agcctagagaaggctgtgagc- caaggagggagggtcttcctttggcatgggatggggatgaagtaagga- gagggactggaccccc tggaagctgattcactatgggggagggtgatt- gaagtcctccagacaaccctcagatttgatgatttcctagtagaactcacagaaata aagagctgttatactgtg (SEQ ID No: 30; GenBank Accession No. NM_001030049). In another embodiment, the KLK3 protein is encoded by residues 42-758 of SEQ ID No: 30. In another embodiment, the KLK3 protein is encoded by a homologue of SEQ ID No: 30. In another embodiment, the KLK3 protein is encoded by a variant of SEQ ID No: 30. In another embodiment, the KLK3 protein is encoded by an isomer of SEQ ID No: 30. In another embodiment, the KLK3 protein is encoded by a fragment of SEQ ID No: 30. Each possibility represents a separate embodiment of the methods and compositions as provided herein.

In another embodiment, the KLK3 protein has the sequence: MWVPVVFLTLSVTWIGAAPLILSRIVGG- WECEKHSQPWQVLVASRGRAVCGGVLV HPQWVL- TAAHCIRKPGDDSSHDLMLLRLSEPAELTDAVKVM- DLPTQEPALGTTCYA SGWGSIEPEEFLTPKKLQCVDLHVISNDVCAQVH- PQKVTKFMLCAGRWTGGKSTCS GDSGGPLVCNGV- LQGITSWGSEPCALPERPSLYTKVVHYRKWIKDTI- VANP (SEQ ID No: 31; GenBank Accession No. NP_001025219). In another embodiment, the KLK3 protein is a homologue of SEQ ID No: 31. In another embodiment, the KLK3 protein is a variant of SEQ ID No: 31. In another embodiment, the KLK3 protein is an isomer of SEQ ID No: 31. In another embodiment, the KLK3 protein is a fragment of SEQ ID No: 31. Each possibility represents a separate embodiment of the methods and compositions as provided herein.

In another embodiment, the KLK3 protein is encoded by a nucleotide molecule having the sequence: agccccaagcttac- cacctgcacccggagagctgtgtcaccatgtgggtcccggttgtcttcctcaccct- gtccgtgacgtggattggt gctgcacccctcatcctgtctcggattgtgggag- gctgggagtgcgagaagcattcccaaccctggcaggtgcttgtggcctctcgtg gcagggcagtctgcggcggtgttctggtgcacccccagtgggtcctcacagct- gcccactgcatcaggaagccaggtgatgactcc agccacgacctcatgctgctc- cgcctgtcagagcctgccgagctcacggatgctgtgaaggtcatggacctgc- ccacccaggagcc agcactggggaccacctgctacgcctcaggctggggcagcattgaaccagag- gagttcttgacccaaagaaacttcagtgtgtgga cctccatgttatttccaat- gacgtgtgtgcgcaagttcaccctcagaaggtgaccaagttcatgctgtgtgctg- acgctggacagggg gcaaaagcacctgctcgggtgattctgggggcccacttgtctgtaatggtgtgct- tcaaggtatcacgtcatggggcagtgaaccatg tgccctgcccgaaaggccttc- cctgtacaccaaggtggtgcattaccaaggacaccatcgtggccaacccctgag- caccccctatcaa ccccctattgtagtaaacttggaaccttggaaatgaccaggccaagactcaagc- ctccccagttctactgacctttgtccttaggtgtgag gtccagggttgctag- gaaaagaaatcagcagacacaggtgtagaccagagtgtttcttaaatggtg- taattttgtctctctctgtgtcctgg ggaatactggccatgcctggagacatatcactcaatttctctgaggacacagatag- gatggggtgtctgtgttatttgtgggtacagag atgaaagaggggtgggatcca- cactgagagagtggagagtgacatgtgctggacactgtccatgaagcact- gagcagaagctgga ggcacaacgcaccagacactcacagcaaggatggagctgaaaacataac- ccactctgtcctggaggcactgggaagcctagaa ggctgtgagc- caaggagggagggtcttcctttggcatgggatggggatgaagtaagga- gagggactggaccccctggaagctgatt cactatgggggaggtgtattgaagtcctccagacaaccctcagatttgatgattc- ctagtagaactcacagaaataaagagctgttat actgtg (SEQ ID No: 32; GenBank Accession No. NM_001030048). In another embodiment, the KLK3 protein is encoded by residues 42-758 of SEQ ID No: 32. In another embodiment, the KLK3 protein is encoded by a homologue of SEQ ID No: 32. In another embodiment, the KLK3 protein is encoded by a variant of SEQ ID No: 32. In another embodiment, the KLK3 protein is encoded by an isomer of SEQ ID No: 32. In another embodiment, the KLK3 protein is encoded by a fragment of SEQ ID No: 32. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSHDLMLLRLSEPAELTDAVKVMDLPTQEPAL-GTTCYASGWGSIEPEEFLTPK KLQCVDLHVISNDV-CAQVHPQKVTKFMLCAGRWTGGKSTCSGDSGG-PLVCNGVLQ GITSWGSEPCALPERPSLYTKVVHYRKWIKDTIVANP (SEQ ID No: 33; GenBank Accession No. NP_001639). In another embodiment, the KLK3 protein is a homologue of SEQ ID No: 33. In another embodiment, the KLK3 protein is a variant of SEQ ID No: 33. In another embodiment, the KLK3 protein is an isomer of SEQ ID No: 33. In another embodiment, the KLK3 protein is a fragment of SEQ ID No: 33. Each possibility represents a separate embodiment of the methods and compositions as provided herein.

In another embodiment, the KLK3 protein is encoded by a nucleotide molecule having the sequence: agccccaagcttac-cacctgcacccggagagctgtgtcaccatgtgggtcccggttgtcttcctcaccct-gtccgtgacgtggattggt gctgcacccctcatcctgtctcggattgtgggag-gctgggagtgcgagaagcattcccaaccctggcaggtgcttgtggcctctcgtg gcagggcagtctgcggcggtgttctggtgcacccccagtgggtcctcacagct-gcccactgcatcaggaacaaaagcgtgatcttgc tgggtcggcacagcct-gtttcatcctgaagacacaggccaggtatttcaggtcagccacagcttcccacac-ccgctctacgatatgag cctcctgaagaatcgattcctcaggccaggtgatgactccagccacgacctcat-gctgctccgcctgtcagagcctgccgagctcacg gatgctgtgaaggtcatg-gacctgcccacccaggagccagcactggggaccacctgctacgcctcag-gctggggcagcattgaac cagaggagttcttgaccccaaagaaacttcagtgtgtggacctccatgttatttc-caatgacgtgtgtgcgcaagttcaccctcagaagg tgaccaagttcatgctgtgt-gctggacgctggacaggggggcaaaagcacctgctcgggtgattctgggggc-ccacttgtctgtaatgg tgtgcttcaaggtatcacgtcatggggcagtgaaccatgtgccctgc-ccgaaaggccttccctgtacaccaaggtggtgcattaccgg aagtggat-caaggacaccatcgtggccaacccctgagcaccccctatcaactccctattgtag-taaacttggaaccttggaaatgacca ggccaagactcaagcctcccagttctactgacctttgtccttaggtgtgaggtcca-gggttgctaggaaaagaaatcagcagacaca ggtgtagaccagagtgtttct-taaatggtgtaattttgtcctctctgtgtcctggggaatactggccatgcctggaga-catatcactcaattt ctctgaggacacagataggatggggtgtctgtgttatttgtggggtacagagat-gaaagagggtgggatccacactgagagagtgg agagtgacatgtgctgga-cactgtccatgaagcactgagcagaagctggaggcacaacgcaccagacact-cacagcaaggatgga gctgaaaacataacccactctgtcctggaggcactgggaagcctagagaaggct-gtgagccaaggagggagggtcttcctttggcat gggatggggatgaag-taaggagagggactggaccccctggaagctgattcactatgggggaggtgtatt-gaagtcctccagacaa ccctcagatttgatgatttcctagtagaactcacagaaataaagagctgttatactgtg (SEQ ID No: 34; GenBank Accession No. NM_001648). In another embodiment, the KLK3 protein is encoded by residues 42-827 of SEQ ID No: 34. In another embodiment, the KLK3 protein is encoded by a homologue of SEQ ID No: 34. In another embodiment, the KLK3 protein is encoded by a variant of SEQ ID No: 34. In another embodiment, the KLK3 protein is encoded by an isomer of SEQ ID No: 34. In another embodiment, the KLK3 protein is encoded by a fragment of SEQ ID No: 34. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSHDLMLLRLSEPAELTDAVKVMDLPTQEPAL-GTTCYASGWGSIEPEEFLTPK KLQCVDLHVISNDV-CAQVHPQKVTKFMLCAGRWTGGKSTCSGDSGG-PLVCNGVLQ GITSWGSEPCALPERPSLYTKVVHYRKWIKDTIVANP (SEQ ID No: 35 GenBank Accession No. AAX29407.1). In another embodiment, the KLK3 protein is a homologue of SEQ ID No: 35. In another embodiment, the KLK3 protein is a variant of SEQ ID No: 35. In another embodiment, the KLK3 protein is an isomer of SEQ ID No: 35. In another embodiment, the sequence of the KLK3 protein comprises SEQ ID No: 35. In another embodiment, the KLK3 protein is a fragment of SEQ ID No: 35. Each possibility represents a separate embodiment of the methods and compositions as provided herein.

In another embodiment, the KLK3 protein is encoded by a nucleotide molecule having the sequence: gggggagc-cccaagcttaccacctgcacccggagagctgtgtcaccatgtgggtcccggtt-gtcttcctcaccctgtccgtgacgtgg attggtgctgcacccctcatcctgtctcg-gattgtgggaggctgggagtgcgagaagcattcccaaccctggcaggtgcttgt ggcctc tcgtggcagggcagtctgcggcggtgttctggtgcacccca-gtgggtcctcacagctgcccactgcatcaggaacaaaagcgtgat ctt-gctgggtcggcacagcctgtttcatcctgaagacacaggccaggtatttcaggtca-gccacagcttcccacacccgctctacgata tgagcctcctgaagaatcgattcctcaggccaggtgatgactccagccacgacct-catgctgctccgcctgtcagagcctgccgagct cacggatgctgtgaaggtcatg-gacctgcccacccaggagccagcactggggaccacctgctacgcctcag-gctggggcagcatt gaaccagaggagttcttgaccccaaagaaacttcagtgtgtggacctccatgtt-atttccaatgacgtgtgtgcgcaagttcaccctcag aaggtgaccaagttcatgct-gtgtgctggacgctggacaggggggcaaaagcacctgctcgggtgat-tctgggggcccacttgtctgta atggtgtgcttcaaggtatcacgtcatggggcagtgaaccatgtgccctgc-ccgaaaggccttccctgtacaccaaggtggtgcattac cggaagtggat-caaggacaccatcgtggccaacccctgagcaccccctatcaactccctattgtag-taaacttggaaccttggaaatga ccaggccaagactcaggcctcccagttctactgacctttgtccttaggtgtgag-gtccagggttgctaggaaaagaaatcagcagac acaggtgtagaccagagt-gtttcttaaatggtgtaattttgtcctctctgtgtcctggggaatactggccatgcctg-gagacatatcactca atttctctgaggacacagataggatggggtgtctgtgttatttgtggggtacaga-gatgaaagagggtgggatccacactgagagag tggagagtgacatgtgctg-gacactgtccatgaagcactgagcagaagctggaggcacaacgcaccaga-cactcacagcaaggat ggagctgaaaacataacccactctgtcctggaggcactgggaagcctaga-gaaggctgtgagccaaggagggagggtcttcctttg gcatgggatggggat-gaagtagggagagggactggaccccctggaagctgattcactatgggggag-gtgtattgaagtcctccag acaaccctcagatttgatgatttcctagtagaactcacagaaataaagagctgt-tatactgcgaaaaaaaaaaaaaaaaaaaaaaaaa (SEQ ID No: 36; GenBank Accession No. BC056665). In another embodiment, the KLK3 protein is encoded by residues 47-832 of SEQ ID No: 36. In another embodiment, the KLK3 protein is encoded by a homologue of SEQ ID No: 36. In another embodiment, the KLK3 protein is encoded by a variant of SEQ ID No: 36. In another embodiment, the KLK3 protein is encoded by an isomer of SEQ ID No: 36. In another embodiment, the KLK3 protein is encoded by a fragment of SEQ ID No: 36. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSIEPEEFLTPKKLQCVDLHVISNDVCAQVH-PQKVTKFMLCAGRWTGGKSTCS GDSGGPLVCNGV-LQGITSWGSEPCALPERPSLYTKVVHYRKWIKDTIVA (SEQ ID No: 37; GenBank Accession No. AJ459782). In another embodiment, the KLK3 protein is a homologue of SEQ ID No: 37. In another embodiment, the KLK3 protein is a variant of SEQ ID No: 37. In another embodiment, the KLK3 protein is an isomer of SEQ ID No: 37. In another embodiment, the KLK3 protein is a fragment of SEQ ID No: 37. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSHDLMLLRLSEPAELTDAVKVMDLPTQEPAL-GTTCYASGWGSIEPEEFLTPK KLQCVDLHVISNDV-CAQVHPQKVTKFMLCAGRWTGGKSTCSVSH-PYSQDLEGKGE WGP (SEQ ID No: 38, GenBank Accession No. AJ512346). In another embodiment, the KLK3 protein is a homologue of SEQ ID No: 38. In another embodiment, the KLK3 protein is a variant of SEQ ID No: 38. In another embodiment, the KLK3 protein is an isomer of SEQ ID No: 38. In another embodiment, the sequence of the KLK3 protein comprises SEQ ID No: 38. In another embodiment, the KLK3 protein is a fragment of SEQ ID No: 38. Each possibility represents a separate embodiment of the methods and compositions as provided herein.

In another embodiment, the KLK3 protein has the sequence: MWVPVVFLTLSVTWIGERGHGWGDAGE-GASPDCQAEALSPPTQHPSPDRELGSFLS LPA-PLQAHTPSPSILQQSSLPHQVPAPSHLPQNFLPIAQ-PAPCSQLLY (SEQ ID No: 39 GenBank Accession No. AJ459784). In another embodiment, the KLK3 protein is a homologue of SEQ ID No: 39. In another embodiment, the KLK3 protein is a variant of SEQ ID No: 39. In another embodiment, the sequence of the KLK3 protein comprises SEQ ID No: 39. In another embodiment, the KLK3 protein is an isomer of SEQ ID No: 39. In another embodiment, the KLK3 protein is a fragment of SEQ ID No: 39. Each possibility represents a separate embodiment of the methods and compositions as provided herein.

In another embodiment, the KLK3 protein has the sequence: MWVPVVFLTLSVTWIGAAPLILSRIVGG-WECEKHSQPWQVLVASRGRAVCGGVLV HPQWVL-TAAHCIRNKSVILLGRHSLFHPEDTGQVFQVSHSFPH-PLYDMSLLKNRFLR PGDDSSHDLMLLRLSEPAELTDAVKVMDLPTQEPAL-GTTCYASGWGSIEPEEFLTPK KLQCVDLHVISNDV-CAQVHPQKVTKFMLCAGRWTGGKSTCSGDSGG-PLVCNGVLQ GITSWGSEPCALPERPSLYTKVVHYRKWIKDTIVANP (SEQ ID No: 40 GenBank Accession No. AJ459783). In another embodiment, the KLK3 protein is a homologue of SEQ ID No: 40. In another embodiment, the KLK3 protein is a variant of SEQ ID No: 40. In another embodiment, the KLK3 protein is an isomer of SEQ ID No: 40. In another embodiment, the KLK3 protein is a fragment of SEQ ID No: 40. Each possibility represents a separate embodiment of the methods and compositions as provided herein.

In another embodiment, the KLK3 protein is encoded by a nucleotide molecule having the sequence: aagtttcccttctc-ccagtccaagaccccaaatcaccacaaaggacccaatccccagactcaaga-tatggtctgggcgctgtcttgtgt ctcctaccctgatccctgggttcaactctgctc-ccagagcatgaagcctctccaccagcaccagccaccaacctgcaaacctagggaa gattgacagaattcccagcctttcccagctcccccctgcccatgtcccaggactc-ccagccttggttctctgcccccgtgtcttttcaaacc cacatcctaaatccatctc-ctatccgagtcccccagttcctcctgtcaaccctgattcccctgatctagcac-ccccctcgcaggtgctgca ccccctcatcctgtctcggattgtgggaggctgggagtgcgagaagcattcccaac-cctggcaggtgcttgtagcctctcgtggcaggg cagtctgcggcggtgttctggt-gcacccccagtgggtcctcacagctacccactgcatcaggaacaaaagcgt-gatcttgctgggtcg gcacagcctgtttcatcctgaagacacaggccaggtatttcaggtcagccacagct-tcccacacccgctctacgatatgagcctcctga agaatcgattcctcaggccag-gtgatgactccagccacgacctcatgctgctccgcctgtcagagcctgccgagct-cacggatgctat gaaggtcatggacctgcccacccaggagccagcactggggaccacctgc-tacgcctcaggctggggcagcattgaaccagagga gttcttgac-cccaaagaaacttcagtgtgtggacctccatgttatttccaatgacgtgtgtgcg-caagttcaccctcagaaggtgaccaa gttcatgctgtgtgctggacgctggacaggggggcaaaagcacctgctcgggtgat-tctggggcccacttgtctgtaatggtgtgcttc aaggtatcacgtcatggggca-gtgaaccatgtgccctgcccgaaaggccttccctgtacaccaaggtggtgcattac-cggaagtgga tcaaggacaccatcgtggccaacccctgagcaccccctatcaactccctattgtag-taaacttggaaccttggaaatgaccaggccaag actcaggcctccccagttc-tactgacctttgtccttaggtgtgaggtccagggttgctaggaaaagaaatcagca-gacacaggtgtaga ccagagtgtttcttaaatggtgtaatttgtctctctgtgtcctggggaatactggccat-gcctggagacatatcactcaatttctctgagg acacagataggatggggtgtctgt-gttatttgtgggtacagagatgaaagaggggtgggatccacactgagagagtg-gagagtgac atgtgctggacactgtccatgaagcactgagcagaagctggaggcacaacgcac-cagacactcacagcaaggatggagctgaaaa cataacccactctgtcctggag-gcactgggaagcctagagaaggctgtgaaccaaggagggagggtcttcctttg-gcatgggatgg ggatgaagtaaggagagggactgaccccctggaagctgattcac-tatgggggaggtgtattgaagtcctccagacaaccctcagat ttgatgatttc-ctagtagaactcacagaaataaagagctgttatactgtgaa (SEQ ID No: 41; GenBank Accession No. X07730). In another embodiment, the KLK3 protein is encoded by residues 67-1088 of SEQ ID No: 41. In another embodiment, the KLK3 protein is encoded by a homologue of SEQ ID No: 41. In another embodiment, the KLK3 protein is encoded by a variant of SEQ ID No: 41. In another embodiment, the KLK3 protein is encoded by an isomer of SEQ ID No: 41. In another embodiment, the KLK3 protein is encoded by a fragment of SEQ ID No: 41. Each possibility represents a separate embodiment of the methods and compositions as provided herein.

In another embodiment, the KLK3 protein is encoded by a sequence set forth in one of the following GenBank Accession Numbers: BC005307, AJ310938, AJ310937, AF335478, AF335477, M27274, and M26663. In another embodiment, the KLK3 protein is encoded by a sequence set forth in one of the above GenBank Accession Numbers. Each possibility represents a separate embodiment of the methods and compositions as provided herein.

In another embodiment, the KLK3 protein is encoded by a sequence set forth in one of the following GenBank Accession Numbers: NM_001030050, NM_001030049, NM_001030048, NM_001030047, NM_001648, AJ459782, AJ512346, or AJ459784. Each possibility represents a separate embodiment of the methods and compositions as provided herein. In one embodiment, the KLK3 protein is encoded by a variation of any of the sequences described herein wherein the sequence lacks MWVPVVFLTLS-VTWIGAAPLILSR (SEQ ID NO: 55).

In another embodiment, the KLK3 protein has the sequence that comprises a sequence set forth in one of the following GenBank Accession Numbers: X13943, X13942, X13940, X13941, and X13944. Each possibility represents a separate embodiment of the methods and compositions as provided herein.

In another embodiment, the KLK3 protein is any other KLK3 protein known in the art. Each KLK3 protein represents a separate embodiment of the methods and compositions as provided herein.

In another embodiment, the KLK3 peptide is any other KLK3 peptide known in the art. In another embodiment, the KLK3 peptide is a fragment of any other KLK3 peptide known in the art. Each type of KLK3 peptide represents a separate embodiment of the methods and compositions as provided herein.

"KLK3 peptide" refers, in another embodiment, to a full-length KLK3 protein. In another embodiment, the term refers to a fragment of a KLK3 protein. In another embodiment, the term refers to a fragment of a KLK3 protein that is lacking the KLK3 signal peptide. In another embodiment, the term refers to a KLK3 protein that contains the entire KLK3 sequence except the KLK3 signal peptide. "KLK3 signal sequence" refers, in another embodiment, to any signal sequence found in nature on a KLK3 protein. In another embodiment, a KLK3 protein of methods and compositions as provided herein does not contain any signal sequence. Each possibility represents a separate embodiment of the methods and compositions as provided herein.

In another embodiment, the kallikrein-related peptidase 3 (KLK3 protein) that is the source of a KLK3 peptide for use in the methods and compositions as provided herein is a PSA protein. In another embodiment, the KLK3 protein is a P-30 antigen protein. In another embodiment, the KLK3 protein is a gamma-seminoprotein protein. In another embodiment, the KLK3 protein is a kallikrein 3 protein. In another embodiment, the KLK3 protein is a semenogelase protein. In another embodiment, the KLK3 protein is a seminin protein. In another embodiment, the KLK3 protein is any other type of KLK3 protein that is known in the art. Each possibility represents a separate embodiment of the methods and compositions as provided herein.

In another embodiment, the KLK3 protein is a splice variant 1 KLK3 protein. In another embodiment, the KLK3 protein is a splice variant 2 KLK3 protein. In another embodiment, the KLK3 protein is a splice variant 3 KLK3 protein. In another embodiment, the KLK3 protein is a transcript variant 1 KLK3 protein. In another embodiment, the KLK3 protein is a transcript variant 2 KLK3 protein. In another embodiment, the KLK3 protein is a transcript variant 3 KLK3 protein. In another embodiment, the KLK3 protein is a transcript variant 4 KLK3 protein. In another embodiment, the KLK3 protein is a transcript variant 5 KLK3 protein. In another embodiment, the KLK3 protein is a transcript variant 6 KLK3 protein. In another embodiment, the KLK3 protein is a splice variant RP5 KLK3 protein. In another embodiment, the KLK3 protein is any other splice variant KLK3 protein known in the art. In another embodiment, the KLK3 protein is any other transcript variant KLK3 protein known in the art. Each possibility represents a separate embodiment of the methods and compositions as provided herein.

In another embodiment, the KLK3 protein is a mature KLK3 protein. In another embodiment, the KLK3 protein is a pro-KLK3 protein. In another embodiment, the leader sequence has been removed from a mature KLK3 protein of methods and compositions as provided herein. Each possibility represents a separate embodiment of the methods and compositions as provided herein.

In another embodiment, the KLK3 protein that is the source of a KLK3 peptide of methods and compositions as provided herein is a human KLK3 protein. In another embodiment, the KLK3 protein is a primate KLK3 protein. In another embodiment, the KLK3 protein is a KLK3 protein of any other species known in the art. In another embodiment, one of the above KLK3 proteins is referred to in the art as a "KLK3 protein." Each possibility represents a separate embodiment of the methods and compositions as provided herein.

In another embodiment, the antigen of interest is a KLK9 polypeptide.

In another embodiment, the antigen of interest is HPV-E7. In another embodiment, the antigen is HPV-E6. In another embodiment, the antigen is Her-2/neu. In another embodiment, the antigen is NY-ESO-1. In another embodiment, the antigen is telomerase (TERT). In another embodiment, the antigen is SCCE. In another embodiment, the antigen is CEA. In another embodiment, the antigen is LMP-1. In another embodiment, the antigen is p53. In another embodiment, the antigen is carboxic anhydrase IX (CAIX). In another embodiment, the antigen is PSMA. In another embodiment, the antigen is prostate stem cell antigen (PSCA). In another embodiment, the antigen is HMW-MAA. In another embodiment, the antigen is WT-1. In another embodiment, the antigen is HIV-1 Gag. In another embodiment, the antigen is Proteinase 3. In another embodiment, the antigen is Tyrosinase related protein 2. In another embodiment, the antigen is PSA (prostate-specific antigen). In another embodiment, the antigen is selected from HPV-E7, HPV-E6, Her-2, NY-ESO-1, telomerase (TERT), SCCE, HMW-MAA, WT-1, HIV-1 Gag, CEA, LMP-1, p53, PSMA, PSCA, Proteinase 3, Tyrosinase related protein 2, Muc1, PSA (prostate-specific antigen), or a combination thereof.

In another embodiment, the antigen is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, gp100, a MART1 antigen associated with melanoma, or the PSA antigen associated with prostate cancer. In another embodiment, the antigen for the compositions and methods as provided herein are melanoma-associated antigens, which in one embodiment are TRP-2, MAGE-1, MAGE-3, gp-100, tyrosinase, HSP-70, beta-HCG, or a combination thereof.

In one embodiment, the first and second nucleic acids may encode two separate antigens that serve as tumor targets, which in one embodiment are Prostate Specific Antigen (PSA) and Prostate Cancer Stem Cell (PSCA) antigen. In one embodiment, the polypeptide encoded by the second nucleic acid may complement or synergize the immune response to the first nucleic acid encoding an antigenic polypeptide. In another embodiment, the polypeptide encoded by the second nucleic acid affects vascular growth. In one embodiment, the first and second nucleic acid may encode two polypeptides that affect vascular growth, which in one embodiment, work via distinct mechanisms to affect vascular growth. In one embodiment, such polypeptides are EGFR-III, HMW-MAA, or a combination thereof. In one embodiment, a polypeptide may serve as both a tumor antigen an angiogenic factor. In one embodiment, the first nucleic acid may encode a tumor antigen, and the second nucleic acid may encode a polypeptide that is an inhibitor of the function or expression of ARG-1 or NOS or combination. In one embodiment, an inhibitor of NOS is $N^G$-monomethyl-L-arginine (L-NMMA), $N^G$-nitro-L-arginine methyl ester (L-NAME), 7-NI, L-NIL, or L-NIO. In one embodiment, N-omega-nitro-L-arginine a nitric oxide synthase inhibitor and L-arginine competitive inhibitor may be encoded by the nucleic acid. In one embodiment, the second nucleic acid may encode an mRNA that inhibits function or expression of ARG-1 or NOS.

In one embodiment, a polypeptide expressed by the *Listeria* of the present invention may be a neuropeptide growth factor antagonist, which in one embodiment is [D-Arg1, D-Phe5, D-Trp-7,9, Leu11]substance P, [Arg6, D-Trp-7,9, NmePhe8]substance P(6-11). These and related embodiments embodiments are understood by one of skill in the art.

In another embodiment, the antigen is an infectious disease antigen. In one embodiment, the antigen is an auto antigen or a self-antigen.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, *pneumococcus* antigens, respiratory syncytial virus antigens, *Haemophilus influenza* outer membrane proteins, *Helicobacter pylori urease, Neisseria meningitidis* pilins, *N. gonorrhoeae* pilins, human papilloma virus antigens E1 and E2 from type HPV-16, -18, -31, -33, -35 or -45 human papilloma viruses, or a combination thereof.

In other embodiments, the antigen is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis. Each antigen represents a separate embodiment of the methods and compositions as provided herein.

The immune response induced by methods and compositions as provided herein is, in another embodiment, a T cell response. In another embodiment, the immune response comprises a T cell response. In another embodiment, the response is a $CD8^+$ T cell response. In another embodiment, the response comprises a $CD8^+$ T cell response. Each possibility represents a separate embodiment as provided herein.

In one embodiment, a recombinant *Listeria* of the compositions and methods as provided herein comprise an angiogenic polypeptide. In another embodiment, anti-angiogenic approaches to cancer therapy are very promising, and in one embodiment, one type of such anti-angiogenic therapy targets pericytes. In another embodiment, molecular targets on vascular endothelial cells and pericytes are important targets for antitumor therapies. In another embodiment, the platelet-derived growth factor receptor (PDGF-B/PDGFR-β) signaling is important to recruit pericytes to newly formed blood vessels. Thus, in one embodiment, angiogenic polypeptides as provided herein inhibit molecules involved in pericyte signaling, which in one embodiment, is PDGFR-β.

In one embodiment, the compositions of the present invention comprise an angiogenic factor, or an immunogenic fragment thereof, where in one embodiment, the immunogenic fragment comprises one or more epitopes recognized by the host immune system. In one embodiment, an angiogenic factor is a molecule involved in the formation of new blood vessels. In one embodiment, the angiogenic factor is VEGFR2. In another embodiment, an angiogenic factor of the present invention is Angiogenin; Angiopoietin-1; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF). In another embodiment, an angiogenic factor is an angiogenic protein. In one embodiment, a growth factor is an angiogenic protein. In one embodiment, an angiogenic protein for use in the compositions and methods of the present invention is Fibroblast growth factors (FGF); VEGF; VEGFR and Neuropilin 1 (NRP-1); Angiopoietin 1 (Ang1) and Tie2; Platelet-derived growth factor (PDGF; BB-homodimer) and PDGFR; Transforming growth factor-beta (TGF-β), endoglin and TGF-β receptors; monocyte chemotactic protein-1 (MCP-1); Integrins αVβ3, αVβ5 and α5β1; VE-cadherin and CD31; ephrin; plasminogen activators; plasminogen activator inhibitor-1; Nitric oxide synthase (NOS) and COX-2; AC133; or Id1/Id3. In one embodiment, an angiogenic protein for use in the compositions and methods of the present invention is an angiopoietin, which in one embodiment, is Angiopoietin 1, Angiopoietin 3, Angiopoietin 4 or Angiopoietin 6. In one embodiment, endoglin is also known as CD105; EDG; HHT1; ORW; or ORW1. In one embodiment, endoglin is a TGFbeta co-receptor.

In one embodiment, cancer vaccines as provided herein generate effector T cells that are able to infiltrate the tumor, destroy tumor cells and eradicate the disease. In one embodiment, naturally occurring tumor infiltrating lymphocytes (TILs) are associated with better prognosis in several tumors, such as colon, ovarian and melanoma. In colon cancer, tumors without signs of micrometastasis have an increased infiltration of immune cells and a Th1 expression profile, which correlate with an improved survival of patients. Moreover, the infiltration of the tumor by T cells has been associated with success of immunotherapeutic approaches in both pre-clinical and human trials. In one embodiment, the infiltration of lymphocytes into the tumor site is dependent on the up-regulation of adhesion molecules in the endothelial cells of the tumor vasculature, generally by proinflammatory cytokines, such as IFN-γ, TNF-α and IL-1. Several adhesion molecules have been implicated in the process of lymphocyte infiltration into tumors, including intercellular adhesion molecule 1 (ICAM-1), vascular endothelial cell adhesion molecule 1 (V-CAM-1), vascular adhesion protein 1 (VAP-1) and E-selectin. However, these cell-adhesion molecules are commonly down-regulated in the tumor vasculature. Thus, in one embodiment, cancer vaccines as provided herein increase TILs, up-regulate adhesion molecules (in one embodiment, ICAM-1, V-CAM-1, VAP-1, E-selectin, or a combination thereof), up-regulate proinflammatory cytokines (in one embodiment, IFN-γ, TNF-α, IL-1, or a combination thereof), or a combination thereof.

In one embodiment, the compositions and methods as provided herein provide anti-angiogenesis therapy, which in one embodiment, may improve immunotherapy strategies. In one embodiment, the compositions and methods as provided herein circumvent endothelial cell anergy in vivo by up-regulating adhesion molecules in tumor vessels and enhancing leukocyte-vessel interactions, which increases the number of tumor infiltrating leukocytes, such as CD8+ T cells. Interestingly, enhanced anti-tumor protection correlates with an increased number of activated CD4+ and CD8+ tumor-infiltrating T cells and a pronounced decrease in the number of regulatory T cells in the tumor upon VEGF blockade.

In one embodiment, delivery of anti-angiogenic antigen simultaneously with a tumor-associated antigen to a host afflicted by a tumor as described herein, will have a synergistic effect in impacting tumor growth and a more potent therapeutic efficacy.

In another embodiment, targeting pericytes through vaccination will lead to cytotoxic T lymphocyte (CTL) infiltration, destruction of pericytes, blood vessel destabilization and vascular inflammation, which in another embodiment is associated with up-regulation of adhesion molecules in the endothelial cells that are important for lymphocyte adherence and transmigration, ultimately improving the ability of lymphocytes to infiltrate the tumor tissue. In another embodiment, concomitant delivery of a tumor-specific antigen generate lymphocytes able to invade the tumor site and kill tumor cells.

In one embodiment, the platelet-derived growth factor receptor (PDGF-B/PDGFR-β) signaling is important to recruit pericytes to newly formed blood vessels. In another embodiment, inhibition of VEGFR-2 and PDGFR-β con-comitantly induces endothelial cell apoptosis and regression of tumor blood vessels, in one embodiment, approximately 40% of tumor blood vessels.

In another embodiment, said recombinant Listeria strain is an auxotrophic Listeria strain. In another embodiment, said auxotrophic Listeria strain is a dal/dat mutant. In another embodiment, the nucleic acid molecule is stably maintained in the recombinant bacterial strain in the absence of antibiotic selection.

In one embodiment, auxotrophic mutants useful as vaccine vectors may be generated in a number of ways. In another embodiment, D-alanine auxotrophic mutants can be generated, in one embodiment, via the disruption of both the dal gene and the dat gene to generate an attenuated auxotrophic strain of Listeria which requires exogenously added D-alanine for growth.

In one embodiment, the generation of AA strains of Listeria deficient in D-alanine, for example, may be accomplished in a number of ways that are well known to those of skill in the art, including deletion mutagenesis, insertion mutagenesis, and mutagenesis which results in the generation of frameshift mutations, mutations which cause premature termination of a protein, or mutation of regulatory sequences which affect gene expression. In another embodiment, mutagenesis can be accomplished using recombinant DNA techniques or using traditional mutagenesis technology using mutagenic chemicals or radiation and subsequent selection of mutants. In another embodiment, deletion mutants are preferred because of the accompanying low probability of reversion of the auxotrophic phenotype. In another embodiment, mutants of D-alanine which are generated according to the protocols presented herein may be tested for the ability to grow in the absence of D-alanine in a simple laboratory culture assay. In another embodiment, those mutants which are unable to grow in the absence of this compound are selected for further study.

In another embodiment, in addition to the aforementioned D-alanine associated genes, other genes involved in synthesis of a metabolic enzyme, as provided herein, may be used as targets for mutagenesis of Listeria.

In one embodiment, said auxotrophic Listeria strain comprises an episomal expression vector comprising a metabolic enzyme that complements the auxotrophy of said auxotrophic Listeria strain. In another embodiment, the construct is contained in the Listeria strain in an episomal fashion. In another embodiment, the foreign antigen is expressed from a vector harbored by the recombinant Listeria strain. In another embodiment, said episomal expression vector lacks an antibiotic resistance marker. In one embodiment, an antigen of the methods and compositions as provided herein is genetically fused to an oligopeptide comprising a PEST sequence. In another embodiment, said endogenous polypeptide comprising a PEST sequence is LLO. In another embodiment, said endogenous polypeptide comprising a PEST sequence is ActA. Each possibility represents a separate embodiment of the methods and compositions as provided herein.

In another embodiment, the metabolic enzyme complements an endogenous metabolic gene that is lacking in the remainder of the chromosome of the recombinant bacterial strain. In one embodiment, the endogenous metabolic gene is mutated in the chromosome. In another embodiment, the endogenous metabolic gene is deleted from the chromosome. In another embodiment, said metabolic enzyme is an amino acid metabolism enzyme. In another embodiment, said metabolic enzyme catalyzes a formation of an amino acid used for a cell wall synthesis in said recombinant

*Listeria* strain. In another embodiment, said metabolic enzyme is an alanine racemase enzyme. In another embodiment, said metabolic enzyme is a D-amino acid transferase enzyme. Each possibility represents a separate embodiment of the methods and compositions as provided herein.

In another embodiment, the metabolic enzyme catalyzes the formation of an amino acid (AA) used in cell wall synthesis. In another embodiment, the metabolic enzyme catalyzes synthesis of an AA used in cell wall synthesis. In another embodiment, the metabolic enzyme is involved in synthesis of an AA used in cell wall synthesis. In another embodiment, the AA is used in cell wall biogenesis. Each possibility represents a separate embodiment of the methods and compositions as provided herein.

In another embodiment, the metabolic enzyme is a synthetic enzyme for D-glutamic acid, a cell wall component.

In another embodiment, the metabolic enzyme is encoded by an alanine racemase gene (dal) gene. In another embodiment, the dal gene encodes alanine racemase, which catalyzes the reaction L-alanine H⇌D-alanine.

The dal gene of methods and compositions of the methods and compositions as provided herein is encoded, in another embodiment, by the sequence:
atggtgacaggctggcatcgtccaacatggattgaaatagaccgcgcagcaattcgcgaaaatataaaaaatgaacaa aataaactcccggaaagtgtcgacttatgggcagtagtcaaagctaatgcatatggtcacggaattatcgaagttgctaggacggcga
aagaagctggagcaaaaggtttctgcgtagccattttagatgaggcactggctcttagagaagctggatttcaagatgactttattcttgt gcttggtgcaaccagaaaagaagatgctaatctggcagccaaaaaccacatttcacttactgtttttagagaagattggctagagaatct
aacgctagaagcaacacttcgaattcatttaaaagtagatagcggtatggggcgtctcggtattcgtacgactgaagaagcacggcga attgaagcaaccagtactaatgatcaccaattacaactggaaggtatttacacgcattttgcaacagccgaccagctagaaactagttatt
ttgaacaacaattagctaagttccaaacgattttaacgagtttaaaaaaacgaccaacttatgttcatacagccaattcagctgcttcattgt tacagccacaaatcgggtttgatgcgattcgctttggtatttcgatgtatggattaactccctccacagaaatcaaaactagcttgccgttt
gagcttaaacctgcacttgcactctataccgagatggttcatgtgaaagaacttgcaccaggcgatagcgttagctacggagcaacttat acagcaacagagcgagaatgggttgcgacattaccaattggctatgcggatggattgattcgtcattacagtggtttccatgttttagtag
acggtgaaccagctccaatcattggtcgagtttgtatggatcaaaccatcataaaactaccacgtgaatttcaaactggttcaaaagtaac gataattggcaaagatcatggtaacacggtaacagcagatgatgccgctcaatatttagatacaattaattatgaggtaacttgtttgttaa atgagcgcatacctagaaaatacatccattag (SEQ ID No: 42; GenBank Accession No: AF038438). In another embodiment, the nucleotide encoding dal is homologous to SEQ ID No: 42. In another embodiment, the nucleotide encoding dal is a variant of SEQ ID No: 42. In another embodiment, the nucleotide encoding dal is a fragment of SEQ ID No: 42. In another embodiment, the dal protein is encoded by any other dal gene known in the art. Each possibility represents a separate embodiment of the methods and compositions as provided herein.

In another embodiment, the dal protein has the sequence:
MVTGWHRPTWIEIDRAAIRENIKNEQNKLPES-VDLWAVVKANAYGHGIIEV ARTAKEAGAKG-FCVAILDEALALREAGFQDDFILVLGATRKEDAN-LAAKNHISLTVF
REDWLENLTLEATLRIHLKVDSGMGRLGIRTTEEAR-RIEATSTNDHQLQLEGIYTHFA TADQLETSY-FEQQLAKFQTILTSLKKRPTYVHTANSAASLLQPQI-GFDAIRFGISMYG
LTPSTEIKTSLPFELKPALALYTEMVHVKELAPGDS-VSYGATYTATEREWVATLPIGY ADGLIRHYSGFHV-LVDGEPAPIIGRVCMDQTIIKLPREFQTGSKVTIIGKD-HGNTVTA DDAAQYLDTINYEVTCLLNERIPRKYIH (SEQ ID No: 43; GenBank Accession No: AF038428). In another embodiment, the dal protein is homologous to SEQ ID No: 43. In another embodiment, the dal protein is a variant of SEQ ID No: 43. In another embodiment, the dal protein is an isomer of SEQ ID No: 43. In another embodiment, the dal protein is a fragment of SEQ ID No: 43. In another embodiment, the dal protein is a fragment of a homologue of SEQ ID No: 43. In another embodiment, the dal protein is a fragment of a variant of SEQ ID No: 43. In another embodiment, the dal protein is a fragment of an isomer of SEQ ID No: 43.

In another embodiment, the dal protein is any other *Listeria* dal protein known in the art. In another embodiment, the dal protein is any other gram-positive dal protein known in the art. In another embodiment, the dal protein is any other dal protein known in the art. Each possibility represents a separate embodiment of the methods and compositions as provided herein.

In another embodiment, the dal protein of methods and compositions as provided herein retains its enzymatic activity. In another embodiment, the dal protein retains 90% of wild-type activity. In another embodiment, the dal protein retains 80% of wild-type activity. In another embodiment, the dal protein retains 70% of wild-type activity. In another embodiment, the dal protein retains 60% of wild-type activity. In another embodiment, the dal protein retains 50% of wild-type activity. In another embodiment, the dal protein retains 40% of wild-type activity. In another embodiment, the dal protein retains 30% of wild-type activity. In another embodiment, the dal protein retains 20% of wild-type activity. In another embodiment, the dal protein retains 10% of wild-type activity. In another embodiment, the dal protein retains 5% of wild-type activity. Each possibility represents a separate embodiment of the methods and compositions as provided herein.

In another embodiment, the metabolic enzyme is encoded by a D-amino acid aminotransferase gene (dat). D-glutamic acid synthesis is controlled in part by the dat gene, which is involved in the conversion of D-glu+pyr to alpha-ketoglutarate+D-ala, and the reverse reaction.

In another embodiment, a dat gene utilized in the present invention has the sequence set forth in GenBank Accession Number AF038439. In another embodiment, the dat gene is any another dat gene known in the art. Each possibility represents a separate embodiment of the methods and compositions as provided herein.

The dat gene of methods and compositions of the methods and compositions as provided herein is encoded, in another embodiment, by the sequence:
atgaaagtattagtaaataaccatttagttgaaagagaagatgccacagttgacattgaagaccgcggatatcagtttggt gatggtgtatatgaagtagttcgtctatataatggaaaattctttacttataatgaacacattgatcgcttatatgctagtgcagcaaaaattgacttagttattccttattccaaagaagagct acgtgaat
tacttgaaaaattagttgccgaaaataatatcaatacagggaatgtctatttacaagtgactcgtggtgttcaaaacccacgtaatcatgtaatccctgatgatttccctctagaaggcgttttaacagcagcagctcgtgaagt acctagaaacgagcgtcaattcgttgaa ggtggaacggcgattacagaagaagatg tgcgctggttacgctgtgatattaagagcttaaaccttttaggaaatattctagcaaaaaataaagcacatcaacaaaatgctttggaagctattttacatcgcggggaacaagtaacagaat gttctgcttcaaacgtttcta ttattaaagatggtgtattatggacgcatgcggcagataacttaatcttaaatggtatcactcgtcaagttat cattgatgttgcgaaaaagaatggcattcctgttaaagaagcgatttcacttttaacagaccttcgtgaagcggatgaagtgttcatttca agtacaactattgaaattacacctattacgcatattgacggagttcaagtagctgacggaaaacgtggaccaattacagcgcaacttcat caatattttgtagaagaaat cactcgtgcatgtggcgaattagagttttgcaaaataa (SEQ ID No: 44; GenBank Accession No: AF038439). In another embodiment, the nucleotide encoding dat is homologous to SEQ ID No: 44. In another embodiment, the nucleotide encoding dat is a variant of SEQ ID No: 44. In another embodiment, the nucleotide encoding dat is a fragment of SEQ ID No: 44. In another embodiment, the dat protein is encoded by any other dat gene known in the art. Each possibility represents a separate embodiment of the methods and compositions as provided herein.

In another embodiment, the dat protein has the sequence: MKVLVNNHLVEREDATVDIEDRGYQFGDGVYEVVRLYNGKFFTYNEHIDR LYASAAKIDLVIPYSKEELRELLEKLVAENNINTGNVYLQVTRGVQNPRNHVIPDDFP LEGVLTAAAREVPRNERQFVEGGTAITEEDVRWLRCDIKSLNLLGNILAKNKAHQQ NALEAILHRGEQVTECSASNVSIIKDGVLWTHAADNLILNGITRQVIIDVAKKNGIPV KEADFTLTDLREADEVFISSTTIEITPITHIDGVQVADGKRGPITAQLHQYFVEEITRAC GELEFAK (SEQ ID No: 45; GenBank Accession No: AF038439). In another embodiment, the dat protein is homologous to SEQ ID No: 45. In another embodiment, the dat protein is a variant of SEQ ID No: 45. In another embodiment, the dat protein is an isomer of SEQ ID No: 45. In another embodiment, the dat protein is a fragment of SEQ ID No: 45. In another embodiment, the dat protein is a fragment of a homologue of SEQ ID No: 45. In another embodiment, the dat protein is a fragment of a variant of SEQ ID No: 45. In another embodiment, the dat protein is a fragment of an isomer of SEQ ID No: 45.

In another embodiment, the dat protein is any other *Listeria* dat protein known in the art. In another embodiment, the dat protein is any other gram-positive dat protein known in the art. In another embodiment, the dat protein is any other dat protein known in the art. Each possibility represents a separate embodiment of the methods and compositions as provided herein.

In another embodiment, the dat protein of methods and compositions of the methods and compositions as provided herein retains its enzymatic activity. In another embodiment, the dat protein retains 90% of wild-type activity. In another embodiment, the dat protein retains 80% of wild-type activity. In another embodiment, the dat protein retains 70% of wild-type activity. In another embodiment, the dat protein retains 60% of wild-type activity. In another embodiment, the dat protein retains 50% of wild-type activity. In another embodiment, the dat protein retains 40% of wild-type activity. In another embodiment, the dat protein retains 30% of wild-type activity. In another embodiment, the dat protein retains 20% of wild-type activity. In another embodiment, the dat protein retains 10% of wild-type activity. In another embodiment, the dat protein retains 5% of wild-type activity. Each possibility represents a separate embodiment of the methods and compositions as provided herein.

In another embodiment, the metabolic enzyme is encoded by dga. D-glutamic acid synthesis is also controlled in part by the dga gene, and an auxotrophic mutant for D-glutamic acid synthesis will not grow in the absence of D-glutamic acid (Pucci et al, 1995, J. Bacteriol. 177: 336-342). In another rembodiment, the recombinant *Listeria* is auxotrophic for D-glutamic acid. A further example includes a gene involved in the synthesis of diaminopimelic acid. Such synthesis genes encode beta-semialdehyde dehydrogenase, and when inactivated, renders a mutant auxotrophic for this synthesis pathway (Sizemore et al, 1995, Science 270: 299-302). In another embodiment, the dga protein is any other *Listeria* dga protein known in the art. In another embodiment, the dga protein is any other gram-positive dga protein known in the art. Each possibility represents a separate embodiment of the methods and compositions as provided herein.

In another embodiment, the metabolic enzyme is encoded by an alr (alanine racemase) gene. In another embodiment, the metabolic enzyme is any other enzyme known in the art that is involved in alanine synthesis. In another embodiment, the metabolic enzyme is any other enzyme known in the art that is involved in L-alanine synthesis. In another embodiment, the metabolic enzyme is any other enzyme known in the art that is involved in D-alanine synthesis. In another rembodiment, the recombinant *Listeria* is auxotrophic for D-alanine. Bacteria auxotrophic for alanine synthesis are well known in the art, and are described in, for example, *E. coli* (Strych et al, 2002, J. Bacteriol. 184:4321-4325), *Corynebacterium glutamicum* (Tauch et al, 2002, J. Biotechnol 99:79-91), and *Listeria* to monocytogenes (Frankel et al, U.S. Pat. No. 6,099,848)), *Lactococcus* species, and *Lactobacillus* species, (Bron et al, 2002, Appl Environ Microbiol, 68: 5663-70). In another embodiment, any D-alanine synthesis gene known in the art is inactivated. Each possibility represents a separate embodiment of the methods and compositions as provided herein.

In another embodiment, the metabolic enzyme is an amino acid aminotransferase.

In another embodiment, the metabolic enzyme is encoded by serC, a phosphoserine aminotransferase. In another embodiment, the metabolic enzyme is encoded by asd (aspartate beta-semialdehyde dehydrogenase), involved in synthesis of the cell wall constituent diaminopimelic acid. In another embodiment, the metabolic enzyme is encoded by gsaB-glutamate-1-semialdehyde aminotransferase, which catalyzes the formation of 5-aminolevulinate from (S)-4-amino-5-oxopentanoate. In another embodiment, the metabolic enzyme is encoded by HemL, which catalyzes the formation of 5-aminolevulinate from (S)-4-amino-5-oxopentanoate. In another embodiment, the metabolic enzyme is encoded by aspB, an aspartate aminotransferase that catalyzes the formation of oxalozcetate and L-glutamate from L-aspartate and 2-oxoglutarate. In another embodiment, the metabolic enzyme is encoded by argF-1, involved in arginine biosynthesis. In another embodiment, the metabolic enzyme is encoded by aroE, involved in amino acid biosynthesis. In another embodiment, the metabolic enzyme is encoded by aroB, involved in 3-dehydroquinate biosynthesis. In another embodiment, the metabolic enzyme is encoded by aroD, involved in amino acid biosynthesis. In another embodiment, the metabolic enzyme is encoded by aroC, involved in amino acid biosynthesis. In another embodiment, the metabolic enzyme is encoded by hisB, involved in histidine biosynthesis. In another embodiment, the metabolic enzyme is encoded by hisD, involved in histidine biosynthesis. In another embodiment, the metabolic enzyme is encoded by hisG, involved in histidine biosynthesis. In another embodiment, the metabolic enzyme is encoded by metX, involved in methionine biosynthesis. In another embodiment, the metabolic enzyme is encoded by proB, involved in proline biosynthesis. In another embodiment, the metabolic enzyme is encoded by argR, involved in arginine biosynthesis. In another embodiment, the metabolic enzyme is encoded by argJ, involved in arginine biosynthesis. In another embodiment, the metabolic enzyme is encoded by thiI, involved in thiamine biosynthesis. In another embodiment, the metabolic enzyme is encoded by LMOf2365_1652, involved in tryptophan biosynthesis. In another embodiment, the metabolic enzyme is encoded by aroA, involved in tryptophan biosynthesis. In another embodiment, the metabolic enzyme is encoded by ilvD, involved in valine and isoleucine biosynthesis. In another embodiment, the metabolic enzyme is encoded by ilvC, involved in valine and isoleucine biosynthesis. In another embodiment, the metabolic enzyme is encoded by leuA, involved in leucine biosynthesis. In another embodiment, the metabolic enzyme is encoded by dapF, involved in lysine biosynthesis. In another embodiment, the metabolic enzyme is encoded by thrB, involved in threonine biosynthesis (all GenBank Accession No. NC_002973).

In another embodiment, the metabolic enzyme is a tRNA synthetase. In another embodiment, the metabolic enzyme is encoded by the trpS gene, encoding tryptophanyltRNA synthetase. In another embodiment, the metabolic enzyme is any other tRNA synthetase known in the art. Each possibility represents a separate embodiment of the methods and compositions as provided herein.

In another embodiment, a recombinant *Listeria* strain as provided herein has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the passaging attenuates the strain, or in another embodiment, makes the strain less virulent. Methods for passaging a recombinant *Listeria* strain through an animal host are well known in the art, and are described, for example, in U.S. patent application Ser. No. 10/541,614. Each possibility represents a separate embodiment of the methods and compositions as provided herein.

The recombinant *Listeria* strain of the methods and compositions as provided herein is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment as provided herein. In another embodiment, the sequences of *Listeria* proteins for use in the methods and compositions as provided herein are from any of the above-described strains.

In one embodiment, a *Listeria monocytogenes* strain as provided herein is the EGD strain, the 10403S strain, the NICPBP 54002 strain, the S3 strain, the NCTC 5348 strain, the NICPBP 54006 strain, the M7 strain, the S19 strain, or another strain of *Listeria monocytogenes* which is known in the art.

In another embodiment, the recombinant *Listeria* strain is a vaccine strain, which in one embodiment, is a bacterial vaccine strain.

In one embodiment, a vaccine is a composition which elicits an immune response to an antigen or polypeptide in the composition as a result of exposure to the composition.

In another embodiment, the vaccine additionally comprises an adjuvant, cytokine, chemokine, or combination thereof. In another embodiment, the vaccine or composition additionally comprises antigen presenting cells (APCs), which in one embodiment are autologous, while in another embodiment, they are allogeneic to the subject.

In one embodiment, a "vaccine" is a composition which elicits an immune response in a host to an antigen or polypeptide in the composition as a result of exposure to the composition. In one embodiment, the immune response is to a particular antigen or to a particular epitope on the antigen. In one embodiment, the vaccine may be a peptide vaccine, in another embodiment, a DNA vaccine. In another embodiment, the vaccine may be contained within and, in another embodiment, delivered by, a cell, which in one embodiment is a bacterial cell, which in one embodiment, is a *Listeria*. In one embodiment, a vaccine may prevent a subject from contracting or developing a disease or condition, wherein in another embodiment, a vaccine may be therapeutic to a subject having a disease or condition. In one embodiment, a vaccine of the present invention comprises a composition of the present invention and an adjuvant, cytokine, chemokine, or combination thereof.

In another embodiment, the present invention provides an immunogenic composition comprising a recombinant *Listeria* of the present invention. In another embodiment, the immunogenic composition of methods and compositions of the present invention comprises a recombinant vaccine vector of the present invention. In another embodiment, the immunogenic composition comprises a plasmid of the present invention. In another embodiment, the immunogenic composition comprises an adjuvant. In one embodiment, a vector of the present invention may be administered as part of a vaccine composition. Each possibility represents a separate embodiment of the present invention.

In another embodiment, a vaccine of the present invention is delivered with an adjuvant. In one embodiment, the adjuvant favors a predominantly Th1-mediated immune response. In another embodiment, the adjuvant favors a Th1-type immune response. In another embodiment, the adjuvant favors a Th1-mediated immune response. In another embodiment, the adjuvant favors a cell-mediated immune response over an antibody-mediated response. In another embodiment, the adjuvant is any other type of adjuvant known in the art. In another embodiment, the immunogenic composition induces the formation of a T cell immune response against the target protein.

In another embodiment, the adjuvant is MPL. In another embodiment, the adjuvant is QS21. In another embodiment, the adjuvant is a TLR agonist. In another embodiment, the adjuvant is a TLR4 agonist. In another embodiment, the adjuvant is a TLR9 agonist. In another embodiment, the adjuvant is Resiquimod®. In another embodiment, the adjuvant is imiquimod. In another embodiment, the adjuvant is a CpG oligonucleotide. In another embodiment, the adjuvant is a cytokine or a nucleic acid encoding same. In another embodiment, the adjuvant is a chemokine or a nucleic acid encoding same. In another embodiment, the adjuvant is IL-12 or a nucleic acid encoding same. In another embodiment, the adjuvant is IL-6 or a nucleic acid encoding same. In another embodiment, the adjuvant is a lipopolysaccharide. In another embodiment, the adjuvant is as described in Fundamental Immunology, 5th ed (August 2003): William E. Paul (Editor); Lippincott Williams & Wilkins Publishers; Chapter 43: Vaccines, GJV Nossal, which is hereby incorporated by reference. In another embodiment, the adjuvant is any other adjuvant known in the art. Each possibility represents a separate embodiment of the methods and compositions as provided herein.

In one embodiment, provided herein is a method of inducing an immune response to an antigen in a subject comprising administering a recombinant *Listeria* strain to said subject. In one embodiment, provided herein is a method of inducing an anti-angiogenic immune response to an antigen in a subject comprising administering a recombinant *Listeria* strain to said subject. In another embodiment, said recombinant *Listeria* strain comprises a first and second nucleic acid molecule. In another embodiment, each said nucleic acid molecule encodes a heterologous antigen. In yet another embodiment, said first nucleic acid molecule is operably integrated into the *Listeria* genome as an open reading frame with an endogenous polypeptide comprising a PEST sequence.

In one embodiment, provided herein is a method of treating, suppressing, or inhibiting at least one cancer in a subject comprising administering a recombinant *Listeria* strain to said subject. In another embodiment, said recombinant *Listeria* strain comprises a first and second nucleic acid molecule. In another embodiment, each said nucleic acid molecule encoding a heterologous antigen. In yet another embodiment, said first nucleic acid molecule is operably integrated into the *Listeria* genome as an open reading frame with a nucleic acid sequence encoding an endogenous polypeptide comprising a PEST sequence. In another embodiment, at least one of said antigens is expressed by at least one cell of said cancer cells.

In one embodiment, provided herein is a method of delaying the onset to a cancer in a subject comprising administering a recombinant *Listeria* strain to said subject. In another embodiment, provided herein is a method of delaying the progression to a cancer in a subject comprising administering a recombinant *Listeria* strain to said subject. In another embodiment, provided herein is a method of extending the remission to a cancer in a subject comprising administering a recombinant *Listeria* strain to said subject. In another embodiment, provided herein is a method of decreasing the size of an existing tumor in a subject comprising administering a recombinant *Listeria* strain to said subject. In another embodiment, provided herein is a method of preventing the growth of an existing tumor in a subject comprising administering a recombinant *Listeria* strain to said subject. In another embodiment, provided herein is a method of preventing the growth of new or additional tumors in a subject comprising administering a recombinant *Listeria* strain to said subject.

In one embodiment, cancer or tumors may be prevented in specific populations known to be susceptible to a particular cancer or tumor. In one embodiment, such susceptibilty may be due to environmental factors, such as smoking, which in one embodiment, may cause a population to be subject to lung cancer, while in another embodiment, such susceptbility may be due to genetic factors, for example a population with BRCA1/2 mutations may be susceptible, in one embodiment, to breast cancer, and in another embodiment, to ovarian cancer. In another embodiment, one or more mutations on chromosome 8q24, chromosome 17q12, and chromosome 17q24.3 may increase susceptibility to prostate cancer, as is known in the art. Other genetic and environmental factors contributing to cancer susceptibility are known in the art.

In another embodiment, a method of present invention further comprises the step of boosting the human subject with a recombinant *Listeria* strain as provided herein. In another embodiment, the recombinant *Listeria* strain used in the booster inoculation is the same as the strain used in the initial "priming" inoculation. In another embodiment, the booster strain is different from the priming strain. In another embodiment, the same doses are used in the priming and boosting inoculations. In another embodiment, a larger dose is used in the booster. In another embodiment, a smaller dose is used in the booster. Each possibility represents a separate embodiment of the methods and compositions as provided herein.

In one embodiment, the first or second nucleic acid molecule encodes a prostate specific antigen (PSA) and the method is for treating, inhibiting or suppressing prostate cancer. In another embodiment, the first or second nucleic acid molecule encodes PSA and the method is for treating, inhibiting or suppressing ovarian cancer. In another embodiment, the first or second nucleic acid molecule encodes PSA and the method is treating, inhibiting, or suppressing metastasis of prostate cancer, which in one embodiment, comprises metastasis to bone, and in another embodiment, comprises metastasis to other organs. In another embodiment, the first or second nucleic acid molecule encodes PSA and the method is for treating, inhibiting or suppressing metastasis of prostate cancer to bones. In yet another embodiment the method is for treating, inhibiting, or suppressing metastatis of prostate cancer to other organs. In another embodiment, the first or second nucleic acid molecule encodes PSA and the method is for treating, inhibiting or suppressing breast cancer. In another embodiment, the first or second nucleic acid molecule encodes PSA and the method is for treating, inhibiting or suppressing both ovarian and breast cancer.

In one embodiment, the first or second nucleic acid molecule encodes a High Molecular Weight-Melanoma Associated Antigen (HMW-MAA) and the method is for treating, inhibiting or suppressing melanoma. In another embodiment, the first or second nucleic acid molecule encodes HMW-MAA and the method is for treating, inhibiting or suppressing breast cancer. In another embodiment, the first or second nucleic acid molecule encodes HMW-MAA and the method is for treating, inhibiting or suppressing ovarian cancer. In another embodiment, the first or second nucleic acid molecule encodes HMW-MAA and the method is for treating, inhibiting or suppressing benign nevi lesions. In another embodiment, the first or second nucleic acid molecule encodes HMW-MAA and the method is for treating, inhibiting or suppressing basal cell carcinoma. In another embodiment, the first or second nucleic acid molecule encodes HMW-MAA and the method is for treating, inhibiting or suppressing a tumor of neural crest origin, which in one embodiment, is an astrocytoma, glioma, neuroblastoma, sarcoma, or combination thereof. In another embodiment, the first or second nucleic acid molecule encodes HMW-MAA and the method is for treating, inhibiting or suppressing a childhood leukemia, which in one embodiment, is Childhood Acute Lymphoblastic Leukemia, and in another embodiment, is Childhood Acute Myeloid Leukemia (which in one embodiment, is acute myelogenous leukemia, acute myeloid leukemia, acute myelocytic leukemia, or acute non-lymphocytic leukemia) and in another embodiment, is acute lymphocytic leukemia (which in one embodiment, is called acute lymphoblastic leukemia, and in another embodiment, is acute myelogenous leukemia (also called acute myeloid leukemia, acute myelocytic leukemia, or acute non-lymphocytic leukemia) and in another embodiment, is Hybrid or mixed lineage leukemia. In another embodiment, the first or second nucleic acid molecule encodes HMW-MAA and the method is for treating, inhibiting or suppressing Chronic myelogenous leukemia or Juvenile Myelomonocytic Leukemia (JMML). In another embodiment, the first or second nucleic acid molecule encodes HMW-MAA and the method is for treating, inhibiting or suppressing lobular breast carcinoma lesions.

The cancer that is the target of methods and compositions as provided herein is, in another embodiment, a melanoma. In another embodiment, the cancer is a sarcoma. In another embodiment, the cancer is a carcinoma. In another embodiment, the cancer is a mesothelioma (e.g. malignant mesothelioma). In another embodiment, the cancer is a glioma. In another embodiment, the cancer is a germ cell tumor. In another embodiment, the cancer is a choriocarcinoma.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is a non-small cell lung cancer (NSCLC). In another embodiment, the cancer is a colon cancer. In another embodiment, the cancer is a lung cancer. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma. Each possibility represents a separate embodiment of the methods and compositions as provided herein.

In one embodiment, the compositions and methods as provided herein can be used to treat solid tumors related to or resulting from any of the cancers as described hereinabove. In another embodiment, the tumor is a Wilms' tumor. In another embodiment, the tumor is a desmoplastic small round cell tumor.

In another embodiment, the present invention provides a method of impeding angiogenesis of a solid tumor in a subject, comprising administering to the subject a composition comprising a recombinant *Listeria* encoding a heterologous antigen. In another embodiment, the antigen is HMW-MAA. In another embodiment, the antigen is fibroblast growth factor (FGF). In another embodiment, the antigen is vascular endothelial growth factor (VEGF). In another embodiment, the antigen is any other antigen known in the art to be involved in angiogenesis. In another embodiment, the methods and compositions of impeding angiogenesis of a solid tumor in a subject, as provided herein, comprise administering to the subject a composition comprising a recombinant *Listeria* encoding two heterologous antigens. In another embodiment, one of the two heterologous antigens is HMW-MAA. In another embodiment, the antigen is any other antigen known in the art to be involved in angiogenesis. Each possibility represents a separate embodiment of the methods and compositions as provided herein.

Methods for assessing efficacy of prostate cancer vaccines are well known in the art, and are described, for example, in Dzojic H et al (Adenovirus-mediated CD40 ligand therapy induces tumor cell apoptosis and systemic immunity in the TRAMP-C2 mouse prostate cancer model. Prostate. 2006 Jun. 1; 66(8):831-8), Naruishi K et al (Adenoviral vector-mediated RTVP-1 gene-modified tumor cell-based vaccine suppresses the development of experimental prostate cancer. Cancer Gene Ther. 2006 July; 13(7):658-63), Sehgal I et al (Cancer Cell Int. 2006 Aug. 23; 6:21), and Heinrich J E et al (Vaccination against prostate cancer using a live tissue factor deficient cell line in Lobund-Wistar rats. Cancer Immunol Immunother 2007; 56(5):725-30). Each possibility represents a separate embodiment as provided herein.

In another embodiment, the prostate cancer model used to test methods and compositions as provided herein is the TPSA23 (derived from TRAMP-C1 cell line stably expressing PSA) mouse model. In another embodiment, the prostate cancer model is a 178-2 BMA cell model. In another embodiment, the prostate cancer model is a PAIII adenocarcinoma cells model. In another embodiment, the prostate cancer model is a PC-3M model. In another embodiment, the prostate cancer model is any other prostate cancer model known in the art. Each possibility represents a separate embodiment of the methods and compositions as provided herein.

In another embodiment, the vaccine is tested in human subjects, and efficacy is monitored using methods well known in the art, e.g. directly measuring $CD4^+$ and $CD8^+$ T cell responses, or measuring disease progression, e.g. by determining the number or size of tumor metastases, or monitoring disease symptoms (cough, chest pain, weight loss, etc). Methods for assessing the efficacy of a prostate cancer vaccine in human subjects are well known in the art, and are described, for example, in Uenaka A et al (T cell immunomonitoring and tumor responses in patients immunized with a complex of cholesterol-bearing hydrophobized pullulan (CHP) and NY-ESO-1 protein. Cancer Immun. 2007 Apr. 19; 7:9) and Thomas-Kaskel A K et al (Vaccination of advanced prostate cancer patients with PSCA and PSA peptide-loaded dendritic cells induces DTH responses that correlate with superior overall survival. Int J Cancer. 2006 Nov. 15; 119(10):2428-34). Each method represents a separate embodiment of the methods and compositions as provided herein.

In another embodiment, the present invention provides a method of treating benign prostate hyperplasia (BPH) in a subject. In another embodiment, the present invention provides a method of treating Prostatic Intraepithelial Neoplasia (PIN) in a subject In one embodiment, provided herein is a recombinant *Listeria* strain comprising a nucleic acid molecule operably integrated into the *Listeria* genome. In another embodiment said nucleic acid molecule encodes (a) an endogenous polypeptide comprising a PEST sequence and (b) a polypeptide comprising an antigen in an open reading frame.

In one embodiment, provided herein is a method of treating, suppressing, or inhibiting at least one tumor in a subject, comprising administering a recombinant *Listeria* strain to said subject. In another embodiment, said recombinant *Listeria* strain comprises a first and second nucleic acid molecule. In another embodiment, each said nucleic acid molecule encodes a heterologous antigen. In another embodiment, said first nucleic acid molecule is operably integrated into the Listeria genome as an open reading frame with a native polypeptide comprising a PEST sequence and wherein said antigen is expressed by at least one cell of said tumor.

In one embodiment, "antigen" is used herein to refer to a substance that when placed in contact with an organism, results in a detectable immune response from the organism. An antigen may be a lipid, peptide, protein, carbohydrate, nucleic acid, or combinations and variations thereof.

In one embodiment, "variant" refers to an amino acid or nucleic acid sequence (or in other embodiments, an organism or tissue) that is different from the majority of the population but is still sufficiently similar to the common mode to be considered to be one of them, for example splice variants.

In one embodiment, "isoform" refers to a version of a molecule, for example, a protein, with only slight differences compared to another isoform, or version, of the same protein. In one embodiment, isoforms may be produced from different but related genes, or in another embodiment, may arise from the same gene by alternative splicing. In another embodiment, isoforms are caused by single nucleotide polymorphisms.

In one embodiment, "fragment" refers to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In one embodiment, the fragment is a functional fragment. In another embodiment, the fragment is an immunogenic fragment. In one embodiment, a fragment has 10-20 nucleic or amino acids, while in another embodiment, a fragment has more than 5 nucleic or amino acids, while in another embodiment, a fragment has 100-200 nucleic or amino acids, while in another embodiment, a fragment has 100-500 nucleic or amino acids, while in another embodiment, a fragment has 50-200 nucleic or amino acids, while in another embodiment, a fragment has 10-250 nucleic or amino acids.

In one embodiment, "immunogenicity" or "immunogenic" is used herein to refer to the innate ability of a protein, peptide, nucleic acid, antigen or organism to elicit an immune response in an animal when the protein, peptide, nucleic acid, antigen or organism is administered to the animal. Thus, "enhancing the immunogenicity" in one embodiment, refers to increasing the ability of a protein, peptide, nucleic acid, antigen or organism to elicit an immune response in an animal when the protein, peptide, nucleic acid, antigen or organism is administered to an animal. The increased ability of a protein, peptide, nucleic acid, antigen or organism to elicit an immune response can be measured by, in one embodiment, a greater number of antibodies to a protein, peptide, nucleic acid, antigen or organism, a greater diversity of antibodies to an antigen or organism, a greater number of T-cells specific for a protein, peptide, nucleic acid, antigen or organism, a greater cytotoxic or helper T-cell response to a protein, peptide, nucleic acid, antigen or organism, and the like.

In one embodiment, a "homologue" refers to a nucleic acid or amino acid sequence which shares a certain percentage of sequence identity with a particular nucleic acid or amino acid sequence. In one embodiment, a sequence useful in the composition and methods as provided herein may be a homologue of a particular LLO sequence or N-terminal fragment thereof, ActA sequence or N-terminal fragment thereof, or PEST-like sequence described herein or known in the art. In one embodiment, such a homolog maintains In another embodiment, a sequence useful in the composition and methods as provided herein may be a homologue of an antigenic polypeptide, which in one embodiment, is KLK3 or HMW-MAA or a functional fragment thereof. In one embodiment, a homolog of a polypeptide and, in one embodiment, the nucleic acid encoding such a homolog, of the present invention maintains the functional characteristics of the parent polypeptide. For example, in one embodiment, a homolog of an antigenic polypeptide of the present invention maintains the antigenic characteristic of the parent polypeptide. In another embodiment, a sequence useful in the composition and methods as provided herein may be a homologue of any sequence described herein. In one embodiment, a homologue shares at least 70% identity with a particular sequence. In another embodiment, a homologue shares at least 72% identity with a particular sequence. In another embodiment, a homologue shares at least 75% identity with a particular sequence. In another embodiment, a homologue shares at least 78% identity with a particular sequence. In another embodiment, a homologue shares at least 80% identity with a particular sequence. In another embodiment, a homologue shares at least 82% identity with a particular sequence. In another embodiment, a homologue shares at least 83% identity with a particular sequence. In another embodiment, a homologue shares at least 85% identity with a particular sequence. In another embodiment, a homologue shares at least 87% identity with a particular sequence. In another embodiment, a homologue shares at least 88% identity with a particular sequence. In another embodiment, a homologue shares at least 90% identity with a particular sequence. In another embodiment, a homologue shares at least 92% identity with a particular sequence. In another embodiment, a homologue shares at least 93% identity with a particular sequence. In another embodiment, a homologue shares at least 95% identity with a particular sequence. In another embodiment, a homologue shares at least 96% identity with a particular sequence. In another embodiment, a homologue shares at least 97% identity with a particular sequence. In another embodiment, a homologue shares at least 98% identity with a particular sequence. In another embodiment, a homologue shares at least 99% identity with a particular sequence. In another embodiment, a homologue shares 100% identity with a particular sequence. Each possibility represents a separate embodiment as provided herein.

In one embodiment, it is to be understood that a homolog of any of the sequences as provided herein and/or as described herein is considered to be a part of the invention.

In one embodiment, "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

In one embodiment, "treating" refers to both therapeutic treatment and prophylactic or preventative measures, wherein the object is to prevent or lessen the targeted pathologic condition or disorder as described herein. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" or "impeding" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a particular disease or disorder, while in one embodiment, "secondary" refers to a symptom that is derived from or consequent to a primary cause. In one embodiment, the compounds for use in the present invention treat primary or secondary symptoms or secondary complications. In another embodiment, "symptoms" may be any manifestation of a disease or pathological condition.

In some embodiments, the term "comprising" refers to the inclusion of other recombinant polypeptides, amino acid sequences, or nucleic acid sequences, as well as inclusion of other polypeptides, amino acid sequences, or nucleic acid sequences, that may be known in the art, which in one embodiment may comprise antigens or *Listeria* polypeptides, amino acid sequences, or nucleic acid sequences. In some embodiments, the term "consisting essentially of" refers to a composition for use in the methods as provided herein, which has the specific recombinant polypeptide, amino acid sequence, or nucleic acid sequence, or fragment thereof. However, other polypeptides, amino acid sequences, or nucleic acid sequences may be included that are not involved directly in the utility of the recombinant polypeptide(s). In some embodiments, the term "consisting" refers to a composition for use in the methods as provided herein having a particular recombinant polypeptide, amino acid sequence, or nucleic acid sequence, or fragment or combination of recombinant polypeptides, amino acid sequences, or nucleic acid sequences or fragments as provided herein, in any form or embodiment as described herein.

In one embodiment, the compositions for use in the methods as provided herein are administered intravenously. In another embodiment, the vaccine is administered orally, whereas in another embodiment, the vaccine is administered parenterally (e.g., subcutaneously, intramuscularly, and the like).

Further, in another embodiment, the compositions or vaccines are administered as a suppository, for example a rectal suppository or a urethral suppository. Further, in another embodiment, the pharmaceutical compositions are administered by subcutaneous implantation of a pellet. In a further embodiment, the pellet provides for controlled release of an agent over a period of time. In yet another embodiment, the pharmaceutical compositions are administered in the form of a capsule.

In one embodiment, the route of administration may be parenteral. In another embodiment, the route may be intraocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation (aerosol), nasal aspiration (spray), intranasal (drops), sublingual, oral, aerosol or suppository or a combination thereof. For intranasal administration or application by inhalation, solutions or suspensions of the compounds mixed and aerosolized or nebulized in the presence of the appropriate carrier suitable. Such an aerosol may comprise any agent described herein. In one embodiment, the compositions as set forth herein may be in a form suitable for intracranial administration, which in one embodiment, is intrathecal and intracerebroventricular administration. In one embodiment, the regimen of administration will be determined by skilled clinicians, based on factors such as exact nature of the condition being treated, the severity of the condition, the age and general physical condition of the patient, body weight, and response of the individual patient, etc.

In one embodiment, parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

In one embodiment, sustained or directed release compositions can be formulated, e.g., liposomes or those wherein the active compound is protected with differentially degradable coatings, e.g., by microencapsulation, multiple coatings, etc. Such compositions may be formulated for immediate or slow release. It is also possible to freeze-dry the new compounds and use the lyophilisates obtained, for example, for the preparation of products for injection.

In one embodiment, for liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, a composition of or used in the methods of this invention may be administered alone or within a composition. In another embodiment, compositions of this invention admixture with conventional excipients, i.e., pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the compositions for use of the methods and compositions as provided herein may be administered with a carrier/diluent. Solid carriers/diluents include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In one embodiment, the compositions of the methods and compositions as provided herein may comprise the composition of this invention and one or more additional compounds effective in preventing or treating cancer. In some embodiments, the additional compound may comprise a compound useful in chemotherapy, which in one embodiment, is Cisplatin. In another embodiment, Ifosfamide, Fluorouracilor5-FU, Irinotecan, Paclitaxel (Taxol), Docetaxel, Gemcitabine, Topotecan or a combination thereof, may be administered with a composition as provided herein for use in the methods as provided herein. In another embodiment, Amsacrine, Bleomycin, Busulfan, Capecitabine, Carboplatin, Carmustine, Chlorambucil, Cisplatin, Cladribine, Clofarabine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Gliadelimplants, Hydroxycarbamide, Idarubicin, Ifosfamide, Irinotecan, Leucovorin, Liposomaldoxorubicin, Liposomaldaunorubicin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Satraplatin, Streptozocin, Tegafur-uracil, Temozolomide, Teniposide, Thiotepa, Tioguanine, Topotecan, Treosulfan, Vinblastine, Vincristine, Vindesine, Vinorelbine, or a combination thereof, may be administered with a composition as provided herein for use in the methods as provided herein.

In another embodiment, fusion proteins as provided herein are prepared by a process comprising subcloning of appropriate sequences, followed by expression of the resulting nucleotide. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid. In another embodiment, a similar strategy is used to produce a protein wherein an HMW-MAA fragment is embedded within a heterologous peptide.

In one embodiment, the present invention also provides a recombinant Listeria comprising a nucleic acid molecule encoding a heterologous antigenic polypeptide or fragment thereof, wherein said nucleic acid molecule is operably integrated into the Listeria genome as an open reading frame with an endogenous polypeptide comprising a PEST sequence.

In one embodiment, provided herein is a recombinant Listeria capable of expressing and secreting two distinct heterologous antigens comprising a first antigen that is operably integrated in the genome as an open reading frame with a first polypeptide or fragment thereof comprising a PEST sequence and a second antigen that is operably integrated in the genome as an open reading frame with a second polypeptide or fragment thereof comprising a PEST sequence. In another embodiment, said first or second polypeptide or fragment thereof is ActA, or LLO. In another embodiment, said first or second antigen is prostate tumor-associated antigen (PSA), or High Molecular Weight-Melanoma Associated Antigen (HMWMAA). In another embodiment, said fragment is an immunogenic fragment. In yet another embodiment, said episomal expression vector lacks an antibiotic resistance marker.

In another embodiment, the first and second antigen are distinct. In another embodiment, said first and second antigens are concomitantly expressed. In another embodiment, said first or second antigen are expressed at the same level. In another embodiment, said first or second antigen are differentially expressed. In another embodiment, gene or protein expression is determined by methods that are well known in the art which in another embodiment comprise real-time PCR, northern blotting, immunoblotting, etc. In another embodiment, said first or second antigen's expression is controlled by an inducible system, while in another embodiment, said first or second antigen's expression is controlled by a constitutive promoter. In another embodiment, inducible expression systems are well known in the art.

In one embodiment, provided herein is a method of preparing a recombinant Listeria capable of expressing and secreting two distinct heterologous antigens that target tumor cells and angiogenesis concomitantly. In another embodiment, said method of preparing said recombinant Listeria comprises the steps of genetically fusing a first antigen into the genome that is operably linked to an open reading frame encoding a first polypeptide or fragment thereof comprising a PEST sequence and transforming said recombinant Listeria with an episomal expression vector encoding a second antigen that is operably linked to an open reading frame encoding a second polypeptide or fragment thereof comprising a PEST sequence. In another embodiment, said method of preparing said recombinant Listeria comprises the steps of genetically fusing a first antigen into the genome that is operably linked to an open reading frame encoding a first polypeptide or fragment thereof comprising a PEST sequence and genetically fusing a second antigen that is operably linked to an open reading frame encoding a second polypeptide or fragment thereof comprising a PEST sequence.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the Listeria vaccine strain as provided herein is transformed by electroporation. Each method represents a separate embodiment of the methods and compositions as provided herein.

In one embodiment, provided herein is a method of inducing an immune response to an antigen in a subject comprising administering a recombinant Listeria strain to said subject, wherein said recombinant Listeria strain comprises a first and second nucleic acid molecule, each said nucleic acid molecule encoding a heterologous antigenic polypeptide or fragment thereof, wherein said first nucleic acid molecule is operably integrated into the Listeria genome as an open reading frame with a nucleic acid encoding an endogenous polypeptide comprising a PEST sequence.

In another embodiment, provided herein is a method of inhibiting the onset of cancer, said method comprising the step of administering a recombinant Listeria composition that expresses two distinct heterologous antigens specifically expressed in said cancer.

In one embodiment, provided herein is a method of treating a first and a second tumor in a subject, said method comprising the step of administering a recombinant Listeria composition that expresses two distinct heterologous antigens specifically expressed on said first and second tumor.

In another embodiment, provided herein is a method of ameliorating symptoms that are associated with a cancer in a subject, said method comprising the step of administering a recombinant Listeria composition that expresses two distinct heterologous antigens specifically expressed in said cancer.

In one embodiment, provided herein is a method of protecting a subject from cancer, said method comprising the step of administering a recombinant Listeria composition that expresses two distinct heterologous antigens specifically expressed in said cancer In another embodiment, provided herein is a method of delaying onset of cancer, said method comprising the step of administering a recombinant Listeria composition that expresses two distinct heterologous antigens specifically expressed in said cancer. In another embodiment, provided herein is a method of treating metastatic cancer, said method comprising the step of administering a recombinant Listeria composition that expresses two distinct heterologous antigens specifically expressed in said cancer. In another embodiment, provided herein is a method of preventing metastatic canceror micrometastatis, said method comprising the step of administering a recombinant Listeria composition that expresses two distinct heterologous antigens specifically expressed in said cancer. In another embodiment, the recombinant Listeria composition is administered orally or parenterally.

In one embodiment, the present invention provides a method of producing a recombinant Listeria strain expressing two antigens, the method comprising: (a) genetically fusing a first nucleic acid encoding a first antigen into the Listeria genome in an open reading frame with an endogenous PEST-containing gene; (b) transforming said recombinant Listeria with an episomal expression vector comprising a second nucleic acid encoding a second antigen; and (c) expressing said first and second antigens under conditions conducive to antigenic expression in said recombinant Listeria strain. In another embodiment, the present invention provides a method of producing a recombinant Listeria strain expressing two antigens, the method comprising: (a) genetically fusing a first nucleic acid encoding a first antigen and a second nucleic acid encoding a second antigen into the Listeria genome in an open reading frame with an endogenous PEST-containing gene; and (b) expressing said first and second antigens under conditions conducive to antigenic expression in said recombinant Listeria strain. In one embodiment, genetic fusion is via homologous recombination, as described herein. In one embodiment, conditions conducive to antigenic expression are known in the art.

In another embodiment of the methods and compositions as provided herein, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment as provided herein.

The terms "polypeptide," "peptide" and "recombinant peptide" refer, in another embodiment, to a peptide or polypeptide of any length. In another embodiment, a peptide or recombinant peptide as provided herein has one of the lengths enumerated above for an HMW-MAA fragment.

Each possibility represents a separate embodiment of the methods and compositions as provided herein. In one embodiment, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In one embodiment, "antigenic polypeptide" is used herein to refer to a polypeptide, peptide or recombinant peptide as described hereinabove that is foreign to a host and leads to the mounting of an immune response when present in, or, in another embodiment, detected by, the host.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), *-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides as provided herein may also include one or more modified amino acids or one or more non-amino acid monomers (e.g. fatty acids, complex carbohydrates etc).

In one embodiment, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than 500 generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the methods and compositions as provided herein.

In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see, e.g., Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS1992); Mulligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described, e.g., in WO 97/03211; WO 96/39154; Mata (1997) Toxicol. Appi. Pharmacol. 144:189-197. Other synthetic backbones encompasses by the term include methylphosphonate linkages or alternating methylphosphonate and phosphodiester linkages (Strauss-Soukup (1997) Biochemistry 36:8692-8698), and benzylphosphonate linkages (Samstag (1996) Antisense Nucleic Acid Drug Dev. 6:153-156). The term nucleic acid is used interchangeably with gene, cDNA, mRNA, oligonucleotide primer, probe and amplification product.

In one embodiment of the methods and compositions as provided herein, the term "recombination site" or "site-specific recombination site" refers to a sequence of bases in a nucleic acid molecule that is recognized by a recombinase (along with associated proteins, in some cases) that mediates exchange or excision of the nucleic acid segments flanking the recombination sites. The recombinases and associated proteins are collectively referred to as "recombination proteins" see, e.g., Landy, A., (Current Opinion in Genetics & Development) 3:699-707; 1993).

A "phage expression vector" or "phagemid" refers to any phage-based recombinant expression system for the purpose of expressing a nucleic acid sequence of the methods and compositions as provided herein in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

In one embodiment, the term "operably linked" as used herein means that the transcriptional and translational regulatory nucleic acid, is positioned relative to any coding sequences in such a manner that transcription is initiated. Generally, this will mean that the promoter and transcriptional initiation or start sequences are positioned 5' to the coding region.

In one embodiment, an "open reading frame" or "ORF" is a portion of an organism's genome which contains a sequence of bases that could potentially encode a protein. In another embodiment, the start and stop ends of the ORF are not equivalent to the ends of the mRNA, but they are usually contained within the mRNA. In one embodiment, ORFs are located between the start-code sequence (initiation codon) and the stop-codon sequence (termination codon) of a gene. Thus, in one embodiment, a nucleic acid molecule operably integrated into a genome as an open reading frame with an endogenous polypeptide is a nucleic acid molecule that has integrated into a genome in the same open reading frame as an endogenous polypeptide.

In one embodiment, the present invention provides a fusion polypeptide comprising a linker sequence. In one embodiment, a "linker sequence" refers to an amino acid sequence that joins two heterologous polypeptides, or fragments or domains thereof. In general, as used herein, a linker is an amino acid sequence that covalently links the polypeptides to form a fusion polypeptide. A linker typically includes the amino acids translated from the remaining recombination signal after removal of a reporter gene from a display vector to create a fusion protein comprising an amino acid sequence encoded by an open reading frame and the display protein. As appreciated by one of skill in the art, the linker can comprise additional amino acids, such as glycine and other small neutral amino acids.

In one embodiment, "endogenous" as used herein describes an item that has developed or originated within the reference organism or arisen from causes within the reference organism. In another embodiment, endogenous refers to native.

In one embodiment, "heterologous" as used herein describes a nucleic acid, amino acid, peptide, polypeptide, or protein derived from a different species than the reference species. Thus, for example, a *Listeria* strain expressing a heterologous polypeptide, in one embodiment, would express a polypeptide that is not native or endogenous to the *Listeria* strain, or in another embodiment, a polypeptide that is not normally expressed by the *Listeria* strain, or in another embodiment, a polypeptide from a source other than the *Listeria* strain. In another embodiment, heterologous may be used to describe something derived from a different organism within the same species. In another embodiment, the heterologous antigen is expressed by a recombinant strain of *Listeria*, and is processed and presented to cytotoxic T-cells upon infection of mammalian cells by the recombinant strain. In another embodiment, the heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal.

In one embodiment, an "episomal expression vector" as described herein refers to a nucleic acid vector which may be linear or circular, and which is usually double-stranded in form. In one embodiment, an episomal expression vector comprises a gene of interest. In another embodiment, the inserted gene of interest is not interrupted or subjected to regulatory constraints which often occur from integration into cellular DNA. In another embodiment, the presence of the inserted heterologous gene does not lead to rearrangement or interruption of the cell's own important regions. In another embodiment, episomal vectors persist in multiple copies in the bacterial cytoplasm, resulting in amplification of the gene of interest, and, in another embodiment, viral trans-acting factors are supplied when necessary. In another embodiment, in stable transfection procedures, the use of episomal vectors often results in higher transfection efficiency than the use of chromosome-integrating plasmids (Belt, P. B. G. M., et al (1991) Efficient cDNA cloning by direct phenotypic correction of a mutant human cell line (HPRT2) using an Epstein-Barr virus-derived cDNA expression vector. Nucleic Acids Res. 19, 4861-4866; Mazda, O., et al. (1997) Extremely efficient gene transfection into lympho-hematopoietic cell lines by Epstein-Barr virus-based vectors. J. Immunol. Methods 204, 143-151). In one embodiment, the episomal expression vectors of the methods and compositions as provided herein may be delivered to cells in vivo, ex vivo, or in vitro by any of a variety of the methods employed to deliver DNA molecules to cells. The vectors may also be delivered alone or in the form of a pharmaceutical composition that enhances delivery to cells of a subject.

In one embodiment, "fused" refers to linkage by covalent bonding.

"Transforming," in one embodiment, refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the methods and compositions as provided herein.

In another embodiment, conjugation is used to introduce genetic material and/or plasmids into bacteria. Methods for conjugation are well known in the art, and are described, for example, in Nikodinovic J et al (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102(35):12554-9). Each method represents a separate embodiment of the methods and compositions as provided herein.

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient.

Each possibility represents a separate embodiment of the methods and compositions as provided herein.

In one embodiment, the term "attenuation," as used herein, is meant a diminution in the ability of the bacterium to cause disease in an animal. In other words, the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria, the lethal dose at which 50% of inoculated animals survive* (LD.sub.50) is preferably increased above the LD.sub.50 of wild-type *Listeria* by at least about 10-fold, more preferably by at least about 100-fold, more preferably at least about 1,000 fold, even more preferably at least about 10,000 fold, and most preferably at least about 100.000-fold. An attenuated strain of *Listeria* is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. In one embodiment, the term "subject" does not exclude an individual that is healthy in all respects and does not have or show signs of disease or disorder.

In one embodiment, the *Listeria* as provided herein expresses a heterologous polypeptide, as described herein, in another embodiment, the *Listeria* as provided herein secretes a heterologous polypeptide, as described herein, and in another embodiment, the *Listeria* as provided herein expresses and secretes a heterologous polypeptide, as described herein. In another embodiment, the *Listeria* as provided herein comprises a heterologous polypeptide, and in another embodiment, comprises a nucleic acid that encodes a heterologous polypeptide.

In one embodiment, *Listeria* strains as provided herein may be used in the preparation of vaccines. In one embodiment, *Listeria* strains as provided herein may be used in the preparation of peptide vaccines. Methods for preparing peptide vaccines are well known in the art and are described, for example, in EP1408048, United States Patent Application Number 20070154953, and OGASAWARA et al (Proc. Natl. Acad. Sci. USA Vol. 89, pp. 8995-8999, October 1992). In one embodiment, peptide evolution techniques are used to create an antigen with higher immunogenicity. Techniques for peptide evolution are well known in the art and are described, for example in U.S. Pat. No. 6,773,900.

In one embodiment, the vaccines of the methods and compositions as provided herein may be administered to a host vertebrate animal, preferably a mammal, and more preferably a human, either alone or in combination with a pharmaceutically acceptable carrier. In another embodiment, the vaccine is administered in an amount effective to induce an immune response to the *Listeria* strain itself or to a heterologous antigen which the *Listeria* species has been modified to express. In another embodiment, the amount of vaccine to be administered may be routinely determined by one of skill in the art when in possession of the present disclosure. In another embodiment, a pharmaceutically acceptable carrier may include, but is not limited to, sterile distilled water, saline, phosphate buffered solutions or bicarbonate buffered solutions. In another embodiment, the pharmaceutically acceptable carrier selected and the amount of carrier to be used will depend upon several factors including the mode of administration, the strain of *Listeria* and the age and disease state of the vaccinee. In another embodiment, administration of the vaccine may be by an oral route, or it may be parenteral, intranasal, intramuscular, intravascular, intrarectal, intraperitoneal, or any one of a variety of well-known routes of administration. In another embodiment, the route of administration may be selected in accordance with the type of infectious agent or tumor to be treated.

In one embodiment, the present invention provides a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, the present invention provides a method of inducing an immune response to an antigen in a subject comprising administering a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, the present invention provides a method of treating, suppressing, or inhibiting a cancer in a subject comprising administering a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, the present invention provides a method of treating, suppressing, or inhibiting at least one tumor in a subject comprising administering a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, the present invention provides a method of producing a recombinant *Listeria* strain expressing an antigen, the method comprising genetically fusing a first nucleic acid encoding an antigen into the *Listeria* genome in an open reading frame with an endogenous PEST-containing gene; and expressing said antigen under conditions conducive to antigenic expression in said recombinant *Listeria* strain.

In another embodiment, the present invention provides any of the methods described hereinabove using a recombinant *Listeria* strain comprising a nucleic acid molecule encoding a heterologous antigenic polypeptide or fragment thereof, wherein said nucleic acid molecule is operably integrated into the *Listeria* genome in an open reading frame with an endogenous PEST-containing gene.

In another embodiment, the present invention provides a kit for conveniently practicing the methods as provided herein comprising one or more *Listeria* strains as provided herein, an applicator, and instructional material that describes how to use the kit components in practicing the methods as provided herein.

The following examples are presented in order to more fully illustrate the preferred embodiments of the invention. They should in no way be construed, however, as limiting the broad scope of the invention.

EXAMPLES

We developed a recombinant Lm that secretes PSA fused to tLLO (Lm-LLO-PSA), which elicits a potent PSA-specific immune response associated with regression of tumors in a mouse model for prostate cancer, wherein the expression of tLLO-PSA is derived from a plasmid based on pGG55 (Table 1), which confers antibiotic resistance to the vector. We recently developed a new strain for the PSA vaccine based on the pADV142 plasmid, which has no antibiotic resistance markers, and referred as LmddA-142 (Table 1). This new strain is times more attenuated than Lm-LLO-PSA. In addition, LmddA-142 was slightly more immunogenic and significantly more efficacious in regressing PSA expressing tumors than the Lm-LLO-PSA.

TABLE 1

Plasmids and strains

| Plasmids | Features |
|---|---|
| pGG55 | pAM401/pGB354 shuttle plasmid with gram(−) and gram(+) cm resistance, LLO-E7 expression cassette and a copy of Lm prfA gene |
| pTV3 | Derived from pGG55 by deleting cm genes and inserting the Lm dal gene |
| pADV119 | Derived from pTV3 by deleting the prfA gene |
| pADV134 | Derived from pADV119 by replacing the Lm dal gene by the *Bacillus* dal gene |
| pADV142 | Derived from pADV134 by replacing HPV16 e7 with klk3 |
| pADV168 | Derived from pADV134 by replacing HPV16 e7 with hmw-$maa_{2160-2258}$ |
| Strains | Genotype |
| 10403S | Wild-type *Listeria monocytogenes*:: str |
| XFL-7 | 10403S $prfA^{(-)}$ |
| Lmdd | 10403S $dal^{(-)}$ $dat^{(-)}$ |
| LmddA | 10403S $dal^{(-)}$ $dat^{(-)}$ $actA^{(-)}$ |
| LmddA-134 | 10403S $dal^{(-)}$ $dat^{(-)}$ $actA^{(-)}$ pADV134 |
| LmddA-142 | 10403S $dal^{(-)}$ $dat^{(-)}$ $actA^{(-)}$ pADV142 |
| Lmdd-143 | 10403S $dal^{(-)}$ $dat^{(-)}$ with klk3 fused to the hly gene in the chromosome |
| LmddA-143 | 10403S $dal^{(-)}$ $dat^{(-)}$ $actA^{(-)}$ with klk3 fused to the hly gene in the chromosome |
| LmddA-168 | 10403S $dal^{(-)}$ $dat^{(-)}$ $actA^{(-)}$ pADV168 |
| Lmdd-143/134 | Lmdd-143 pADV134 |
| LmddA-143/134 | LmddA-143 pADV134 |
| Lmdd-143/168 | Lmdd-143 pADV168 |
| LmddA-143/168 | LmddA-143 pADV168 |

-continued

```
gtcagcagaatatgtgatacaggatatattccgatcctcgctca ctgactcgctacgctcggtcgttcgactgcggcgagcggaaatg gcttacgaacggggcggagatttcctggaagatgccaggaagat acttaacagggaagtgagagggccgcggcaaagccgtttttcca taggctccgcccccctgacaagcatcacgaaatctgacgctcaa atcagtggtggcgaaacccgacaggactataaagataccaggcg tttccccctggcggctccctcgtgcgctctcctgttcctgcctt tcggtttaccggtgtcattccgctgttatggccgcgtttgtctc attccacgcctgacactcagttccgggtaggcagttcgctccaa gctggactgtatgcacgaacccccgttcagtccgaccgctgcg ccttatccggtaactatcgtcttgagtccaacccggaaagacat gcaaaagcaccactggcagcagccactggtaattgatttagagg agttagtcttgaagtcatgcgccggttaaggctaaactgaaagg acaagttttggtgactgcgctcctccaagccagttacctcggtt
```

The sequence of the plasmid pAdv142 (6523 bp) was as follows:

```
This plasmid was sequenced at Genewiz facility
from the E. coli strain on 2-20-08.
                                   (SEQ ID NO: 46)
cggagtgtatactggcttactatgaggcactgatgagggtgtca gtgaagtgcttcatgtggcaggagaaaaaaggctgcaccggtgc
```

-continued

```
caaagagttggtagctcagagaaccttcgaaaaaccgccctgca aggcggtttttttcgttttcagagcaagagattacgcgcagacca aaacgatctcaagaagatcatcttattaatcagataaaatattt ctagccctcctttgattagtatattcctatcttaaagttacttt tatgtggaggcattaacatagttaatgacgtcaaaaggatagca
```

-continued agactagaataaagctataaagcaagcatatataatattgcgat
catattagaagcgaatttcgccaatattataattatcaaaagag
aggggtggcaaacggtatttggcattattaggttaaaaaatgta
gaaggagagtgaaacccatgaaaaaataatgctagtttttaca
cttatattagttagtctaccaattgcgcaacaaactgaagcaaa
ggatgcatctgcattcaataaagaaaattcaatttcatccatgg
caccaccagcatctccgcctgcaagtcctaagacgccaatcgaa
aagaaacacgcggatgaaatcgataagtatatacaaggattgga
ttacaataaaaacaatgtattagtataccacggagatgcagtga
caaatgtgccgccaagaaaaggttacaaagatggaaatgaatat
attgagtggagaaaaagaagaaatccatcaatcaaaataatgca
gacattcaagagtgaatgcaatttcgagcctaacctatccaggt
gctctcgtaaaagcgaattcggaattagtagaaaatcaaccaga
tgactccctgtaaaacgtgattcattaacactcagcattgatttt
gccaggtatgactaatcaagacaataaaatagagtaaaaatgc
cactaaatcaaacgttaacaacgcagtaaatacattagtggaaa
gatggaatgaaaaatatgctcaagcttatccaaatgtaagtgca
aaaattgattatgatgacgaaatggcttacagtgaatcacaatt
aattgcgaaataggtacagcatttaaagctgtaaataatagctt
gaatgtaaacttcggcgcaatcagtgaagggaaaatgcaagaag
aagtcattagattaaacaaatttactataacgtgaatgttaatg
aacctacaagaccaccagattatcggcaaagctgttactaaaga
gcagagcaagcgcttggagtgaatgcagaaaatcctcctgcata
tatctcaagtgtggcgtatggccgtcaagatatttgaaattatc
aactaattcccatagtactaaagtaaaagctgatttgatgctgc
cgtaagcggaaaatctgtctcaggtgatgtagaactaacaaata
tcatcaaaaattatcatcaaagccgtaatttacggaggaccgca
aaagatgaagttcaaatcatcgacggcaacctcggagacttacg
cgatattagaaaaaggcgctactataatcgagaaacaccagga
gacccattgcttatacaacaaacttcctaaaagacaatgaatta
gctgttattaaaaacaactcagaatatattgaaacaacttcaaa
agcttatacagatggaaaaattaacatcgatcactctggaggat
acgttgctcaattcaacatttcttgggatgaagtaaattatgat
ctcgag<u>attgtgggaggctgggagtgcgagaagcattcccaa</u>
<u>ccctggcaggtgcttgtggcctctcgtggcagggcagtctgcgg</u>
<u>cggtgttctggtgcaccccagtgggtcctcacagctgccact</u>

-continued

<u>gcatcaggaacaaaagcgtgatcttgctgggtcggcacagcctg</u>
<u>tttcatcctgaagacacaggccaggtatttcaggtcagccacag</u>
<u>cttcccacacccgctctacgatatgagcctcctgaagaatcgat</u>
<u>tcctcaggccaggtgatgactccagccacgacctcatgctgctc</u>
<u>cgcctgtcagagcctgccgagctcacggatgctgtgaaggtcat</u>
<u>ggacctgcccacccaggagccagcactggggaccacctgctacg</u>
<u>cctcaggctggggcagcattgaaccagaggagttcttgacccca</u>
<u>aagaaacttcagtgtgtggacctccatgttatttccaatgacgt</u>
<u>gtgtgcgcaagttcaccctcagaaggtgaccaagttcatgcttg</u>
<u>tgctggacgctggacaggggcaaaagcacctgctcgggtgatt</u>
<u>ctgggggcccacttgtctgttatggtgtgcttcaaggtatcacg</u>
<u>tcatggggcagtgaaccatgtgcctgcccgaaaggccttccct</u>
<u>gtacaccaaggtggtgcattaccggaagtggatcaaggacacca</u>
<u>tcgtggccaaccccTAA</u>cccgggccactaactcaacgctagtag
tggatttaatcccaaatgagccaacagaaccagaaccagaaaca
gaacaagtaacattggagttagaaatggaagaagaaaaaagcaa
tgatttcgtgtgaataatgcacgaaatcattgcttattatttaa
aaagcgatatactagatataacgaaacaacgaactgaataaaga
atacaaaaaaagagccacgaccagttaaagcctgagaaactttta
actgcgagccttaattgattaccaccaatcaattaaagaagtcg
agacccaaaatttggtaaagtatttaattactttattaatcaga
tacttaaatatctgtaaacccattatatcgggttttttgagggga
tttcaagtattaagaagataccaggcaatcaattaagaaaaact
tagttgattgccattagagtgattcaactagatcgtagcttcta
actaattaattttcgtaagaaaggagaacagctgaatgaatatc
ccttttgttgtagaaactgtgcttcatgacggcttgttaaagta
caaatttaaaaatagtaaaattcgctcaatcactaccaagccag
gtaaaagtaaaggggctatattgcgtatcgctcaaaaaaaagca
tgattggcggacgtggcgttgactgacttccgaagaagcgattc
acgaaaatcaagatacatttacgcattggacaccaaacgatatc
gttatggtacgtatgcagacgaaaaccgttcatacactaaagga
cattctgaaaacaatttaagacaaatcaataccactttattgat -continued

```
tagatattcacacggaaaagaaactatttcagcaagcgatatt
ttaacaacagctattgatttaggttttatgcctacgttaattat
caaatctgataaaggttatcaagcatattttgttttagaaacgc
cagtctatgtgacttcaaaatcagaatttaaatctgtcaaagca
gccaaaataatctcgcaaaatatccgagaatattttggaaagtc
tttgccagttgatctaacgtgcaatcattttgggattgctcgta
taccaagaacggacaatgtagaattttttgatcccaattaccgt
tattctttcaaagaatggcaagattggtatttcaaacaaacaga
taataagggctttactcgttcaagtctaacggttttaagcggta
cagaaggcaaaaaacaagtagatgaaccctggtttaatctctta
ttgcacgaaacgaaattttcaggagaaaagggtttagtagggcg
caatagcgttatgtttaccctctctttagcctactttagttcag
gctattcaatcgaaacgtgcgaatataatatgtttgagtttaat
aatcgattagatcaacccttagaagaaaaagaagtaatcaaaat
tgttagaagtgcctattcagaaaactatcaaggggctaataggg
aatacattaccattctttgcaaagcttgggtatcaagtgattta
accagtaaagatttatagtccgtcaagggtggataaattcaaga
aaaaaagaagcgaacgtcaacgtgttcatttgtcagaatggaaa
gaagatttaatggcttatattagcgaaaaaagcgatgtatacaa
gccttatttagcgacgaccaaaaaagagattagagaagtgctag
gcattcctgaacggacattagataaattgctgaaggtactgaag
gcgaatcaggaaattttctttaagattaaaccaggaagaaatgg
tggcattcaacttgctagtgttaaatcattgttgctatcgatca
ttaaattaaaaaaagaagaacgagaaagctatataaggcgctg
acagcttcgataatttagaacgtacatttattcaagaaactcta
aacaaattggcagaacgccccaaaacggacccacaactcgattt
gatagctacgatacaggctgaaaataaaacccgcactatgccat
tacatttatatctatgatacgtgtttgttttttctttgctggcta
gcttaattgcttatatttacctgcaataaaggatttcttacttc
cattatactcccattttccaaaaacatacggggaacacgggaac
ttattgtacaggccacctcatagttaatggatcgagccacctgc
aatctcatccatggaaatatattcatcccctgccggcctatta
atgtgacttttgtgcccggcggatattcctgatccagctccacc
ataaattggtccatgcaaattcggccggcaattacaggcgattc
catcacaaggatgtcggtccattcaattacggagccagccgtcc
gcatagcctacaggcaccgtcccgatccatgtgtattaccgctg
tgtactcggctccgtagctgacgctctcgccattctgatcagat
gacatgtgacagtgtcgaatgcagggtaaatgccggacgcagct
gaaacggtatctcgtccgacatgtcagcagacgggcgaaggcca
tacatgccgatgccgaatctgactgcattaaaaaagcctatttc
agccggagtccagcggcgctgttcgcgcagtggaccattagatt
ctttaacggcagcggagcaatcagctctttaaagcgctcaaact
gcattaagaaatagcctctttcttttcatccgctgtcgcaaaa
tgggtaaataccccttgcactttaaacgagggttgcggtcaag
aattgccatcacgttctgaacttcttcctctgttttacaccaa
cgttgttcatccccgtatcgaccttcagatgaaaatgaagagaa
cctttttcgtgtggcgggctgcctcctgaagccattcaacaga
ataacctgttaaggtcacgtcatactcagcagcgattgccacat
actccggggaaccgcgccaagcaccaatataggcgccttcaat
ccctttttgcgcagtgaaatcgcttcatccaaatggccacggcc
aagcatgaagcaacctgcgtcaagagcagcctttgctgtttctg
catcaccatgcccgtaggcgtttgctttcacaactgccatcaag
tggacatgttcaccgatatgattttttcatattgctgacatttt
cctttatcgcggacaagtcaatttccgcccacgtatctctgtaa
aaaggttttgtgctcatggaaaactcctctchttttcagaaaat
cccagtacgtaattaagtatttgagaattaattttatattgatt
aatactaagtttacccagttttcacctaaaaaacaaatgatgag
ataatagctccaaaggctaaagaggactataccaactatttgtt
aattaa.
```

Example 1

Construction of Attenuated Listeria Strain-LmddΔactA and Insertion of the Human klk3 Gene in Frame to the hly Gene in the Lmdd and Lmdda Strains The strain Lm dal dat (Lmdd) was attenuated by the irreversible deletion of the virulence factor, ActA. An in-frame deletion of actA in the Lmdaldat (Lmdd) background was constructed to avoid any polar effects on the expression of downstream genes. The Lm dal dat ΔactA contains the first 19 amino acids at the N-terminal and 28 amino acid residues of the C-terminal with a deletion of 591 amino acids of ActA.

The actA deletion mutant was produced by amplifying the chromosomal region corresponding to the upstream (657 bp-oligo's Adv 271/272) and downstream (625 bp-oligo's Adv 273/274) portions of actA and joining by PCR. The sequence of the primers used for this amplification is given in the Table 2. The upstream and downstream DNA regions of actA were cloned in the pNEB193 at the EcoRI/PstI restriction site and from this plasmid, the EcoRI/PstI was further cloned in the temperature sensitive plasmid pKSV7, resulting in ΔactA/pKSV7 (pAdv120).

TABLE 2

Sequence of primers that was used for the amplification of DNA sequences upstream and downstream of actA

| Primer | Sequence | SEQ ID NO: |
|---|---|---|
| Adv271-actAF1 | cg GAATTCGGATCCgcgccaaatcattggttgattg | 47 |
| Adv272-actAR1 | gcgaGTCGACgtcggggttaatcgtaatgcaattggc | 48 |
| Adv273-actAF2 | gcgaGTCGACccatacgacgttaattcttgcaatg | 49 |
| Adv274-actAR2 | gataCTGCAGGGATCCttcccttctcggtaatcagtcac | 50 |

Figure 1:
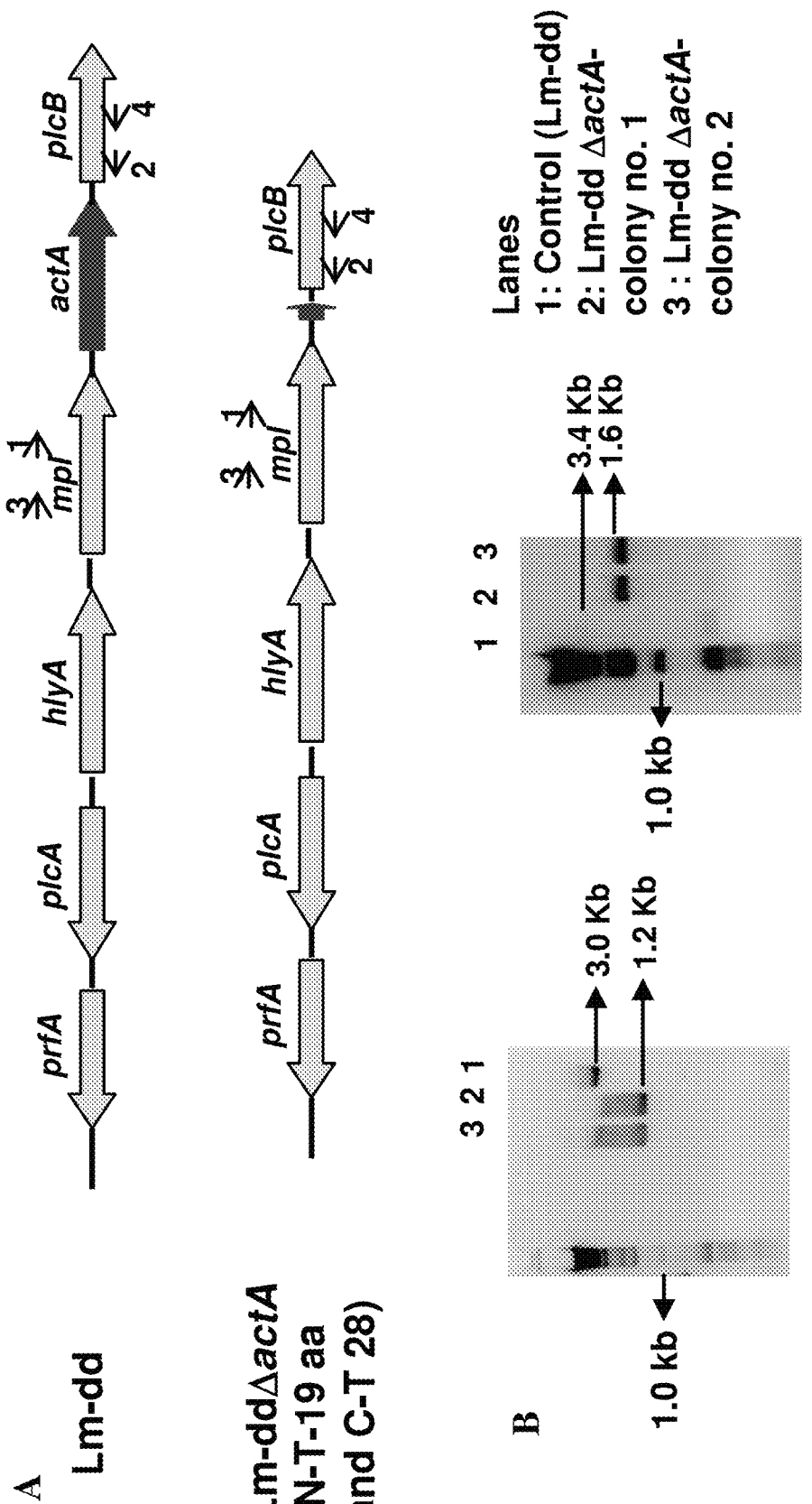
FIG. 1. (A) Schematic representation of the chromosomal region of the Lmdd-143 and LmddA-143 after klk3 integration and actA deletion; (B) The klk3 gene is integrated into the Lmdd and LmddA chromosome. PCR from chromosomal DNA preparation from each construct using klk3 specific primers amplifies a band of 714 bp corresponding to the klk3 gene, lacking the secretion signal sequence of the wild type protein.

The deletion of the gene from its chromosomal location was verified using primers that bind externally to the actA deletion region, which are shown in FIG. 1 as primer 3 (Adv 305-tgggatggccaagaaattc, SEQ ID NO: 51) and primer 4 (Adv304-ctaccatgtcttccgttgcttg; SEQ ID NO: 52). The PCR analysis was performed on the chromosomal DNA isolated from Lmdd and LmddΔactA. The sizes of the DNA fragments after amplification with two different sets of primer pairs 1/2 and 3/4 in Lmdd chromosomal DNA was expected to be 3.0 Kb and 3.4 Kb. On the other hand, the expected sizes of PCR using the primer pairs 1/2 and 3/4 for the LmddΔactA was 1.2 Kb and 1.6 Kb. Thus, PCR analysis in FIG. 1 confirms that the 1.8 kb region of actA was deleted in the LmddΔactA strain. DNA sequencing was also performed on PCR products to confirm the deletion of actA containing region in the strain, LmddΔactA.

Example 2

Construction of the Antibiotic-Independent Episomal Expression System for Antigen Delivery by Lm Vectors The antibiotic-independent episomal expression system for antigen delivery by Lm vectors (pAdv142) is the next generation of the antibiotic-free plasmid pTV3 (Verch et al., Infect Immun, 2004. 72(11):6418-25, incorporated herein by reference). The gene for virulence gene transcription activator, prfA was deleted from pTV3 since Listeria strain Lmdd contains a copy of prfA gene in the chromosome. Additionally, the cassette for p60-Listeria dal at the NheI/PacI restriction site was replaced by p60-Bacillus subtilis dal resulting in plasmid pAdv134 (FIG. 2A). The similarity of the Listeria and Bacillus dal genes is ~30%, virtually eliminating the chance of recombination between the plasmid and the remaining fragment of the dal gene in the Lmdd chromosome. The plasmid pAdv134 contained the antigen expression cassette tLLO-E7. The LmddA strain was transformed with the pADV134 plasmid and expression of the LLO-E7 protein from selected clones confirmed by Western blot (FIG. 2B). The Lmdd system derived from the 10403S wild-type strain lacks antibiotic resistance markers, except for the Lmdd streptomycin resistance.

Further, pAdv134 was restricted with XhoI/XmaI to clone human PSA, klk3 resulting in the plasmid, pAdv142. The new plasmid, pAdv142 (FIG. 2C, Table 1) contains Bacillus dal (B-Dal) under the control of Listeria p60 promoter. The shuttle plasmid, pAdv142 complemented the growth of both E. coli ala drx MB2159 as well as Listeria monocytogenes strain Lmdd in the absence of exogenous D-alanine. The antigen expression cassette in the plasmid pAdv142 consists of hly promoter and LLO-PSA fusion protein (FIG. 2C).

The plasmid pAdv142 was transformed to the Listeria background strains, LmddactA strain resulting in Lm-ddA-LLO-PSA. The expression and secretion of LLO-PSA fusion protein by the strain, Lm-ddA-LLO-PSA was confirmed by Western Blot using anti-LLO and anti-PSA antibody (FIG. 2D). There was stable expression and secretion of LLO-PSA fusion protein by the strain, Lm-ddA-LLO-PSA after two in vivo passages.

Example 3

In Vitro and In Vivo Stability of the Strain LmddA-LLO-PSA

The in vitro stability of the plasmid was examined by culturing the LmddA-LLO-PSA Listeria strain in the presence or absence of selective pressure for eight days. The selective pressure for the strain LmddA-LLO-PSA is D-alanine. Therefore, the strain LmddA-LLO-PSA was passaged in Brain-Heart Infusion (BHI) and BHI+ 100 μg/ml D-alanine. CFUs were determined for each day after plating on selective (BHI) and non-selective (BHI+D-alanine) medium. It was expected that a loss of plasmid will result in higher CFU after plating on non-selective medium (BHI+D-alanine). As depicted in FIG. 3A, there was no difference between the number of CFU in selective and non-selective medium. This suggests that the plasmid pAdv142 was stable for at least 50 generations, when the experiment was terminated.

Plasmid maintenance in vivo was determined by intravenous injection of 5×10$^7$ CFU LmddA-LLO-PSA, in C57BL/6 mice. Viable bacteria were isolated from spleens homogenized in PBS at 24 h and 48 h. CFUs for each sample were determined at each time point on BHI plates and BHI+100 μg/ml D-alanine. After plating the splenocytes on selective and non-selective medium, the colonies were recovered after 24 h. Since this strain is highly attenuated, the bacterial load is cleared in vivo in 24 h. No significant differences of CFUs were detected on selective and non-selective plates, indicating the stable presence of the recombinant plasmid in all isolated bacteria (FIG. 3B).

Example 4

In Vivo Passaging, Virulence and Clearance of the Strain LmddA-142 (LmddA-LLO-PSA)

LmddA-142 is a recombinant Listeria strain that secretes the episomally expressed tLLO-PSA fusion protein. To determine a safe dose, mice were immunized with LmddA-LLO-PSA at various doses and toxic effects were determined. LmddA-LLO-PSA caused minimum toxic effects (data not shown). The results suggested that a dose of $10^8$ CFU of LmddA-LLO-PSA was well tolerated by mice. Virulence studies indicate that the strain LmddA-LLO-PSA was highly attenuated.

The in vivo clearance of LmddA-LLO-PSA after administration of the safe dose, $10^8$ CFU intraperitoneally in C57BL/6 mice, was determined. There were no detectable colonies in the liver and spleen of mice immunized with LmddA-LLO-PSA after day 2. Since this strain is highly attenuated, it was completely cleared in vivo at 48 h (FIG. 4A).

To determine if the attenuation of LmddA-LLO-PSA attenuated the ability of the strain LmddA-LLO-PSA to infect macrophages and grow intracellularly, we performed a cell infection assay. Mouse macrophage-like cell line such as J774A.1 were infected in vitro with Listeria constructs and intracellular growth was quantified. The positive control strain, wild type Listeria strain 10403S grows intracellularly, and the negative control XFL7, a prfA mutant, cannot escape the phagolysosome and thus does not grow in J774 cells. The intracytoplasmic growth of LmddA-LLO-PSA was slower than 10403S due to the loss of the ability of this strain to spread from cell to cell (FIG. 4B). The results indicate that LmddA-LLO-PSA has the ability to infect macrophages and grow intracytoplasmically.

Example 5

Immunogenicity of the Strain-LmddA-LLO-PSA in C57BL/6 Mice

The PSA-specific immune responses elicited by the construct LmddA-LLO-PSA in C57BL/6 mice were determined using PSA tetramer staining. Mice were immunized twice with LmddA-LLO-PSA at one week intervals and the splenocytes were stained for PSA tetramer on day 6 after the boost. Staining of splenocytes with the PSA-specific tetramer showed that LmddA-LLO-PSA elicited 23% of PSA tetramer$^+$CD8$^+$ CD62L$^{low}$ cells (FIG. 5A).

The functional ability of the PSA-specific T cells to secrete IFN-γ after stimulation with PSA peptide for 5 h was examined using intracellular cytokine staining. There was a 200-fold increase in the percentage of CD8$^+$ CD62L$^{low}$IFN-γ secreting cells stimulated with PSA peptide in the LmddA-LLO-PSA group compared to the naïve mice (FIG. 5B), indicating that the LmddA-LLO-PSA strain is very immunogenic and primes high levels of functionally active PSA CD8$^+$ T cell responses against PSA in the spleen.

To determine the functional activity of cytotoxic T cells generated against PSA after immunizing mice with LmddA-LLO-PSA, we tested the ability of PSA-specific CTLs to lyse cells EL4 cells pulsed with H-2D$^b$ peptide in an in vitro assay. A FACS-based caspase assay (FIG. 5C) and Europium release (FIG. 5D) were used to measure cell lysis. Splenocytes of mice immunized with LmddA-LLO-PSA contained CTLs with high cytolytic activity for the cells that display PSA peptide as a target antigen.

Elispot was performed to determine the functional ability of effector T cells to secrete IFN-γ after 24 h stimulation with antigen. Using ELISpot, we observed there was a 20-fold increase in the number of spots for IFN-γ in splenocytes from mice immunized with LmddA-LLO-PSA stimulated with specific peptide when compared to the splenocytes of the naïve mice (FIG. 5E).

Example 6

Immunization with the LmddA-142 Strains Induces Regression of a Tumor Expressing PSA and Infiltration of the Tumor by PSA-Specific CTLs The therapeutic efficacy of the construct LmddA-142 (LmddA-LLO-PSA) was determined using a prostrate adenocarcinoma cell line engineered to express PSA (Tramp-C1-PSA (TPSA); Shahabi et al., 2008). Mice were subcutaneously implanted with $2 \times 10^6$ TPSA cells. When tumors reached the palpable size of 4-6 mm, on day 6 after tumor inoculation, mice were immunized three times at one week intervals with $10^8$ CFU LmddA-142, $10^7$ CFU Lm-LLO-PSA (positive control) or left untreated. The naïve mice developed tumors gradually (FIG. 6A). The mice immunized with LmddA-142 were all tumor-free until day 35 and gradually 3 out of 8 mice developed tumors, which grew at a much slower rate as compared to the naïve mice (FIG. 6B). Five out of eight mice remained tumor free through day 70. As expected, Lm-LLO-PSA-vaccinated mice had fewer tumors than naïve controls and tumors developed more slowly than in controls (FIG. 6C). Thus, the construct LmddA-LLO-PSA could regress 60% of the tumors established by TPSA cell line and slow the growth of tumors in other mice. Cured mice that remained tumor free were rechallenged with TPSA tumors on day 68.

Immunization of mice with the LmddA-142 can control the growth and induce regression of 7-day established Tramp-C1 tumors that were engineered to express PSA in more than 60% of the experimental animals (FIG. 6B), compared to none in the untreated group (FIG. 6A). The LmddA-142 was constructed using a highly attenuated vector (LmddA) and the plasmid pADV142 (Table 1).

Further, the ability of PSA-specific CD8 lymphocytes generated by the LmddA-LLO-PSA construct to infiltrate tumors was investigated. Mice were subcutaneously implanted with a mixture of tumors and matrigel followed by two immunizations at seven day intervals with naïve or control (Lm-LLO-E7) Listeria, or with LmddA-LLO-PSA. Tumors were excised on day 21 and were analyzed for the population of CD8$^+$ CD62L$^{low}$ PSA$^{tetramer+}$ and CD4$^+$ CD25$^+$FoxP3$^+$ regulatory T cells infiltrating in the tumors.

A very low number of CD8$^+$ CD62L$^{low}$ PSA$^{tetramer+}$ tumor infiltrating lymphocytes (TILs) specific for PSA that were present in the both naïve and Lm-LLO-E7 control immunized mice was observed. However, there was a 10-30-fold increase in the percentage of PSA-specific CD8$^+$ CD62L$^{low}$ PSA$^{tetramer+}$ TILs in the mice immunized with LmddA-LLO-PSA (FIG. 7A). Interestingly, the population of CD8$^+$ CD62L$^{low}$ PSA$^{tetramer+}$ cells in spleen was 7.5 fold less than in tumor (FIG. 7A).

In addition, the presence of CD4$^+$/CD25$^+$/Foxp3$^+$ T regulatory cells (regs) in the tumors of untreated mice and Listeria immunized mice was determined. Interestingly, immunization with Listeria resulted in a considerable decrease in the number of CD4$^+$ CD25$^+$ FoxP3$^+$ T-regs in tumor but not in spleen (FIG. 7B). However, the construct LmddA-LLO-PSA had a stronger impact in decreasing the frequency of CD4$^+$ CD25$^+$FoxP3$^+$ T-regs in tumors when compared to the naïve and Lm-LLO-E7 immunized group (FIG. 7B).

Thus, the LmddA-142 vaccine can induce PSA-specific CD8$^+$ T cells that are able to infiltrate the tumor site (FIG. 7A). Interestingly, Immunization with LmddA-142 was associated with a decreased number of regulatory T cells in the tumor (FIG. 7B), probably creating a more favorable environment for an efficient anti-tumor CTL activity.

Example 7

Lmdd-143 and LmddA-143 Secretes a Functional LLO Despite the PSA Fusion

The Lmdd-143 and LmddA-143 contain the full-length human klk3 gene, which encodes the PSA protein, inserted by homologous recombination downstream and in frame with the hly gene in the chromosome. These constructs were made by homologous recombination using the pKSV7 plasmid (Smith and Youngman, Biochimie. 1992; 74 (7-8) p705-711), which has a temperature-sensitive replicon, carrying the hly-klk3-mpl recombination cassette. Because of the plasmid excision after the second recombination event, the antibiotic resistance marker used for integration selection is lost. Additionally, the actA gene is deleted in the LmddA-143 strain (FIG. 8A). The insertion of klk3 in frame with hly into the chromosome was verified by PCR (FIG. 8B) and sequencing (data not shown) in both constructs.

One important aspect of these chromosomal constructs is that the production of LLO-PSA would not completely abolish the function of LLO, which is required for escape of *Listeria* from the phagosome, cytosol invasion and efficient immunity generated by *L. monocytogenes*. Western-blot analysis of secreted proteins from Lmdd-143 and LmddA-143 culture supernatants revealed an ~81 kDa band corresponding to the LLO-PSA fusion protein and an ~60 kDa band, which is the expected size of LLO (FIG. 9A), indicating that LLO is either cleaved from the LLO-PSA fusion or still produced as a single protein by *L. monocytogenes*, despite the fusion gene in the chromosome. The LLO secreted by Lmdd-143 and LmddA-143 retained 50% of the hemolytic activity, as compared to the wild-type *L. monocytogenes* 10403S (FIG. 9B). In agreement with these results, both Lmdd-143 and LmddA-143 were able to replicate intracellularly in the macrophage-like J774 cell line (FIG. 9C).

Example 8

Both Lmdd-143 and LmddA-143 Elicit Cell-Mediated Immune Responses Against the PSA Antigen After showing that both Lmdd-143 and LmddA-143 are able to secrete PSA fused to LLO, we investigated if these strains could elicit PSA-specific immune responses in vivo. C57Bl/6 mice were either left untreated or immunized twice with the Lmdd-143, LmddA-143 or LmddA-142. PSA-specific CD8$^+$ T cell responses were measured by stimulating splenocytes with the PSA$_{65-74}$ peptide and intracellular staining for IFN-γ. As shown in FIG. 10, the immune response induced by the chromosomal and the plasmid-based vectors is similar.

Example 9

A Recombinant Lm Strain Secreting a LLO-HMW-MAA Fusion Protein Results in a Broad Antitumor Response Three Lm-based vaccines expressing distinct HMW-MAA fragments based on the position of previously mapped and predicted HLA-A2 epitopes were designed (FIG. 11A). The Lm-tLLO-HMW-MMA$_{2160-2258}$ (also referred as Lm-LLO-HMW-MAA-C) is based on the avirulent Lm XFL-7 strain and a pGG55-based plasmid. This strain secretes a ~62 kDa band corresponding to the tLLO-HMW-MAA$_{2160-2258}$ fusion protein (FIG. 11B). The secretion of tLLO-HMW-MAA$_{2160-2258}$ is relatively weak likely due to the high hydrophobicity of this fragment, which corresponds to the HMW-MAA transmembrane domain. Using B16F10 melanoma cells transfected with the full-length HMW-MAA gene, we observed that up to 62.5% of the mice immunized with the Lm-LLO-HMW-MAA-C could impede the growth of established tumors (FIG. 11C). This result shows that HMW-MAA can be used as a target antigen in vaccination strategies. Interestingly, we also observed that immunization of mice with Lm-LLO-HMW-MAA-C significantly impaired the growth of tumors not engineered to express HMW-MAA, such as B16F10, RENCA and NT-2 (FIG. 11D), which were derived from distinct mouse strains. In the NT-2 tumor model, which is a mammary carcinoma cell line expressing the rat HER-2/neu protein and is derived from the FVB/N transgenic mice, immunization with Lm-LLO-HMW-MAA-C 7 days after tumor inoculation not only impaired tumor growth but also induced regression of the tumor in 1 out of 5 mice (FIG. 11D).

Example 10

Immunization of Mice with Lm-LLO-HMW-MAA-C Induces Infiltration of the Tumor Stroma by CD8$^+$ T Cells and a Significant Reduction in the Pericyte Coverage in the Tumor Vasculature Although NT-2 cells do not express the HMW-MAA homolog NG2, immunization of FVB/N mice with Lm-LLO-HMW-MAA-C significantly impaired the growth of NT-2 tumors and eventually led to tumor regression (FIG. 11D). This tumor model was used to evaluate CD8$^+$ T cells and pericytes in the tumor site by immunofluorescence. Staining of NT-2 tumor sections for CD8 showed infiltration of CD8$^+$ T cells into the tumors and around blood vessels in mice immunized with the Lm-LLO-HMW-MAA-C vaccine, but not in mice immunized with the control vaccine (FIG. 12A). Pericytes in NT-2 tumors were also analyzed by double staining with αSMA and NG2 (murine homolog of HMW-MAA) antibodies. Data analysis from three independent NT-2 tumors showed a significant decrease in the number of pericytes in mice immunized with Lm-LLO-HMW-MAA-C, as compared to control (P≤0.05) (FIG. 12B). Similar results were obtained when the analysis was restricted to cells stained for αSMA, which is not targeted by the vaccine (data not shown). Thus, Lm-LLO-HMW-MAA-C vaccination impacts blood vessel formation in the tumor site by targeting pericytes.

Example 11

Development of a Recombinant *L. monocytogenes* Vector with Enhanced Anti-Tumor Activity by Concomitant Expression and Secretion of LLO-PSA and tLLO-HMW-MAA$_{2160-2258}$ Fusion Proteins, Eliciting Immune Responses to Both Heterologous Antigens.

Materials and Methods:
Construction of the pADV168 Plasmid.

The HMW-MAA-C fragment is excised from a pCR2.1-HMW-MAA$_{2160-2258}$ plasmid by double digestion with XhoI and XmaI restriction endonucleases. This fragment is cloned in the pADV134 plasmid already digested with XhoI and XmaI to excise the E7 gene. The pADV168 plasmid is electroporated into electrocompetent the dal$^{(-)}$ dat$^{(-)}$ E. coli strain MB2159 and positive clones screened for RFLP and sequence analysis.

Construction of Lmdd-143/168, LmddA-143/168 and the Control Strains LmddA-168, Lmdd-143/134 and LmddA-143/134.

Lmdd, Lmdd-143 and LmddA-143 is transformed with either pADV168 or pADV134 plasmid. Transformants are selected on Brain-Heart Infusion-agar plates supplemented with streptomycin (250 μg/ml) and without D-alanine (BHIs medium). Individual clones are screened for LLO-PSA, tLLO-HMW-MAA$_{2160-2258}$ and tLLO-E7 secretion in bacterial culture supernatants by Western-blot using an anti-LLO, anti-PSA or anti-E7 antibody. A selected clone from each strain will be evaluated for in vitro and in vivo virulence. Each strain is passaged twice in vivo to select the most stable recombinant clones. Briefly, a selected clone from each construct is grown and injected i.p to a group of 4 mice at 1×10$^8$ CFU/mouse. Spleens are harvested on days 1 and 3, homogenized and plated on BHIs-agar plates. After the first passage, one colony from each strain is selected and passaged in vivo for a second time. To prevent further attenuation of the vector, to a level impairing its viability, constructs in two vectors with distinct attenuation levels (Lmdd-143/168, LmddA-143/168) are generated.

In Vitro Virulence Determination by Intracellular Replication in J774 Cells.

Uptake of Lm by macrophages, followed by cytosolic invasion and intracellular proliferation are required for successful antigen delivery and presentation by Lm-based vaccines. An in vitro invasion assay, using a macrophage-like J774 cell line is used to test these properties in new recombinant Lm strains. Briefly, J774 cells are infected for 1 hour in medium without antibiotics at MOI of 1:1 with either the control wild-type Lm strain 10403S or the new Lm strains to be tested. Extracellular bacteria are killed by 1 hour incubation in medium 10 μg/ml of gentamicin. Samples are harvested at regular intervals and cells lysed with water. Ten-fold serial dilutions of the lysates are plated in duplicates on BHIs plates and colony-forming units (CFU) counted in each sample.

In Vivo Virulence Studies.

Groups of four C57BL/6 mice (7 weeks old) are injected i.p. with two different doses (1×10$^8$ and 1×10$^9$ CFUs/dose) of Lmdd-143/168, LmddA-143/168, LmddA-168, Lmdd-143/134 or LmddA-143/134 strains. Mice are followed-up for 2 weeks for survival and LD$_{50}$ estimation. An LD$_{50}$ of >1×10$^8$ constitutes an acceptable value based on previous experience with other Lm-based vaccines.

Results

Once the pADV168 plasmid is successfully constructed, it is sequenced for the presence of the correct HMW-MAA sequence. This plasmid in these new strains express and secrete the LLO fusion proteins specific for each construct. These strains are highly attenuated, with an LD50 of at least 1×10$^8$ CFU and likely higher than 1×10$^9$ CFU for the actA-deficient (LmddA) strains, which lack the actA gene and consequently the ability of cell-to-cell spread. The construct is tested and the one that has a better balance between attenuation and therapeutic efficacy is selected.

Example 12

Detection of Immune Responses and Anti-Tumor Effects Elicited Upon Immunization with Lmdd-143/168 and LmddA-143/168

Immune responses to PSA and HMW-MAA are studied in mice upon immunization with Lmdd-143/168 and LmddA-143/168 strains using standard methods, such as detection of IFN-γ production and specific CTL activity against these antigens. The therapeutic efficacy of dual-expression vectors are tested in the TPSA23 tumor model.

Intracellular Cytokine Staining for IFN-γ.

C57BL/6 mice (3 mice per treatment group) are immunized twice at 1-week intervals with the Lmdd-143/168 and LmddA-143/168 strains. As controls for this experiment, mice are immunized with Lmdd-143, LmddA-143, LmddA-142, LmddA-168, Lmdd-143/134, LmddA-143/134 or left untreated (naïve group). Spleens are harvested after 7 days and a single cell suspension of splenocytes are prepared. These splenocytes are plated at 2×10$^6$ cells/well in a round bottom 96-well plate, in freshly prepared complete RPMI medium with IL-2 (50 U/ml) and stimulated with either the PSA H-2 Db peptide, HCIRNKSVIL, (SEQ ID NO: 53), or the HPV16 E7 H-2 Db control peptide RAHYNIVTF (SEQ ID NO: 54) at a final concentration of 1 μM. Since HMW-MAA-epitopes have not been mapped in the C57Bl/6 mouse, HMW-MAA-specific immune responses are detected by incubating 2×10$^6$ splenocytes with 2×10$^5$ EL4-HMW-MAA cells. The cells are incubated for 5 hours in the presence of monensin to retain the intracellular IFN-γ in the cells. After incubation, cells are stained with anti-mouse CD8-FITC, CD3-PerCP, CD62L-APC antibodies. They are then permeabilized and stained for IFNγ-PE and analyzed in a four-color FACS Calibur (BD Biosciences).

Cytotoxicity Assay.

To investigate the effector activity of the PSA and HMW-MAA specific T cells generated upon vaccinations, isolated splenocytes are incubated for 5 days in complete RPMI medium containing 20 U/ml of mouse IL-2 (Sigma), in the presence of stimulator cells (mitomycin C treated MC57G cells infected with either PSA or HMW-MAA vaccinia). For the cytotoxicity assay, EL4 target cells are labeled for 15 minutes with DDAO-SE (0.6 M) (Molecular Probes) and washed twice with complete medium. The labeled target cells are pulsed for 1 hour with either the PSA H-2 Db peptide, or the HPV16 E7 H-2 Db control peptide, at a final concentration of 5 μM. For HMW-MAA-specific cytotoxic responses, the EL4-HMW-MAA cells are used as targets. The cytotoxicity assay is performed for 2 hours by incubating the target cells (T) with effector cells (E) at different E:T ratios for 2-3 hours. Cells are fixed with formalin, permeabilized and stained for cleaved caspase-3 to detect induction of apoptosis in the target cells.

Anti-Tumor Efficacy.

The anti-tumor efficacy of the Lmdd-143/168 and LmddA-143/168 strains are compared to that of LmddA-142 and LmddA-168, using the T-PSA23 tumor model (TrampC-1/PSA). Groups of 8 male C57BL/6 mice (6-8 weeks old) are inoculated s.c. with 2×10$^6$ T-PSA23 cells and 7 days later immunized i.p. with 0.1×LD50 dose of Lmdd-143/168, LmddA-143/168, LmddA-142 and LmddA-168. As controls, mice are either left untreated or immunized with an Lm control strain (LmddA-134). Each group receives two additional doses of the vaccines with 7 day intervals. Tumors are monitored for 60 days or until they reach a size of 2 cm, at which point mice are sacrificed.

Results

Immunization of mice with LmddA-168 results in the induction of specific responses against HMW-MAA. Similarly, Lmdd-143/168 and LmddA-143/168 elicits an immune response against PSA and HMW-MAA that is comparable to the immune responses generated by L. monocytogenes vectors expressing each antigen individually. Immunization of T-PSA-23-bearing mice with the Lmdd-143/168 and LmddA-143/168 results in a better anti-tumor therapeutic efficacy than the immunization with either LmddA-142 or LmddA-168.

Example 13

Immunization with Either Lmdd-143/168 or LmddA-143/168 Results in Pericyte Destruction, Up-Regulation of Adhesion Molecules in Endothelial Cells and Enhanced Infiltration of TILs Specific for PSA Characterization of Tumor Infiltrating Lymphocytes and Endothelial Cell-Adhesion Molecules Induced Upon Immunization with Lmdd-143/168 or LmddA-143/168.

The tumors from mice immunized with either Lmdd-143/168 or LmddA-143/168 are analyzed by immunofluorescence to study expression of adhesion molecules by endothelial cells, blood vessel density and pericyte coverage in the tumor vasculature, as well as infiltration of the tumor by immune cells, including CD8 and CD4 T cells. TILs specific for the PSA antigen are characterized by tetramer analysis and functional tests.

Analysis of Tumor Infiltrating Lymphocytes (TILs).

TPSA23 cells embedded in matrigel are inoculated s.c in mice (n=3 per group), which are immunized on days 7 and 14 with either Lmdd-143/168 or LmddA-143/168, depending on which one is the more effective according to results obtained in anti-tumor studies. For comparison, mice are immunized with LmddA-142, LmddA-168, a control Lm vaccine or left untreated. On day 21, the tumors are surgically excised, washed in ice-cold PBS and minced with a scalpel. The tumors are treated with dispase to solubilize the Matrigel and release single cells for analysis. PSA-specific $CD8^+$ T cells are stained with a PSA65-74 H-2 Db tetramer-PE and anti-mouse CD8-FITC, CD3-PerCP-Cy5.5 and CD62L-APC antibodies. To analyze regulatory T cell in the tumor, TILs are stained with CD4-FITC, CD3-PerCP-Cy5.5 and CD25-APC and subsequently permeabilized for FoxP3 staining (anti-FoxP3-PE, Milteny Biotec). Cells are analyzed by a FACS Calibur cytometer and CellQuestPro software (BD Biosciences).

Immunofluorescence.

On day 21 post tumor inoculation, the TPSA23 tumors embedded in matrigel are surgically excised and a fragment immediately cryopreserved in OCT freezing medium. The tumor fragments are cryosectioned for 8-10 μm thick sections. For immunofluorescence, samples are thawed and fixed using 4% formalin. After blocking, sections are stained with antibodies in blocking solution in a humidified chamber at 37° C. for 1 hour. DAPI (Invitrogen) staining are performed according to manufacturer instructions. For intracellular stains (αSMA), incubation is performed in PBS/0.1% Tween/1% BSA solution. Slides are cover-slipped using a mounting solution (Biomeda) with anti-fading agents, set for 24 hours and kept at 4° C. until imaging using Spot Image Software (2006) and BX51 series Olympus fluorescent microscope. CD8, CD4, FoxP3, αSMA, NG2, CD31, ICAM-1, VCAM-1 and VAP-1 are evaluated by immunofluorescence.

Statistical Analysis:

Non-parametric Mann-Whitney and Kruskal-Wallis tests are applied to compare tumor sizes among different treatment groups. Tumor sizes are compared at the latest timepoint with the highest number of mice in each group (8 mice). A p-value of less than 0.05 is considered statistically significant in these analyses.

Results

Immunization of TPSA23-bearing mice with the Lmdd-143/168 and LmddA-143/168 results in higher numbers of effector TILs specific to PSA and also decreases pericyte coverage of the tumor vasculature. Further, cell-adhesion markers are significantly up-regulated in immunized mice.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A recombinant *Listeria* strain comprising a nucleic acid molecule encoding a fusion polypeptide, wherein said fusion polypeptide comprises a heterologous antigen fused to an N-terminal LLO, wherein said recombinant *Listeria* is an attenuated *Listeria* comprising a mutation in the dal/dat genes, wherein said *Listeria* comprises an episomal vector comprising a nucleic acid sequence encoding a metabolic enzyme that complements said dal/dat mutation, wherein said episomal vector is stably maintained in said recombinant *Listeria* in the absence of antibiotic selection, and wherein said *Listeria* comprises a deletion of the endogenous actA gene.

2. The recombinant *Listeria* of claim 1, wherein said nucleic acid molecule is integrated into the *Listeria* genome.

3. The recombinant *Listeria* of claim 1, wherein said nucleic acid molecule is in said episomal vector in said recombinant *Listeria* strain.

4. The recombinant *Listeria* of claim 3, wherein said episomal vector does not confer antibiotic resistance upon said recombinant *Listeria*.

5. The recombinant *Listeria* of claim 1, wherein said metabolic enzyme is an alanine racemase enzyme or a D-amino acid transferase enzyme.

6. The recombinant *Listeria* of claim 1, wherein the heterologous antigen is Prostate Specific Antigen (PSA) or a fragment thereof, or Human Papilloma Virus E7 (HPV-E7) or a fragment thereof.

7. An immunogenic composition comprising the recombinant *Listeria* of claim 6, and an adjuvant.

8. The recombinant *Listeria* of claim 7, wherein said adjuvant comprises a granulocyte/macrophage colony-stimulating factor (GM-CSF) protein, a nucleic acid molecule encoding a GM-CSF protein, saponin QS21, monophosphoryl lipid A, or an unmethylated CpG-containing oligonucleotide.

9. The recombinant *Listeria* of claim 1, wherein said *Listeria* is a *Listeria monocytogenes* strain.

10. A recombinant *Listeria* strain comprising a nucleic acid molecule encoding a fusion polypeptide, wherein said fusion polypeptide comprises a Prostate Specific Antigen (PSA) or fragment thereof fused to an N-terminal LLO, wherein said recombinant *Listeria* is an attenuated *Listeria* comprising a mutation in the dal/dat genes, wherein said *Listeria* comprises a metabolic enzyme that complements said dal/dat mutation, and wherein said *Listeria* comprises a deletion of the endogenous actA gene.

* * * * *